United States Patent
Hermanson et al.

(10) Patent No.: US 9,180,162 B2
(45) Date of Patent: *Nov. 10, 2015

(54) CODON-OPTIMIZED POLYNUCLEOTIDE-BASED VACCINES AGAINST HUMAN CYTOMEGALOVIRUS INFECTION

(71) Applicant: Vical Incorporated, San Diego, CA (US)

(72) Inventors: Gary G. Hermanson, Encinitas, CA (US); Andrew J. Geall, Cambridge, MA (US); Mary Kopke Wloch, San Diego, CA (US)

(73) Assignee: Vical Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/176,813

(22) Filed: Feb. 10, 2014

(65) Prior Publication Data

US 2014/0186382 A1 Jul. 3, 2014

Related U.S. Application Data

(63) Continuation of application No. 13/525,814, filed on Jun. 18, 2012, now Pat. No. 8,673,317, which is a continuation of application No. 13/013,752, filed on Jan. 25, 2011, now Pat. No. 8,278,093, which is a continuation of application No. 11/892,020, filed on Aug. 17, 2007, now Pat. No. 7,888,112, which is a continuation of application No. 10/738,986, filed on Dec. 19, 2003, now Pat. No. 7,410,795.

(60) Provisional application No. 60/435,549, filed on Dec. 23, 2002.

(51) Int. Cl.
| | | |
|---|---|---|
| *C07K 14/005* | (2006.01) | |
| *A61K 39/245* | (2006.01) | |
| *A61K 38/16* | (2006.01) | |
| *C07H 21/00* | (2006.01) | |
| *A61K 39/12* | (2006.01) | |
| *C07K 14/045* | (2006.01) | |
| *A61K 39/00* | (2006.01) | |
| *A61K 35/763* | (2015.01) | |

(52) U.S. Cl.
CPC .................. *A61K 38/16* (2013.01); *A61K 39/12* (2013.01); *A61K 39/245* (2013.01); *C07H 21/00* (2013.01); *C07K 14/005* (2013.01); *C07K 14/045* (2013.01); *A61K 35/763* (2013.01); *A61K 38/162* (2013.01); *A61K 39/00* (2013.01); *A61K 2039/53* (2013.01); *A61K 2039/55522* (2013.01); *A61K 2039/55555* (2013.01); *A61K 2039/55572* (2013.01); *C12N 2710/16122* (2013.01); *C12N 2710/16134* (2013.01); *C12N 2800/22* (2013.01)

(58) Field of Classification Search
CPC . A61K 39/12; A61K 39/245; A61K 2039/53; A61K 39/00; A61K 35/763; A61K 39/25; A61K 2039/6075; C12N 2710/16134; C12N 7/00; C12N 2710/16122; C12N 2710/16121; C12N 2710/16162; C12N 2710/16234
See application file for complete search history.

(56) References Cited

U.S. PATENT DOCUMENTS

| | | | |
|---|---|---|---|
| 5,124,440 A | | 6/1992 | Gehrz et al. |
| 5,547,834 A | | 8/1996 | Spaete et al. |
| 5,800,981 A | | 9/1998 | Bruggeman et al. |
| 5,834,307 A | | 11/1998 | Spaete et al. |
| 5,925,751 A | * | 7/1999 | Spaete et al. ............... 536/23.72 |
| 5,972,596 A | * | 10/1999 | Pavlakis et al. ................... 435/5 |
| 6,074,648 A | | 6/2000 | Lee |

(Continued)

FOREIGN PATENT DOCUMENTS

| | | |
|---|---|---|
| EP | 0 609 580 A1 | 8/1994 |
| EP | 1 156 112 A1 | 11/2001 |

(Continued)

OTHER PUBLICATIONS

Selinsky C, Luke C, Wloch M, Geall A, Hermanson G, Kaslow D, Evans T. A DNA-based vaccine for the prevention of human cytomegalovirus-associated diseases. Hum Vaccin. Jan.-Feb. 2005;1(1):16-23. Epub Jan. 25, 2005.*

(Continued)

*Primary Examiner* — Benjamin P Blumel
*Assistant Examiner* — Rachel Gill
(74) *Attorney, Agent, or Firm* — Sughrue Mion, PLLC

(57) ABSTRACT

The invention is related to polynucleotide-based cytomegalovirus vaccines. In particular, the invention is plasmids operably encoding HCMV antigens, in which the naturally-occurring coding regions for the HCMV antigens have been modified for improved translation in human or other mammalian cells through codon optimization. HCMV antigens which are useful in the invention include, but are not limited to pp65, glycoprotein B (gB), IE1, and fragments, variants or derivatives of either of these antigens. In certain embodiments, sequences have been deleted, e.g., the Arg435-Lys438 putative kinase in pp65 and the membrane anchor and endocellular domains in gB. The invention is further directed to methods to induce an immune response to HCMV in a mammal, for example, a human, comprising delivering a plasmid encoding a codon-optimized HCMV antigen as described above. The invention is also directed to pharmaceutical compositions comprising plasmids encoding a codon-optimized HCMV antigen as described above, and further comprising adjuvants, excipients, or immune modulators.

10 Claims, 30 Drawing Sheets

(56) References Cited

U.S. PATENT DOCUMENTS

| | | | |
|---|---|---|---|
| 6,100,064 | A | 8/2000 | Burke et al. |
| 6,133,433 | A | 10/2000 | Pande et al. |
| 6,156,317 | A | 12/2000 | Diamond et al. |
| 6,162,620 | A | 12/2000 | Smith et al. |
| 6,242,567 | B1 | 6/2001 | Pande et al. |
| 6,251,399 | B1 | 6/2001 | Diamond |
| 6,586,409 | B1 * | 7/2003 | Wheeler ............ 514/44 R |
| 7,410,795 | B2 * | 8/2008 | Hermanson et al. ....... 435/320.1 |
| 7,888,112 | B2 * | 2/2011 | Hermanson et al. ....... 435/320.1 |
| 8,278,093 | B2 * | 10/2012 | Hermanson et al. ....... 435/320.1 |
| 8,673,317 | B2 * | 3/2014 | Hermanson et al. ....... 424/230.1 |
| 2002/0081318 | A1 | 6/2002 | Zaia |
| 2002/0110567 | A1 | 8/2002 | Gerdts et al. |

FOREIGN PATENT DOCUMENTS

| | | |
|---|---|---|
| WO | WO 89/07143 A1 | 8/1989 |
| WO | WO 97/11086 A1 | 3/1997 |
| WO | WO 97/40165 A1 | 10/1997 |
| WO | WO 99/02694 A1 | 1/1999 |
| WO | WO 01/52888 A2 | 7/2001 |
| WO | WO 02/00844 A2 | 1/2002 |

OTHER PUBLICATIONS

Yao ZQ, Gallez-Hawkins G, Lomeli NA, Li X, Molinder KM, Diamond DJ, Zaia JA. Site-directed mutation in a conserved kinase domain of human cytomegalovirus-pp65 with preservation of cytotoxic T lymphocyte targeting. Vaccine. Feb. 8, 2001;19(13-14):1628-35.*

Gallez-Hawkins G, Lomeli NA, L Li X, Yao ZQ, La Rosa C, Diamond DJ, Zaia JA. Kinase-deficient CMVpp65 triggers a CMVpp65 specific T-cell immune response in HLA-A*0201.Kb transgenic mice after DNA immunization. Scand J Immunol. Jun. 2002;55(6):592-8. Erratum in: Scand J Immunol Aug. 2002;56(2):217.*

Endresz V, Kari L, Berencsi K, Kari C, Gyulai Z, Jeney C, Pincus S, Rodeck U, Méric C, Plotkin SA, Gönczöl E. Induction of human cytomegalovirus (HCMV)-glycoprotein B (gB)-specific neutralizing antibody and phosphoprotein 65 (pp65)-specific cytotoxic T lymphocyte responses by naked DNA immunization. Vaccine. Jan. 1999;17(1):50-8.*

Chee et. al. "pp65, Tegument protein UL83, Human herpesvirus 5 strain AD169." GenBank P06725. Dep. Feb. 1, 1991.*

Chee et. al. Human herpesvirus 5 strain AD169. GenBank X17403. Dep. Jul. 1, 1992.*

Plotkin, S.A., et al., "Candidate Cytomegalovirus Strain for Human Vaccination", 12(3):521-527 (1975).

Davison, A.J., et al.,"The Human Cytomegalovirus Genome Revisited: Comparison with the Chimpanzee Cytomegalovirus Genome", 84(1):17-28(2003).

Baldridge, J., et al.,"Monophosphoryl Lipid A (MPL) Formulations for the Next Generation of Vaccines", 19(1):103-107 (1999).

Wheeler, C.J., et al., "A novel cationic lipid greatly enhances plasmid DNA delivery and expression in mouse lung", Proc. Natl. Acad. Sci. USA 93(21):11454-9 (1996).

Cranage, M.P., et al., "Identification of the human cytomegalovirus glycoprotein B gene and induction of neutralizing antibodies via its expression in recombinant vaccinia virus", Journal EMBO J. 5(11):3057-3063 (1986).

Rueger, B., et al., "Primary structure and transcription of the genes encoding for the two virion phosphoproteins pp 65 and pp71 of human cytomegalovirus", J. Virol. 61:446-453 (1987).

Akrigg, A., et al., "The structure of the major immediate early gene of human cytomegalovirus strain AD169," Virus Res. 2:107-121, Elsevier (1985).

Allen, L.B., et al., "Novel method for evaluating antiviral drugs against human cytomegalovirus in mice," Antimicrob. Agents Chemother. 36:206-208, American Society for Microbiology (1992).

Amadei, C., et al., "Human anti-cytomegalovirus (CMV) immunoglobulins secreted by EBV-transformed B-lymphocyte cell lines," Dev. Biol. Stand. 57:283-286, S. Karger (1984).

Andre, S., et al., "Increased immune response elicited by DNA vaccination with a cynthetic gp120 sequence with optimized codon usage," J. Virol. 72:1497-1503, American Society for Microbiology (1998).

Arrode, G., et al., "Cross-presentation of human cytomegalovirus pp65 (UL83) to CD8 T cells is regulated by virus-induced, soluable mediator-dependent maturation of dendritic cells," J. Virol. 76:142-150, American Society for Microbiology (2002).

Berensi, K., et al., "The N-terminal 303 amino acids of human cytomegalovirus envelope glycoprotein B (UL55) and the exon 4 region of the major immediate early protein 1 (UL123) induce a cytotoxic T-cell response," Vaccine 14:369-374, Elsevier Science (1996).

Bidanset, D.J., et al., "Replication of human cytomegalovirus in sever combined immunodeficient mice implanted with human retinal tissue", J. Infect. Dis. 184:192-195, Univ. of Chicago Press (2001).

Chee, M.S., et al., "Analysis of the protein-coding of the sequence of human cytomegalovirus strain AS169," in Cytomegalovirus, McDougall, J.K. ed 126-169 (1990).

Davignon, J-L., et al., "Anti-human cytomegalovirus activity of cytokines produced by CD4 T-cell clones specifically activated by IE1 peptides in vitro," J. Virol. 70:2162-2169, American Society for Microbiology (1996).

Deml, L., et al., " Multiple effects of codon usage optimization on expression and immunogenicity of DNA candidate vaccines encoding the human immunodeficiency virus type 1 gag protein," J. Virol. 75:10991-11001, American Society for Microbiology (2001).

Diamond, D.J., et al., "Development of a candidate HLA A*0201 restricted peptide-based vaccine against human cytomegalovirus infection," Blood 90:1751-1767, American Society of Hematology (1997).

Donnelly, J.J., et al., "DNA vaccines", Annu. Rev. Immunol. 15:617-648, Annual Reviews, Inc. (1997).

Egan, M.A., et al., "The use of cytokines and chemokines as genetic adjuvants for plasmid DNA vaccines", Clin. Appl. Immunol. Rev. 2:255-287, Elsevier (2002).

Elek, S.D., et al., "Development of a vaccine against mental retardation caused by cytomegalovirus infection in utero", Lancet 1:1-5, The Lancet (1974).

Elkington, R., et al., "Ex vivo profiling of CD8 -T-cells responses to human cytomegalovirus reveals broad and multispecific reactivities in healthy virus carriers", J. Virol. 77:5226-5240, American Society for Microbiology (2003).

EMBL-EBI Database, Accession No. P06173, Cranage, M.P., et al., Entry Date 1988, Updated Feb. 2006.

Endresz, V., et al., "Optimization of DNA immunization against human cytomegalovirus", Vaccine 19:3972-3980, Elsevier Science (2001).

Endresz, V., et al., "Induction of Human Cytomegalovirus (HCMV)-Glycoprotein B (gB)-Specific Neutralizing Antibody and Phosphoprotein 65 (pp65)-Specific Cytotoxic T Lymphocyte Responses by Naked DNA Immunization," Vaccine 17:50-58, Elsevier Science Ltd. (1999).

Fowler, K.B., et al., "The outcome of congenital cytomegalovirus infection in relation to maternal antibody status", N. Eng. J. Med. 326:663-667, Massachusetts Medical Society (1992).

Gallez-Hawkins, G., et la., "kinase-deficient CMVpp65 triggers a CMVpp65 specific T-Cell immune response in HLA-A*0201.K Transgenic mice after DNA immunization", Scand. J. Immunol. 5:592-598, Blackwell Science (2002).

Gautier, N., et al., "Characterization of an epitope of the human cytomegalovirus protein IE1 recognized by a CD4 T cell clone", Eur. J. Immunol. 36:1110-1117, VCH Verlagsgesellschaft mbH (1996).

Geissler, M., et al., "Differential cellular and humoral immune responses to HCV core and HBV envelope proteins after genetic immunizations using chimeric constructs", Vaccine 16:857-867, Elsevier Science (1998).

Gonczol, E., et al., "Development of a cytomegalovirus vaccine: lessons from recent trials," Exp. Opin. Biol. Ther. 1: 401-412, Ashely Publication (2001).

(56) References Cited

OTHER PUBLICATIONS

Griscelli, F., et al., "Quantification of Human cytomegalovirus DNA in bone marrow transplant recipients by real-time PCR", J. Clin. Microbiol. 39:4362-4369, American Society for Microbiology (2001).

Guiver, M., et al., "Evaluation of CMV viral load using Taqman CMV quantitative PCR and comparison with CMV antigenemia in heart and lung transplant recipients", Transplantation 71:1609-1615, Lippincott Williams & Wilkins (2001).

Gyulai, Z., et al., "Cytotoxic T lymphocyte (CTL) responses to human cytomegalovirus pp65, IE-Exon4, gB, pp150, and pp28 in healthy individulas: reevaluation of prevalence of IE-1-specific CTLS", J. Infect. Dis. 181:1537-1546, University of Chicago Press (2000).

Hayward, G.S., et al., "Cytomegalovirus, herpesviridae, betaherpesvirinae", in The Springer Index of Viruses, Tidona, C.A., eds., Springer, N.Y. pp. 416-422 (2002).

Kern, F., et al., "Cytomegalovirus (CMV) phosphorprotein 65 makes a large contribution to shaping the T cell repertoire in CMV-exposed individuals", J. Infect. Dis. 185:1709-1716, University of Chicago Press (2002).

Khan, N., et al., "Comparative analysis of CD8 T cell responses against human cytomegalovirus proteins pp56 and immediate early 1 shows similarities in precursor frequency,oligoclonality and phenotype", J. Infect. Dis. 185:000-000, University of Chicago press (2000).

Khattub, B.A-M., et al., "The t-cell epitopes within the C-terminal 265 amino acids of the matric protein pp65 of human cytomegalovirus recognized by human lymphocytes", J. Med. Virol. 52:68-76, Wiley-Liss, Inc. (1997).

Kotsopoulou, et al., "A rev-independent human immunodeficiency virus type 1 (HIV-1) based vector that exploits a codon-optimized HIV-1 gag-pol gene," J. Virol. 74:4839-4852, American Society for Microbiology (2000).

Laycock, K.A., et al., "An in vivo model of human cytomegalovirus retinal infection", Am. J. Ophthalmol. 124:181-189, Elsevier Science (1997).

Limaye, A.P., et al., "High incidence of ganciclovir-resistant cytomegalovirus infection among lung transplant recipients receiving preemptive therapy", J. Infect. Dis. 185:20-27, University of Chicago Press (2002).

Liu, Y., et al., "Molecular analysis of the immune response to human cytomegalovirus glycoprotein B.I. mapping of HLA-restricted helper T cell epitopes on gp93", J. Gen. Virol. 74:2207-2214, Society for general microbiology (1993).

Loomis-Huff, J.E., et al., "Immunogenicity of DNA vaccine against herpes B virus in mice and rhesus macaques", Vaccine 19:4865-4873, Elsevier Science, Ltd (2001).

Lurain, N.S., et al., "Human cytomegalovirus UL144 open reading frame: sequence hypervariabilit in low-passage clinical isolates", J. Virol. 73:10040-10050, American Society for Microbiology (1999).

Malone, C.L., et al., " Transactivation of a human cytomegalovirus early promoter by gene products from the immediate-early gene IE2 and augmentation by IE1: mutational analysis of the viral proteins", J. Virol. 64:1498-1506, American Society for Microbiology (1990).

Manickan, E., et al., "DNA vaccines—a modern gimmick or a boon to vaccinology?" Crit. Rev. Immunol. 17:139-154, Begell House (1997).

Masuoka, M., et al., "Identification of the HLA-A24 peptide epitope within cytomegalovirus protein pp65 recognized by CMV-specific cytotoxic T lymphocytes", Viral. Immunol. 14:369-377, Mary Ann Liebert (2001).

Minamishima, Y., et al., "Murine model for immunoprophylaxis of cytomegalovirus infection", Microbiol. Immunol. 22:693-700, Japanese Society for Bacteriology (1978).

Mocarski, Jr., E.S., Cytomegaloviruses (herpesviridae), in Encyclopedia of Virology, 2nd ed., vol. I, Granoff, A., and Webster, R.G., ed., Academic Press, San Diego, CA, pp. 344-358.

Mocarski, Jr., E.S., et al., "Cytomegaloviruses and their replication", in Fields Virology, 4th ed., Knipe, D.M., et al., eds., Lippincott Williams & Wilkins, Philadelphia, PA, pp. 2629-2674 (2001).

Morello, C.S.,e t al., "Development of a vaccine against murine cytomegalovirus (MCMV), consisting of a plasmid DNA and formalin-inactivated MCMV, that provides long-term, complete protection against viral replication", J. Virol. 76:4822-4835, American Society for Microbiology (2002).

Nagata, T., et al., "Codon optimization effect on translational efficiency of DNA vaccine in mammalian cells: analysis of plasmid DNA encoding a CTL epitop derived from microorganisms", Biochem. Biophys. Res. Comm. 261:445-451, Academic Press (1999).

Nakamura, Y., et al., "codon usage tabulated from international DNA sequence databases: status for the year 2000", Nucl. Acids Res. 28:292, Oxford University Press (2000).

Navarro, D., et al., "Humoral immune response to functional regions of human cytomegalovirus glycoprotein B", J. Med. Virol. 52:451-459, Wiley-Liss, Inc (1997).

Nossal, G., et al., "Living up to the legacy", Nat. <ed. 4:475-476, Nature America, Inc. (1998).

Ohlin, M., et al., "Characterization of human monoclonal antibodies directed against the pp65-kD matrix antigen of human cytomegalovirus", Clin. Exp. Immunol. 84:508-514, Blackwell Scientific Publications (1991).

Ohlin, M., et al., "Fine specificity of the human immune response to the major neutralization epitopes expressed on cytomegalovirus gp58/116 (gB), as determined with human monoclonal antibodies", J. Virol. 67:703-710, American Society for Microbiology (1993).

Pajovic, S., et al., "Identification of a viral kinase that phosphorylates specific E2Fs and pocket proteins", Mol. Cell Biol. 17:6459-6464, American Society for Microbiology (1997).

Pande, H., et al., "Human cytomegalovirus strain towne pp65 gene: nucleotide sequence and expression in *Escherichia* colo", Virology 182:220-228, Academic Press, Inc. (1991).

Pari, G.S., et al., "Generation of a nude mouse tumor model for in vivo replication of human cytomegalovirus", J. Infect. Dis. 177:523-528, University of Chicago Press (1998).

Pass, R.F., et al., "Cytomegalovirus", in Fileds Virology, 4th ed, vol. 2, Knipe, D.M., et al., eds., Lippincott Williams and Wilkins, Philadelphia, PA pp. 2675-2698 (2001).

Plotkin, S.A., et al., "Vaccination against cytomegalovirus, the changeling demon", Pediatr. Infect. Dis. J. 18:313-326, Lippencott Williams & Wilkins, Inc. (1999).

Ruger, B., et al., Primary structure and transcription of the genes coding for the two virion phosphorporitens pp65 and pp71 of human cytomegalovirus, J. Virol. 61:446-453, American Society for Microbiology (1987).

Schmolka, I.R., et al., "A review of block polymer surfactants", J. Am. Oil Chem. 54:110-116, The American Oil Chemists' Society (1997).

Segondy, M., et al., "Cytomegalovirus-specific in vitro antibody production by peripheral blood lymphocytes from renal transplant recipients with CMV infection", J. Med. Virol. 40:200-203, Wiley-Liss, Inc. (1993).

Sequar, G., et al., "Experimental coninfection of rhesus macaques with rhesus cytomegalovirus and simian immunodeficiency virus: pathogenesis", J. Virol. 76:7661-7671, American Society for Microbiology (2002).

Shiver, J.W., et al., "Replication-incompetent adenoviral vaccine vector elicits effective anti-immunodeficiency-virus immunity", Nature 415:331-335, Macmillan Magazines, Ltd (2002).

Solache, A>, et al., "Identification of three HLA-A*0201-restricted cytotoxic T cell epitopes in the cytomegalovirus protein pp65 that are conserved between eight strains of the virus", J. Immunol. 163:5512-5518, American Association of Immunologists (1999).

Spaete, R.R., et al., "Human cytomegalovirus structural proteins", J. Gen. Virol. 75:3287-3308, Society for General Microbiology (1994).

Speckner, A., et al., "Antigenic domain 1 of human cytomegalovirus glycoprotein B induces a multitude of different antibodies which, when combined, results in incomplete virus neutralization", J. Gen. Virol. 80:2183-2191, Society for General Microbiology (1999).

(56) References Cited

OTHER PUBLICATIONS

Spiller, O.B., et al., "Development of a model for cytomegalovirus infection of oligodendrocytes", J. Gen. Virol. 78:3349-3356, Society for General Microbiology (1997).

Staczek, J., "Animal cytomegaloviruses", Microbiol. Rev. 54:247-265, American Society for Microbiology (1994).

Storch, G.A., et al., "Comparison of PCR and pp65 antigenemia assay with quantitative shell vial culture for detection of cytomegalovirus in blood leukocytes from solid-organ transplant recipients", J. Clin. Microbiol. 32:997-1003, American Society for Microbiology (1994).

Tugizov, S., et al., "Mutated forms for human cytomegalovirus glycoprotein B are impaired by inducing syncytium formation", Virology 209:580-591, Academic Press, Inc. (1995).

Vaz-Santiago, J., et al., "IE1-pp65 recombinant protein from human CMV combined with a nanoparticulate carrier, SMBV, as a potential source for the development of anti-human CMV adoptive immunotherapy", Cytotherapy 4:11-19, Martin Dunitz Taylor & Francis Group (2002).

Yang, Z-y., et al.,"Overcoming immunity to a viral vaccine by DNA proming before vector boosting", J. Virol. 77:799-803, American Society for Microbiology (2003).

Yao, Z-Q., et al., "Site-directed mutation in a conserved kinase domain of human cytomegalovirus-pp65 with preservation of cytotoxic T lymphocyte targeting", Vaccine 19:1628-1635, Elsevier (2001).

Ye, M., et al., "Strong CD8 Tcell responses following coimmunization with plasmids expressing the dominant pp89 and subdominant M84 antigens of murine cytomegalovirus correlate with long-term protection against subsequent viral challenge", J. Virol. 76:2100-2112, American Society for Microbiology (2002).

Zaia, J.A., et al., "Status of cytomegalovirus prevention and treatment in 2000", Hematology pp. 339-355, Taylor & Francis Health Sciences (2000).

Zheng, Z., et al., "Mutations in the carboxyl-terminal hydrophobic sequence of human cytomegalovirus glycoprotein B alter transport and protein chaperone binding", J. Virol. 70:8029-8040, American Society for Microbiology (1996).

"Performance chemical products: pluronic and pluronic R block copolymer surfactants", BASF Corporation, at http://www.basf.com/static/openmarket/Xcelerate/preview_cid-982931199819_pubid-974236, view Dec. 13, 2002.

European Examination Report for European Application No. 03 814 236.0-2405, EPO, Munich.

NCBI Entrez, Genbank Report, Accession No. X17403, from Chee et al. (1999).

Go Vera, et al., "A cytomegalovirus vaccine for transplantation: Are we closer?" Journal of Infectious Diseases, 197(12):1631-1633 (2008).

Wloch, M., et al., "Safety and immunogenicity of a bivalent cytomegalovirus DNA vaccine in health adult subjects", Journal of Infectious Diseases, 197(12):1634-1642 (2008).

Tang, J., et al., "Building a Mouse Model Hallmarking the Congenital Human Cytomegalovirus infection in central nervous system," Arch. Virol. 147:1189-1195, Springer-Verlag (Jun. 2002).

Narum, D.L., et al., "Codon Optimization of Gene Fragments Encoding Plasmodium falciparum merzoite proteins enhances DNA vaccine protein expression and immunogenicity in Mice," Infect. Immun. 69:7250-7523, American Society for Microbiology (Dec. 2001).

Communication pursuant to Article 94(3) EPC issued Aug. 31, 2008 with respect to European Patent Application No. 03 814 236.0.

European Search Report issued Mar. 10, 2011 with respect to European Patent Application No. 10 00 6227.

\* cited by examiner

Figure 1

```
  1  atg gag tcg cgc ggt cgc cgt tgt ccc gaa atg ata tcc gta ctg ggt ccc
      M   E   S   R   G   R   R   C   P   E   M   I   S   V   L   G   P 52  att tcg ggg cac gtg ctg aaa gcc gtg ttt agt cgc ggc gat acg ccg gtg
      I   S   G   H   V   L   K   A   V   F   S   R   G   D   T   P   V 103  ctg ccg cac gag acg cga ctc ctg cag acg ggt atc cac gta cgc gtg agc
      L   P   H   E   T   R   L   L   Q   T   G   I   H   V   R   V   S 154  cag ccc tcg ctg atc ttg gta tcg cag tac acg ccc gac tcg acg cca tgc
      Q   P   S   L   I   L   V   S   Q   Y   T   P   D   S   T   P   C 205  cac cgc ggc gac aat cag ctg cag gtg cag cac acg tac ttt acg ggc agc
      H   R   G   D   N   Q   L   Q   V   Q   H   T   Y   F   T   G   S 256  gag gtg gag aac gtg tcg gtc aac gtg cac aac ccc acg ggc cga agc atc
      E   V   E   N   V   S   V   N   V   H   N   P   T   G   R   S   I 307  tgc ccc agc cag gag ccc atg tcg atc tat gtg tac gcg ctg ccg ctc aag
      C   P   S   Q   E   P   M   S   I   Y   V   Y   A   L   P   L   K 358  atg ctg aac atc ccc agc atc aac gtg cac cac tac ccg tcg gcg gcc gag
      M   L   N   I   P   S   I   N   V   H   H   Y   P   S   A   A   E 409  cgc aaa cac cga cac ctg ccc gta gct gac gct gtg att cac gcg tcg ggc
      R   K   H   R   H   L   P   V   A   D   A   V   I   H   A   S   G 460  aag cag atg tgg cag gcg cgt ctc acg gtc tcg gga ctg gcc tgg acg cgt
      K   Q   M   W   Q   A   R   L   T   V   S   G   L   A   W   T   R 511  cag cag aac cag tgg aaa gag ccc gac gtc tac tac acg tca gcg ttc gtg
      Q   Q   N   Q   W   K   E   P   D   V   Y   Y   T   S   A   F   V 562  ttt ccc acc aag gac gtg gca ctg cgg cac gtg gtg tgc gcg cac gag ctg
      F   P   T   K   D   V   A   L   R   H   V   V   C   A   H   E   L 613  gtt tgc tcc atg gag aac acg cgc gca acc aag atg cag gtg ata ggt gac
      V   C   S   M   E   N   T   R   A   T   K   M   Q   V   I   G   D 664  cag tac gtc aag gtg tac ctg gag tcc ttc tgc gag gac gtg ccc tcc ggc
      Q   Y   V   K   V   Y   L   E   S   F   C   E   D   V   P   S   G 715  aag ctc ttt atg cac gtc acg ctg ggc tct gac gtg gaa gag gac ctg acg
      K   L   F   M   H   V   T   L   G   S   D   V   E   E   D   L   T 766  atg acc cgc aac ccg caa ccc ttc atg cgc ccc cac gag cgc aac ggc ttt
      M   T   R   N   P   Q   P   F   M   R   P   H   E   R   N   G   F 817  acg gtg ttg tgt ccc aaa aat atg ata atc aaa ccg ggc aag atc tcg cac
      T   V   L   C   P   K   N   M   I   I   K   P   G   K   I   S   H 868  atc atg ctg gat gtg gct ttt acc tca cac gag cat ttt ggg ctg ctg tgt
      I   M   L   D   V   A   F   T   S   H   E   H   F   G   L   L   C 919  ccc aag agc atc ccg ggc ctg agc atc tca ggt aac ctg ttg atg aac ggg
      P   K   S   I   P   G   L   S   I   S   G   N   L   L   M   N   G 970  cag cag atc ttc ctg gag gta caa gcc ata cgc gag acc gtg aaa ctg cgt
      Q   Q   I   F   L   E   V   Q   A   I   R   E   T   V   E   L   R
```

Figure 1 (cont'd)

```
1021 cag tac gat ccc gtg gct gcg ctc ttc ttt ttc gat atc gac ttg ctg ctg
      Q   Y   D   P   V   A   A   L   F   F   F   D   I   D   L   L   L 1072 cag cgc ggg cct cag tac agc gag cac ccc acc ttc acc agc cag tat cgc
      Q   R   G   P   Q   Y   S   E   H   P   T   F   T   S   Q   Y   R 1123 atc cag ggc aag ctt gag tac cga cac acc tgg gac cgg cac gac gag ggt
      I   Q   G   K   L   E   Y   R   H   T   W   D   R   H   D   E   G 1174 gcc gcc cag ggc gac gac gac gtc tgg acc agc gga tcg gac tcc gac gaa
      A   A   Q   G   D   D   D   V   W   T   S   G   S   D   S   D   E 1225 gaa ctc gta acc acc gag cgc aag acg ccc cgc gtc acc ggc ggc ggc gcc
      E   L   V   T   T   E   R   K   T   P   R   V   T   G   G   G   A 1276 atg gcg ggc gcc tcc act tcc gcg ggc cgc aaa cgc aaa tca gca tcc tcg
      M   A   G   A   S   T   S   A   G   R   K   R   K   S   A   S   S 1327 gcg acg gcg tgc acg tcg ggc gtt atg aca cgc ggc cgc ctt aag gcc gag
      A   T   A   C   T   S   G   V   M   T   R   G   R   L   K   A   E 1378 tcc acc gtc gcg ccc gaa gag gac acc gac gag gat tcc gac aac gaa atc
      S   T   V   A   P   E   E   D   T   D   E   D   S   D   N   E   I 1429 cac aat ccg gcc gtg ttc acc tgg ccg ccc tgg cag gcc ggc atc ctg gcc
      H   N   P   A   V   F   T   W   P   P   W   Q   A   G   I   L   A 1480 cgc aac ctg gtg ccc atg gtg gct acg gtt cag ggt cag aat ctg aag tac
      R   N   L   V   P   M   V   A   T   V   Q   G   Q   N   L   K   Y 1531 cag gaa ttc ttc tgg gac gcc aac gac atc tac cgc atc ttc gcc gaa ttg
      Q   E   F   F   W   D   A   N   D   I   Y   R   I   F   A   E   L 1582 gaa ggc gta tgg cag ccc gct gcg caa ccc aaa cgt cgc cgc cac cgg caa
      E   G   V   W   Q   P   A   A   Q   P   K   R   R   R   H   R   Q 1633 gac gcc ttg ccc ggg cca tgc atc gcc tcg acg ccc aaa aag cac cga ggt
      D   A   L   P   G   P   C   I   A   S   T   P   K   K   H   R   G
```

Figure 2

```
  1    atggagtcccgcggtcgccgctgtcccgaaatgatatccgtactgggtcccatttccggg   60
  1     M  E  S  R  G  R  R  C  P  E  M  I  S  V  L  G  P  I  S  G    20

61    cacgtgctgaaagccgtgtttagtcgcggcgataccccgtgctgccccacgagacccga   120
 21     H  V  L  K  A  V  F  S  R  G  D  T  P  V  L  P  H  E  T  R    40

121    ctcctgcagaccggtatccacgtacgcgtgagccagccctccctgatcttggtatcccag  180
 41     L  L  Q  T  G  I  H  V  R  V  S  Q  P  S  L  I  L  V  S  Q    60

181    tacaccccgactccaccccatgccaccgcggcgacaatcagctgcaggtgcagcacacc   240
 61     Y  T  P  D  S  T  P  C  H  R  G  D  N  Q  L  Q  V  Q  H  T    80

241    tactttaccggcagcgaggtggagaacgtgtccgtcaacgtgcacaacccaccggccga   300
 81     Y  F  T  G  S  E  V  E  N  V  S  V  N  V  H  N  P  T  G  R   100

301    agcatctgccccagccaggagcccatgtccatctatgtgtacgccctgcccctcaagatg  360
101     S  I  C  P  S  Q  E  P  M  S  I  Y  V  Y  A  L  P  L  K  M   120

361    ctgaacatccccagcatcaacgtgcaccactaccctccgccgccgagcgcaaacaccga   420
121     L  N  I  P  S  I  N  V  H  H  Y  P  S  A  A  E  R  K  H  R   140

421    cacctgcccgtagctgacgctgtgattcacgcctccggcaagcagatgtggcaggcccgc  480
141     H  L  P  V  A  D  A  V  I  H  A  S  G  K  Q  M  W  Q  A  R   160

481    ctcaccgtctccggactggcctggacccgccagcagaaccagtggaaagagcccgacgtc  540
161     L  T  V  S  G  L  A  W  T  R  Q  Q  N  Q  W  K  E  P  D  V   180

541    tactacacctcagccttcgtgtttccaccaaggacgtggcactgcggcacgtggtgtgc   600
181     Y  Y  T  S  A  F  V  F  P  T  K  D  V  A  L  R  H  V  V  C   200

601    gcccacgagctggtttgctccatggagaacacccgcgcaaccaagatgcaggtgataggt  660
201     A  H  E  L  V  C  S  M  E  N  T  R  A  T  K  M  Q  V  I  G   220

661    gaccagtacgtcaaggtgtacctggagtccttctgcgaggacgtgccctccggcaagctc  720
221     D  Q  Y  V  K  V  Y  L  E  S  F  C  E  D  V  P  S  G  K  L   240

721    tttatgcacgtcaccctgggctctgacgtggaagaggacctgaccatgacccgcaacccc  780
241     F  M  H  V  T  L  G  S  D  V  E  E  D  L  T  M  T  R  N  P   260

781    caacccttcatgcgcccccacgagcgcaacggctttaccgtgttgtgtcccaaaaatatg  840
261     Q  P  F  M  R  P  H  E  R  N  G  F  T  V  L  C  P  K  N  M   280

841    ataatcaaacccggcaagatctcccacatcatgctggatgtggcttttacctcacacgag  900
281     I  I  K  P  G  K  I  S  H  I  M  L  D  V  A  F  T  S  H  E   300
```

Figure 2 (cont'd)

```
 901   catttgggctgctgtgtcccaagagcatccccggcctgagcatctcaggtaacctgttg    960
 301    H  F  G  L  L  C  P  K  S  I  P  G  L  S  I  S  G  N  L  L    320

961   atgaacgggcagcagatcttcctggaggtacaagccatacgcgagaccgtggaactgcgc   1020
 321    M  N  G  Q  Q  I  F  L  E  V  Q  A  I  R  E  T  V  E  L  R    340

1021   cagtacgatcccgtggctgccctcttcttttcgatatcgacttgctgctgcagcgcggg   1080
 341    Q  Y  D  P  V  A  A  L  F  F  F  D  I  D  L  L  L  Q  R  G    360

1081   cctcagtacagcgagcaccccaccttcaccagccagtatcgcatccagggcaagcttgag   1140
 361    P  Q  Y  S  E  H  P  T  F  T  S  Q  Y  R  I  Q  G  K  L  E    380

1141   taccgacacacctgggaccggcacgacgagggtgccgcccagggcgacgacgacgtctgg   1200
 381    Y  R  H  T  W  D  R  H  D  E  G  A  A  Q  G  D  D  D  V  W    400

1201   accagcggatccgactccgacgaagaactcgtaaccaccgagcgcaagacccccgcgtc   1260
 401    T  S  G  S  D  S  D  E  E  L  V  T  T  E  R  K  T  P  R  V    420

1261   accggcggcggcgccatggccggcgcctccacttccgccgg d cgcaaacgcaaa tcagca   1320
 421    T  G  G  A  M  A  G  A  S  T  S  A  G    R  K  R  K    S  A    440

1321   tcctccgccaccgcctgcacctccggcgttatgacacgcggccgccttaaggccgagtcc   1380
 441    S  S  A  T  A  C  T  S  G  V  M  T  R  G  R  L  K  A  E  S    460

1381   accgtcgcccccgaagaggacaccgacgaggattccgacaacgaaatccacaatcccgcc   1440
 461    T  V  A  P  E  E  D  T  D  E  D  S  D  N  E  I  H  N  P  A    480

1441   gtgttcacctggccacctggcaggccggcatcctggcccgcaacctggtgccatggtg   1500
 481    V  F  T  W  P  P  W  Q  A  G  I  L  A  R  N  L  V  P  M  V    500

1501   gctaccgttcagggtcagaatctgaagtaccaggaattcttctgggacgccaacgacatc   1560
 501    A  T  V  Q  G  Q  N  L  K  Y  E  E  F  F  W  D  A  N  D  I    520

1561   taccgcatcttcgccgaattggaaggcgtatggcagcccgctgcccaacccaaacgccgc   1620
 521    Y  R  I  F  A  E  L  E  G  V  W  Q  P  A  A  Q  P  K  R  R    540

1621   cgccaccggcaagacgccttgcccgggccatgcatcgcctccaccccaaaaagcaccga   1680
 541    R  H  R  Q  D  A  L  P  G  P  C  I  A  S  T  P  K  K  H  R    560

1681   ggt                                                            1700
 561    G                                                             580
```

Figure 3A

```
  1 ATGGAGTCGCGCGGTCGCCGTTGTCCCGAAATGATATCCGTACTGGGTCC       50
    ||||.||.||.|||.|.||||||||.||.|||||...|||.||.||.||
  1 ATGGAATCTCGAGGTAGACGTTGTCCGGAGATGATCAGCGTGCTAGGACC       50

51 CATTTCGGGGCACGTGCTGAAAGCCGTGTTTAGTCGCGGCGATACGCCGG      100
    .||....|||||||||.|||||.||.||||||....|.||.||||||||.|
 51 AATAAGTGGGCACGTCCTGAAGGCTGTGTTTTCAAGGGGGGATACGCCAG      100

101 TGCTGCCGCACGAGACGCGACTCCTGCAGACGGGTATCCACGTACGCGTG      150
    ||||.||.|||||||||.||.||.||.||.||.|||||.||||..|.||.
101 TGCTCCCACACGAGACCCGCCTGCTACAAACAGGTATTCACGTTAGGGTC      150

151 AGCCAGCCCTCGCTGATCTTGGTATCGCAGTACACGCCCGACTCGACGCC      200
    ...||||||...||.||.|||||....||||.||.||||||||.||.||
151 TCACAGCCCAGCCTAATTTTGGTTAGCCAGTATACACCCGACTCCACCCC      200

201 ATGCCACCGCGGCGACAATCAGCTGCAGGTGCAGCACACGTACTTTACGG      250
    .||.||.|||||||||||.||||||||.|||||.||.||.||.||.||.|
201 TTGTCATCGCGGCGACAACCAGCTGCAAGTCCAGCATACTTATTTCACAG      250

251 GCAGCGAGGTGGAGAACGTGTCGGTCAACGTGCACAACCCCACGGGCCGA      300
    |||||||||||||.||.|||||||||.||||.|||||.||||.||.||.
251 GCAGCGAGGTGGAAAATGTGTCGGTCAATGTGCATAACCCTACCGGGCGT      300

301 AGCATCTGCCCCAGCCAGGAGCCCATGTCGATCTATGTGTACGCGCTGCC      350
    ..||||||||....||||||||.|||||.|||||.|||||.||..|.||
301 TCCATCTGCCCTTCACAGGAGCCTATGTCTATCTACGTGTATGCTTTACC      350

351 GCTCAAGATGCTGAACATCCCCAGCATCAACGTGCACCACTACCCGTCGG      400
    ..|.||||||.|.|||||||||...|||||.||||||||||.||.||.|
351 TTTGAAGATGTTAAACATCCCCTCTATCAATGTGCACCATTATCCTTCAG      400
```

Figure 3B

```
401 CGGCCGAGCGCAAACACCGACACCTGCCCGTAGCTGACGCTGTGATTCAC   450
    ||||·||||| ||||||||·|||·|·|||||·||||||||·||·||·|||
401 CGGCTGAGCGGAAACACCGCCACTTACCCGTGGCTGACGCAGTCATACAC   450

451 GCGTCGGGCAAGCAGATGTGGCAGGCGCGTCTCACGGTCTCGGGACTGGC   500
    |||···||·||||||||||||||·||·||·||·||||||||·||·|||||
451 GCGAGCGGTAAGCAGATGTGGCAAGCACGACTGACGGTCTCCGGTCTGGC   500

501 CTGGACGCGTCAGCAGAACCAGTGGAAAGAGCCCGACGTCTACTACACGT   550
    ·|||||··|·|||||||||·||||||||·||·||·||·||·|||||||··
501 TTGGACTAGACAGCAGAATCAGTGGAAGGAACCTGATGTGTACTACACCA   550

551 CAGCGTTCGTGTTTCCCACCAAGGACGTGGCACTGCGGCACGTGGTGTGC   600
    ··||·||·||·||·|||||·||||||||||||||·|||||·||||||
551 GCGCATTTGTCTTCCCAACCAAAGACGTGGCACTGCGCCACGTAGTGTGC   600

601 GCGCACGAGCTGGTTTGCTCCATGGAGAACACGCGCGCAACCAAGATGCA   650
    ||·||·||·|||||·||·|||||||||||||||·||·|||||||||||||
601 GCCCATGAACTGGTGTGTTCCATGGAGAACACCCGGGCAACCAAGATGCA   650

651 GGTGATAGGTGACCAGTACGTCAAGGTGTACCTGGAGTCCTTCTGCGAGG   700
    |||·||·||·||·|||||·||·||·||·|||||·||||||||·||·||||
651 GGTAATTGGCGATCAGTATGTGAAAGTTTACCTTGAGTCCTTTTGTGAGG   700

701 ACGTGCCCTCCGGCAAGCTCTTTATGCACGTCACGCTGGGCTCTGACGTG   750
    |·||·|||··||||||||·||·|||||·|||·|||·||||··|||||||
701 ATGTACCCAGCGGCAAGCTGTTCATGCATGTGACGTTGGGCAGTGACGTG   750

751 GAAGAGGACCTGACGATGACCCGCAACCCGCAACCCTTCATGCGCCCCCA   800
    |||||||||||||·|||||·||·||·|||||·||·|||·|·||·||
751 GAAGAGGACCTGACAATGACTCGAAATCCACAACCATTTATGAGGCCGCA   800
```

Figure 3C

```
 801  CGAGCGCAACGGCTTTACGGTGTTGTGTCCCAAAAATATGATAATCAAAC   850
      |||..|.|||||.|||||.|||.|.||.||.||.||.|||||.|||||.|
 801  CGAAAGAAACGGGTTTACAGTGCTCTGCCCAAAGAACATGATCATCAAGC   850

851  CGGGCAAGATCTCGCACATCATGCTGGATGTGGCTTTTACCTCACACGAG   900
      |.||.|||||....||.||.|||||.|||||.||.||.|||...|||||.
 851  CCGGGAAGATTAGTCATATTATGCTCGATGTTGCCTTCACCAGTCACGAA   900

901  CATTTTGGGCTGCTGTGTCCCAAGAGCATCCCGGGCCTGAGCATCTCAGG   950
      ||||||||.||.||.||.|||||...||||||.|||.||...||.|||||
 901  CATTTTGGACTCCTTTGCCCCAAATCCATCCCAGGCTTGTCAATTTCAGG   950

951  TAACCTGTTGATGAACGGGCAGCAGATCTTCCTGGAGGTACAAGCCATAC  1000
      .||.||..|.|||||||||.||||||||.|||||||||.|||||.||.|
 951  CAATCTCCTCATGAACGGACAGCAGATTTTCCTGGAGGTGCAAGCGATCC  1000

1001  GCGAGACCGTGGAACTGCGTCAGTACGATCCCGTGGCTGCGCTCTTCTTT  1050
      |.|||||.||.||.|||.|.|||||.|||||.||.||.||.||.|||||.
1001  GGGAGACTGTAGAGCTGAGACAGTATGATCCTGTTGCAGCCCTGTTCTTC  1050

1051  TTCGATATCGACTTGCTGCTGCAGCGCGGGCCTCAGTACAGCGAGCACCC  1100
      |||||||||||.|.||.||.|||||.||.||.|||||||||||.|||||
1051  TTCGATATCGACCTTCTCCTTCAGCGAGGCCCGCAGTACAGCGAACACCC  1100

1101  CACCTTCACCAGCCAGTATCGCATCCAGGGCAAGCTTGAGTACCGACACA  1150
      .|||||.||....|||||.||||||||.|||.||.||.|||||.||.||.|
1101  AACCTTTACATCTCAGTACCGCATCCAAGGGAAACTGGAGTATCGTCATA  1150

1151  CCTGGGACCGGCACGACGAGGGTGCCGCCCAGGGCGACGACGACGTCTGG  1200
      ||||||||.||||.|||||.||.||||||.||.||.|||||.||.||.|||
1151  CCTGGGACAGGCATGACGAAGGGGCCGCTCAAGGAGACGATGATGTGTGG  1200
```

Figure 3D

```
1201 ACCAGCGGATCGGACTCCGACGAAGAACTCGTAACCACCGAGCGCAAGAC 1250
     ||·||·||·|||||·|||||·||·||···|·||·||·|||||··|·|||||
1201 ACAAGTGGCTCGGATTCCGATGAGGAGTTGGTGACAACCGAAAGAAAGAC 1250

1251 GCCCCGCGTCACCGGCGGCGGCGCCATGGCGGGCGCCTCCACTTCCGCGG 1300
     ·|||·|·||·|||||·||·||·||·|||||·||·||·|||||||··|||·|
1251 TCCCAGGGTTACCGGAGGAGGAGCAATGGCAGGTGCTTCCACTAGCGCTG 1300

1301 GCCGCAAACGCAAATCAGCATCCTCGGCGACGGCGTGCACGTCGGGCGTT 1350
     ||·|·|||||·|||···||·|||···||·||·||·|||||·||·||||||·
1301 GCAGGAAACGGAAAAGCGCCTCCAGTGCCACAGCCTGCACTTCTGGCGTC 1350

1351 ATGACACGCGGCCGCCTTAAGGCCGAGTCCACCGTCGCGCCCGAAGAGGA 1400
     |||||··|·||·||·||·||·|||||·||·||·||·||·||·||·|||||
1351 ATGACGAGGGGGCGGCTGAAAGCCGAATCTACTGTAGCCCCTGAGGAGGA 1400

1401 CACCGACGAGGATTCCGACAACGAAATCCACAATCCGGCCGTGTTCACCT 1450
     |||·|||||||||||·|||||·|||||·|||||||·||·||·||·||·|
1401 CACTGACGAGGATTCTGACAATGAAATTCACAATCCCGCGGTTTTTACAT 1450

1451 GGCCGCCCTGGCAGGCCGGCATCCTGGCCCGCAACCTGGTGCCCATGGTG 1500
     ||||·||·||||||||||||·||·||||||||·|||||·||||||||||·
1451 GGCCCCCTTGGCAGGCCGGAATTCTGGCCCGGAACCTTGTGCCCATGGTC 1500

1501 GCTACGGTTCAGGGTCAGAATCTGAAGTACCAGGAATTCTTCTGGGACGC 1550
     ||·||·||·||·||·|||||·|||||||||||||||||·||||||||·||
1501 GCCACAGTCCAAGGCCAGAACCTGAAGTACCAGGAATTTTTCTGGGATGC 1550

1551 CAACGACATCTACCGCATCTTCGCCGAATTGGAAGGCGTATGGCAGCCCG 1600
     |||||||||·|||·|·|||||||||·|||·||||·||·||·|||||||||
1551 CAACGACATATACAGAATCTTCGCAGAACTGGAGGGAGTTTGGCAGCCCG 1600
```

Figure 3E

```
1601 CTGCGCAACCCAAACGTCGCCGCCACCGGCAAGACGCCTTGCCCGGGCCA      1650
     ||||·||·||·|||||··|·||·|||·|·||·||||||·|·||·|||||·
1601 CTGCTCAGCCTAAACGCAGACGGCACAGACAGGACGCCCTCCCAGGGCCG      1650

1651 TGCATCGCCTCGACGCCCAAAAAGCACCGAGGT      1683
     |||||·|||||·||·||·||·|||||||||·|||
1651 TGCATAGCCTCTACCCCAAAGAAGCACCGCGGT      1683
```

Figure 4A

```
  1 atggaatccaggatctggtgcctggtagtctgcgttaacctgtgtatcgtctgtctgggt  60
  1 M  E  S  R  I  W  C  L  V  V  C  V  N  L  C  I  V  C  L  G   20

61 gctgcggtttcctcttctagtacttcccatgcaacttcttctactcacaatggaagccat 120
 21 A  A  V  S  S  S  T  S  H  A  T  S  S  T  H  N  G  S  H   40

121 acttctcgtacgacgtctgctcaaacccggtcagtctattctcaacacgtaacgtcttct 180
 41 T  S  R  T  T  S  A  Q  T  R  S  V  Y  S  Q  H  V  T  S  S   60

181 gaagccgtcagtcatagagccaacgagactatctacaacactaccctcaagtacggagat 240
 61 E  A  V  S  H  R  A  N  E  T  I  Y  N  T  T  L  K  Y  G  D   80

241 gtggtgggagtcaacactaccaagtaccccctatcgcgtgtgttctatggcccagggtacg 300
 81 V  V  G  V  N  T  T  K  Y  P  Y  R  V  C  S  M  A  Q  G  T  100

301 gatcttattcgctttgaacgtaatatcatctgcacctcgatgaagcctatcaatgaagac 360
101 D  L  I  R  F  E  R  N  I  I  C  T  S  M  K  P  I  N  E  D  120

361 ttggatgagggcatcatggtggtctacaagcgcaacatcgtggcgcacacctttaaggta 420
121 L  D  E  G  I  M  V  V  Y  K  R  N  I  V  A  H  T  F  K  V  140

421 cgggtctaccaaaaggttttgacgtttcgtcgtagctacgcttacatctacaccacttat 480
141 R  V  Y  Q  K  V  L  T  F  R  R  S  Y  A  Y  I  Y  T  T  Y  160

481 ctgctgggcagcaatacggaatacgtggcgcctcctatgtgggagattcatcacatcaac 540
161 L  L  G  S  N  T  E  Y  V  A  P  P  M  W  E  I  H  H  I  N  180

541 aagtttgctcaatgctacagttcctacagccgcgttataggaggcacggttttcgtggca 600
181 K  F  A  Q  C  Y  S  S  Y  S  R  V  I  G  G  T  V  F  V  A  200
```

Figure 4B

```
 601 tatcatagggacagttatgaaaacaaaaccatgcaattaattcccgacgattattccaac  660
 201 Y  H  R  D  S  Y  E  N  K  T  M  Q  L  I  P  D  D  Y  S  N   220

661 acccacagtacccgttacgtgacggtcaaggatcagtggcacagccgcggcagcacctgg  720
 221 T  H  S  T  R  Y  V  T  V  K  D  Q  W  H  S  R  G  S  T  W   240

721 ctctatcgtgagacctgtaatctgaactgtatgctgaccatcactactgcgcgctccaag  780
 241 L  Y  R  E  T  C  N  L  N  C  M  L  T  I  T  T  A  R  S  K   260

781 tatccttatcattttttttgcaacttccacgggtgatgtggtttacatttctcctttctac  840
 261 Y  P  Y  H  F  F  A  T  S  G  D  V  V  Y  I  S  P  F  Y       280

841 aacggaaccaatcgcaatgccagctactttggagaaaacgccgacaagttttcatttc    900
 281 N  G  T  N  R  N  A  S  Y  F  G  E  N  A  D  K  F  F  I  F   300

901 ccgaactacaccatcgtttccgactttggaagacccaacgctgcgccagaaacccatagg  960
 301 P  N  Y  T  I  V  S  D  F  G  R  P  N  A  A  P  E  T  H  R   320

961 ttggtggcttttctcgaacgtgccgactcggtgatctcttgggatatacaggacgagaag 1020
 321 L  V  A  F  L  E  R  A  D  S  V  I  S  W  D  I  Q  D  E  K   340

1021 aatgtcacctgccagctcaccttctgggaagcctcggaacgtactatccgttccgaagcc 1080
 341 N  V  T  C  Q  L  T  F  W  E  A  S  E  R  T  I  R  S  E  A   360

1081 gaagactcgtaccactttttcttctgccaaaatgactgcaacttttctgtctaagaaacaa 1140
 361 E  D  S  Y  H  F  S  S  A  K  M  T  A  T  F  L  S  K  Q      380

1141 gaagtgaacatgtccgactccgcgctggactgcgtacgtgatgaggctataaataagtta 1200
 381 E  V  N  M  S  D  S  A  L  D  C  V  R  D  E  A  I  N  K  L   400
```

Figure 4C

```
1201 cagcagatttcaatacttcatacaatcaaacatatgaaaaatacggaaacgtgtccgtc 1260
 401  Q  Q  I  F  N  T  S  Y  N  Q  T  Y  E  K  Y  G  N  V  S  V  420

1261 ttcgaaaccagcggcggtctggtggtgttctggcaaggcatcaagcaaaaatctttggtg 1320
 421  F  E  T  S  G  G  L  V  V  F  W  Q  G  I  K  Q  K  S  L  V  440

1321 gaattggaacgtttggccaatcgatccagtctgaatatcactcataggaccagaagaagt 1380
 441  E  L  E  R  L  A  N  R  S  S  L  N  I  T  H  R  T  R  R  S  460

1381 acgagtgacaataatacaactcatttgtccagcatggaatcggtgcacaatctggtctac 1440
 461  T  S  D  N  N  T  T  H  L  S  S  M  E  S  V  H  N  L  V  Y  480

1441 gcccagctgcagttcacctatgacacgttgcgcggttacatcaaccgggcgctggcgcaa 1500
 481  A  Q  L  Q  F  T  Y  D  T  L  R  G  Y  I  N  R  A  L  A  Q  500

1501 atcgcagaagcctggtgtgtggatcaacggcgcaccctagaggtcttcaaggaactcagc 1560
 501  I  A  E  A  W  C  V  D  Q  R  R  T  L  E  V  F  K  E  L  S  520

1561 aagatcaacccgtcagccattctctcggccatttacaacaaaccgattgccgcgcgtttc 1620
 521  K  I  N  P  S  A  I  L  S  A  I  Y  N  K  P  I  A  A  R  F  540

1621 atgggtgatgtcttgggcctggccagctgcgtgaccatcaaccaaaccagcgtcaaggtg 1680
 541  M  G  D  V  L  G  L  A  S  C  V  T  I  N  Q  T  S  V  K  V  560

1681 ctgcgtgatatgaacgtgaaggaatcgccaggacgctgctactcacgacccgtggtcatc 1740
 561  L  R  D  M  N  V  K  E  S  P  G  R  C  Y  S  R  P  V  V  I  580

1741 tttaatttcgccaacagctcgtacgtgcagtacggtcaactgggcgaggacaacgaaatc 1800
 581  F  N  F  A  N  S  S  Y  V  Q  Y  G  Q  L  G  E  D  N  E  I  600
```

Figure 4D

```
1801 ctgttgggcaaccaccgcactgaggaatgtcagcttcccagcctcaagatcttcatcgcc 1860
 601 L  L  G  N  H  R  T  E  E  C  Q  L  P  S  L  K  I  F  I  A   620

1861 gggaactcggcctacgagtacgtggactacctcttcaaacgcatgattgacctcagcagt 1920
 621 G  N  S  A  Y  E  Y  V  D  Y  L  F  K  R  M  I  D  L  S  S   640

1921 atctccaccgtcgacagcatgatcgccctggatatcgacccgctggaaaataccgacttc 1980
 641 I  S  T  V  D  S  M  I  A  L  D  I  D  P  L  E  N  T  D  F   660

1981 agggtactggaactttactcgcagaaagagctgcgttccagcaacgttttgacctcgaa 2040
 661 R  V  L  E  L  Y  S  Q  K  E  L  R  S  S  N  V  F  D  L  E   680

2041 gagatcatgcgcgaattcaactcgtacaagcagcgggtaaagtacgtggaggacaaggta 2100
 681 E  I  M  R  E  F  N  S  Y  K  Q  R  V  K  Y  V  E  D  K  V   700

2101 gtcgacccgctaccgccctacctcaagggtctggacgacctcatgagcggcctgggcgcc 2160
 701 V  D  P  L  P  P  Y  L  K  G  L  D  D  L  M  S  G  L  G  A   720

2161 gcgggaaaggccgttggcgtagccattggggccgtgggtggcgcggtggcctccgtggtc 2220
 721 A  G  K  A  V  G  V  A  I  G  A  V  G  G  A  V  A  S  V  V   740

2221 gaaggcgttgccaccttcctcaaaaacccttcggagccttcaccatcatcctcgtggcc 2280
 741 E  G  V  A  T  F  L  K  N  P  F  G  A  F  T  I  I  L  V  A   760

2281 atagccgtagtcattatcacttatttgatctatactcgacagcggcgtctgtgcacgcag 2340
 761 I  A  V  V  I  I  T  Y  L  I  Y  T  R  Q  R  R  L  C  T  Q   780

2341 ccgctgcagaacctctttccctatctggtgtccgccgacgggaccaccgtgacgtcgggc 2400
 781 P  L  Q  N  L  F  P  Y  L  V  S  A  D  G  T  T  V  T  S  G   800
```

Figure 4E

```
2401 agcaccaaagacacgtcgttacaggctccgccttcctacgaggaaagtgtttataattct 2460
 801 S   T   K   D   T   S   L   Q   A   P   P   S   Y   E   E   S   V   Y   N   S   820

2461 ggtcgcaaaggaccgggaccaccgtcgtctgatgcatccacggcggctccgccttacacc 2520
 821 G   R   K   G   P   G   P   P   S   S   D   A   S   T   A   A   P   P   Y   T   840

2521 aacgagcaggcttaccagatgcttctggccctggccgtctggacgcagagcagcgagcg 2580
 841 N   E   Q   A   Y   Q   M   L   L   A   L   A   R   L   D   A   E   Q   R   A   860

2581 cagcagaacggtacagattctttggacggacagactggcacgcaggacaagggacagaag 2640
 861 Q   Q   N   G   T   D   S   L   D   G   Q   T   G   T   Q   D   K   G   Q   K   880

2641 cctaacctgctagaccggctgcgacatcgcaaaaacggctacagacacttgaaagactcc 2700
 881 P   N   L   L   D   R   L   R   H   R   K   N   G   Y   R   H   L   K   D   S   900

2701 gacgaagaagagaacgtc 2718
 901 D   E   E   E   N   V   906
```

Figure 5A

```
  1 atggaatccaggatctggtgcctggtagtctgcgttaacctgtgtatcgtctgtctgggt  60
  1 M  E  S  R  I  W  C  L  V  V  C  V  N  L  C  I  V  C  L  G   20

61 gctgccgtttcctcttctagtacttcccatgcaacttcttctactcacaatggaagccat 120
 21 A  A  V  S  S  S  S  T  S  H  A  T  S  S  T  H  N  G  S  H   40

121 acttctcgcaccacctctgctcaaacccggtcagtctattctcaacacgtaacctcttct 180
 41 T  S  R  T  T  S  A  Q  T  R  S  V  Y  S  Q  H  V  T  S  S   60

181 gaagccgtcagtcatagagccaacgagactatctacaacactaccctcaagtacggagat 240
 61 E  A  V  S  H  R  A  N  E  T  I  Y  N  T  T  L  K  Y  G  D   80

241 gtggtgggagtcaacactaccaagtaccctatcgcgtgtgttctatggcccagggtacc  300
 81 V  V  G  V  N  T  T  K  Y  P  Y  R  V  C  S  M  A  Q  G  T  100

301 gatcttattcgctttgaacgcaatatcatctgcacctccatgaagcctatcaatgaagac 360
101 D  L  I  R  F  E  R  N  I  I  C  T  S  M  K  P  I  N  E  D  120

361 ttggatgagggcatcatggtggtctacaagcgcaacatcgtggcccacacctttaaggta 420
121 L  D  E  G  I  M  V  V  Y  K  R  N  I  V  A  H  T  F  K  V  140

421 cgggtctaccaaaaggttttgacctttcgccgcagctacgcttacatctacaccacttat 480
141 R  V  Y  Q  K  V  L  T  F  R  R  S  Y  A  Y  I  Y  T  T  Y  160

481 ctgctgggcagcaataccgaatacgtggcccctcctatgtgggagattcatcacatcaac 540
161 L  L  G  S  N  T  E  Y  V  A  P  P  M  W  E  I  H  H  I  N  180

541 aagtttgctcaatgctacagttcctacagccgcgttataggaggcaccgtttttcgtggca 600
181 K  F  A  Q  C  Y  S  S  Y  S  R  V  I  G  G  T  V  F  V  A  200
```

Figure 5B

```
 601 tatcatagggacagttatgaaaacaaaaccatgcaattaattcccgacgattattccaac  660
 201 Y  H  R  D  S  Y  E  N  K  T  M  Q  L  I  P  D  D  Y  S  N   220

661 acccacagtacccgctacgtgaccgtcaaggatcagtggcacagccgcggcagcacctgg  720
 221 T  H  S  T  R  Y  V  T  V  K  D  Q  W  H  S  R  G  S  T  W   240

721 ctctatcgcgagacctgtaatctgaactgtatgctgaccatcactactgcccgctccaag  780
 241 L  Y  R  E  T  C  N  L  N  C  M  L  T  I  T  T  A  R  S  K   260

781 tatccttatcatttttttgcaacttccaccggtgatgtggtttacatttctcctttctac  840
 261 Y  P  Y  H  F  F  A  T  S  G  D  V  V  Y  I  S  P  F  Y      280

841 aacggaaccaatcgcaatgccagctactttggagaaaacgccgacaagttttctcattttc  900
 281 N  G  T  N  R  N  A  S  Y  F  G  E  N  A  D  K  F  F  I  F   300

901 cccaactacaccatcgtttccgactttggaagacccaacgctgccccagaaacccatagg  960
 301 P  N  Y  T  I  V  S  D  F  G  R  P  N  A  A  P  E  T  H  R   320

961 ttggtggcttttctcgaacgcgccgactccgtgatctcttgggatatacaggacgagaag 1020
 321 L  V  A  F  L  E  R  A  D  S  V  I  S  W  D  I  Q  D  E  K   340

1021 aatgtcacctgccagctcaccttctgggaagcctccgaacgcactatccgctccgaagcc 1080
 341 N  V  T  C  Q  L  T  F  W  E  A  S  E  R  T  I  R  S  E  A   360

1081 gaagactcctaccacttttcttctgccaaaatgactgcaacttttctgtctaagaaacaa 1140
 361 E  D  S  Y  H  F  S  S  A  K  M  T  A  T  F  L  S  K  K  Q   380

1141 gaagtgaacatgtccgactccgccctggactgcgtacgcgatgaggctataaataagtta 1200
 381 E  V  N  M  S  D  S  A  L  D  C  V  R  D  E  A  I  N  K  L   400
```

Figure 5C

```
1201 cagcagatttcaatacttcatacaatcaaacatatgaaaaatacggaaacgtgtccgtc 1260
 401  Q  Q  I  F  N  T  S  Y  N  Q  T  Y  E  K  Y  G  N  V  S  V   420

1261 ttcgaaaccagcggcggtctggtggtgttctggcaaggcatcaagcaaaaatctttggtg 1320
 421  F  E  T  S  G  G  L  V  V  F  W  Q  G  I  K  Q  K  S  L  V   440

1321 gaattggaacgcttggccaatcgatccagtctgaatatcactcataggaccagaagaagt 1380
 441  E  L  E  R  L  A  N  R  S  S  L  N  I  T  H  R  T  R  R  S   460

1381 accagtgacaataatacaactcatttgtccagcatggaatccgtgcacaatctggtctac 1440
 461  T  S  D  N  N  T  T  H  L  S  S  M  E  S  V  H  N  L  V  Y   480

1441 gcccagctgcagttcacctatgacaccttgcgcggttacatcaaccgggccctggcccaa 1500
 481  A  Q  L  Q  F  T  Y  D  T  L  R  G  Y  I  N  R  A  L  A  Q   500

1501 atcgcagaagcctggtgtgtggatcaacggcgcaccctagaggtcttcaaggaactcagc 1560
 501  I  A  E  A  W  C  V  D  Q  R  R  T  L  E  V  F  K  E  L  S   520

1561 aagatcaaccccctcagccattctctccgccatttacaacaaacccattgccgcccgcttc 1620
 521  K  I  N  P  S  A  I  L  S  A  I  Y  N  K  P  I  A  A  R  F   540

1621 atgggtgatgtcttgggcctggccagctgcgtgaccatcaaccaaaccagcgtcaaggtg 1680
 541  M  G  D  V  L  G  L  A  S  C  V  T  I  N  Q  T  S  V  K  V   560

1681 ctgcgcgatatgaacgtgaaggaatccccaggacgctgctactcacgaccgtggtcatc 1740
 561  L  R  D  M  N  V  K  E  S  P  G  R  C  Y  S  R  P  V  V  I   580

1741 tttaatttcgccaacagctcctacgtgcagtacggtcaactgggcgaggacaacgaaatc 1800
 581  F  N  F  A  N  S  S  Y  V  Q  Y  G  Q  L  G  E  D  N  E  I   600
```

Figure 5D

```
1801 ctgttgggcaaccaccgcactgaggaatgtcagcttccagcctcaagatcttcatcgcc 1860
 601  L  L  G  N  H  R  T  E  E  C  Q  L  P  S  L  K  I  F  I  A  620

1861 gggaactccgcctacgagtacgtggactacctcttcaaacgcatgattgacctcagcagt 1920
 621  G  N  S  A  Y  E  Y  V  D  Y  L  F  K  R  M  I  D  L  S  S  640

1921 atctccaccgtcgacagcatgatcgccctggatatcgacccctggaaaataccgacttc 1980
 641  I  S  T  V  D  S  M  I  A  L  D  I  D  P  L  E  N  T  D  F  660

1981 agggtactggaactttactcccagaaagagctgcgctccagcaacgttttttgacctcgaa 2040
 661  R  V  L  E  L  Y  S  Q  K  E  L  R  S  S  N  V  F  D  L  E  680

2041 gagatcatgcgcgaattcaactcctacaagcagcgggtaaagtacgtggaggacaaggta 2100
 681  E  I  M  R  E  F  N  S  Y  K  Q  R  V  K  Y  V  E  D  K  V  700

2101 gtcgacccactacctccctacctcaagggtctggacgac 2139
 701  V  D  P  L  P  P  Y  L  K  G  L  D  D  713
```

Figure 6A

```
  1 ATGGAATCCAGGATCTGGTGCCTGGTAGTCTGCGTTAACCTGTGTATCGT   50
    ||||||||||||||||||||-||-||-|||||-||-|||||-||||||||
  1 ATGGAATCCAGGATCTGGTGTCTCGTCGTCTGTGTCAACCTTTGTATCGT   50

51 CTGTCTGGGTGCTGCGGTTTC---CTCTTCTAGTACTTCCCATGCAACTT   97
    -||..||||-|||||-|||..    |...||-|..|.|   |||||-||..
 51 TTGCTTGGGAGCTGCCGTTAGTAGCAGCTCCACAAGT---CATGCCACCA   97

98 CTTCTACTCACAATGGAAGCCATACTTCTCGTACGACGTCTGCTCAAACC  147
    ....|||-||-||-||-|||||-||-||-||-||-|||---|||||-||-
 98 GCAGTACCCATAACGGTAGCCACACCTCACGGACAACGAGCGCTCAGACT  147

148 CGGTCAGTCTATTCTCAACACGTAACGTCTTCTGAAGCCGTCAGTCATAG  197
    ||-||-||-||-||-||-|||||-||-||-||-||-||-||---|||-|
148 CGTTCCGTGTACTCGCAGCACGTTACCTCCTCAGAGGCAGTGTCCCATCG  197

198 AGCCAACGAGACTATCTACAACACTACCCTCAAGTACGGAGATGTGGTGG  247
    -||-||||||-|||||||||||||-||-|||||||||-||-||-||||
198 CGCTAACGAAACTATCTACAACACCACACTCAAGTATGGCGACGTAGTGG  247

248 GAGTCAACACTACCAAGTACCCCTATCGCGTGTGTTCTATGGCCCAGGGT  297
    |-||-||-||-||-||-|||||-|||-|-|||||-||-|||||||||||.
248 GTGTAAATACGACAAAATACCCATATAGAGTGTGCTCAATGGCCCAGGGC  297

298 ACGGATCTTATTCGCTTTGAACGTAATATCATCTGCACCTCGATGAAGCC  347
    ||-||||||-||-||-||-|||..|-|||||-||||||||||-|||||-||
298 ACCGATCTGATCCGGTTCGAGAGAAATATAATCTGCACCTCTATGAAACC  347

348 TATCAATGAAGACTTGGATGAGGGCATCATGGTGGTCTACAAGCGCAACA  397
    |||||||||-||..||||-|||||-||||||||||||-||-|||-|-||-|
348 TATCAATGAGGATCTGGACGAGGGGATCATGGTGGTGTATAAGAGAAATA  397
```

Figure 6B

```
398  TCGTGGCGCACACCTTTAAGGTACGGGTCTACCAAAAGGTTTTGACGTTT  447
     |.||.||.||.||||||||.||.||.||.||.||||||||.||.||.||.
398  TTGTCGCCCATACCTTTAAAGTGCGCGTTTATCAAAAGGTGTTAACTTTC  447

448  CGTCGTAGCTACGCTTACATCTACACCACTTATCTGCTGGGCAGCAATAC  497
     .|..|...||||||||||.|||||||||.||.|||||.|||..||||||
448  AGAAGGTCCTACGCTTATATCTACACCACGTACCTGCTCGGCTCCAATAC  497

498  GGAATACGTGGCGCCTCCTATGTGGGAGATTCATCACATCAACAAGTTTG  547
     .||.||||||.||.||||||.||||||||.||||.||.|||||||||.|
498  AGAGTACGTCGCTCCTCCCATGTGGGAAATTCACCATATCAACAAGTTCG  547

548  CTCAATGCTACAGTTCCTACAGCCGCGTTATAGGAGGCACGGTTTTCGTG  597
     |.||.||||||...||.|||...|||||.||.|||||.||.||.||||||
548  CCCAGTGCTACTCCTCTTACTCACGCGTGATCGGAGGGACCGTGTTCGTG  597

598  GCATATCATAGGGACAGTTATGAAAACAAAACCATGCAATTAATTCCCGA  647
     ||||||||..|.||...|||.||||||||.||.|||||..|.||.||.||
598  GCATATCACCGAGATTCTTACGAAAACAAGACAATGCAGCTGATCCCTGA  647

648  CGATTATTCCAACACCCACAGTACCCGTTACGTGACGGTCAAGGATCAGT  697
     .||.||.||.||.||.|||...||||||||.||||||.||.||||||||.|
648  TGACTACTCTAATACACACTCAACCCGTTATGTGACCGTAAAGGATCAAT  697

698  GGCACAGCCGCGGCAGCACCTGGCTCTATCGTGAGACCTGTAATCTGAAC  747
     |||||..||||||....||||||||||||..|.||.||.||.||.|||||.
698  GGCACTCCGCGGGTCTACCTGGCTCTACAGGGAAACGTGCAACCTGAAT  747

748  TGTATGCTGACCATCACTACTGCGCGCTCCAAGTATCCTTATCATTTTTT  797
     |||||||||||.||.||.||||..|.||.|||||.||.||.||.|||||
748  TGTATGCTGACAATAACGACTGCTAGGTCAAAGTACCCCTACCACTTTTT  797
```

Figure 6C

```
798  TGCAACTTCCACGGGTGATGTGGTTTACATTTCTCCTTTCTACAACGGAA  847
     ||||||·||·||·||·||·||||||||·|||··|||||||||||||||||
798  TGCAACCTCTACCGGCGACGTGGTTTATATTAGTCCTTTCTACAACGGAA  847

848  CCAATCGCAATGCCAGCTACTTTGGAGAAAACGCCGACAAGTTTTTCATT  897
     ||||·||·|||||·||·||·||·||·|||||||·||||||||||||||||
848  CCAACCGTAATGCGAGTTATTTCGGTGAAAACGCAGACAAGTTTTTCATT  897

898  TTCCCGAACTACACCATCGTTTCCGACTTTGGAAGACCCAACGCTGCGCC  947
     |||||·|||||·||·||||····||||·|||||||||·||·||·||·||
898  TTCCCCAACTATACTATCGTGAGTGACTTCGGAAGACCTAATGCAGCCCC  947

948  AGAAACCCATAGGTTGGTGGCTTTTCTCGAACGTGCCGACTCGGTGATCT  997
     |||·||·|||·|··|||||||·||·||||||·|·|||||····|||||||
948  AGAGACTCATCGCCTGGTGGCCTTCCTCGAAAGAGCCGATAGCGTGATCT  997

998  CTTGGGATATACAGGACGAGAAGAATGTCACCTGCCAGCTCACCTTCTGG  1047
     |·||||||||·|||||||||||||·||·||·|||||·|||||||·|||
998  CCTGGGATATTCAGGACGAGAAGAACGTGACTTGCCAACTCACCTTTTGG  1047

1048 GAAGCCTCGGAACGTACTATCCGTTCCGAAGCCGAAGACTCGTACCACTT  1097
     ||·||·||·||·||·|||||·||···|||||||||||||||·||·||·||
1048 GAGGCGTCTGAGCGCACTATACGAAGCGAAGCCGAAGACTCTTATCATTT  1097

1098 TTCTTCTGCCAAAATGACTGCAACTTTTCTGTCTAAGAAACAAGAAGTGA  1147
     ······|||·||·|||||·||·|||||··||||·||·|||||·||·||·|
1098 CAGCAGTGCAAAGATGACAGCCACTTTCTTGTCCAAAAACAGGAGGTTA  1147

1148 ACATGTCCGACTCCGCGCTGGACTGCGTACGTGATGAGGCTATAAATAAG  1197
     |||||||·||||||·|||||·|||||·||·||·||·|||||·||·||·|·
1148 ACATGTCTGACTCAGCGCTAGACTGTGTGCGGGACGAGGCGATCAACAAA  1197
```

Figure 6D

```
1198  TTACAGCAGATTTTCAATACTTCATACAATCAAACATATGAAAAATACGG  1247
      .|.||.||.||.|||||.||....|||||.||.||.||.||.||.||.||
1198  CTGCAACAAATATTCAACACGAGCTACAACCAGACCTACGAGAAGTATGG  1247

1248  AAACGTGTCCGTCTTCGAAACCAGCGGCGGTCTGGTGGTGTTCTGGCAAG  1297
      .||.|||||.||.||.||.||.|||||||||.|||||.||.||.||||.|
1248  CAATGTGTCAGTATTTGAGACTAGCGGCGGACTGGTAGTATTTTGGCAGG  1297

1298  GCATCAAGCAAAAATCTTTGGTGGAATTGGAACGTTTGGCCAATCGATCC  1347
      |.||.||.||.||.|||.|.||.|||.|.||.||..||||||||||....
1298  GGATTAAACAGAAGTCTCTCGTCGAACTCGAGCGGCTGGCCAATCGCAGT  1347

1348  AGTCTGAATATCACTCATAGGACCAGAAGAAGTACGAGTGACAATAATAC  1397
      ||||||||.|||||.||.|||||..||||...|||....||.||||||||
1348  AGTCTGAACATCACACACAGGACACGAAGGTCTACTTCCGATAATAATAC  1397

1398  AACTCATTTGTCCAGCATGGAATCGGTGCACAATCTGGTCTACGCCCAGC  1447
      .||.||..|.|||...|||||.||||||||||.|||||.|||||.|||.
1398  CACCCACCTCTCCTCTATGGAGTCGGTGCACAACCTGGTGTACGCTCAGT  1447

1448  TGCAGTTCACCTATGACACGTTGCGCGGTTACATCAACCGGGCGCTGGCG  1497
      ||||||||.||.||.|||||..|||||||.||.||.|||.|.||||||||.
1448  TGCAGTTTACATACGACACCCTGCGCGGGTATATTAACAGAGCGCTGGCA  1497

1498  CAAATCGCAGAAGCCTGGTGTGTGGATCAACGGCGCACCCTAGAGGTCTT  1547
      ||.||||||.|||||.|||||.||.||.|||||.||.||.||.||||||||
1498  CAGATCGCCGAAGCATGGTGCGTCGACCAACGTCGAACGCTGGAGGTCTT  1547

1548  CAAGGAACTCAGCAAGATCAACCCGTCAGCCATTCTCTCGGCCATTTACA  1597
      ||||||.||...||||||.|||||....|||||||||.||.||.|||||||
1548  CAAGGAGCTATCCAAGATTAACCCAAGTGCCATTCTATCTGCAATTTACA  1597
```

Figure 6E

```
1598 ACAAACCGATTGCCGCGCGTTTCATGGGTGATGTCTTGGGCCTGGCCAGC  1647
     |.||.|||||||||||..|.||.|||||.|||||..||||.|||||.|||
1598 ATAAGCCGATTGCCGCTAGGTTTATGGGCGATGTTCTGGGACTGGCGAGC  1647

1648 TGCGTGACCATCAACCAAACCAGCGTCAAGGTGCTGCGTGATATGAACGT  1697
     ||.|||||.||.||||||||....|||||||||||..|.||.||||||||
1648 TGTGTGACTATAAACCAAACGTCAGTCAAGGTGCTTAGGGACATGAACGT  1697

1698 GAAGGAATCGCCAGGACGCTGCTACTCACGACCCGTGGTCATCTTTAATT  1747
     .||||||||.||.||.||.||.||.||.||.||.||.|||||.|||||||
1698 TAAGGAATCCCCTGGCCGGTGTTATTCGCGGCCTGTTGTCATATTTAATT  1747

1748 TCGCCAACAGCTCGTACGTGCAGTACGGTCAACTGGGCGAGGACAACGAA  1797
     |.|||||...|||.|||||||||||||||.||..|.||||||||||||||
1748 TTGCCAATTCCTCTTACGTGCAGTACGGCCAGTTAGGCGAGGACAACGAA  1797

1798 ATCCTGTTGGGCAACCACCGCACTGAGGAATGTCAGCTTCCCAGCCTCAA  1847
     ||..|.|||||||.||.|||||.|||||||||.|||.|.||.|||||.||
1798 ATTTTATTGGGCAATCATCGCACCGAGGAATGCCAGTTGCCGAGCCTGAA  1847

1848 GATCTTCATCGCCGGGAACTCGGCCTACGAGTACGTGGACTACCTCTTCA  1897
     .|||||.||.||.|||||...|.||||||||||||.|||||.|||||.|
1848 AATCTTTATAGCTGGGAACAGCGCTTACGAGTACGTCGACTATCTCTTTA  1897

1898 AACGCATGATTGACCTCAGCAGTATCTCCACCGTCGACAGCATGATCGCC  1947
     |.||.|||||||.||.|||...|||..|||.||||||...|||||||||
1898 AGCGGATGATTGATCTGAGCTCGATCAGCACAGTCGACTCTATGATCGCC  1947

1948 CTGGATATCGACCCGCTGGAAAATACCGACTTCAGGGTACTGGAACTTTA  1997
     ||||||||.|||||||||||.|||||.||.|||||.||.||.|||.|.||
1948 CTGGATATTGACCCGCTGGAGAATACAGATTTCAGAGTGCTTGAATTATA  1997
```

Figure 6F

```
1998 CTCGCAGAAAGAGCTGCGTTCCAGCAACGTTTTTGACCTCGAAGAGATCA 2047
     .||.||||||||||||...|...||.||.||.||.||.||.||.||.|
1998 TTCACAGAAAGAGCTGCGGAGCTCAAATGTGTTCGATCTTGAGGAAATTA 2047

2048 TGCGCGAATTCAACTCGTACAAGCAGCGGGTAAAGTACGTGGAGGACAAG 2097
     ||||.|||||||||...|||||||.|||||.|||||||||||||||||
2048 TGCGGGAATTCAACAGCTACAAGCAACGGGTCAAGTACGTGGAGGACAAG 2097

2098 GTAGTCGACCCGCTACCGCCCTACCTCAAGGGTCTGGACGACCTCATGAG 2147
     ||.||.|||||.||.||.||||||.|.||.||||||||.||.||||||||
2098 GTGGTGGACCCACTGCCCCCTACTTGAAAGGTCTGGATGATCTCATGAG 2147

2148 CGGCCTGGGCGCCGCGGGAAAGGCCGTTGGCGTAGCCATTGGGGCCGTGG 2197
     |||.||.||.||.||.||.||.||||||||.|||||.||.||.||||.|
2148 CGGTCTTGGAGCGGCTGGCAAAGCCGTTGGAGTAGCAATCGGCGCCGTTG 2197

2198 GTGGCGCGGTGGCCTCCGTGGTCGAAGGCGTTGCCACCTTCCTCAAAAAC 2247
     |.||.||.|||||.||.||.||.||.|||||||||.|||||..|.||.|||
2198 GAGGGGCCGTGGCTTCTGTAGTGGAGGGCGTTGCTACCTTTTTGAAGAAC 2247

2248 CCCTTCGGAGCCTTCACCATCATCCTCGTGGCCATAGCCGTAGTCATTAT 2297
     ||||||||.|||||.||.||||||.||.||.||.||.||.||.||.||
2248 CCCTTCGGGGCCTTTACTATCATTCTAGTCGCTATTGCAGTCGTGATAAT 2297

2298 CACTTATTTGATCTATACTCGACAGCGGCGTCTGTGCACGCAGCCGCTGC 2347
     |||.||||||||||||||||.|||.|.||..|.|||||.|||||.||.|
2298 CACATATTTGATCTATACTCGGCAGAGACGCTTATGCACACAGCCCCTTC 2347

2348 AGAACCTCTTTCCCTATCTGGTGTCCGCCGACGGGACCACCGTGACGTCG 2397
     ||||.||||||.||||||||||.||||||.|||||||.||.||||||....
2348 AGAATCTCTTCCCCTATCTGGTCTCCGCAGATGGGACAACAGTGACAAGT 2397
```

Figure 6G

```
2398  GGCAGCACCAAAGACACGTCGTTACAGGCTCCGCCTTCCTACGAGGAAAG  2447
      |||...||.||.||.||....||.||.||||||.||....||||.||.||
2398  GGCTCGACTAAGGATACCAGCTTGCAAGCTCCCCCAAGTTACGAAGAGAG  2447

2448  TGTTTATAATTCTGGTCGCAAAGGACCGGGACCACCGTCGTCTGATGCAT  2497
      .||||||||.||.|||.|.|||||||||.||.|||||----||.||||||||
2448  CGTTTATAACTCCGGTAGGAAAGGACCAGGTCCACCTAGCTCAGATGCAT  2497

2498  CCACGGCGGCTCCGCCTTACACCAACGAGCAGGCTTACCAGATGCTTCTG  2547
      |.||.||.||.||.||.||.||.||.||.|||||||||.||.|||||||||.||.
2498  CAACCGCTGCCCCACCCTATACTAATGAGCAGGCCTATCAGATGCTGCTT  2547

2548  GCCCTGGCCCGTCTGGACGCAGAGCAGCGAGCGCAGCAGAACGGTACAGA  2597
      ||.||.|||.|.||||||||.||||||||||.|||||||||.||.|||||
2548  GCACTCGCCAGACTGGACGCCGAGCAGCGAGCCCAGCAGAATGGGACAGA  2597

2598  TTCTTTGGACGGACAGACTGGCACGCAGGACAAGGGACAGAAGCCTAACC  2647
      .||..|.|||||.|||||||||.||.|||||.||.|||||||.|||||.|
2598  CTCCCTCGACGGGCAGACTGGAACCCAGGATAAAGGACAGAAACCTAATC  2647

2648  TGCTAGACCGGCTGCGACATCGCAAAAACGGCTACAGACACTTGAAAGAC  2697
      ||||.||||||.||..||||..|.|||||-|||||||.|||.|.||||||.
2648  TGCTTGACCGACTAAGACACAGGAAAAATGGCTACAGGCACCTAAAGAT  2697

2698  TCCGACGAAGAAGAGAACGTC  2718
      ...||.||||||||||||||
2698  AGTGATGAAGAAGAGAACGTC  2718
```

Figure 7A

```
  1 atggagtcctctgccaagagaaagatggaccctgataatcctgacgagggcccttcctcc  60
  1 M  E  S  S  A  K  R  K  M  D  P  D  N  P  D  E  G  P  S  S   20

61 aaggtgccacggcccgagacacccgtgaccaaggccacgacgttcctgcagactatgttg 120
 21 K  V  P  R  P  E  T  P  V  T  K  A  T  T  F  L  Q  T  M  L   40

121 aggaaggaggttaacagtcagctgagtctgggagacccgctgtttccagagttggccgaa 180
 41 R  K  E  V  N  S  Q  L  S  L  G  D  P  L  F  P  E  L  A  E   60

181 gaatccctcaaaacttttgaacaagtgaccgaggattgcaacgagaaccccgagaaagat 240
 61 E  S  L  K  T  F  E  Q  V  T  E  D  C  N  E  N  P  E  K  D   80

241 gtcctggcagaactcgtcaaacagattaaggttcgagtggacatggtgcggcatagaatc 300
 81 V  L  A  E  L  V  K  Q  I  K  V  R  V  D  M  V  R  H  R  I  100

301 aaggagcacatgctgaaaaaatatacccagacggaagagaaattcactggcgcctttaat 360
101 K  E  H  M  L  K  K  Y  T  Q  T  E  E  K  F  T  G  A  F  N  120

361 atgatgggaggatgtttgcagaatgccttagatatcttagataaggttcatgagcctttc 420
121 M  M  G  G  C  L  Q  N  A  L  D  I  L  D  K  V  H  E  P  F  140

421 gaggagatgaagtgtattgggctaactatgcagagcatgtatgagaactacattgtacct 480
141 E  E  M  K  C  I  G  L  T  M  Q  S  M  Y  E  N  Y  I  V  P  160

481 gaggataagcgggagatgtggatggcttgtattaaggagctgcatgatgtgagcaagggc 540
161 E  D  K  R  E  M  W  M  A  C  I  K  E  L  H  D  V  S  K  G  180

541 gccgctaacaagttggggggtgcactgcaggctaaggcccgtgctaaaaaggatgaactt 600
181 A  A  N  K  L  G  G  A  L  Q  A  K  A  R  A  K  K  D  E  L  200

601 aggagaaagatgatgtatatgtgctacaggaatatagagttcttttaccaagaactcagcc 660
201 R  R  K  M  M  Y  M  C  Y  R  N  I  E  F  F  T  K  N  S  A  220

661 ttccctaagaccaccaatggctgcagtcaggccatggcggcactgcagaacttgcctcag 720
221 F  P  K  T  T  N  G  C  S  Q  A  M  A  A  L  Q  N  L  P  Q  240

721 tgctcccctgatgagattatggcttatgcccagaaaatatttaagattttggatgaggag 780
241 C  S  P  D  E  I  M  A  Y  A  Q  K  I  F  K  I  L  D  E  E  260

781 agagacaaggtgctcacgcacattgatcacatatttatggatatcctcactacatgtgtg 840
261 R  D  K  V  L  T  H  I  D  H  I  F  M  D  I  L  T  T  C  V  280

841 gaaacaatgtgtaatgagtacaaggtcactagtgacgcttgtatgatgaccatgtacggg 900
281 E  T  M  C  N  E  Y  K  V  T  S  D  A  C  M  M  T  M  Y  G  300
```

Figure 7B

```
 901 ggcatctctctcttaagtgagttctgtcgggtgctgtgctgctatgtcttagaggagact  960
 301 G  I  S  L  L  S  E  F  C  R  V  L  C  C  Y  V  L  E  E  T   320

961 agtgtgatgctggccaagcggcctctgataaccaagcctgaggttatcagtgtaatgaag 1020
 321 S  V  M  L  A  K  R  P  L  I  T  K  P  E  V  I  S  V  M  K   340

1021 cgccgcattgaggagatctgcatgaaggtctttgcccagtacattctgggggccgatcct 1080
 341 R  R  I  E  E  I  C  M  K  V  F  A  Q  Y  I  L  G  A  D  P   360

1081 ctgagagtctgctctcctagtgtggatgacctacgggccatcgccgaggagtcagatgag 1140
 361 L  R  V  C  S  P  S  V  D  D  L  R  A  I  A  E  E  S  D  E   380

1141 gaagaggctattgtagcctacactttggccaccgctggtgtcagctcctctgattctctg 1200
 381 E  E  A  I  V  A  Y  T  L  A  T  A  G  V  S  S  S  D  S  L   400

1201 gtgtcaccccagagtccctgtacccgcgactatccctctgtcctcagtaattgtggct  1260
 401 V  S  P  P  E  S  P  V  P  A  T  I  P  L  S  S  V  I  V  A   420

1261 gagaacagtgatcaggaagaaagtgagcagagtgatgaggaagaggaggagggtgctcag 1320
 421 E  N  S  D  Q  E  E  S  E  Q  S  D  E  E  E  E  G  A  Q      440

1321 gaggagcgggaggacactgtgtctgtcaagtctgagccagtgtctgagatagaggaagtt 1380
 441 E  E  R  E  D  T  V  S  V  K  S  E  P  V  S  E  I  E  E  V   460

1381 gccccagaggaagaggaggatggtgctgaggaacccaccgcctctggaggcaagagcacc 1440
 461 A  P  E  E  E  D  G  A  E  E  P  T  A  S  G  G  K  S  T      480

1441 caccctatggtgactagaagcaaggctgaccag 1473
 481 H  P  M  V  T  R  S  K  A  D  Q   491
```

CODON-OPTIMIZED POLYNUCLEOTIDE-BASED VACCINES AGAINST HUMAN CYTOMEGALOVIRUS INFECTION

CROSS-REFERENCE TO RELATED APPLICATIONS

The present application is a continuation application of U.S. application Ser. No. 13/525,814, filed Jun. 18, 2012, which is a continuation application of U.S. application Ser. No. 13/013,752, filed Jan. 25, 2011, now U.S. Pat. No. 8,278,093, issued Oct. 2, 2012, which is a continuation application of U.S. application Ser. No. 11/892,020, filed Aug. 17, 2007, now U.S. Pat. No. 7,888,112, issued Feb. 15, 2011, which is a continuation application of U.S. application Ser. No. 10/738,986, filed Dec. 19, 2003, now U.S. Pat. No. 7,410,795, issued Aug. 12, 2008, which claims benefit of U.S. Provisional Application No. 60/435,549, filed Dec. 23, 2002, all of which are incorporated herein by reference in their entirety.

BACKGROUND OF THE INVENTION

Human cytomegalovirus ("HCMV") infects between 50% and 85% of adults by 40 years of age (Gerson A. A., et al., in *Viral Infections of Humans*, Evans A. S. and Kaslow, R. A., eds., Plenum Press, New York, N.Y. (1997)). Although HCMV infection is benign in most healthy adults, it can result in deadly pneumonitis, as well as colitis, esophagitis, leukopenia, and retinitis in transplant and other immunocompromised patients, especially those with HIV. In solid organ transplant (SOT) or hematopoeitic cell transplant (HCT) populations, HCMV disease can occur either from new infection transmitted from the donor organ or HCT, or can recur as a result of reactivation of latent virus in the recipient.

Despite licensed therapies, HCMV-associated disease remains severely debilitating and life-threatening in HIV patients and the allogeneic related HCT and SOT settings. In addition, HCMV is the most common intrauterine infection in the United States, and results in death or severe sequelae in over 8,000 infants per year. For these reasons, HCMV was ranked in the list of the top 10 vaccines most in need of development in the United States (*Vaccines for the 21$^{st}$ century: a tool for decision making*, National Academy of Sciences (1999)).

Existing therapies include the use of immunoglobulins and anti-viral agents such as ganciclovir and its derivatives, which are most effective when used prophylactically or very early during infection in at risk populations. However, these therapies are characterized by significant toxicity and limited efficacy, especially for late onset disease (onset after the first 100 days) (Fillet, A. M., *Drugs Aging* 19:343-354 (2002); von Bueltzingsloewen, A., et al., *Bone Marrow Transplant* 12:197-202 (1993); Winston, D. J., et al., *Ann. Intern. Med.* 118:179-184 (1993); Goodrich, J. M., et al., *Ann. Intern. Med.* 118:173-178 (1993); Boeckh, M., et al., *Blood* 88:4063-4071 (1996); Salzberger, B., et al., *Blood* 90:2502-2508 (1997); Preiser, W., et al., *J. Clin. Virol.* 20:59-70 (2001); Grangeot-Keros, L., and Cointe, D., *J. Clin. Virol.* 21:213-221 (2001); Boeckh, M., and Bowden, R., *Cancer Treat. Res.* 76:97-136 (1995); Zaia, J. A., et al., *Hematology* (Am. Soc. Hematol. Educ. Program) 339-355 (2000)).

In addition to developing more rapid and sensitive diagnostics, molecular biological methods enable the development of defined subunit vaccines for human pathogens. Indeed, safe, effective recombinant subunit vaccines would significantly reduce, and perhaps eliminate, the need for therapeutic treatments. In the case of HCMV, control of infection has been correlated with antibody and T cell recognition of at least three viral proteins: pp65, glycoprotein B (gB), and the immediate early-1 protein (IE1).

The 65kD viral protein pp65, also known as ppUL83, lower matrix protein, ICP27, PK68, and pp64, is one of the most abundantly expressed structural proteins (FIG. 1). It is encoded by the UL83 gene of the viral genome (nucleotides 119352-121037 of the HCMV strain AD169 genomic sequence, Genbank X17403). This protein is believed to be processed for MHC presentation shortly after viral entry into cells, which allows it to be presented before other viral proteins shut down the antigen processing pathway in infected cells. Therefore, T cell recognition of this protein is important for infection control (Solache, et al. *J. Immunol.* 163:5512-5518 (1999)), which is herein incorporated by reference in its entirety.

Glycoprotein B (gB) is a 906 amino acid envelope glycoprotein (FIG. 4) encoded by UL55, nucleotides 80772-83495 of Genbank X17403). It is a type I integral membrane protein that participates in the fusion of the virion envelope with the cell membrane, is required for infectivity, is highly immunogenic, and has a high degree of conservation among HCMV strains, making this protein an attractive target for vaccines. The full-length protein contains an amino-terminal signal peptide (amino acids 1-24), an extracellular domain (amino acids 25-713), a putative trans-membrane anchor domain (amino acids 714-771) and an intracellular domain (amino acids 772-906). Deletion of the transmembrane anchor domain results in secretion of gB (Zheng et al. *J. Virol.* 70:8029-8040 (1996)). Additionally, the full-length protein is cleaved by host furin proteases between amino acids 460 and 461 to form the gp93 and gp55 cleavage products that remain tightly associated as a heterodimer. (Mocarski E. S. and C. T. Courcelle, pp. 2629-2674, Field's Virology, 4th ed., Eds. Knipe D M and Howley P M, Lippincott Williams & Wilkins, Philadelphia (2001)). Each of the references cited in this paragraph is incorporated herein by reference in its entirety.

IE1 is a 491 amino acid protein (FIG. 7) encoded by HCMV ORF UL123 (Genbank X17403, nucleotides 171006-172765). The gene encodes a 1.9 Kb mRNA comprising four exons, with only exons 2-4 being translated. The 85 N-terminal amino acids are encoded by exons 2 and 3, with the remainder encoded by exon 4. IE2 is a related family of proteins that share exons 1-3 and an exon 5, with many splice variations. Together, IE1 and IE2 transactivate the HCMV major immediate early promoter to regulate viral transcription (Malone, C L. et al. *J. Virol.* 64:1498-1506 (1990); Mocarski, E. *Fields Virology* Ed. Field et al., 3$^{rd}$ ed., pp. 2447-2491, Lippincott-Raven Publishers, Philadelphia (1996); Chee M. S. et al., *Curr Topics Microbiol. Immunol.* 154:125-169 (1990)). Each of the references cited in this paragraph is incorporated herein by reference in its entirety.

IE1 has a kinase activity that is dependent on an ATP binding site encoded by amino acids 173-196. IE1 can autophosphorylate or phosphorylate cellular factors to transactivate E2F dependent transcription. Both exons 3 and 4 are required for viral transactivation, with the required regions in exon 4 being broadly distributed throughout the exon. The portion of the protein encoded by exon 4 is known to have a high degree of secondary structure. Although IE1 is transported to the nucleus, no nuclear localization signal has been identified. (Pajovic, S. et al. *Mol. Cell. Bio.* 17:6459-6464 (1997)). Gyulai et al. showed high levels of CTL response in vitro to effector cells expressing a nucleotide fragment consisting of exon 4 (Gyulai et al. *J. Infectious Diseases* 181:

1537-1546 (2000)). Each of the references cited in this paragraph is incorporated herein by reference in its entirety.

No vaccine is currently available for HCMV. However, clinical trials have been performed with live-attenuated HCMV vaccines, a canarypox-based vaccine, and a recombinant gB vaccine (Plotkin, S. A., *Pediatr. Infect. Dis. J.* 18:313-325 (1999)). The first HCMV vaccine tested in humans was a live attenuated virus vaccine made from the AD169 laboratory-adapted strain (Elek, S. D. and Stern, H., *Lancet* 1:1-5 (1974)). Local reactions were common, but HCMV was not isolated from any of the vaccine recipients. This vaccine was not investigated beyond initial Phase I studies.

Immune responses to HCMV have been determined by the study of acute and chronic HCMV infections in both animal models and in man. Antibody appears critical in the prevention of maternal-fetal transmission, and is primarily directed to the envelope glycoproteins, especially gB (Plotkin, S. A., *Pediatr. Infect. Dis. J.* 18:313-325 (1999); Fowler, K. B., *N. Engl. J. Med.* 326:663-667 (1992)).

In contrast, the control of HCMV infection in transplant recipients and HIV-infected persons is associated with preserved cellular immune responses, including CD4+, CD8+, and NK T cells. The CD8+ T-cell responses are directed primarily at the immediate early (IE) protein of HCMV and at the abundant tegument protein pp65 (Gyulai, Z., et al., *J. Infect. Dis.* 181:1537-1546 (2000); Tabi, Z., et al., *J. Immunol.* 166:5695-5703 (2001); Wills, M. R., et al., *J. Virol.* 70:7569-7579 (1996); Frankenberg, N., et al., *Virology* 295: 208-216 (2002); Retiere, C., et al., *J. Virol.* 74:3948-3952 (2000); Koszinowski, U. H., et al., *J. Virol.* 61:2054-2058 (1987); Kern, F., et al., *J. Infect. Dis.* 185:1709-1716 (2002)). Approximately 92% of persons have CD8+ responses to pp65 and another 76% to exon 4 of IE1 (Gyulai, Z., et al., *J. Infect. Dis.* 181:1537-1546 (2000); Kern, F., et al., *J. Infect. Dis.* 185:1709-1716 (2002)). In addition, another one third of infected individuals have CTL responses to gB. Almost all infected persons have CD4+ responses to HCMV, although the gene and epitope mapping of these responses is not as fully investigated as those for CD8+ T cells (Kern, F., et al., *J. Infect. Dis.* 185:1709-1716 (2002); Davignon, J. L., et al., *J. Virol.* 70:2162-2169 (1996); He, H., et al., *J. Gen. Virol.* 76:1603-1610 (1995); Beninga, J., et al., *J. Gen. Virol.* 76:153-160 (1995). The helper T-cell responses in infected, healthy persons are sufficiently robust that HCMV is frequently used as a positive control in the development of methods for the measurement of CD4+ T-cell responses (Kern, F., et al., *J. Infect. Dis.* 185:1709-1716 (2002); Currier, J. R., et al., *J. Immunol. Methods* 260:157-172 (2002); Picker, L. J., et al., *Blood* 86:1408-1419 (1995)).

Other attempts to develop vaccines for HCMV have focused on administering purified or recombinant viral polypeptides, either full-length, modified, or short epitopes, to induce immune responses. In a review published by the American Society for Hematology, Zaia et al. describes various peptide-based approaches to developing HCMV vaccines, including using DNA vaccines to express wild-type and mutated proteins (Zaia, J. A. et al. *Hematology* 2000, *Am Soc Hematol Educ Program*, pp. 339-355, Am. Soc. Hematol. (2000)). Endresz et al. describes eliciting HCMV-specific CTL in mice immunized with plasmids encoding HCMV Towne strain full-length gB, expressed constitutively or under a tetracycline-regulatable promoter, and pp65 or a gB with the deletion of amino acids 715-772 (Endresv, V. et al. *Vaccine* 17:50-8 (1999); Endresz, V. et al. *Vaccine* 19:3972-80 (2001)). U.S. Pat. No. 6,100,064 describes a method of producing secreted gB polypeptides lacking the transmembrane domain but retaining the C terminal domain. U.S. Pat. Nos. 5,547,834 and 5,834,307 describe a gB polypeptide with amino acid substitutions at the endoproteolytic cleavage site to prevent proteolytic processing. U.S. Pat. Nos. 6,251,399 and 6,156,317 describe vaccines using short peptide fragments of pp65 comprising immunogenic epitopes. A number of other groups have analyzed epitopes in HCMV pp65 and gB for eliciting a strong immune response (Liu, Y N. et al. *J. Gen. Virol.* 74:2207-14 (1993); Ohlin, M. et al. *J. Virol.* 67:703-10 (1993); Navarro, D. et al. *J. Med. Virol.* 52:451-9 (1997); Khattab B A. et al. *J. Med. Virol.* 52:68-76 (1997); Diamond, D J. et al. *Blood* 90:1751067 (1997); Solache, A. et al. *J. Immunol.* 163:5512-8 (1999). U.S. Pat. No. 6,162,620 is directed to a polynucleotide encoding a wild-type gB or a gB lacking the membrane sequences. U.S. Pat. No. 6,133,433 is directed to a nucleotide encoding a full-length, wild-type pp65 or a specific 721 nt fragment thereof. Each of the references cited in this paragraph is incorporated herein by reference in its entirety.

During the past few years there has been substantial interest in testing DNA-based vaccines for a number of infectious diseases where the need for a vaccine, or an improved vaccine, exists. Several well-recognized advantages of DNA-based vaccines include the speed, ease and cost of manufacture, the versatility of developing and testing multivalent vaccines, the finding that DNA vaccines can produce a robust cellular response in a wide variety of animal models as well as in man, and the proven safety of using plasmid DNA as a delivery vector (Donnelly, J. J., et al., *Annu. Rev. Immunol.* 15:617-648 (1997); Manickan, E., et al., *Crit. Rev. Immunol.* 17(2):139-154 (1997)). DNA vaccines represent the next generation in the development of vaccines (Nossal, G., *Nat. Med.* 4:475-476 (1998)) and numerous DNA vaccines are in clinical trials. Each of the references cited in this paragraph is incorporated herein by reference in its entirety.

The immunotherapeutic product design is based on the concept of immunization by direct gene transfer. Plasmid-based immunotherapeutics offer the positive attributes of immune stimulation inherent to live-attenuated vaccines combined with the safety of recombinant subunit vaccines in an adjuvant formulation.

In the transplant population, control of HCMV disease is associated with a cellular immune response (Riddell, S. R., "Pathogenesis of cytomegalovirus pneumonia in immuno-compromised hosts," *Semin. Respir. Infect.* 10:199-208 (1995)) and thus an effective product should induce CD4+ and CD8+ T-cell responses. Formulated plasmid has been shown to induce such cellular immune responses, and does not have the safety concerns associated with the use of live vectors in the transplant setting (Shiver, J. W., et al., *Nature* 415:331-335 (2002)).

Retooling coding regions encoding polypeptides from pathogens using codon frequencies preferred in a given mammalian species often results in a significant increase in expression in the cells of that mammalian species, and concomitant increase in immunogenicity. See, e.g., Deml, L., et al., *J. Virol.* 75:10991-11001 (2001), and Narum, D L, et al., *Infect. Immun.* 69:7250-7253 (2001), all of which are herein incorporated by reference in its entirety.

There remains a need in the art for convenient, safe, and efficacious immunogenic compounds to protect humans against HCMV infection. The present invention provides safe yet effective immunogenic compounds and methods to protect humans, especially transplant recipients and immunocompromised individuals, against HCMV infection using such immunogenic compounds.

SUMMARY OF THE INVENTION

The present invention is directed to enhancing immune response of a human in need of protection against HCMV infection by administering in vivo, into a tissue of the human, a polynucleotide comprising a codon-optimized coding region encoding an HCMV polypeptide or a nucleic acid fragment of such a coding region encoding a fragment, a variant, or a derivative thereof. Nucleic acid fragments of the present invention are altered from their native state in one or more of the following ways. First, a nucleic acid fragment which encodes an HCMV polypeptide may be part or all of a codon-optimized coding region, optimized according to codon usage in humans. In addition, a nucleic acid fragment which encodes an HCMV polypeptide may be a fragment which encodes only a portion of a full-length polypeptide, and/or may be mutated so as to, for example, remove from the encoded polypeptide adventitious protein motifs present in the encoded polypeptide or virulence factors associated with the encoded polypeptide. For example, the nucleic acid sequence could be mutated so as not to encode adventitious anchoring motifs that prevent secretion of the polypeptide. Upon delivery, the polynucleotide of the invention is incorporated into the cells of the human in vivo, and a prophylactically or therapeutically effective amount of an HCMV polypeptide or fragment thereof is produced in vivo.

The invention further provides immunogenic compositions comprising a polynucleotide which comprises one or more codon-optimized coding regions encoding polypeptides of HCMV or nucleic acid fragments of such coding regions encoding fragments, variants, or derivatives thereof. Such compositions may include various transfection facilitating or immunity enhancing agents, such as poloxamers, cationic lipids, or adjuvants.

The present invention further provides plasmids and other polynucleotide constructs for delivery of nucleic acid coding sequences to a vertebrate which provide expression of HCMV polypeptides, or fragments, variants, or derivatives thereof. The present inventions further provides carriers, excipients, transfection-facilitating agents, immunogenicity-enhancing agents, e.g. adjuvants, or other agent or agents to enhance the transfection, expression, or efficacy of the administered gene and its gene product.

The invention further provides methods for enhancing the immune response of a human to HCMV infection by administering to the tissues of a human one or more polynucleotides comprising one or more codon-optimized coding regions encoding polypeptides of HCMV or nucleic acid fragments of such coding regions encoding fragments, variants, or derivatives thereof. In certain embodiments, the invention further provides methods for enhancing the immune response of a human patient to HCMV infection by sequentially administering two or more different immunogenic compositions to the tissues of the vertebrate. Such methods comprise initially administering one or more polynucleotides comprising one or more codon-optimized coding regions encoding polypeptides of HCMV or nucleic acid fragments of such coding regions encoding fragments, variants, or derivatives thereof, to prime immunity, and then administering subsequently a different immunogenic composition, for example a recombinant viral vaccine, a protein subunit vaccine, or a recombinant or killed bacterial vaccine or vaccines to boost the anti-HCMV immune response in a human.

The invention further provides methods for enhancing the immune response of a human patient to HCMV by administering to the tissues of a human one or more polynucleotides comprising one or more codon-optimized coding regions encoding polypeptides of HCMV, and also HCMV polypeptides or fragments, variants or derivatives thereof; or one or more non-optimized polynucleotides encoding HCMV polypeptides, fragments, variants or derivatives thereof.

The combination of HCMV polypeptides or polynucleotides encoding HCMV polypeptides or fragments, variants or derivatives thereof, with the codon-optimized nucleic acid compositions provides for therapeutically beneficial effects at dose sparing concentrations. For example, immunological responses sufficient for a therapeutically beneficial effect may be attained by using less of a conventional-type vaccine when supplemented or enhanced with the appropriate amount of a codon-optimized nucleic acid.

Conventional-type vaccines, include vaccine compositions comprising either dead, inert or fragments of a virus or bacteria, or bacterial or viral proteins or protein fragments, injected into the patient to elicit action by the immune system. With regard to the present invention, conventional-type vaccines include compositions comprising immunogenic polypeptides or nucleotides encoding immunogenic polypeptides, fragments, variants, or derivatives thereof, and vectors comprising nucleotides encoding immunogenic polypeptides, fragments, variants, or derivatives thereof, that are not products of, or do not contain codon-optimized polynucleotides as described herein. Thus, genetically engineered vaccines, are included in conventional-type vaccines, such as genetically engineered live vaccines, live chimeric vaccines, live replication-defective vaccines, subunit vaccines, peptide vaccines in various modifications of monovalent, multivalent, or chimeric subunit vaccines delivered as individual components or incorporated into virus-like particles for improved immunogenicity, and polynucleotide vaccines. Auxiliary agents, as described herein, are also considered components of conventional-type vaccines.

Thus, dose sparing is contemplated by administration of the combinatorial polynucleotide vaccine compositions of the present invention.

In particular, the dose of conventional-type vaccine may be reduced by at least 5%, at least 10%, at least 20%, at least 30%, at least 40%, at least 50%, at least 60% or at least 70% when administered in combination, or prior to, or subsequent to, the codon-optimized nucleic acid compositions of the invention.

Similarly, a desirable level of an immunological response afforded by a DNA based pharmaceutical alone may be attained with less DNA by including a conventional-type DNA vaccine. Further, using a combination of a conventional-type vaccine and a codon-optimized DNA-based vaccine may allow both materials to be used in lesser amounts while still affording the desired level of immune response arising from administration of either component alone in higher amounts (e.g. one may use less of either immunological product when they are used in combination). This reduction in amounts of materials being delivered may be for each administration, in addition to reducing the number of administrations, in a vaccination regimen (e.g. 2 versus 3 or 4 injections). Further, the combination may also provide for reducing the kinetics of the immunological response (e.g. desired response levels are attained in 3 weeks instead of 6 after immunization).

In particular, the dose of a DNA based pharmaceutical, may be reduced by at least 5%, at least 10%, at least 20%, at least 30%, at least 40%, at least 50%, at least 60% or at least 70% when administered in combination with conventional CMV vaccines.

Determining the precise amounts of DNA based pharmaceutical and conventional antigen is based on a number of factors as described herein, and is readily determined by one of ordinary skill in the art.

In addition to dose sparing, the claimed combinatorial compositions provide for a broadening of the immune response and/or enhanced beneficial immune responses. Such broadened or enhanced immune responses are achieved by: adding DNA to enhance cellular responses to a conventional-type vaccine; adding a conventional-type vaccine to a DNA pharmaceutical to enhanced humoral response; using a combination that induces additional epitopes (both humoral and/or cellular) to be recognized and/or more desirably responded to (epitope broadening); employing a DNA-conventional vaccine combination designed for a particular desired spectrum of immunological responses; obtaining a desirable spectrum by using higher amounts of either component. The broadened immune response is measurable by one of ordinary skill in the art by various standard immunological assays specific for the desirable response spectrum, which are described in more detail herein.

Both broadening and dose sparing may be obtained simultaneously.

BRIEF DESCRIPTION OF THE FIGURES

FIG. 1 shows the wild-type nucleotide sequence (SEQ ID NO:1) and amino acid translation (SEQ ID NO:2) of full-length, native HCMV pp65 (Genbank WMBE65) from HCMV strain AD 169.

FIG. 2 shows a fully codon-optimized nucleotide sequence (SEQ ID NO:3) and amino acid translation (SEQ ID NO:4) of native HCMV pp65. The putative kinase site at amino acids Arg435-Lys438 is underlined.

FIGS. 3A-3E show the alignment of wild-type ("wt") (SEQ ID NO:1) and fully codon-optimized ("opt") (SEQ ID NO:9) nucleotide sequences encoding native HCMV pp65.

FIGS. 4A-4E show the wild-type nucleotide sequence (SEQ ID NO:11) and amino acid translation (SEQ ID NO:12) of HCMV gB strain AD169. SEQ ID NO:11 contains a nucleic acid fragment encoding the open reading frame for full-length HCMV gB (nucleotides 157-3125 of Genbank X04606). The host proteolytic cleavage site between amino acids 460 and 461 is marked by a colon.

FIGS. 5A-5D show a minimally codon-optimized nucleotide sequence (SEQ ID NO:13) and amino acid sequence (SEQ ID NO:14) of a truncated, secreted HCMV gB. SEQ ID NO:13 contains a nucleic acid encoding a minimal human codon-optimized secreted gB (SEQ ID NO:14).

FIGS. 6A-6G show the alignment of wild-type ("wt") (SEQ ID NO:11) and fully codon-optimized ("opt") (SEQ ID NO:16) nucleotide sequences encoding full-length wild-type HCMV gB.

FIGS. 7A-7B show the wild-type IE1 nucleotide sequence (SEQ ID NO:19), and amino acid translation (SEQ ID NO:20) of full-length, native IE1.

DETAILED DESCRIPTION OF THE INVENTION

Figure 8:
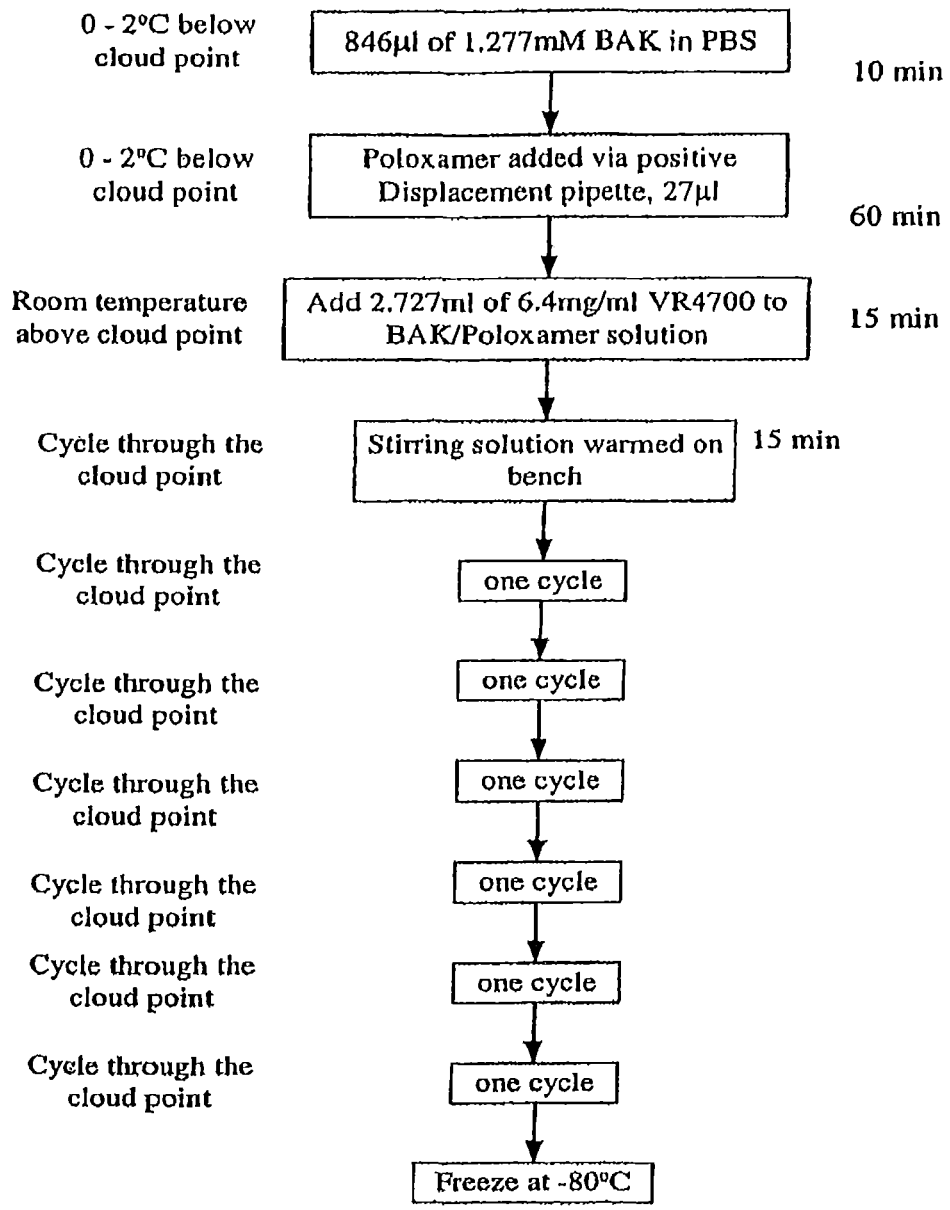
FIG. 8 shows the protocol for the preparation of a formulation comprising 0.3 mM BAK, 7.5 mg/ml CRL 1005, and 5 mg/ml of DNA in a final volume of 3.6 ml, through the use of thermal cycling.

The present invention is directed to compositions and methods for enhancing the immune response of a human in need of protection against HCMV infection by administering in vivo, into a tissue of a human, a polynucleotide comprising a human codon-optimized coding region encoding a polypeptide of HCMV, or a nucleic acid fragment of such a coding region encoding a fragment, variant, or derivative thereof. The polynucleotides are incorporated into the cells of the human in vivo, and an immunologically effective amount of the HCMV polypeptide, or fragment or variant is produced in vivo.

The present invention provides polynucleotide-based vaccines and methods for delivery of HCMV coding sequences to a human with optimal expression and safety conferred through codon optimization and/or other manipulations. These polynucleotide-based vaccines are prepared and administered in such a manner that the encoded gene products are optimally expressed in humans. As a result, these compositions and methods are useful in stimulating an immune response against HCMV infection. Also included in the invention are expression systems, delivery systems, and codon-optimized HCMV coding regions.

A polynucleotide vaccine of the present invention is capable of eliciting an immune response in a human against HCMV when administered to that human. Such polynucleotides are referred to herein as polynucleotide vaccines.

It is to be noted that the term "a" or "an" entity refers to one or more of that entity; for example, "a polynucleotide," is understood to represent one or more polynucleotides. As such, the terms "a" (or "an"), "one or more," and "at least one" can be used interchangeably herein.

The terms "nucleic acid" or "nucleic acid fragment" refers to any one or more nucleic acid segments, e.g., DNA or RNA fragments, present in a polynucleotide or construct. While the terms "nucleic acid," as used herein, is meant to include any nucleic acid, the term "nucleic acid fragment" is used herein to specifically denote a fragment of a designed or synthetic codon-optimized coding region encoding a polypeptide, or fragment, variant, or derivative thereof, which has been optimized according to the codon usage of a given species. As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, and the like, are not part of a coding region. Two or more nucleic' acids or nucleic acid fragments of the present invention can be present in a single polynucleotide construct, e.g., on a single plasmid, or in separate polynucleotide constructs, e.g., on separate plasmids. Furthermore, any nucleic acid or nucleic acid fragment may encode a single polypeptide, e.g., a single antigen, cytokine, or regulatory polypeptide, or may encode more than one polypeptide, e.g., a nucleic acid may encode two or more polypeptides. In addition, a nucleic acid may encode a regulatory element such as a promoter or a transcription terminator, or may encode heterologous coding regions, e.g. specialized elements or motifs, such as a secretory signal peptide or a functional domain.

The terms "fragment," "variant," "derivative" and "analog" when referring to HCMV polypeptides of the present invention include any polypeptides which retain at least some of the immunogenicity or antigenicity of the corresponding native polypeptide. Fragments of HCMV polypeptides of the present invention include proteolytic fragments, deletion fragments and in particular, fragments of HCMV polypeptides which exhibit increased secretion from the cell or higher immunogenicity when delivered to an animal. Polypeptide fragments further include any portion of the polypeptide which comprises an antigenic or immunogenic epitope of the native polypeptide, including linear as well as three-dimensional epitopes. Variants of HCMV polypeptides of the present invention includes fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome or genome of an organism or virus. *Genes II*, Lewin, B., ed., John Wiley & Sons, New York (1985), which is incorporated herein by reference. For example, as used herein, variations in a given gene product, e.g., pp65, between HCMV strains, e.g. Towne and AD169, would be considered "allelic variants." Non-naturally occurring variants may be produced using art-known mutagenesis techniques. Variant polypeptides may comprise conservative or non-conservative amino acid substitutions, deletions or additions. Derivatives of HCMV polypeptides of the present invention, are polypeptides which have been altered so as to exhibit additional features not found on the native polypeptide. Examples include fusion proteins. An analog is another form of an HCMV polypeptide of the present invention. An example is a proprotein which can be activated by cleavage of the proprotein to produce an active mature polypeptide.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., *Gene Therapy* 4:1341-1349 (1997)) comprising a polynucleotide. A nucleic acid may be provided in linear (e.g., mRNA), circular (e.g., plasmid), or branched form as well as double-stranded or single-stranded forms. A polynucleotide may comprise a conventional phosphodiester bond or a non-conventional bond (e.g., an amide bond, such as found in peptide nucleic acids (PNA)).

The terms "infectious polynucleotide" or "infectious nucleic acid" are intended to encompass isolated viral polynucleotides and/or nucleic acids which are solely sufficient to mediate the synthesis of complete infectious virus particles upon uptake by permissive cells. "Isolated" means that the viral nucleic acid does not require pre-synthesized copies of any of the polypeptides it encodes, e.g., viral replicases, in order to initiate its replication cycle.

The terms "non-infectious polynucleotide" or "non-infectious nucleic acid" as defined herein are polynucleotides or nucleic acids which cannot, without additional added materials, e.g., polypeptides, mediate the synthesis of complete infectious virus particles upon uptake by permissive cells. An infectious polynucleotide or nucleic acid is not made "non-infectious" simply because it is taken up by a non-permissive cell. For example, an infectious viral polynucleotide from a virus with limited host range is infectious if it is capable of mediating the synthesis of complete infectious virus particles when taken up by cells derived from a permissive host (i.e., a host permissive for the virus itself). The fact that uptake by cells derived from a non-permissive host does not result in the synthesis of complete infectious virus particles does not make the nucleic acid "non-infectious." In other words, the term is not qualified by the nature of the host cell, the tissue type, or the species.

In some cases, an isolated infectious polynucleotide or nucleic acid may produce fully-infectious virus particles in a host cell population which lacks receptors for the virus particles, i.e., is non-permissive for virus entry. Thus viruses produced will not infect surrounding cells. However, if the supernatant containing the virus particles is transferred to cells which are permissive for the virus, infection will take place.

The terms "replicating polynucleotide" or "replicating nucleic acid" are meant to encompass those polynucleotides and/or nucleic acids which, upon being taken up by a permissive host cell, are capable of producing multiple, e.g., one or more copies of the same polynucleotide or nucleic acid. Infectious polynucleotides and nucleic acids are a subset of replicating polynucleotides and nucleic acids; the terms are not synonymous. For example, a defective virus genome lacking the genes for virus coat proteins may replicate, e.g., produce multiple copies of itself, but is NOT infectious because it is incapable of mediating the synthesis of complete infectious virus particles unless the coat proteins, or another nucleic acid encoding the coat proteins, are exogenously provided.

In certain embodiments, the polynucleotide, nucleic acid, or nucleic acid fragment is DNA. In the case of DNA, a polynucleotide comprising a nucleic acid which encodes a polypeptide normally also comprises a promoter operably associated with the polypeptide-encoding nucleic acid. An operable association is when a nucleic acid encoding a gene product, e.g., a polypeptide, is associated with one or more regulatory sequences in such a way as to place expression of the gene product under the influence or control of the regulatory sequence(s). Two DNA fragments (such as a polypeptide-encoding nucleic acid and a promoter associated with the 5' end of the nucleic acid) are "operably associated" if induction of promoter function results in the transcription of mRNA encoding the desired gene product and if the nature of the linkage between the two DNA fragments does not (1) result in the introduction of a frame-shift mutation, (2) interfere with the ability of the expression regulatory sequences to direct the expression of the gene product, or (3) interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), retroviruses (such as Rous sarcoma virus), and picornaviruses (particularly an internal ribosome entry site, or IRES, also referred to as a CITE sequence). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

In one embodiment, a DNA polynucleotide of the present invention is a circular or linearized plasmid, or other linear DNA which is, in certain embodiments, non-infectious and nonintegrating (i.e., does not integrate into the genome of vertebrate cells). A linearized plasmid is a plasmid that was previously circular but has been linearized, for example, by digestion with a restriction endonuclease.

Alternatively, DNA virus genomes may be used to administer DNA polynucleotides into vertebrate cells. In certain embodiments, a DNA virus genome of the present invention is noninfectious, and nonintegrating. Suitable DNA virus genomes include herpesvirus genomes, adenovirus genomes, adeno-associated virus genomes, and poxvirus genomes. References citing methods for the in vivo introduction of non-infectious virus genomes to vertebrate tissues are well known to those of ordinary skill in the art, and are cited supra.

In other embodiments, a polynucleotide of the present invention is RNA. In a suitable embodiment, the RNA is in the form of messenger RNA (mRNA). Methods for introducing RNA sequences into vertebrate cells are described in U.S. Pat. No. 5,580,859, the disclosure of which is incorporated herein by reference in its entirety.

Polynucleotide, nucleic acids, and nucleic acid fragments of the present invention may be associated with additional nucleic acids which encode secretory or signal peptides, which direct the secretion of a polypeptide encoded by a nucleic acid or polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native leader sequence is used, or a functional derivative of that sequence that retains the ability to direct the secretion of the polypeptide that is operably associated with it. Alternatively, a heterologous mammalian leader sequence, or a functional derivative thereof, may be used. For example, the wild-type leader sequence may be substituted with the leader sequence of human tissue plasminogen activator (TPA) or mouse β-glucuronidase.

In accordance with one aspect of the present invention, there is provided a plasmid for expression of an HCMV gB-derived or pp65-derived coding sequence optimized for expression in human cells, to be delivered to a human to be treated or immunized. Additional HCMV-derived coding sequences, e.g. coding for IE1, may also be included on the plasmid, or on a separate plasmid, and expressed, either using native codons or codons optimized for expression in humans to be treated or immunized. When such a plasmid encoding one or more optimized HCMV sequences is delivered, in vivo to a tissue of the human to be treated or immunized, the transcriptional unit will thus express the one or more encoded gene product(s). The level of expression of the gene product(s) will depend to a significant extent on the strength of the associated promoter and the presence and activation of an associated enhancer element, as well as the optimization of the coding region.

As used herein, the term "plasmid" refers to a construct made up of genetic material (i.e., nucleic acids). Typically a plasmid contains an origin of replication which is functional in bacterial host cells, e.g., *Eschericha coli*, and selectable markers for detecting bacterial host cells comprising the plasmid. Plasmids of the present invention may include genetic elements as described herein arranged such that an inserted coding sequence can be transcribed and translated in eukaryotic cells. Also, while the plasmid may include a sequence from a viral nucleic acid, such viral sequence normally does not cause the incorporation of the plasmid into a viral particle, and the plasmid is therefore a non-viral vector. In certain embodiments described herein, a plasmid is a closed circular DNA molecule.

The term "expression" refers to the biological production of a product encoded by a coding sequence. In most cases a DNA sequence, including the coding sequence, is transcribed to form a messenger-RNA (mRNA). The messenger-RNA is translated to form a polypeptide product which has a relevant biological activity. Also, the process of expression may involve further processing steps to the RNA product of transcription, such as splicing to remove introns, and/or post-translational processing of a polypeptide product.

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" may be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

Also included as polypeptides of the present invention are fragments, derivatives, analogs, or variants of the foregoing polypeptides, and any combination thereof. Polypeptides, and fragments, derivatives, analogs, or variants thereof of the present invention can be antigenic and immunogenic polypeptides related to HCMV polypeptides, which are used to prevent or treat, i.e., cure, ameliorate, lessen the severity of, or prevent or reduce contagion of infectious disease caused by HCMV.

As used herein, an antigenic polypeptide or an immunogenic polypeptide is a polypeptide which, when introduced into a human, reacts with the human's immune system molecules, i.e., is antigenic, and/or induces an immune response in the human, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides of the present invention include, but are not limited to, HCMV pp65 or fragments or variants thereof, e.g. pp65-delArg435-Lys468; gB, or fragments thereof, e.g. consisting of amino acids 1-713, or variants thereof; and IE1 or fragments or variants thereof, e.g. ex4-IE1-delATP and derivatives thereof, e.g., any of the foregoing polypeptides fused to a TPA signal peptide.

The term "epitopes," as used herein, refers to portions of a polypeptide having antigenic or immunogenic activity in an animal, for example a mammal, for example, a human. An "immunogenic epitope," as used herein, is defined as a portion of a protein that elicits an immune response in an animal, as determined by any method known in the art. The term "antigenic epitope," as used herein, is defined as a portion of a protein to which an antibody can immunospecifically bind its antigen as determined by any method well known in the art. Immunospecific binding excludes non-specific binding but does not necessarily exclude cross-reactivity with other antigens. Antigenic epitopes need not necessarily be immunogenic.

In the present invention, antigenic epitopes preferably contain a sequence of at least 4, at least 5, at least 6, at least 7, at least 8, at least 9, at least 10, at least 15, at least 20, at least 25, or between about 15 to about 30 amino acids contained within the amino acid sequence of a polypeptide of the invention. Certain polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic as well as immunogenic epitopes may be linear, i.e., be comprised of contiguous amino acids in a polypeptide, or may be three dimensional, i.e., where an epitope is comprised of non-contiguous amino acids which come together due to the secondary or tertiary structure of the polypeptide, thereby forming an epitope.

As to the selection of peptides or polypeptides bearing an antigenic epitope (e.g., that contain a region of a protein molecule to which an antibody or T cell receptor can bind), it is well known in that art that relatively short synthetic peptides that mimic part of a protein sequence are routinely capable of eliciting an antiserum that reacts with the partially mimicked protein. See, e.g., Sutcliffe, J. G., et al., *Science* 219:660-666 (1983).

Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins. Non-limiting examples of antigenic polypeptides or peptides for HCMV pp65, gB and IE1 epitopes known to elicit cellular or humoral immune responses are listed in Table 1.

TABLE 1

Epitopes for immune recognition for HCMV proteins pp65, gB, and IE1. All of the references herein are incorporated by reference in its entirety.

| HCMV polypeptide | Position | Reference |
| --- | --- | --- |
| gB | aa 178-194<br>aa 190-204<br>aa 250-264<br>aa 420-434 | Liu, YN. et al. *J. Gen. Virol.* 74: 2207-14 (1993) |
| gB | aa 67-86<br>aa 549-635<br>aa 570-579<br>aa 606-619 | Ohlin, M. et al. *J. Virol.* 67: 703-10 (1993). |
| gB | aa 548-618 | Navarro, D. et al. *J. Med. Virol.* 52: 451-9 (1997) |

TABLE 1-continued

Epitopes for immune recognition for HCMV proteins pp65, gB, and IE1. All of the references herein are incorporated by reference in its entirety.

| HCMV polypeptide | Position | Reference |
| --- | --- | --- |
| pp65 | aa 361-376<br>aa 485-499 | Khattab BA. et al. *J. Med. Virol.* 52: 68-76 (1997) |
| pp65 | aa 495-503 | Diamond, DJ. et al. *Blood* 90: 1751067 (1997) |
| pp65 | aa 14-22<br>aa 120-128<br>aa 495-503 | Solache, A. et al. *J. Immunol.* 163: 5512-8 (1999) |
| IE1 (UL123) | aa 199-207<br>aa 279-287<br>aa 309-317<br>aa 315-323<br>aa 378-389<br>aa 379-387 | Khan, N. et al. *J. Inf. Dis.* 185: 000-000 (2002);<br>Elkington, R. et al. *J. Virol.* 77(9): 5226-5240 (2003). |
| IE1 Class II | aa 91-110<br>aa 162-175<br>aa 96-115 | Davignon, J. et al. *J. Virol.* 70: 2162-2169 (1996);<br>Gautier, N. et al. *Eur. J. Immunol.* 26(5): 1110-7 (1996). |

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g. about 9 amino acids) can bind and displace the larger peptides in immunoprecipitation assays. See, for instance, Wilson, et al., *Cell* 37:767-778 (1984) at 777. The anti-peptide antibodies of the invention also are useful for purification of the mimicked protein, for instance, by adsorption chromatography using methods well known in the art.

In certain embodiments, the present invention is directed to polynucleotides comprising nucleic acids and fragments thereof comprising codon-optimized coding regions which encode polypeptides of HCMV, and in particular, HCMV gB or pp65, and fragments, variants, or derivatives thereof, alone or in combination with additional codon-optimized or non-codon-optimized HCMV-derived coding sequences, for example IE1 (SEQ ID NO:19).

"Codon optimization" is defined as modifying a nucleic acid sequence for enhanced expression in the cells of the vertebrate of interest, e.g. human, by replacing at least one, more than one, or a significant number, of codons of the native sequence with codons that are more frequently or most frequently used in the genes of that vertebrate. Various species exhibit particular bias for certain codons of a particular amino acid.

The present invention relates to polynucleotides comprising nucleic acid fragments of codon-optimized coding regions which encode HCMV polypeptides, or fragments, variants, or derivatives thereof, with the codon usage adapted for optimized expression in human cells. These polynucleotides are prepared by incorporating codons preferred for use in human genes into the DNA sequence. Also provided are polynucleotide expression constructs, vectors, and host cells comprising nucleic acid fragments of codon-optimized coding regions which encode HCMV polypeptides, and fragments, variants, or derivatives thereof, and various methods of using the polynucleotide expression constructs, vectors, host cells to treat or prevent HCMV disease in a human.

Polynucleotides comprising nucleic acid fragments of codon-optimized coding regions which encode polypeptides from nonhuman cytomegaloviruses, or fragments, variants, or derivatives thereof, may be optimized for expression in the cells of the vertebrate that can be infected by the nonhuman cytomegalovirus using the methods described herein. A partial list of known vertebrate cytomegaloviruses include murine CMV (MCMV), hamster CMV, guinea pig CMV, rat CMV, rabbit CMV, porcine CMV, bovine CMV, equine CMV, rhesus macaque CMV, African green monkey CMV, and chimpanzee CMV, as well as others (Staczek, J., *Am. Soc. Microbiol*. 545:247-265 (1990)). For example, an MCMV gene would be optimized for expressing in mouse cells, and an equine CMV gene would be optimized for expression in horse cells.

Codon Optimization

As used herein the term "codon-optimized coding region" means a nucleic acid coding region that has been adapted for expression in the cells of a given vertebrate by replacing at least one, or more than one, or a significant number, of codons with one or more codons that are more frequently used in the genes of that vertebrate.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 2

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at www_kazusa_orjp/codon/ (visited Jul. 9, 2002), and these tables can be adapted in a number of ways. See Nakamura, Y., et al. "Codon usage tabulated from the international DNA sequence databases: status for the year 2000" *Nucl. Acids Res*. 28:292 (2000). The codon usage table for human, calculated from GenBank Release 128.0 [15 Feb. 2002], is reproduced below as Table 3. These tables use mRNA nomenclature, and so instead of thymine (T) which is found in DNA, the tables use uracil (U) which is found in RNA. The tables have been adapted so that frequencies are calculated for each amino acid, rather than for all 64 codons. For comparison, the codon usage table for human cytomegalovirus is reproduced below as Table 4.

TABLE 3

Codon Usage Table for Human Genes (*Homo sapiens*)

| Amino Acid | Codon | Number | Frequency |
|---|---|---|---|
| Phe | UUU | 326146 | 0.4525 |
| Phe | UUC | 394680 | 0.5475 |
| Total | | 720826 | |
| Leu | UUA | 139249 | 0.0728 |
| Leu | UUG | 242151 | 0.1266 |
| Leu | CUU | 246206 | 0.1287 |
| Leu | CUC | 374262 | 0.1956 |
| Leu | CUA | 133980 | 0.0700 |
| Leu | CUG | 777077 | 0.4062 |
| Total | | 1912925 | |
| Ile | AUU | 303721 | 0.3554 |
| Ile | AUC | 414483 | 0.4850 |
| Ile | AUA | 136399 | 0.1596 |
| Total | | 854603 | |
| Met | AUG | 430946 | 1.0000 |
| Total | | 430946 | |
| Val | GUU | 210423 | 0.1773 |
| Val | GUC | 282445 | 0.2380 |
| Val | GUA | 134991 | 0.1137 |
| Val | GUG | 559044 | 0.4710 |
| Total | | 1186903 | |
| Ser | UCU | 282407 | 0.1840 |
| Ser | UCC | 336349 | 0.2191 |
| Ser | UCA | 225963 | 0.1472 |
| Ser | UCG | 86761 | 0.0565 |
| Ser | AGU | 230047 | 0.1499 |
| Ser | AGC | 373362 | 0.2433 |
| Total | | 1534889 | |
| Pro | CCU | 333705 | 0.2834 |
| Pro | CCC | 386462 | 0.3281 |

TABLE 3-continued

Codon Usage Table for Human Genes (*Homo sapiens*)

| Amino Acid | Codon | Number | Frequency |
|---|---|---|---|
| Pro | CCA | 322220 | 0.2736 |
| Pro | CCG | 135317 | 0.1149 |
| Total | | 1177704 | |
| Thr | ACU | 247913 | 0.2419 |
| Thr | ACC | 371420 | 0.3624 |
| Thr | ACA | 285655 | 0.2787 |
| Thr | ACG | 120022 | 0.1171 |
| Total | | 1025010 | |
| Ala | GCU | 360146 | 0.2637 |
| Ala | GCC | 551452 | 0.4037 |
| Ala | GCA | 308034 | 0.2255 |
| Ala | GCG | 146233 | 0.1071 |
| Total | | 1365865 | |
| Tyr | UAU | 232240 | 0.4347 |
| Tyr | UAC | 301978 | 0.5653 |
| Total | | 534218 | |
| His | CAU | 201389 | 0.4113 |
| His | CAC | 288200 | 0.5887 |
| Total | | 489589 | |
| Gln | CAA | 227742 | 0.2541 |
| Gln | CAG | 668391 | 0.7459 |
| Total | | 896133 | |
| Asn | AAU | 322271 | 0.4614 |
| Asn | AAC | 376210 | 0.5386 |
| Total | | 698481 | |
| Lys | AAA | 462660 | 0.4212 |
| Lys | AAG | 635755 | 0.5788 |
| Total | | 1098415 | |
| Asp | GAU | 430744 | 0.4613 |
| Asp | GAC | 502940 | 0.5387 |
| Total | | 933684 | |
| Glu | GAA | 561277 | 0.4161 |
| Glu | GAG | 787712 | 0.5839 |
| Total | | 1348989 | |
| Cys | UGU | 190962 | 0.4468 |
| Cys | UGC | 236400 | 0.5532 |
| Total | | 427362 | |
| Trp | UGG | 248083 | 1.0000 |
| Total | | 248083 | |
| Arg | CGU | 90899 | 0.0830 |
| Arg | CGC | 210931 | 0.1927 |
| Arg | CGA | 122555 | 0.1120 |
| Arg | CGG | 228970 | 0.2092 |
| Arg | AGA | 221221 | 0.2021 |
| Arg | AGG | 220119 | 0.2011 |
| Total | | 1094695 | |
| Gly | GGU | 209450 | 0.1632 |
| Gly | GGC | 441320 | 0.3438 |
| Gly | GGA | 315726 | 0.2459 |
| Gly | GGG | 317263 | 0.2471 |
| Total | | 1283759 | |
| Stop | UAA | 13963 | |
| Stop | UAG | 10631 | |
| Stop | UGA | 24607 | |

TABLE 4

Codon Usage Table for Human Cytomegalovirus (human herpesvirus 5)

| Amino Acid | Codon | Number | Frequency |
|---|---|---|---|
| Phe | UUU | 5435 | 0.5456 |
| Phe | UUC | 4527 | 0.4544 |
| Total | | 9962 | |
| Leu | UUA | 1191 | 0.0510 |
| Leu | UUG | 3683 | 0.1578 |
| Leu | CUU | 2162 | 0.0926 |
| Leu | CUC | 5473 | 0.2344 |
| Leu | CUA | 1771 | 0.0759 |
| Leu | CUG | 9066 | 0.3883 |
| Total | | 23346 | |
| Ile | AUU | 2452 | 0.2538 |
| Ile | AUC | 6135 | 0.6350 |
| Ile | AUA | 1075 | 0.1113 |
| Total | | 9662 | |
| Met | AUG | 5051 | 1.0000 |
| Total | | 430946 | |
| Val | GUU | 2271 | 0.1167 |
| Val | GUC | 5082 | 0.2611 |
| Val | GUA | 2570 | 0.1320 |
| Val | GUG | 9541 | 0.4902 |
| Total | | 19464 | |
| Ser | UCU | 2350 | 0.1234 |
| Ser | UCC | 3911 | 0.2054 |
| Ser | UCA | 1296 | 0.0681 |
| Ser | UCG | 4876 | 0.2561 |
| Ser | AGU | 1927 | 0.1012 |
| Ser | AGC | 4677 | 0.2457 |
| Total | | 19037 | |
| Pro | CCU | 1817 | 0.1439 |
| Pro | CCC | 4425 | 0.3506 |
| Pro | CCA | 1391 | 0.1102 |
| Pro | CCG | 4990 | 0.3953 |
| Total | | 12623 | |
| Thr | ACU | 2156 | 0.1368 |
| Thr | ACC | 5648 | 0.3584 |
| Thr | ACA | 1782 | 0.1131 |
| Thr | ACG | 6173 | 0.3917 |
| Total | | 15759 | |
| Ala | GCU | 2559 | 0.1491 |
| Ala | GCC | 8013 | 0.4668 |
| Ala | GCA | 1386 | 0.0807 |
| Ala | GCG | 5209 | 0.3034 |
| Total | | 17167 | |
| Tyr | UAU | 2321 | 0.2629 |
| Tyr | UAC | 6509 | 0.7371 |
| Total | | 8830 | |
| His | CAU | 1906 | 0.2753 |
| His | CAC | 5018 | 0.7247 |
| Total | | 6924 | |
| Gln | CAA | 2894 | 0.3398 |
| Gln | CAG | 5623 | 0.6602 |
| Total | | 8517 | |
| Asn | AAU | 2268 | 0.2892 |
| Asn | AAC | 5574 | 0.7108 |
| Total | | 7842 | |
| Lys | AAA | 3313 | 0.4408 |
| Lys | AAG | 4203 | 0.5592 |
| Total | | 7516 | |
| Asp | GAU | 3514 | 0.3023 |
| Asp | GAC | 8110 | 0.6977 |
| Total | | 11624 | |

TABLE 4-continued

Codon Usage Table for Human Cytomegalovirus
(human herpesvirus 5)

| Amino Acid | Codon | Number | Frequency |
|---|---|---|---|
| Glu | GAA | 4310 | 0.3684 |
| Glu | GAG | 7390 | 0.6316 |
| Total | | 11700 | |
| Cys | UGU | 3059 | 0.4265 |
| Cys | UGC | 4113 | 0.5735 |
| Total | | 7172 | |
| Trp | UGG | 2797 | 1.0000 |
| Total | | 2797 | |
| Arg | CGU | 3747 | 0.2186 |
| Arg | CGC | 6349 | 0.3703 |
| Arg | CGA | 1826 | 0.1065 |
| Arg | CGG | 3285 | 0.1916 |
| Arg | AGA | 1185 | 0.0691 |
| Arg | AGG | 752 | 0.0439 |
| Total | | 17144 | |
| Gly | GGU | 3521 | 0.2430 |
| Gly | GGC | 6952 | 0.4797 |
| Gly | GGA | 1885 | 0.1301 |
| Gly | GGG | 2133 | 0.1472 |
| Total | | 14491 | |
| Stop | UAA | 310 | |
| Stop | UAG | 69 | |
| Stop | UGA | 234 | |

By utilizing these or similar tables, one of ordinary skill in the art can apply the frequencies to any given polypeptide sequence, and produce a nucleic acid fragment of a codon-optimized coding region which encodes the polypeptide, but which uses codons more optimal for a given species. Codon-optimized coding regions can be designed by various different methods.

In one method, termed "uniform optimization," a codon usage table is used to find the single most frequent codon used for any given amino acid, and that codon is used each time that particular amino acid appears in the polypeptide sequence. For example, referring to Table 3 above, for leucine, the most frequent codon is CUG, which is used 41% of the time. Thus all the leucine residues in a given amino acid sequence would be assigned the codon CUG. Human "uniform" codon-optimized nucleotide sequences encoding native pp65 from HCMV strain AD169 (SEQ ID NO:2)) (FIG. 1) and full-length gB from strain AD169 (SEQ ID NO:12) (FIG. 4) are presented herein as SEQ ID NO:7 and SEQ ID NO:15, respectively.

In another method, termed "full-optimization," the actual frequencies of the codons are distributed randomly throughout the coding region. Thus, using this method for optimization, if a hypothetical polypeptide sequence had 100 leucine residues, referring to Table 3 for frequency of usage in the humans, about 7, or 7% of the leucine codons would be UUA, about 13, or 13% of the leucine codons would be UUG, about 13, or 13% of the leucine codons would be CUU, about 20, or 20% of the leucine codons would be CUC, about 7, or 7% of the leucine codons would be CUA, and about 41, or 41% of the leucine codons would be CUG. These frequencies would be distributed randomly throughout the leucine codons in the coding region encoding the hypothetical polypeptide. As will be understood by those of ordinary skill in the art, the distribution of codons in the sequence can vary significantly using this method, however, the sequence always encodes the same polypeptide. Three different human codon-optimized nucleotide sequences encoding native pp65 (SEQ ID NO:2) which have been optimized using this method are presented herein as SEQ ID NO:8, SEQ ID NO:9, and SEQ ID NO:10. Three different human codon-optimized sequences encoding native gB (SEQ ID NO:12) which have been fully optimized using this method are presented herein as SEQ ID NO:16, SEQ ID NO:17 and SEQ ID NO:18, respectively.

In using the "full-optimization" method, an entire polypeptide sequence, or fragment, variant, or derivative thereof is codon-optimized by any of the methods described herein. Various desired fragments, variants or derivatives are designed, and each is then codon-optimized individually. Alternatively, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon-optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

When using the "full-optimization" method, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

In a third method termed "minimal optimization," coding regions are only partially optimized. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a vertebrate species, e.g., humans, in place of a codon that is normally used in the native nucleic acid sequence. Codons that are rarely found in human genes are changed to codons more commonly utilized in human coding regions. To illustrate this method, a comparative chart showing codon usage per thousand of human and HCMV coding regions is presented in Table 5. The data is expressed as the number of times a given codon is used per 1000 codons. For instance, the asterisked codons in Table 5 for alanine, arginine, proline, serine, and threonine are frequently used in the genome of HCMV, but less frequently used in human genes. Starting with the native coding region of the HCMV gene of interest, one or more codons which are infrequently-used may be changed to more commonly-used human codons either by substituting one of the codons more frequently used in human genes. According to this method, these HCMV codons which are used at the same or higher frequency in human genes as compared to HCMV genes are left unchanged.

TABLE 5

Codon Usage Table for Human Genes and HCMV

| Amino Acid | | Codon | Human | hCMV |
|---|---|---|---|---|
| Ala | A | GCA | 16 | 6 |
| * | | GCG | 8 | 22 |
| | | GCC | 19 | 34 |
| | | GCT | 19 | 11 |
| Arg | R | AGA | 12 | 5 |
| | | AGG | 11 | 3 |
| | | CGA | 6 | 8 |
| | | CGG | 12 | 14 |
| | | CGC | 11 | 27 |
| * | | CGT | 5 | 16 |
| Asn | N | AAC | 20 | 24 |
| | | AAT | 17 | 10 |
| Asp | D | GAC | 26 | 34 |
| | | GAT | 22 | 15 |
| Cys | C | TGC | 12 | 17 |
| | | TGT | 10 | 13 |
| Gln | Q | CAA | 12 | 12 |
| | | CAG | 35 | 24 |
| Glu | E | GAA | 30 | 18 |
| | | GAG | 40 | 31 |
| Gly | G | GGA | 16 | 8 |
| | | GGG | 16 | 9 |
| | | GGC | 23 | 29 |
| | | GGT | 11 | 15 |
| His | H | CAC | 15 | 21 |
| | | CAT | 11 | 8 |
| Ile | I | ATA | 7 | 5 |
| | | ATC | 22 | 26 |
| | | ATT | 16 | 10 |
| Leu | L | CTA | 7 | 8 |
| | | CTG | 40 | 38 |
| | | CTC | 20 | 23 |
| | | CTT | 13 | 9 |
| | | TTA | 7 | 5 |
| | | TTG | 13 | 16 |
| Lys | K | AAA | 24 | 14 |
| | | AAG | 33 | 18 |
| Met | M | ATG | 22 | 21 |
| Phe | F | TTC | 21 | 19 |
| | | TTT | 17 | 23 |
| Pro | P | CCA | 17 | 6 |
| * | | CCG | 7 | 21 |
| | | CCC | 20 | 19 |
| | | CCT | 17 | 8 |
| Ser | S | AGC | 19 | 20 |
| | | AGT | 12 | 8 |
| | | TCA | 12 | 6 |
| * | | TCG | 5 | 21 |
| | | TCC | 18 | 17 |
| | | TCT | 15 | 10 |
| Thr | T | ACA | 15 | 8 |
| * | | ACG | 6 | 26 |
| | | ACC | 19 | 24 |
| | | ACT | 13 | 9 |
| Trp | W | TGG | 13 | 12 |
| Tyr | Y | TAC | 16 | 27 |
| | | TAT | 12 | 10 |
| Val | V | GTA | 7 | 11 |
| | | GTG | 29 | 40 |
| | | GTC | 15 | 21 |
| | | GTT | 11 | 10 |

TABLE 5-continued

Codon Usage Table for Human Genes and HCMV

| Amino Acid | Codon | Human | hCMV |
|---|---|---|---|
| Term | TAA | 1 | 1 |
| | TAG | 0.5 | 0 |
| | TGA | 1 | 1 |

Thus, those codons which are used more frequently in the HCMV genome than in human genes are substituted with the most frequently-used human codon. The difference in frequency at which the HCMV codons are substituted may vary based on a number factors as discussed below. For example, codons used at least twice more per thousand in HCMV genes as compared to human genes are substituted with the most frequently used human codon for that amino acid. This ratio may be adjusted higher or lower depending on various factors such as those discussed below. Accordingly, a codon in an HCMV native coding region would be substituted with the codon used most frequently for that amino acid in human coding regions if the codon is used 1.1 times, 1.2 times, 1.3 times, 1.4 times, 1.5 times, 1.6 times, 1.7 times, 1.8 times, 1.9 times, 2.0 times, 2.1 times, 2.2 times, 2.3 times, 2.4 times, 2.5 times, 2.6 times, 2.7 times, 2.8 times, 2.9 times, 3.0 times, 3.1 times, 3.2 times, 3.3, times, 3.4 times, 3.5 times, 3.6 times, 3.7 times, 3.8 times, 3.9 times, 4.0 times, 4.1 times, 4.2 times, 4.3 times, 4.4 times, 4.5 times, 4.6 times, 4.7 times, 4.8 times, 4.9 times, 5.0 times, 5.5 times, 6.0 times, 6.5 times, 7.0 times, 7.5 times, 8.0 times, 8.5 times, 9.0 times, 9.5 times, 10.0 times, 10.5 times, 11.0 times, 11.5 times, 12.0 times, 12.5 times, 13.0 times, 13.5 times, 14.0 times, 14.5 times, 15.0 times, 15.5 times, 16.0 times, 16.5 times, 17.0 times, 17.5 times, 18.0 times, 18.5 times, 19.0 times, 19.5 times, 20 times, 21 times, 22 times, 23 times, 24 times, 25 times, or greater more frequently in HCMV coding regions than in human coding regions.

This minimal human codon optimization for highly variant codons has several advantages, which include but are not limited to the following examples. Since fewer changes are made to the nucleotide sequence of the gene of interest, fewer manipulations are required, which leads to reduced risk of introducing unwanted mutations and lower cost, as well as allowing the use of commercially available site-directed mutagenesis kits, reducing the need for expensive oligonucleotide synthesis. Further, decreasing the number of changes in the nucleotide sequence decreases the potential of altering the secondary structure of the sequence, which can have a significant impact on gene expression in certain host cells. The introduction of undesirable restriction sites is also reduced, facilitating the subcloning of the genes of interest into the plasmid expression vector.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNT1 Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences. For example, the "backtranslation" function is proved on the world wide web by Entelechon GMBH at www_entelechon_com/eng/backtranslation_html (visited Jul. 9, 2002), "backtranseq" function available at bioinfo.p-bi.nrc.ca:—8090/EMBOSS/index.html (visited Oct. 15, 2002). Constructing a rudimentary algorithm to assign codons based on a given frequency can also easily be accomplished with basic mathematical functions by one of ordinary skill in the art.

A number of options are available for synthesizing codon-optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

The codon-optimized coding regions can be versions encoding any gene products from any strain of HCMV, or fragments, variants, or derivatives of such gene products. Described herein are nucleic acid fragments of codon-optimized coding regions encoding the HCMV pp65 polypeptide and the HCMV glycoprotein B (gB) polypeptide, the nucleic acid fragments encoding the complete polypeptide, as well as various fragments, variants, and derivatives thereof, although other pp65 or gB-encoding nucleic acid sources are not excluded. Codon-optimized coding regions encoding other HCMV polypeptides (e.g. IE1), or fragments, variants and derivatives thereof, are included within the present invention. Additional, non-codon-optimized polynucleotides encoding HCMV polypeptides may be included as well.

The present invention is directed to compositions and methods of enhancing the immune response of a human in need of protection against HCMV infection by administering in vivo, into a tissue of a human, a polynucleotide comprising a codon-optimized coding region encoding a polypeptide of HCMV, or a nucleic acid fragment of such a coding region encoding a fragment, variant or derivative thereof. Human-codon optimization is carried out by the methods described herein, for example, in certain embodiments codon-optimized coding regions encoding polypeptides of HCMV, or nucleic acid fragments of such coding regions encoding fragments, variants, or derivatives thereof are optimized according to human codon usage. The polynucleotides of the invention are incorporated into the cells of the human in vivo, and an immunologically effective amount of an HCMV polypeptide is produced in vivo.

In particular, the present invention relates to codon-optimized coding regions encoding polypeptides of HCMV, or nucleic acid fragments of such coding regions fragments, variants, or derivatives thereof which have been optimized according to human codon usage. For example, human codon-optimized coding regions encoding polypeptides of HCMV, or nucleic acid fragments of such coding regions encoding fragments, variants, or derivatives thereof are prepared by substituting one or more codons preferred for use in human genes for the codons naturally used in the DNA sequence encoding the HCMV polypeptide. Also provided are polynucleotides, vectors, and other expression constructs comprising codon-optimized coding regions encoding polypeptides of HCMV, or nucleic acid fragments of such coding regions encoding fragments, variants, or derivatives thereof, and various methods of using such polynucleotides, vectors and other expression constructs. Coding regions encoding HCMV polypeptides may be uniformly optimized, fully optimized, or minimally optimized, as described herein.

The present invention is further directed towards polynucleotides comprising codon-optimized coding regions encoding polypeptides of HCMV antigens, for example, HCMV pp65, gB, and optionally in conjunction with other HCMV antigens, e.g. IE1. The invention is also directed to polynucleotides comprising codon-optimized nucleic acid fragments encoding fragments, variants and derivatives of these polypeptides.

The present invention provides isolated polynucleotides comprising codon-optimized coding regions of HCMV pp65, or fragments, variants, or derivatives thereof. In certain embodiments described herein, a codon-optimized coding region encoding SEQ ID NO:2 is optimized according to codon usage in humans (*Homo sapiens*).

Codon-optimized coding regions encoding SEQ ID NO:2, fully optimized according to codon usage in humans are designed as follows. The amino acid composition of SEQ ID NO:2 is shown in Table 6.

TABLE 6

Amino Acid Composition of Wild-Type HCMV pp65 from strain AD169 (SEQ ID NO: 2).

| Amino Acid | | Number in SEQ ID NO: 2 |
|---|---|---|
| A | Ala | 38 |
| R | Arg | 36 |
| C | Cys | 10 |
| G | Gly | 36 |
| H | His | 24 |
| I | Ile | 25 |
| L | Leu | 41 |
| K | Lys | 22 |
| M | Met | 16 |
| F | Phe | 19 |
| P | Pro | 38 |
| S | Ser | 41 |
| T | Thr | 37 |
| W | Trp | 9 |
| Y | Tyr | 15 |
| V | Val | 44 |
| N | Asn | 18 |
| D | Asp | 28 |
| Q | Gln | 31 |
| E | Glu | 33 |

Using the amino acid composition shown in Table 6, and the human codon usage table shown in Table 3, a human codon-optimized coding region which encodes SEQ ID NO:2 can be designed by any of the methods discussed herein.

In the "uniform optimization" approach, each amino acid is assigned the most frequent codon used in the human genome for that amino acid as indicated on Table 3. According to this method, codons are assigned to the coding region encoding SEQ ID NO:2 as follows: the 19 phenylalanine codons are TTC, the 41 leucine codons are CTG, the 25 isoleucine codons are ATC, the 16 methionine codons are ATG, the 44 valine codons are GTG, the 41 serine codons are AGC, the 38 proline codons are CCC, the 37 threonine codons are ACC, the 38 alanine codons are GCC, the 15 tyrosine codons are TAC, the 24 histidine codons are CAC, the 31 glutamine codons are CAG, the 18 asparagine codons are AAC, the 22 lysine codons are AAG, the 28 aspartic acid codons are GAC, the 33 glutamic acid codons are GAG, the 10 cysteine codons are TGC, the 9 tryptophan codons are TGG, the 36 arginine codons are CGG, AGA, or AGG (the frequencies of usage of these three codons in the human genome are not significantly different), and the 36 glycine codons are GGC. The codon-optimized pp65 coding region designed by this method is presented herein as SEQ ID NO:7.

Alternatively, a "fully codon-optimized" coding region which encodes SEQ ID NO:2 can be designed by randomly assigning each of any given amino acid a codon based on the frequency that codon is used in the human genome. These frequencies are shown in Table 3 above. Using this latter method, codons are assigned to the coding region encoding SEQ ID NO:2 as follows: about 9 of the 19 phenylalanine codons are TTT, and about 10 of the phenylalanine codons are TTC; about 3 of the 41 leucine codons are TTA, about 5 of the leucine codons are TTG, about 5 of the leucine codons are CTT, about 8 of the leucine codons are CTC, about 3 of the leucine codons are CTA, and about 17 of the leucine codons are CTG; about 9 of the 25 isoleucine codons are ATT, about 12 of the isoleucine codons are ATC, and about 4 of the isoleucine codons are ATA; the 16 methionine codons are ATG; about 8 of the 44 valine codons are GTT, about 10 of the valine codons are GTC, about 5 of the valine codons are GTA, and about 21 of the valine codons are GTG; about 8 of the 41 serine codons are TCT, about 9 of the serine codons are TCC, about 6 of the serine codons are TCA, about 2 of the serine codons are TCG, about 6 of the serine codons are AGT, and about 10 of the serine codons are AGC; about 11 of the 38 proline codons are CCT, about 12 of the proline codons are CCC, about 10 of the proline codons are CCA, and about 4 of the proline codons are CCG; about 9 of the 37 threonine codons are ACT, about 13 of the threonine codons are ACC, about 11 of the threonine codons are ACA, and about 4 of the threonine codons are ACG; about 10 of the 38 alanine codons are GCT, about 15 of the alanine codons are GCC, about 9 of the alanine codons are GCA, and about 4 of the alanine codons are GCG; about 7 of the 15 tyrosine codons are TAT and about 8 of the tyrosine codons are TAC; about 10 of the 24 histidine codons are CAT and about 14 of the histidine codons are CAC; about 8 of the 31 glutamine codons are CAA and about 23 of the glutamine codons are CAG; about 8 of the 18 asparagine codons are AAT and about 10 of the asparagine codons are AAC; about 9 of the 22 lysine codons are AAA and about 13 of the lysine codons are AAG; about 13 of the 28 aspartic acid codons are GAT and about 15 of the aspartic acid codons are GAC; about 14 of the 33 glutamic acid codons are GAA and about 19 of the glutamic acid codons are GAG; about 4 of the 10 cysteine codons are TGU and about 6 of the cysteine codons are TGC; the 9 tryptophan codons are TGG; about 3 of the 36 arginine codons are CGT, about 7 of the arginine codons are CGC, about 4 of the arginine codons are CGA, about 8 of the arginine codons are CGG, about 7 of the arginine codons are AGA, and about 7 of the arginine codons are AGG; and about 6 of the 36 glycine codons are GGT, about 12 of the glycine codons are GGC, about 9 of the glycine codons are GGA, and about 9 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

Representative fully-codon-optimized pp65 coding regions designed by this method are presented herein as SEQ ID NOs:8-10.

Additionally, a minimally codon-optimized nucleotide sequence encoding SEQ ID NO:2 can be designed by changing only certain codons found more frequently in HCMV genes than in human genes, as shown in Table 5. For example, if it is desired to substitute more frequently used codons in humans for those codons that occur at least 2.7 times more frequently in HCMV genes, Ala CGC, which occurs 2.75 times more frequently in HCMV genes than in human genes, is changed to, e.g., GCC; Pro CCG, which occurs 3.0 times more frequently in HCMV genes than is human, is changed to, e.g., CCC; Arg CGT, which occurs 3.2 times more frequently in HCMV genes than is human, is changed to, e.g., CGC; Ser TCG, which occurs 4.2 times more frequently in HCMV genes than in human, is changed to, e.g., TCC; and Thr ACG, which occurs 4.3 times more frequently in HCMV genes than is human, is changed to, e.g., ACC. The minimally codon-optimized pp65 coding region designed by this method encoding native HCMV pp65 is presented herein as SEQ ID NO:3. Other methods of "minimal" optimization can be carried out by methods well known to those of ordinary skill in the art.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NO:2, where the nucleic acid fragment is a fragment of a codon-optimized coding region encoding SEQ ID NO:2. The human codon-optimized coding region can be optimized by any of the methods described herein.

In certain embodiments, the present invention provides an isolated polynucleotide comprising a nucleic acid fragment which encodes a polypeptide at least 60%, 65%, 70%, 75%, 80%, 85%, 86%, 87%, 88%, 89%, 90%, 91%, 92%, 93%, 94%, 95%, 96%, 97%, 98%, or 99% identical to SEQ ID NO:2, and where the nucleic acid fragment is a variant of a human codon-optimized coding region encoding SEQ ID NO:2. The human codon-optimized coding region can be optimized by any of the methods described herein.

Further provided is an isolated polynucleotide comprising a minimally codon-optimized nucleic acid (SEQ ID NO:5) which encodes a polypeptide variant of pp65, i.e., SEQ ID NO:6, in which amino acids 435-438 of SEQ ID NO:2 have been deleted. This deletion in the amino acid sequence of pp65 removes putative adventitious substrates for kinase activity present in the amino acid sequence. A human codon-optimized coding region encoding this variant can be optimized by any of the methods described herein. Alternatively amino acids 435-438 could be substituted with different amino acids, or an insertion could be made to remove the motif. Additional fragments, variants, or derivatives of SEQ ID NO:2 may be utilized as well.

The present invention further provides isolated polynucleotides comprising human codon-optimized coding regions of HCMV gB, or fragments, variants, or derivatives thereof. In certain embodiments described herein, a human codon-optimized coding region encoding SEQ ID NO:12 is optimized according to codon usage in humans (*Homo sapiens*). The human codon-optimized coding region can be optimized by any of the methods described herein.

Codon-optimized coding regions encoding SEQ ID NO:12, optimized according to codon usage in humans are designed as follows. The amino acid composition of SEQ ID NO:12 is shown in Table 7, and the amino acid composition of truncated, secreted gB (SEQ ID NO:14) is shown in Table 8.

TABLE 7

Amino Acid Composition of wild typo HCMV gB (SEQ ID NO: 12)

| Amino Acid | | Number in SEQ ID NO: 12 |
|---|---|---|
| A | Ala | 62 |
| R | Arg | 53 |
| C | Cys | 16 |
| G | Gly | 46 |
| H | His | 20 |
| I | Ile | 48 |
| L | Leu | 70 |
| K | Lys | 39 |
| M | Met | 17 |
| F | Phe | 34 |
| P | Pro | 30 |
| S | Ser | 87 |
| T | Thr | 71 |
| W | Trp | 8 |
| Y | Tyr | 51 |
| V | Val | 71 |
| N | Asn | 52 |
| D | Asp | 45 |
| Q | Gln | 37 |
| E | Glu | 49 |

TABLE 8

Amino Acid Composition of secreted HCMV gB, amino acids 1-713 (SEQ ID NO: 14)

| Amino Acid | | Number in SEQ ID NO: 14 |
|---|---|---|
| A | Ala | 41 |
| R | Arg | 43 |
| C | Cys | 15 |
| G | Gly | 27 |
| H | His | 18 |
| I | Ile | 41 |
| L | Leu | 51 |
| K | Lys | 31 |
| M | Met | 15 |
| F | Phe | 30 |
| P | Pro | 19 |
| S | Ser | 73 |
| T | Thr | 56 |
| W | Trp | 8 |
| Y | Tyr | 43 |
| V | Val | 57 |
| N | Asn | 44 |
| D | Asp | 35 |
| Q | Gln | 25 |
| E | Glu | 41 |

Using the amino acid composition shown in Table 7 and the human codon usage, table shown in Table 3, a human codon-optimized coding region which encodes SEQ ID NO:12 can be designed by any of the methods discussed herein. In the "uniform optimization" approach, each amino acid is assigned the most frequent codon used in the human genome for that amino acid as indicated, e.g., in Table 3. According to this method, codons are assigned to the coding region encoding SEQ ID NO:12 as follows: the 34 phenylalanine codons are TTC, the 70 leucine codons are CTG, the 48 isoleucine codons are ATC, the 17 methionine codons are ATG, the 71 valine codons are GTG, the 87 serine codons are AGC, the 30 proline codons are CCC, the 71 threonine codons are ACC, the 62 alanine codons are GCC, the 51 tyrosine codons are TAC, the 20 histidine codons are CAC, the 37 glutamine codons are CAG, the 52 asparagine codons are AAC, the 39 lysine codons are AAG, the 45 aspartic acid codons are GAC, the 49 glutamic acid codons are GAG, the 16 cysteine codons are TGC, the 8 tryptophan codons are TGG, the 53 arginine codons are CGG, AGA, or AGG (the frequencies of usage of these three codons in the human genome are not significantly different), and the 46 glycine codons are GGC. The codon-optimized full-length gB coding region designed by this method is presented herein as SEQ ID NO:15.

Alternatively, a "fully codon-optimized" coding region which encodes SEQ ID NO:12 can be designed by randomly assigning each of any given amino acid a codon based on the frequency that codon is used in the human genome. These frequencies are shown in Table 3 above. Using this latter method, codons are assigned to the coding region encoding SEQ ID NO:12 as follows: about 15 of the 34 phenylalanine codons are TTT and about 19 of the phenylalanine codons are TTC; about 5 of the 70 leucine codons are TTA, about 9 of the leucine codons are TTG, about 9 of the leucine codons are CTT, about 10 of the leucine codons are CTC, about 5 of the leucine codons are CTA, and about 28 of the leucine codons are CTG; about 17 of the 48 soleucine codons are ATT, about 23 of the isoleucine codons are ATC, and about 8 of the isoleucine codons are ATA; the 17 methionine codons are ATG; about 13 of the 71 valine codons are GTT, about 17 of the valine codons are GTC, about 8 of the valine codons are GTA, and about 33 of the valine codons are GTG; about 16 of the 87 serine codons are TCT, about 19 of the serine codons are TCC, about 13 of the serine codons are TCA, about 5 of the serine codons are TCG, about 13 of the serine codons are AGT, and about 21 of the serine codons are AGC; about 9 of the 30 proline codons are CCT, about 10 of the proline codons are CCC, about 8 of the proline codons are CCA, and about 3 of the proline codons are CCG; about 17 of the 71 threonine codons are ACT, about 26 of the threonine codons are ACC, about 20 of the threonine codons are ACA, and about 8 of the threonine codons are ACG; about 16 of the 62 alanine codons are GCT, about 25 of the alanine codons are GCC, about 14 of the alanine codons are GCA, and about 7 of the alanine codons are GCG; about 22 of the 51 tyrosine codons are TAT and about 29 of the tyrosine codons are TAC; about 8 of the 20 histidine codons are CAT and about 12 of the histidine codons are CAC; about 9 of the 37 glutamine codons are CAA and about 28 of the glutamine codons are CAG; about 24 of the 52 asparagine codons are AAT and about 28 of the asparagine codons are AAC; about 16 of the 39 lysine codons are AAA and about 23 of the lysine codons are AAG; about 21 of the 45 aspartic acid codons are GAT and about 24 of the aspartic acid codons are GAC; about 20 of the 49 glutamic acid codons are GAA and about 29 of the glutamic acid codons are GAG; about 7 of the 16 cysteine codons are TGT and about 9 of the cysteine codons are TGC; the 8 tryptophan codons are TOG; about 4 of the 53 arginine codons are CGT, about 10 of the arginine codons are CGC, about 6 of the arginine codons are CGA, about 11 of the arginine codons are CGG, about 11 of the arginine codons are AGA, and about 11 of the arginine codons are AGG; and about 7 of the 46 glycine codons are GGT, about 16 of the glycine codons are GGC, about 12 of the glycine codons are GGA, and about 11 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid. Representative fully codon-optimized gB coding regions designed by this method encoding full-length HCMV gB are presented herein as SEQ ID NOs:16-18.

Additionally, a minimally codon-optimized nucleotide sequence encoding SEQ ID NO:14 can be designed by referring to the amino acid composition of Table 8 and changing only certain codons found more frequently in highly expressing human genes, as shown in Table 5. For example, if it is desired to substitute more frequently used codons in humans for those codons that occur at least 2.7 times more frequently in HCMV genes, Ala CGC, which occurs 2.75 times more frequently in HCMV genes than in human genes, is changed to, e.g., GCC; Pro CCG, which occurs 3.0 times more frequently in HCMV genes than is human, is changed to, e.g., CCC; Arg CGT, which occurs 3.2 times more frequently in HCMV genes than is human, is changed to, e.g., CGC; Ser TCG, which occurs 4.2 times more frequently in HCMV genes than in human, is changed to, e.g., TCC; and Thr ACG, which occurs 4.3 times more frequently in HCMV genes than is human, is changed to, e.g., ACC. The minimally codon-optimized secreted gB coding region encoding SEQ ID NO:14 designed by this method is presented herein as SEQ ID NO:13.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NO:12 or SEQ ID NO:14, where the nucleic acid fragment is a fragment of a human codon-optimized coding region encoding SEQ ID NO:12 or SEQ ID NO:14. The human codon-optimized coding region can be optimized by any of the methods described herein.

In certain embodiments, the present invention provides an isolated polynucleotide comprising a nucleic acid which encodes a polypeptide at least 60%, 65%, 70%, 75%, 80%, 85%, 86%, 87%, 88%, 89%, 90%, 91%, 92%, 93%, 94%, 95%, 96%, 97%, 98%, or 99% identical to gB, i.e., SEQ ID NO:12 or SEQ ID NO:14, and where the nucleic acid is a variant of a codon-optimized coding region encoding SEQ ID NO:12 or SEQ ID NO:14. The human codon-optimized coding region can be optimized by any of the methods described herein.

In this manner, the present invention provides a method of enhancing the level of polypeptide expression from delivered polynucleotides in vivo and/or facilitating uptake of the polynucleotides by the cells of a desired species, for example a vertebrate species, for example a mammalian species, for example humans. Accordingly, the present invention provides a method of treatment and prevention against HCMV infection.

Methods and Administration

The present invention further provides methods for delivering an HCMV polypeptide to a human, which comprise administering to a human one or more of the compositions described herein; such that upon administration of compositions such as those described herein, an HCMV polypeptide is expressed in human cells, in an amount sufficient generate an immune response to HCMV.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equines such as horses, donkeys, and zebras, food animals such as cows, pigs, and sheep; ungulates such as deer and giraffes; and ursids such as bears. In particular, the mammal can be a human subject, a food animal or a companion animal.

The present invention further provides a method for generating, enhancing or modulating an immune response to HCMV comprising administering to a vertebrate one or more of the compositions described herein. In this method, the composition includes an isolated polynucleotide comprising a human codon-optimized coding region encoding a polypeptide of HCMV, or a nucleic acid fragment of such a coding region encoding a fragment, variant, or derivative thereof. The polynucleotides are incorporated into the cells of the vertebrate in vivo, and an antigenic amount of the HCMVs polypeptide, or fragment, variant, or derivative thereof, is produced in vivo. Upon administration of the composition according to this method, the HCMV polypeptide is expressed in the vertebrate in an amount sufficient to elicit an immune response. Such an immune response might be used, for example, to generate antibodies to HCMV for use in diagnostic assays or as laboratory reagents.

The present invention further provides a method for generating, enhancing, or modulating a protective and/or therapeutic immune response to HCMV in a human, comprising administering to a human in need of therapeutic and/or preventative immunity one or more of the compositions described herein. In this method, the composition includes an isolated polynucleotide comprising a human codon-optimized coding region encoding a polypeptide of HCMV, or a nucleic acid fragment of such a coding region encoding a fragment, variant, or derivative thereof. The polynucleotides are incorporated into the cells of the human in vivo, and an immunologically effective amount of the HCMV polypeptide, or fragment or variant is produced in vivo. Upon administration of the composition according to this method, the HCMV polypeptide is expressed in the human in a therapeutically or prophylactically effective amount.

As used herein, an "immune response" refers to the ability of a vertebrate to elicit an immune reaction to a composition delivered to that vertebrate. Examples of immune responses include an antibody response or a cellular, e.g., cytotoxic T-cell, response. One or more compositions of the present invention may be used to prevent HCMV infection in humans, e.g., as a prophylactic vaccine, to establish or enhance immunity to HCMV in a healthy individual prior to exposure to HCMV or contraction of HCMV disease, thus preventing the disease or reducing the severity of disease symptoms.

One or more compositions of the present invention may also be used to treat individuals already exposed to HCMV, or already suffering from HCMV disease to further stimulate the immune system of the human, thus reducing or eliminating the symptoms associated with that disease or disorder. As defined herein, "treatment" refers to the use of one or more compositions of the present invention to prevent, cure, retard, or reduce the severity of HCMV disease symptoms in a human, and/or result in no worsening of HCMV disease over a specified period of time. It is not required that any composition of the present invention provide total immunity to HCMV or totally cure or eliminate all HCMV disease symptoms. As used herein, a "human in need of therapeutic and/or preventative immunity" refers to an individual for whom it is desirable to treat, i.e., to prevent, cure, retard, or reduce the severity of HCMV disease symptoms, and/or result in no worsening of HCMV disease over a specified period of time.

In other embodiments, one or more compositions of the present invention are utilized in a "prime boost" regimen. An example of a "prime boost" regimen may be found in Yang; Z. et al. *J. Virol.* 77:799-803 (2002). In these embodiments, one or more polynucleotide vaccine compositions of the present invention are delivered to a human, thereby priming the immune response of the human to HCMV, and then a second immunogenic composition is utilized as a boost vaccination. One or more polynucleotide vaccine compositions of the present invention are used to prime immunity, and then a second immunogenic composition, e.g., a recombinant viral vaccine or vaccines, a different polynucleotide vaccine, one or more purified subunit HCMV proteins, e.g., gB or pp65, with or without additional HCMV antigens, e.g. IE1, or a variant, fragment, or derivative thereof, is used to boost the anti-HCMV immune response. The polynucleotide vaccine compositions may comprise one or more vectors for expression of one or more HCMV genes as described herein. In addition, a polynucleotide prime vaccine and the later boost vaccine may elicit an immune response to the same or similar antigens, or may elicit responses to different antigens.

In another embodiment, vectors are prepared for expression in the recombinant virus vaccine and in transfected mammalian cells as part of a polynucleotide vaccine.

The terms "priming" or "primary" and "boost" or "boosting" are used herein to refer to the initial and subsequent immunizations, respectively, i.e., in accordance with the definitions these terms normally have in immunology.

The invention further provides methods for enhancing the immune response of a human patient to HCMV by administering to the tissues of a human one or more polynucleotides comprising one or more codon-optimized coding regions encoding polypeptides of HCMV, and also HCMV polypeptides or fragments, variants or derivatives thereof; or one or more non-optimized polynucleotides encoding HCMV polypeptides, fragments, variants or derivatives thereof.

The combination of HCMV polypeptides or polynucleotides encoding HCMV polypeptides or fragments, variants or derivatives thereof, with the codon-optimized nucleic acid compositions provides for therapeutically beneficial effects at dose sparing concentrations. For example, immunological responses sufficient for a therapeutically beneficial effect may be attained by using less of a conventional-type vaccine (that is a vaccine comprising immunogenic polypeptides or nucleotides encoding immunogenic polypeptides, fragments, variants, or derivatives thereof, that are not products of, or have not been codon-optimized as described herein) when supplemented or enhanced with the appropriate amount of a codon-optimized nucleic acid.

Conventional-type vaccines, include vaccine compositions comprising either dead, inert or fragments of a virus or bacteria, or bacterial or viral proteins or protein fragments, injected into the patient to elicit action by the immune system. With regard to the present invention, conventional-type vaccines include compositions comprising immunogenic polypeptides or nucleotides encoding immunogenic polypeptides, fragments, variants, or derivatives thereof, and vectors comprising nucleotides encoding immunogenic polypeptides, fragments, variants, or derivatives thereof, that are not products of, or do not contain codon-optimized polynucleotides as described herein. Thus, genetically engineered vaccines, are included in conventional-type vaccines, such as genetically engineered live vaccines, live chimeric vaccines, live replication-defective vaccines, subunit vaccines, peptide vaccines in various modifications of monovalent, multivalent, or chimeric subunit vaccines delivered as individual components or incorporated into virus-like particles for improved immunogenicity, and polynucleotide vaccines. Auxiliary agents, as described herein, are also considered components of conventional-type vaccines.

Thus, dose sparing is contemplated by administration of the combinatorial polynucleotide-vaccine compositions of the present invention.

In particular, the dose of conventional-type vaccines may be reduced by at least 5%, at least 10%, at least 20%, at least 30%, at least 40%, at least 50%, at least 60% or at least 70% when administered in combination with the codon-optimized nucleic acid compositions of the invention.

Similarly, a desirable level of an immunological response afforded by a DNA based pharmaceutical alone may be attained with less DNA by including a conventional-type DNA vaccine. Further, using a combination of a conventional-type vaccine and a codon-optimized DNA-based vaccine may allow both materials to be used in lesser amounts while still affording the desired level of immune response arising from administration of either component alone in higher amounts (e.g. one may use less of either immunological product when they are used in combination). This reduction in amounts of materials being delivered may be for each administration, in addition to reducing the number of administrations, in a vaccination regimen (e.g. 2 versus 3 or 4 injections). Further, the combination may also provide for reducing the kinetics of the immunological response (e.g. desired response levels are attained in 3 weeks instead of 6 after immunization).

In particular, the dose of DNA based pharmaceuticals, may be reduced by at least 5%, at least 10%, at least 20%, at least 30%, at least 40%, at least 50%, at least 60% or at least 70% when administered in combination with conventional IV vaccines.

Determining the precise amounts of DNA based pharmaceutical and a conventional antigen is based on a number of factors as described herein, and is readily determined by one of ordinary skill in the art.

In addition to dose sparing, the claimed combinatorial compositions provide for a broadening of the immune response and/or enhanced beneficial immune responses. Such broadened or enhanced immune responses are achieved by: adding DNA to enhance cellular responses to a conventional-type vaccine; adding a conventional-type vaccine to a DNA pharmaceutical to enhanced humoral response; using a combination that induces additional epitopes (both humoral and/or cellular) to be recognized and/or more desirably responded to (epitope broadening); employing a DNA-conventional vaccine combination designed for a particular desired spectrum of immunological responses; obtaining a desirable spectrum by using higher amounts of either component. The broadened immune response is measurable by one of ordinary skill in the art by standard immunological assay specific for the desirable response spectrum.

Both broadening and dose sparing may be obtained simultaneously.

In certain embodiments, one or more compositions of the present invention are delivered to a human by methods described herein, thereby achieving an effective therapeutic and/or an effective preventative immune response.

More specifically, the compositions of the present invention may be administered to any tissue of a human, including, but not limited to, muscle, skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage.

Furthermore, the compositions of the present invention may be administered to any internal cavity of a human, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, the ocular cavities, the lumen of a duct of a salivary gland or a liver. When the compositions of the present invention is administered to the lumen of a duct of a salivary gland or liver, the desired polypeptide is expressed in the salivary gland and the liver such that the polypeptide is delivered into the blood stream of the human from each of the salivary gland or the liver. Certain modes for administration to secretory organs of a gastrointestinal system using the salivary gland, liver and pancreas to release a desired polypeptide into the bloodstream is disclosed in U.S. Pat. Nos. 5,837,693 and 6,004,944, both of which are incorporated herein by reference in their entireties.

In one embodiment, the compositions are administered to muscle, either skeletal muscle or cardiac muscle, or to lung tissue. Specific, but non-limiting modes for administration to lung tissue are disclosed in Wheeler, C. J., et al., *Proc. Natl. Acad. Sci. USA* 93:11454-11459 (1996), which is incorporated herein by reference in its entirety.

According to the disclosed methods, compositions of the present invention can be administered by intramuscular (i.m.), subcutaneous (s.c.), or intrapulmonary routes. Other suitable routes of administration include, but not limited to intratracheal, transdermal, intraocular, intranasal, inhalation, intracavity, intravenous (i.v.), intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal; nasal, peritoneal, or intestinal cavities as well as, intrathecal (i.e., into spinal canal), intraventricular (i.e., into the brain ventricles or the heart ventricles), intraatrial (i.e., into the heart atrium) and sub arachnoid (i.e., into the sub arachnoid spaces of the brain) administration.

Any mode of administration can be used so long as the mode results in the expression of the desired peptide or protein, in the desired tissue, in an amount sufficient to generate an immune response to HCMV and/or to generate a prophylactically or therapeutically effective immune response to HCMV in a human in need of such response. Administration means of the present invention include needle injection, catheter infusion, biolistic injectors, particle accelerators (e.g., "gene guns" or pneumatic "needleless" injectors) Med-E-Jet (Vahlsing, H., et al., *J. Immunol. Methods* 171:11-22 (1994)), Pigjet (Schrijver, R., et al., *Vaccine* 15: 1908-1916 (1997)), Biojector (Davis, H., et al., *Vaccine* 12: 1503-1509 (1994); Gramzinski, R., et al., *Mol. Med*. 4: 109-118 (1998)), Advantajet (Linmayer, I., et al., *Diabetes Care* 9:294-297 (1986)), Medi-jector (Martins, J., and Roedl, E. J. *Occup. Med.* 21:821-824 (1979)), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, Y., et al., *Life Sciences* 65: 2193-2203 (1999)) or topical applications during surgery. Certain modes of administration are intramuscular needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir, L. M. et al., *Proc. Natl. Acad. Sci USA* 96:4262-7 (1999); Hartikka, J. et al., *Mol. Ther*. 4:407-15 (2001); Mathiesen, I., *Gene Ther*. 6:508-14 (1999); Rizzuto G. et al., *Hum. Gen. Ther*. 11:1891-900 (2000). Each of the references cited in this paragraph is incorporated herein by reference in its entirety.

Further, antigen constructs alone or in combination may be formulated to enhance the type of immune response (e.g. humoral, cellular, mucosal, etc.) believed to be most beneficial to mount in the host for that particular antigen or antigens. Each such formulation may be administered individually at a separate site in the host, and/or combined and administered with some or all of the other antigen formulations at one or more sites in the host. Each administration may be accomplished using the same or different physical means of administration. Thus, as a non-limiting example, a gB plasmid could be formulated with cationic lipids and administered as a mist intranasaly, in conjunction with administration of a poloxamer formulation of pp65 using a needle free device into skin and muscle of one limb, in conjunction with transdermal intramuscular administration using a conventional syringe and needle of an IE1 plasmid in PBS into a second limb.

Determining an effective amount of one or more compositions of the present invention depends upon a number of factors including, for example, the antigen being expressed, e.g. gB, pp65 or IE1; or fragments, variants, or derivatives thereof, the age and weight of the subject, the precise condition requiring treatment and its severity, and the route of administration. Based on the above factors, determining the precise amount, number of doses, and timing of doses are within the ordinary skill in the art and will be readily determined by the attending physician.

Compositions of the present invention may include various salts, excipients, delivery vehicles and/or auxiliary agents as are disclosed, e.g., in U.S. Patent Application Publication 2002/0019358, published Feb. 14, 2002, which is incorporated herein by reference in its entirety.

Furthermore, compositions of the present invention may include one or more transfection facilitating compounds that facilitate delivery of polynucleotides to the interior of a cell, and/or to a desired location within a cell. As used herein, the terms "transfection facilitating compound," "transfection facilitating agent," and "transfection facilitating material" are synonymous, and may be used interchangeably. It should be noted that certain transfection facilitating compounds may also be "adjuvants" as described infra, e.g., in addition to facilitating delivery of polynucleotides to the interior of a cell, the compound acts to alter or increase the immune response to the antigen encoded by that polynucleotide. Examples of the transfection facilitating compounds include, but are not limited to inorganic materials such as calcium phosphate, alum (aluminum sulfate), and gold particles (e.g., "powder" type delivery vehicles); peptides that are, for example, cationic, intercell targeting (for selective delivery to certain cell types), intracell targeting (for nuclear localization or endosomal escape), and ampipathic (helix forming or pore forming); proteins that are, for example, basic (e.g., positively charged) such as histones, targeting (e.g., asialoprotein), viral (e.g., Sendai virus coat protein), and pore-forming; lipids that are, for example, cationic (e.g., DMRIE, DOSPA, DC-Chol), basic (e.g., steryl amine), neutral (e.g., cholesterol), anionic (e.g., phosphatidyl serine), and zwitterionic (e.g., DOPE, DOPC); and polymers such as dendrimers, star-polymers, "homogenous" poly-amino acids (e.g., poly-lysine, poly-arginine), "heterogenous" poly amino acids (e.g., mixtures of lysine & glycine), co-polymers, polyvinylpyrrolidinone (PVP), poloxamers (e.g. CRL 1005) and polyethylene glycol (PEG). A transfection facilitating material can be used alone or in combination with one or more other transfection facilitating materials. Two or more transfection facilitating materials can be combined by chemical bonding (e.g., covalent and ionic such as in lipidated polylysine, PEGylated polylysine) (Toncheva, et al., *Biochim. Biophys. Acta* 1380(3):354-368 (1988)), mechanical mixing (e.g., free moving materials in liquid or solid phase such as "polylysine+cationic lipids") (Gao and Huang, *Biochemistry* 35:1027-1036 (1996); Trubetskoy, et al., *Biochim. Biophys. Acta* 1131:311-313 (1992)), and aggregation (e.g., co-precipitation, gel forming such as in cationic lipids+poly-lactide, and polylysine+gelatin).

One category of transfection facilitating materials is cationic lipids. Examples of cationic lipids are 5-carboxyspermylglycine dioctadecylamide (DOGS) and dipalmitoyl-phophatidylethanolamine-5-carboxyspermylamide (DPPES). Cationic cholesterol derivatives are also useful, including {3β-[N—N',N'-dimethylamino)ethane]-carbomoyl}-cholesterol(DC-Chol). Dimethyldioctadecyl-ammonium bromide (DDAB), N-(3-aminopropyl)-N,N-(bis-(2-tetradecyloxyethyl))-N-methyl-ammonium bromide (PA-DEMO), N-(3-aminopropyl)-N,N-(bis-(2-dodecyloxyethyl))-N-methyl-ammonium bromide (PA-DELO), N,N,N-tris-(2-dodecyloxy)ethyl-N-(3-amino) propyl-ammonium bromide (PA-TELO), and N1-(3-aminopropyl)((2-dodecyloxy)ethyl)-N2-(2-dodecyloxy) ethyl-1-piperazinaminium bromide (GA-LOE-BP) can also be employed in the present invention.

Non-diether cationic lipids, such as DL-1,2-dioleoyl-3-dimethylaminopropyl-β-hydroxyethylammonium (DORI diester), 1-O-oleyl-2-oleoyl-3-dimethylaminopropyl-β-hydroxyethylammonium (DORI ester/ether), and their salts promote in vivo gene delivery. In some embodiments, cationic lipids comprise groups attached via a heteroatom attached to the quaternary ammonium moiety in the head group. A glycyl spacer can connect the linker to the hydroxyl group.

Specific, but non-limiting cationic lipids for use in certain embodiments of the present invention include DMRIE ((±)-N-(2-hydroxyethyl)-N,N-dimethyl-2,3-bis(tetradecyloxy)-1-propanaminium bromide), GAP-DMORIE ((±)-N-(3-aminopropyl)-N,N-dimethyl-2,3-bis(syn-9-tetradeceneyloxy)-1-propanaminium bromide), and GAP-DLRIE ((±)-N-(3-aminopropyl)-N,N-dimethyl-2,3-(bis-dodecyloxy)-1-propanaminium bromide).

Other specific but non-limiting cationic surfactants for use in certain embodiments of the present invention include Bn-DHRIE, DhxRIE, DhxRIE-OAc, DhxRIE-OBz and Pr-DOctRIE-OAc. These lipids are disclosed in copending U.S. Patent Application Ser. No. 60/435,303. In another aspect of the present invention, the cationic surfactant is Pr-DOctRIE-OAc.

Other cationic lipids include (±)-N,N-dimethyl-N-[2-(sperminecarboxamido)ethyl]-2,3-bis(dioleyloxy)-1-propaniminium pentahydrochloride (DOSPA), (±)-N-(2-aminoethyl)-N,N-dimethyl-2,3-bis(tetradecyloxy)-1-propaniminium bromide(β-aminoethyl-DMRIE or RAE-DMRIE) (Wheeler, et al., *Biochim. Biophys. Acta* 1280:1-11 (1996)), and (±)-N-(3-aminopropyl)-N,N-dimethyl-2,3-bis (dodecyloxy)-1-propaniminium bromide (GAP-DLRIE) (Wheeler, et al., *Proc. Natl. Acad. Sci. USA* 93:11454-11459 (1996)), which have been developed from DMRIE.

Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(3-aminopropyl)-N,N-dimethyl-2,3-(bis-tetradecyloxy)-1-propanaminium bromide (GAP-DMRIE), (±)-N—((N"-methyl)-N'-ureyl)propyl-N,N-dimethyl-2,3-bis(tetradecyloxy)-1-propanaminium bromide (GMU-DMRIE), (±)-N-(2-hydroxyethyl)-N,N-dimethyl-2,3-bis(dodecyloxy)-1-propanaminium bromide (DLRIE), and (±)-N-(2-hydroxyethyl)-N,N-dimethyl-2,3-bis-([Z]-9-octadecenyloxy)propyl-1-propaniminium bromide (HP-DORIE).

In the embodiments where the immunogenic composition comprises a cationic lipid, the cationic lipid may be mixed with one or more co-lipids. For purposes of definition, the term Aco-lipid refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films. One non-limiting class of co-lipids are the zwitterionic phospholipids, which include the phosphatidylethanolamines and the phosphatidylcholines. Examples of phosphatidylethanolamines, include DOPE, DMPE and DPyPE. In certain embodiments, the co-lipid is DPyPE, which comprises two phytanoyl substituents incorporated into the diacylphosphatidylethanolamine skeleton. In other embodiments, the co-lipid is DOPE, CAS name 1,2-dioleyoyl-sn-glycero-3-phosphoethanolamine.

When a composition of the present invention comprises a cationic lipid and co-lipid, the cationic lipid:co-lipid molar ratio may be from about 9:1 to about 1:9, from about 4:1 to about 1:4, from about 2:1 to about 1:2, or about 1:1.

In order to maximize homogeneity, the plasmid and co-lipid components may be dissolved in a solvent such as chloroform, followed by evaporation of the cationic lipid/co-lipid solution under vacuum to dryness as a film on the inner surface of a glass vessel (e.g., a Rotovap round-bottomed flask). Upon suspension in an aqueous solvent, the amphipathic lipid component molecules self-assemble into homogenous lipid vesicles. These lipid vesicles may subsequently be processed to have a selected mean diameter of uniform size prior to complexing with, for example, a codon-optimized polynucleotide of the present invention, according to methods known to those skilled in the art. For example, the sonication of a lipid solution is described in Felgner et al., *Proc. Natl. Acad. Sci. USA* 8:7413-7417 (1987) and in U.S. Pat. No. 5,264,618, the disclosures of which are incorporated herein by reference.

In those embodiments where the composition includes a cationic lipid, polynucleotides of the present invention are complexed with lipids by mixing, for example, a plasmid in aqueous solution and a solution of cationic lipid:co-lipid as prepared herein are mixed. The concentration of each of the constituent solutions can be adjusted prior to mixing such that the desired final plasmid/cationic lipid:co-lipid ratio and the desired plasmid final concentration will be obtained upon mixing the two solutions. The cationic lipid:co-lipid mixtures are suitably prepared by hydrating a thin film of the mixed lipid materials in an appropriate volume of aqueous solvent by vortex mixing at ambient temperatures for about 1 minute. The thin films are prepared by admixing chloroform solutions of the individual components to afford a desired molar solute ratio followed by aliquoting the desired volume of the solutions into a suitable container. The solvent is removed by evaporation, first with a stream of dry, inert gas (e.g. argon) followed by high vacuum treatment.

Other hydrophobic and amphiphilic additives, such as, for example, sterols, fatty acids, gangliosides, glycolipids, lipopeptides, liposaccharides, neobees, niosomes, prostaglandins and sphingolipids, may also be included in compositions of the present invention. In such compositions, these additives may be included in an amount between about 0.1 mol % and about 99.9 mol % (relative to total lipid), about 1-50 mol %, or about 2-25 mol %.

Additional embodiments of the present invention are drawn to compositions comprising an auxiliary agent which is administered before, after, or concurrently with the polynucleotide. As used herein, an "auxiliary agent" is a substance included in a composition for its ability to enhance, relative to a composition which is identical except for the inclusion of the auxiliary agent, the entry of polynucleotides into vertebrate cells in vivo, and/or the in vivo expression of polypeptides encoded by such polynucleotides. Certain auxiliary agents may, in addition to enhancing entry of polynucleotides into cells, enhance an immune response to an immunogen encoded by the polynucleotide. Auxiliary agents of the present invention include nonionic, anionic, cationic, or zwitterionic surfactants or detergents; chelators, DNAse inhibitors, poloxamers, agents that aggregate or condense nucleic acids, emulsifying or solubilizing agents, wetting agents, gel-forming agents, and buffers.

Auxiliary agents for use in compositions of the present invention include, but are not limited to non-ionic detergents and surfactants IGEPAL CA 630® CA 630, NONIDET® NP-40, NONIDET® P40 (2-[2-[4-(2,4,4-trimethylpentan-2-yl)phenoxyl]ethoxyl]ethanol), TWEEN-20™ (2-[2-[3,4-bis (2-hydroxyethoxy)oxolan-2-yl]-2-(2-hydroxyethoxy) ethoxy]ethyl dodecanoate), TWEEN-80™, Pluronic® F68, Pluronic® F77, Pluronic® P65, Triton X-100™, and Triton X-114™; the anionic detergent sodium dodecyl sulfate (SDS); the sugar stachyose; the condensing agent DMSO; and the chelator/DNAse inhibitor EDTA, CRL 1005, and BAK. In certain specific embodiments, the auxiliary agent is DMSO, NONIDET® P40 (2-[2-[4-(2,4,4-trimethylpentan-2-yl)phenoxy]ethoxy]ethanol), Pluronic® F68, Pluronic® F77, Pluronic® P65, Pluronic® L64, and Pluronic® F108. See, e.g., U.S. Patent Application Publication 20020019358, published Feb. 14, 2002, which is incorporated herein by reference in its entirety.

Certain compositions of the present invention may further include one or more adjuvants before, after, or concurrently with the polynucleotide. The term "adjuvant" refers to any material having the ability to (1) alter or increase the immune response to a particular antigen or (2) increase or aid an effect of a pharmacological agent. It should be noted, with respect to polynucleotide vaccines, that an "adjuvant," may be a transfection facilitating material. Similarly, certain "transfection facilitating materials" described supra, may also be an "adjuvant." An adjuvant may be used with a composition comprising a polynucleotide of the present invention. In a prime-boost regimen, as described herein, an adjuvant may be used with either the priming immunization, the booster immunization, or both. Suitable adjuvants include, but are not limited to, cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, poloxamers, and cationic lipids.

A great variety of materials have been shown to have adjuvant activity through a variety of mechanisms. Any compound which may increase the expression, antigenicity or immunogenicity of the polypeptide is a potential adjuvant. The present invention provides an assay to screen for improved immune responses to potential adjuvants. Potential adjuvants which may be screened for their ability to enhance the immune response according to the present invention include, but are not limited to: inert carriers, such as alum, bentonite, latex, and acrylic particles; pluronic block polymers, such as TiterMax™; depot formers, such as Freunds adjuvant, surface active materials, such as saponin, lysolecithin, retinal, Quil A, liposomes, and pluronic polymer formulations; macrophage stimulators, such as bacterial lipopolysaccharide; alternate pathway complement activators; such as insulin, zymosan, endotoxin, and levamisole; and non-ionic surfactants, such as poloxamers, poly(oxyethylene)-poly(oxypropylene)tri-block copolymers. Also included as adjuvants are transfection-facilitating materials, such as those described above.

Poloxamers which may be screened for their ability to enhance the immune response according to the present invention include, but are not limited to commercially available poloxamers such as Pluronic® L121 (ave. MW: 4400; approx. MW of hydrophobe, 3600; approx. wt. % of hydrophile, 10%), Pluronic® L101 (ave. MW: 3800; approx. MW of hydrophobe, 3000; approx. wt. % of hydrophile, 10%), Pluronic® L81 (ave. MW: 2750; approx. MW of hydrophobe, 2400; approx. wt. % of hydrophile, 10%), Pluronic® L61 (ave. MW: 2000; approx. MW of hydrophobe, 1800; approx. wt. % of hydrophile, 10%), Pluronic® L31 (ave. MW: 1100; approx. MW of hydrophobe, 900; approx. wt. % of hydrophile, 10%), Pluronic® L122 (ave. MW: 5000; approx. MW of hydrophobe, 3600; approx. wt. % of hydrophile, 20%), Pluronic® L92 (ave. MW: 3650; approx. MW of hydrophobe, 2700; approx. wt. % of hydrophile; 20%), Pluronic® L72 (ave. MW: 2750; approx. MW of hydrophobe, 2100; approx. wt. % of hydrophile, 20%), Pluronic® L62 (ave. MW: 2500; approx. MW of hydrophobe, 1800; approx. wt. % of hydrophile, 20%), Pluronic® L42 (ave. MW: 1630; approx. MW of hydrophobe, 1200; approx. wt. % of hydrophile, 20%), Pluronic® L63 (ave. MW: 2650; approx. MW of hydrophobe, 1800; approx. wt. % of hydrophile, 30%), Pluronic® L43 (ave. MW: 1850; approx. MW of hydrophobe, 1200; approx. wt. % of hydrophile, 30%), Pluronic® L64 (ave. MW: 2900; approx. MW of hydrophobe, 1800; approx. wt. % of hydrophile, 40%), Pluronic® L44 (ave. MW: 2200; approx. MW of hydrophobe, 1200; approx. wt. % of hydrophile, 40%), Pluronic® L35 (ave. MW: 1900; approx. MW of hydrophobe, 900; approx. wt. % of hydrophile, 50%), Pluronic® P123 (ave. MW: 5750; approx. MW of hydrophobe, 3600; approx. wt. % of hydrophile, 30%), Pluronic® P103 (ave. MW: 4950; approx. MW of hydrophobe, 3000; approx. wt. % of hydrophile, 30%), Pluronic® P104 (ave. MW: 5900; approx. MW of hydrophobe, 3000; approx. wt. % of hydrophile, 40%), Pluronic® P84 (ave. MW: 4200; approx. MW of hydrophobe, 2400; approx. wt. % of hydrophile, 40%), Pluronic® P105 (ave. MW: 6500; approx. MW of hydrophobe, 3000; approx. wt. % of hydrophile, 50%), Pluronic® P85 (ave. MW: 4600; approx. MW of hydrophobe, 2400; approx. wt. % of hydrophile, 50%), Pluronic® P75 (ave. MW: 4150; approx. MW of hydrophobe, 2100; approx. wt. % of hydrophile, 50%), Pluronic® P65 (ave. MW: 3400; approx. MW of hydrophobe, 1800; approx. wt. % of hydrophile, 50%), Pluronic® F127 (ave. MW: 12600; approx. MW of hydrophobe, 3600; approx. wt. % of hydrophile, 70%), Pluronic® F98 (ave. MW: 13000; approx. MW of hydrophobe, 2700; approx. wt. % of hydrophile, 80%), Pluronic® F87 (ave. MW: 7700; approx. MW of hydrophobe, 0.2400; approx. wt. % of hydrophile, 70%), Pluronic® F77 (ave. MW: 6600; approx. MW of hydrophobe, 2100; approx. wt. % of hydrophile, 70%), Pluronic® F108 (ave. MW: 14600; approx. MW of hydrophobe, 3000; approx. wt. % of hydrophile, 80%), Pluronic® F98 (ave. MW: 13000; approx. MW of hydrophobe, 2700; approx. wt. % of hydrophile, 80%), Pluronic® F88 (ave. MW: 11400; approx. MW of hydrophobe, 2400; approx. wt. % of hydrophile, 80%), Pluronic® F68 (ave. MW: 8400; approx. MW of hydrophobe, 1800; approx. wt. % of hydrophile, 80%), Pluronic® F38 (ave. MW: 4700; approx. MW of hydrophobe, 900; approx. wt. % of hydrophile, 80%).

Reverse poloxamers of the present invention include, but are not limited to Pluronic® R 31R1 (ave. MW: 3250; approx. MW of hydrophobe, 3100; approx. wt. % of hydrophile, 10%), Pluronic® R 25R1 (ave. MW: 2700; approx. MW of hydrophobe, 2500; approx. wt. % of hydrophile, 10%), Pluronic® R 17R1 (ave. MW: 1900; approx. MW of hydrophobe, 1700; approx. wt. % of hydrophile, 10%), Pluronic® R 31R2 (ave. MW: 3300; approx. MW of hydrophobe, 3100; approx. wt: % of hydrophile, 20%), Pluronic® R 25R2 (ave. MW: 3100; approx. MW of hydrophobe, 2500; approx. wt. % of hydrophile, 20%), Pluronic® R 17R2 (ave. MW: 2150; approx. MW of hydrophobe, 1700; approx. wt. % of hydrophile, 20%), Pluronic® R 12R3 (ave. MW: 1800; approx. MW of hydrophobe, 1200; approx. wt. % of hydrophile, 30%), Pluronic® R 31R4 (ave. MW: 4150; approx. MW of hydrophobe, 3100; approx. wt. % of hydrophile, 40%), Pluronic® R 25R4 (ave. MW: 3600; approx. MW of hydrophobe, 2500; approx. wt. % of hydrophile, 40%), Pluronic® R 22R4 (ave. MW: 3350; approx. MW of hydrophobe, 2200; approx. wt. % of hydrophile, 40%), Pluronic® R 17R4 (ave. MW: 3650; approx. MW of hydrophobe, 1700; approx. wt. % of hydrophile, 40%), Pluronic® R 25R5 (ave. MW: 4320; approx. MW of hydrophobe, 2500; approx. wt. % of hydrophile, 50%), Pluronic® R 10R5 (ave. MW: 1950; approx. MW of hydrophobe, 1000; approx. wt. % of hydrophile, 50%), Pluronic® R 25R8 (ave. MW: 8550; approx. MW of hydrophobe, 2500; approx. wt. % of hydrophile, 80%), Pluronic® R 17R8 (ave. MW: 7000; approx. MW of hydrophobe, 1700; approx. wt. % of hydrophile, 80%), and Pluronic® R 10R8. (ave. MW: 4550; approx. MW of hydrophobe, 1000; approx. wt. % of hydrophile, 80%).

Other commercially available poloxamers which may be screened for their ability to enhance the immune response according to the present invention include compounds that are block copolymer of polyethylene and polypropylene glycol such as Synperonic® L121, Synperonic® L122, Synperonic® P104, Synperonic® P105, Synperonic® P123, Synperonic® P85 and Synperonic® P94; and compounds that are nonylphenyl polyethylene glycol such as Synperonic® NP10, Synperonic® NP30 and Synperonic® NP5.

Other poloxamers which may be screened for their ability to enhance the immune response according to the present invention include a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; (b) a block copolymer having a polyether segment and a polycation segment, wherein the polyether segment comprises at least an A-type block, and the polycation segment comprises a plurality of cationic repeating units; and (c) a polyether-polycation copolymer comprising a polymer, a polyether segment and a polycationic segment comprising a plurality of cationic repeating units of formula —NH—$R^0$, wherein $R^0$ is a straight chain aliphatic group of 2 to 6 carbon atoms, which may be substituted, wherein said polyether segments comprise at least one of an A-type of B-type segment. See U.S. Pat. No. 5,656,611, by Kabonov, et al., which is incorporated herein by reference in its entirety.

Other auxiliary agents which may be screened for their ability to enhance the immune response according to the present invention include, but are not limited to Acacia (gum arabic); the poloxyethylene ether R—O—$(C_2H_4O)_x$—H (BRIJ®), e.g., polyethylene glycol dodecyl ether (BRIJ® 35, x=23), polyethylene glycol dodecyl ether (BRIJ® 30, x=4), polyethylene glycol hexadecyl ether (BRIJ® 52 x=2), polyethylene glycol hexadecyl ether (BRIJ® 56, x=10), polyethylene glycol hexadecyl ether (BRIJ® 58P, x=20), polyethylene glycol octadecyl ether (BRIJ® 72, x=2), polyethylene glycol octadecyl ether (BRIJ® 76, x=10), polyethylene glycol octadecyl ether (BRIJ® 78P, x=20), polyethylene glycol oleyl ether (BRIJ® 92V, x=2), and polyoxyl 10 oleyl ether (BRIJ® 97, x=10); poly-D-glucosamine (chitosan); chlorbutanol; cholesterol; diethanolamine; digitonin; dimethylsulfoxide (DMSO), ethylenediamine tetraacetic acid (EDTA); glyceryl monosterate; lanolin alcohols; mono- and di-glycerides; monoethanolamine; nonylphenol polyoxyethylene ether (NP-40®); octylphenoxypolyethoxyethanol (NONIDET NP-40 from Amresco); ethyl phenol poly(ethylene glycol ether)", n=11 (Nonidet® P40 from Roche); octyl phenol ethylene oxide condensate with about 9 ethylene oxide units (nonidet P40); IGEPAL CA 630® ((octyl phenoxy)polyethoxyethanol; structurally same as NONIDET NP-40); oleic acid; oleyl alcohol; polyethylene glycol 8000; polyoxyl 20 cetostearyl ether; polyoxyl 35 castor oil; polyoxyl 40 hydrogenated castor oil; polyoxyl 40 stearate; polyoxyethylene sorbitan monolaurate (polysorbate 20, or TWEEN-20®); polyoxyethylene sorbitan monooleate (polysorbate 80, or TWEEN-80®); propylene glycol diacetate; propylene glycol monstearate; protamine sulfate; proteolytic enzymes; sodium dodecyl sulfate (SDS); sodium monolaurate; sodium stearate; sorbitan derivatives (SPAN®), e.g., sorbitan monopalmitate (SPAN® 40), sorbitan monostearate (SPAN® 60), sorbitan tristearate (SPAN® 65), sorbitan monooleate (SPAN® 80), and sorbitan trioleate (SPAN® 85); 2,6,10,15,19,23-hexamethyl-2,6,10,14,18,22-tetracosa-hexaene (squalene); stachyose; stearic acid; sucrose; surfactin (lipopeptide antibiotic from *Bacillus subtilis*); dodecylpoly(ethyleneglycolether)$_9$ (Thesit®) MW 582.9; octyl phenol ethylene oxide condensate with about 9-10 ethylene oxide units (Triton X-100™); octyl phenol ethylene oxide condensate with about 7-8 ethylene oxide units (Triton X-114™); tris(2-hydroxyethyl) amine (trolamine); and emulsifying wax.

In certain adjuvant compositions, the adjuvants are cytokines. A composition of the present invention can comprise one or more cytokines, chemokines, or compounds that induce the production of cytokines and chemokines, or a polynucleotide encoding one or more cytokines, chemokines, or compounds that induce the production of cytokines and chemokines. Examples include, but are not limited to granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNω), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), *Leishmania* elongation initiating factor (LEIF), and Flt-3 ligand.

In certain compositions of the present invention, the polynucleotide construct may be complexed with an adjuvant composition comprising (±)-N-(3-aminopropyl)-N,N-dimethyl-2,3-bis(syn-9-tetradeceneyloxy)-1-propanaminium bromide (GAP-DMORIE). The composition may also comprise one or more co-lipids, e.g., 1,2-dioleoyl-sn-glycero-3-phosphoethanolamine (DOPE), 1,2-diphytanoyl-sn-glycero-3-phosphoethanolamine (DPyPE), and/or 1,2-dimyristoyl-glycer-3-phosphoethanolamine (DMPE). An adjuvant composition comprising; GAP-DMORIE and DPyPE at a 1:1 molar ratio is referred to herein as Vaxfectin™. See, e.g., PCT Publication No. WO 00/57917, which is incorporated herein by reference in its entirety.

The ability of an adjuvant to increase the immune response to an antigen is typically manifested by a significant increase in immune-mediated protection. For example, an increase in humoral immunity is typically manifested by a significant increase in the titer of antibodies raised to the antigen, and an increase in T-cell activity is typically manifested in increased cell proliferation, increased cytokine production and/or antigen specific cytolytic activity. An adjuvant may also alter an immune response, for example, by changing a $Th_2$ response into a $Th_1$ response.

Nucleic acid molecules and/or polynucleotides of the present invention, e.g., pDNA, mRNA, linear DNA or oligonucleotides, may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a human.

Compositions of the present invention can be formulated according to known methods. Suitable preparation methods are described, for example, in *Remington's Pharmaceutical Sciences*, 16th Edition, A. Osol, ed., Mack Publishing Co., Easton, Pa. (1980), and *Remington's Pharmaceutical Sciences*, 19th Edition, A. R. Gennaro, ed., Mack Publishing Co., Easton, Pa. (1995), both of which are incorporated herein by reference in their entireties. Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives.

The following examples are included for purposes of illustration only and are not intended to limit the scope of the present invention, which is defined by the appended claims. All references cited in the Examples are incorporated herein by reference in their entireties.

EXAMPLES

Materials and Methods

The following materials and methods apply generally to all the examples disclosed herein. Specific materials and methods are disclosed in each example, as necessary.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, *Molecular Cloning A Laboratory Manual*, 2nd Ed., Sambrook et al., ed., Cold Spring Harbor Laboratory Press: (1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds: 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); and in Ausubel et al., *Current Protocols in Molecular Biology*, John Wiley and Sons, Baltimore, Md. (1989).

Gene Construction

Constructs of the present invention are constructed based on the sequence information provided herein or in the art utilizing standard molecular biology techniques, including, but not limited to the following. First, a series complementary oligonucleotide pairs of 80-90 nucleotides each in length and spanning the length of the construct are synthesized by standard methods. These oligonucleotide pairs are synthesized such that upon annealing, they form double stranded fragments of 80-90 base pairs, containing cohesive ends. The single-stranded ends of each pair of oligonucleotides are designed to anneal with a single-stranded end of an adjacent oligonucleotide duplex. Several adjacent oligonucleotide pairs prepared in this manner are allowed to anneal, and approximately five to six adjacent oligonucleotide duplex fragments are then allowed to anneal together via the cohesive single stranded ends. This series of annealed oligonucleotide duplex fragments is then ligated together and cloned into a suitable plasmid, such as the TOPO® vector available from Invitrogen Corporation, Carlsbad, Calif. The construct is then sequenced by standard methods. Constructs prepared in this manner, comprising 5 to 6 adjacent 80 to 90 base pair fragments ligated together, i.e., fragments of about 500 base pairs, are prepared, such that the entire desired sequence of the construct is represented in a series of plasmid constructs. The inserts of these plasmids are then cut with appropriate restriction enzymes and ligated together to form the final construct. The final construct is then cloned into a standard bacterial cloning vector, and sequenced. Alternatively, wild sequences can be cloned directly from HCMV-infected cells (e.g. MRC-5 cells, ATCC Accession No. CCL-171, available from the American Type Culture Collection, Manassas, Va.) using PCR primers that amplify the gene of interest. The oligonucleotides and primers referred to herein can easily be designed by a person of skill in the art based on the sequence information provided herein and in the art, and such can be synthesized by any of a number of commercial nucleotide providers, for example Retrogen, San Diego, Calif., and GENEART, Regensburg, Germany.

Plasmid Vector

Constructs of the present invention were inserted into eukaryotic expression vector V10551. This vector is built on a modified pUC18 background (see Yanisch-Perron, C., et al. *Gene* 33:103-119 (1985)), and contains a kanamycin resistance gene, the human cytomegalovirus immediate early 1 promoter/enhancer and intron A, and the bovine growth hormone transcription termination signal, and a polylinker for inserting foreign genes. See Hartikka, J., et al., *Hum. Gene Ther*. 7:1205-1217 (1996). However, other standard commercially available eukaryotic expression vectors may be used in the present invention, including, but not limited to: plasmids pcDNA3, pHCMV/Zeo, pCR3.1, pEF1/His, pIND/GS, pRc/HCMV2, pSV40/Zeo2, pTRACER-HCMV, pUB6N5-His, pVAX1, and pZeoSV2 (available from Invitrogen, San Diego, Calif.), and plasmid pCI (available from Promega, Madison, Wis.).

Plasmid DNA Purification

Plasmid DNA was transformed into *Escherichia coli* DH5α competent cells and highly purified covalently closed circular plasmid DNA was isolated by a modified lysis procedure (Horn, N. A., et al., *Hum. Gene Ther*. 6:565-573 (1995)) followed by standard double CsCl-ethidium bromide gradient ultracentrifugation (Sambrook, J., et al., *Molecular Cloning: A Laboratory Manual*, 2nd Ed., Cold Spring Harbor Laboratory Press, Plainview, N.Y. (1989)). Alternatively, plasmid DNAs are purified using Giga columns from Qiagen (Valencia, Calif.) according to the kit instructions. All plasmid preparations were free of detectable chromosomal DNA, RNA and protein impurities based on gel analysis and the bicinchoninic protein assay (Pierce Chem. Co., Rockford Ill.). Endotoxin levels were measured using *Limulus* Amebocyte Lysate assay (LAL, Associates of Cape Cod, Falmouth, Mass.) and were less than 0.6 Endotoxin Units/mg of plasmid DNA. The spectrophotometric $A_{260}/A_{280}$ ratios of the DNA solutions were typically above 1.8. Plasmids were ethanol precipitated and resuspended in an appropriate solution, e.g., 150 mM sodium phosphate (for other appropriate excipients and auxiliary agents, see U.S. Patent Application Publication 20020019358, published Feb. 14, 2002). DNA was stored at −20° C. until use. DNA was diluted by mixing it with 300 mM salt solutions and by adding appropriate amount of USP water to obtain 1 mg/ml plasmid DNA in the desired salt at the desired molar concentration.

Plasmid Expression in Mammalian Cell Lines

The expression plasmids were analyzed in vitro by transfecting the plasmids into a well characterized mouse melanoma cell line (VM-92, also known as UM-449) available from the American Type Culture Collection, Manassas, Va. Other well-characterized human cell lines may also be used, e.g. MRC-5 cells, ATCC Accession No. CCL-171. The transfection was performed using cationic lipid-based transfection procedures well known to those of skill in the art. Other transfection procedures are well known in the art and may be used, for example electroporation and calcium chloride-mediated transfection (Graham F. L. and A. J. van der Eb *Virology* 52:456-67 (1973)). Following transfection, cell lysates and culture supernatants of transfected cells were evaluated to compare relative levels of expression of HCMV antigen proteins. The samples were assayed by western blots and ELISAs, using commercially available anti-pp65 and anti-gB monoclonal antibodies (available, e.g., from Research Diagnostics Inc., Flanders N.J.), so as to compare both the quality and the quantity of expressed antigen. Additionally, in vitro transfection assays were used to determine the effect of mixing the various plasmids comprising codon-optimized coding regions encoding HCMV pp65 and gB on levels of expression in human cells.

Expression products derived from human cells transfected with the various polynucleotide constructs were examined for molecular weight, and immunoreactive antigens (i.e., to react with HCMV antisera). In addition, a comparison of expression levels (both intra- and extra-cellular) of each class of expression plasmid (e.g., wild-type vs. human codon-optimized; truncated vs. full-length) was made.

Injections of Plasmid DNA

The quadriceps muscles of restrained awake mice (e.g., female 6-12 week old BALB/c mice from Harlan Sprague Dawley, Indianapolis, Ind.) are injected using a disposable sterile, plastic insulin syringe and 28 G ½ needle (Becton-Dickinson, Franklin Likes, N.J., Cat. No. 329430) fitted with a plastic collar cut from a micropipette tip, all as previously described (Hartikka, J., et al., *Hum. Gene Ther*. 7:1205-1217 (1996)). The mice are injected bilaterally in the rectus femoris muscle with 25 μg of plasmid DNA (50 μg total per mouse) formulated in a salt solution (e.g. 150 mM Sodium Phosphate or phosphate buffered saline (PBS)) or with a lipid-based delivery system.

Animal care throughout the study is in compliance with the "Guide for the Use and Care of Laboratory Animals," Institute of Laboratory Animal Resources, Commission on Life Sciences, National Research Council, National Academy Press, Washington, D.C., 1996 as well as with Vical's Institutional Animal Care and Use Committee.

Immune Correlates

Although HCMV can only infect human cells, a number of reliable animal models for HCMV infection are known in the art, as reviewed by Staczek, and may be used with the methods of the present invention, e.g. to test immunogenicity or expression (Staczek, J. *Microbiol Rev* 54:247-65 (1990)). For example, the transgenic human leukocyte antigen (HLA) A*0201.Kb mouse model may be used (Gallez-Hawkins, G. et al. *Scand J Immunol* 55:592-8 (2002)). A mouse model of vertical HCMV transmission is described in Tang, et al., (Tang, J L, et al. *Arch Virol* 147:1189-95 (2002)). Several models infecting human tissue implanted onto immunodeficient SCID or nude mice have been described (Bidanset, D J, et al., *J Infect Dis* 184:192-5 (2001); Pari, G S, et al, *J Infect Dis* 177:523-8 (1998); Mocarski, E S, et al. *Proc Natl Acad Sci USA* 90:104-8 (1993)). Athymic rats have been used to model cytomegalovirus retinitis using HCMV (Laycock, K A, et al. *Am J Ophthalmol* 124:181-9 (1997)). Additionally, animal models using animal cytomegaloviruses to mimic HCMV infection have been described, including primate

Example 1

Construction of an Isolated Polynucleotide Comprising a Minimally Human Codon-Optimized pp65 Coding Region, Encoding Human Cytomegalovirus pp65 with Kinase Site Deleted VCL-6368 encodes an optimized and mutated form of the human CMV antigen pp65 cloned into the expression vector VR10551 described supra. This plasmid encodes a 557 amino acid protein (SEQ ID NO:6) in which amino acids Arg435-Lys438 of the human CMV pp65 antigen have been deleted. The coding sequence was minimally optimized for expression in humans by changing five codons that are rarely used in humans to corresponding codons that are used more frequently. The five codons and changes are: Ala GCG to GCC, Arg CGT to CGC, Pro CCG to CCC, and CCA, Ser TCG to TCC, and Thr ACG to ACC. The optimized sequence is SEQ ID NO:5.

The pp65delArg435-Lys438 insert of VCL-6368 was constructed in two steps by PCR amplification of an optimized hCMV pp65 plasmid synthesized at Retrogen Inc. (San Diego). The TOPO-hCMV-opti-pp65 plasmid (Retrogen product #8041-8081-4) was amplified with Expand DNA polymerase (Boehringer Mannheim) using the primer set T7 (Invitrogen Cat. #N650-02) (SEQ ID NO:21) and 65-delta-rev (SEQ ID NO:22) and the resulting product was gel purified as a 1330 bp fragment. An overlapping 400 bp fragment was amplified from the same parent TOPO plasmid using the primer set M13rev (Invitrogen Cat. #18430017) (SEQ ID NO:23) and 65-delta-for (SEQ ID NO:24) and the product was gel purified. Ten microliters of each of the two PCR fragments were combined in a second PCR reaction and amplified with the T7 (SEQ ID NO:21) and M13rev primer (SEQ ID NO:23) and the 1704 bp fragment was gel purified. This fragment was cut with the restriction enzymes Avr II and Nhe I and ligated with similarly digested plasmid backbone DNA. The ligation mix was transformed into *E. coli* (XL-2 from Stratagene, Inc.) and screened by PCR for recombinant clones using the primers VR10551FOR (SEQ ID NO:25) and hCMVpp65-R (SEQ ID NO:26). Several PCR positive clones were picked and sequenced. A minimally human codon-optimized clone encoding the correct Arg435-Lys438 deletion form of the human CMV pp65 antigen was selected and used for further analysis.

Expression of VR6368 was shown by transfection of VM92 cells and Western blot analysis using a monoclonal anti-pp65 antibody (ViroGen, lot# hCMV-pp65-4). The predicted sized protein was detected in the supernatant and cell lysate. Even though this construct encodes an intracellular protein, a significant amount ends up in the supernatant. This is not a unique or particularly unusual phenomenon.

Example 2

Construction of an Isolated Polynucleotide Comprising a Minimally Human Codon-Optimized Glycoprotein B Coding Region, Encoding the Secreted Human Cytomegalovirus Glycoprotein B VCL-6365 encodes a secreted form of the human CMV antigen gB cloned into the expression vector VR10551 described supra. This plasmid encodes amino acids 1-713 of the human CMV gB antigen (SEQ ID NO:14). Nucleotides 1-2139 of the wild-type gB coding sequence (SEQ ID NO:11) were minimally optimized for expression in humans by changing five codons that are rarely used in humans to five corresponding codons that are used more frequently. The five codons and changes are: Ala GCG to GCC, Arg CGT to CGC, Pro CCG to CCC, CCT, and CCA, Ser TCG to TCC, and Thr ACG to ACC. The optimized sequence is SEQ ID NO:13.

VR6365 was constructed by inserting a 2160 bp synthesized fragment encoding amino acids 1-713 of the human CMV gB antigen inserted into the expression vector VR-10551. Specifically, VR-10551 was digested with the restriction enzymes Nhe I and Avr II, and the 4.5 kb linear vector was gel purified. The gB insert was obtained by digesting the minimally human codon-optimized coding region encoding the secreted gB fragment synthesized by Retrogen Inc. (San Diego, product #7981-8031(2)-1) with the restriction enzymes Nhe I and Avr II, then gel purifying the resulting 2160 bp fragment. The vector and insert fragments were ligated together, transformed into *E. coli* (XL-2 from Stratagene, Inc.) and screened by PCR for recombinant clones using the primers 10551F (SEQ ID NO:25) and hCMVgB-R (SEQ ID NO:27). Several PCR positive clones were sequenced. A clone with the correct nucleotide sequence and was given the designation VR6365. This clone encodes a secreted form of the human CMV antigen gB cloned into the Nhe I-Avr II sites of the expression vector VR10551.

Purified plasmid DNA was used to transfect the murine cell line VM92 to determine secretion of the minimally human-codon-optimized gB.

Secretion of the minimally human-codon-optimized gB was confirmed with an ELISA assay using plates coated with supernatants from the transfected VM92 cells. Expression and secretion was visualized with polyclonal anti-gB serum and a commercially available anti-gB monoclonal antibody (available from Research Diagnostics Inc., Flanders, N.J.).

Example 3

Construction of an Isolated Polynucleotide Comprising a Human Codon-Optimized CMV IE1 Coding Region, Encoding Human Cytomegalovirus IE1

Plasmid VCL-6520 comprises a 1236 base-pair human codon-optimized synthetic DNA construct encoding exons 2 and 4 of the human CMV IE1 gene, inserted into the expression vector VR-10551. The wild type sequence for exons 2 and 4 of the human CMV IE1 gene follows (SEQ ID NO: 50):

GAATTCGCCGCCACCATGGAGTCCTCTGCCAAGAGAAAGATGGACCCTGATAATCCTGACGAGGGCCCT

TCCTCCAAGGTGCCACGGGTCAAACAGATTAAGGTTCGAGTGGACATGGTGCGGCATAGAATCAAGGAG

```
CACATGCTGAAAAAATATACCCAGACGGAAGAGAAATTCACTGGCGCCTTTAATATGATGGGAGGATGT

TTGCAGAATGCCTTAGATATCTTAGATAAGGTTCATGAGCCTTTCGAGGAGATGAAGTGTATTGGGCTA

ACTATGCAGAGCATGTATGAGAACTACATTGTACCTGAGGATAAGCGGGAGATGTGGATGGCTTGTATT

GATGAACTTAGGAGAAAGATGATGTATATGTGCTACAGGAATATAGAGTTCTTTACCAAGAACTCAGCC

TTCCCTAAGACCACCAATGGCTGCAGTCAGGCCATGGCGGCACTGCAGAACTTGCCTCAGTGCTCCCT

GATGAGATTATGGCTTATGCCCAGAAAATATTTAAGATTTTGGATGAGGAGAGAGACAAGGTGCTCACG

CACATTGATCACATATTTATGGATATCCTCACTACATGTGTGGAAACAATGTGTAATGAGTACAAGGTC

ACTAGTGACGCTTGTATGATGACCATGTACGGGGGCATCTCTCTCTTAAGTGAGTTCTGTCGGGTGCTG

TGCTGCTATGTCTTAGAGGAGACTAGTGTGATGCTGGCCAAGCGGCCTCTGATAACCAAGCCTGAGGTT

ATCAGTGTAATGAAGCGCCGCATTGAGGAGATCTGCATGAAGGTCTTTGCCCAGTACATTCTGGGGGCC

GATCCTCTGAGAGTCTGCTCTCCTAGTGTGGATGACCTACGGGCCATCGCCGAGGAGTCAGATGAGGAA

GAGGCTATTGTAGCCTACACTTTGGCCACCGCTGGTGTCAGCTCCTCTGATTCTCTGGTGTCACCCCCA

GAGTCCCCTGTACCCGCGACTATCCCTCTGTCCTCAGTAATTGTGGCTGAGAACAGTGATCAGGAAGAA

AGTGAGCAGAGTGATGAGGAAGAGGAGGAGGTGCTCAGGAGGAGCGGGAGGACACTGTGTCTGTCAAG

TCTGAGCCAGTGTCTGAGATAGAGGAAGTTGCCCCAGAGGAAGAGGAGGATGGTGCTGAGGAACCCACC

GCCTCTGGAGGCAAGAGCACCCACCCTATGGTGACTAGAAGCAAGGCTGACCAGTGAGGATCC
```

The insert in the VCL-6250 construct was synthesized by GENEART www_geneart_de/, Regensburg, Germany). VCL-6250 has the following sequence (SEQ ID NO:28):

```
10ATATCGCCGCCACCATGGAGTCTAGCGCCAAGAGGAAGATGGACCCCGACAACCCTGATGAGGGCC

CTAGCAGCAAGGTGCCCCGGGTGAAGCAGATCAAGGTGCGGGTGGACATGGTGCGGCACAGGATCAAG

GAACACATGCTGAAGAAGTACACCCAGACCGAGGAGAAGTTCACCGGCGCCTTCAATATGATGGGCGG

CTGCCTGCAGAATGCCCTGGACATCCTGGACAAGGTGCACGAGCCCTTCGAGGAGATGAAGTGCATCG

GCCTGACCATGCAGAGCATGTACGAGAACTACATCGTGCCCGAGGACAAGAGGGAGATGTGGATGGCC

TGCATCGACGAGCTGCGGCGGAAGATGATGTACATGTGCTACCGGAACATCGAGTTCTTCACCAAGAA

CAGCGCCTTCCCCAAGACCACCAACGGATGCTCTCAGGCCATGGCCGCCCTGCAGAATCTGCCTCAGT

GCAGCCCCGATGAGATCATGGCCTACGCCCAGAAGATCTTCAAGATCCTGGACGAGGAGAGGGATAAG

GTGCTGACCCACATCGACCACATCTTCATGGACATCCTGACCACCTGCGTGGAGACCATGTGCAACGA

GTACAAGGTGACCAGCGACGCCTGCATGATGACAATGTACGGCGGCATCAGCCTGCTGAGCGAGTTCT

GCAGAGTGCTGTGCTGCTACGTGCTGGAGGAGACCTCTGTGATGCTGGCCAAGAGGCCCCTGATCACC

AAGCCTGAGGTGATCAGCGTGATGAAGCGGCGGATCGAGGAGATCTGCATGAAGGTGTTCGCCCAGTA

CATCCTGGGAGCCGACCCTCTGAGAGTGTGTAGCCCCAGCGTGGATGACCTGAGAGCCATCGCCGAGG

AATCTGATGAAGAGGAGGCCATCGTGGCCTATACACTGGCCACAGCCGGCGTGTCTAGCAGCGATAGC

CTGGTGAGCCCTCCTGAGTCTCCTGTGCCTGCCACAATCCCTCTGAGCAGCGTGATCGTGGCCGAGAA

CAGCGATCAGGAGGAGAGCGAGCAGTCTGATGAGGAAGAGGAAGAGGGAGCCCAGGAGGAGAGAGAGG

ATACCGTGAGCGTGAAGAGCGAGCCTGTGAGCGAGATCGAAGAGGTGGCCCCTGAGGAAGAAGAGGAT

GGCGCCGAGGAGCCTACAGCCAGCGGCGGCAAGTCAACACACCCCATGGTGACCAGAAGCAAGGCCGA

CCAGTAAGGATCC
```

VCL-6250 was constructed by isolating the EcoR5-BamHI IE1 synthetic insert and ligating it into the expression vector VR-10551, described above. Specifically, VR-10551 was digested with restriction enzymes and gel purified, as described in the preceding examples. The vector and insert fragments were ligated together, transformed into E. coli DH10B cells (available, e.g., from Invitrogen). Selected recombinant plasmids were completely sequences using the primers synthesized according to the following table:

TABLE 9

Primers

| Primer | Sequence | SEQ ID NO |
|---|---|---|
| 2944S | CTG CGC CTT ATC CGG TAA CT | SEQ ID NO: 33 |
| 5876 | CAG TGA GGC ACC TAT CTC AG | SEQ ID NO: 34 |
| 5760 | CAC CAT GAG TGA CGA CTG AA | SEQ ID NO: 35 |
| 5761 | TTA ATC GCG GCC TCG AGC AA | SEQ ID NO: 36 |
| 5762 | GGC TCA TGT CCA ACA TTA CC | SEQ ID NO: 37 |
| 931S | GAG ACG CCA TCC ACG CTG TT | SEQ ID NO: 38 |
| 5874 | CAG ACT TAG GCA CAG CAC AA | SEQ ID NO: 39 |
| 5104 | GAG CGA GGA AGC GGA AGA GT | SEQ ID NO: 40 |
| 3054A | CCG CCT ACA TAC CTC GCT CT | SEQ ID NO: 41 |
| 5767 | GAG CAT TAC GCT GAC TTG AC | SEQ ID NO: 42 |
| 5768 | ATG CCT CTT CCG ACC ATC AA | SEQ ID NO: 43 |
| 5770 | GGC GGT AAT GTT GGA CAT GA | SEQ ID NO: 44 |
| 847A | GGC GGA GTT GTT ACG ACA TT | SEQ ID NO: 45 |
| 5772 | CAT TGT GCT GTG CCT AAG TC | SEQ ID NO: 46 |
| GA seqF1 | CCA GAC CGA GGA GAA GTT CA | SEQ ID NO: 47 |
| GA seqF2 | TGC TGG AGG AGA CCT CTG TG | SEQ ID NO: 48 |
| GA seqR2 | TCG ATC CGC CGC TFC ATC AC | SEQ ID NO: 49 |

Purified VCL-6250 DNA was used to transfect the murine cell line VM92 to determine expression of the IE1 protein. Expression of IE1 was confirmed with a Western Blot assay. Expression was visualized with a commercially available anti-IE1 monoclonal antibody (available from Chemicon International, Temecula, Calif.).

Example 4

Preparation of Vaccine Formulations

In each of the following methods, HCMV antigen-encoding plasmids of the present invention are formulated with the poloxamer system, described herein as VF-P1205-02A. VF-P1205-02A refers to a poloxamer-based delivery system consisting of the non-ionic block copolymer, CRL 1005, and a cationic surfactant, BAK (Benzalkonium chloride 50% solution, available from Ruger Chemical Co. Inc.). Specific final concentrations of each component of the formulae are described in the following methods, but for any of these methods, the concentrations of each component may be varied by basic stoichiometric calculations known by those of ordinary skill in the art to make a final solution having the desired concentrations.

For example, the concentration of CRL 1005 is adjusted depending on, for example, transfection efficiency, expression efficiency, or immunogenicity, to achieve a final concentration of between about 1 mg/ml to about 75 mg/ml, for example, about 1 mg/ml, about 2 mg/ml, about 3 mg/ml, about 4 mg/ml, about 5 mg/ml, about 6.5 mg/ml, about 7 mg/ml, about 7.5 mg/ml, about 8 mg/ml, about 9 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 75 mg/ml of CRL 1005.

Similarly the concentration of DNA is adjusted depending on many factors, including the amount of a formulation to be delivered, the age and weight of the subject, the delivery method and route and the immunogenicity of the antigen being delivered. In general, formulations of the present invention are adjusted have a final concentration from about 1 ng/ml to about 30 mg/ml of plasmid (or other polynucleotide). For example, a formulation of the present invention may have a final concentration of about 1 ng/ml, about 5 ng/ml, about 10 ng/ml, about 50 ng/ml, about 100 ng/ml, about 500 ng/ml, about 1 µg/ml, about 5 µg/ml, about 10 µg/ml, about 50 µg/ml, about 200 µg/ml, about 400 µg/ml, about 600 µg/ml, about 800 µg/ml, about 1 mg/ml, about 2 mg/ml, about 2.5, about 3 mg/ml, about 3.5, about 4 mg/ml, about 4.5, about 5 mg/ml, about 5.5 mg/ml, about 6 mg/ml, about 7 mg/ml, about 8 mg/ml, about 9 mg/ml, about 10 mg/ml, about 20 mg/ml, or about 30 mg mg/ml of a plasmid.

Certain formulations of the present invention include a cocktail of plasmids, for example, a mixture of two or more of plasmids VCL-6365, VCL-6368, or VCL-6520 of the present invention, and optionally plasmids comprising codon-optimized or non-codon-optimized coding regions encoding other HCMV antigens, e.g., an antigenic portion if HCMV IE1, and/or plasmids encoding immunity enhancing proteins, e.g., cytokines. Various plasmids desired in a cocktail are combined together in PBS or other diluent prior to the addition to the other ingredients. Furthermore, plasmids may be present in a cocktail at equal proportions, or the ratios may be adjusted based on, for example, relative expression levels of the antigens or the relative immunogenicity of the encoded antigens. Thus, various plasmids in the cocktail may be present in equal proportion, or up to twice or three times, or more, as much of one plasmid may be included relative to other plasmids in the cocktail.

Additionally, the concentration of BAK may be adjusted depending on, for example, a desired particle size and improved stability: Indeed, in certain embodiments, formulations of the present invention include CRL 1005 and DNA, but are free of BAK. In general BAK-containing formulations of the present invention are adjusted to have a final concentration of BAK from about 0.05 mM to about 0.5 mM. For example, a formulation of the present invention may have a final BAK concentration of about 0.05 mM, 0.1 mM, 0.2 mM, 0.3 mM, 0.4 mM, or 0.5 mM.

The total volume of the formulations produced by the methods below may be scaled up or down, by choosing apparatus of proportional size. Finally, in carrying out any of the methods described below, the three components of the formulation, BAK, CRL 1005, and plasmid DNA, may be added in any order. In each of these methods described below the term "cloud point" refers to the point in a temperature shift, or other titration, at which a clear solution becomes cloudy, i.e., when a component dissolved in a solution begins to precipitate out of solution.

A. Thermal Cycling of a Pre-Mixed Formulation

This example describes the preparation of a formulation comprising 0.3 mM BAK, 7.5 mg/ml CRL 1005, and 5 mg/ml of DNA in a total volume of 3.6 ml. The ingredients are combined together at a temperature below the cloud point and then the formulation is thermally cycled to room temperature (above the cloud point) several times, according to the protocol outlined in FIG. 8.

A 1.28 mM solution of BAK is prepared in PBS, 846 µl of the solution is placed into a 15 ml round bottom flask fitted with a magnetic stirring bar, and the solution is stirred with moderate speed, in an ice bath on top of a stirrer/hotplate (hotplate off) for 10 minutes. CRL 1005 (27 µl) is then added using a 100 µl positive displacement pipette and the solution is stirred for a further 60 minutes on ice. Plasmids VCL-6365 and VCL-6368, and optionally, additional plasmids encoding, e.g., additional HCMV antigens, e.g., VLC-6520, are mixed together at desired proportions in PBS. In the present example, 2.73 ml of a solution containing 3.2 mg/ml VCL-6365 and 3.2 mg/ml VCL-6368 (6.4 mg/ml total DNA) is added drop wise, slowly, to the stirring solution over 1 min using a 5 ml pipette. The solution at this point (on ice) is clear since it is below the cloud point of the poloxamer and is further stirred on ice for 15 min. The ice bath is then removed, and the solution is stirred at ambient temperature for 15 minutes to produce a cloudy solution as the poloxamer passes through the cloud point.

The flask is then placed back into the ice bath and stirred for a further 15 minutes to produce a clear solution as the mixture is cooled below the poloxamer cloud point. The ice bath is again removed and the solution stirred at ambient temperature for a further 15 minutes. Stirring for 15 minutes above and below the cloud point (total of 30 minutes), is defined as one thermal cycle. The mixture is cycled six more times. The resulting formulation may be used immediately, or may be placed in a glass vial, cooled below the cloud point, and frozen at −80° C. for use at a later time.

B. Thermal Cycling, Dilution and Filtration of a Pre-Mixed Formulation, Using Increased Concentrations of CRL 1005

Figure 9:
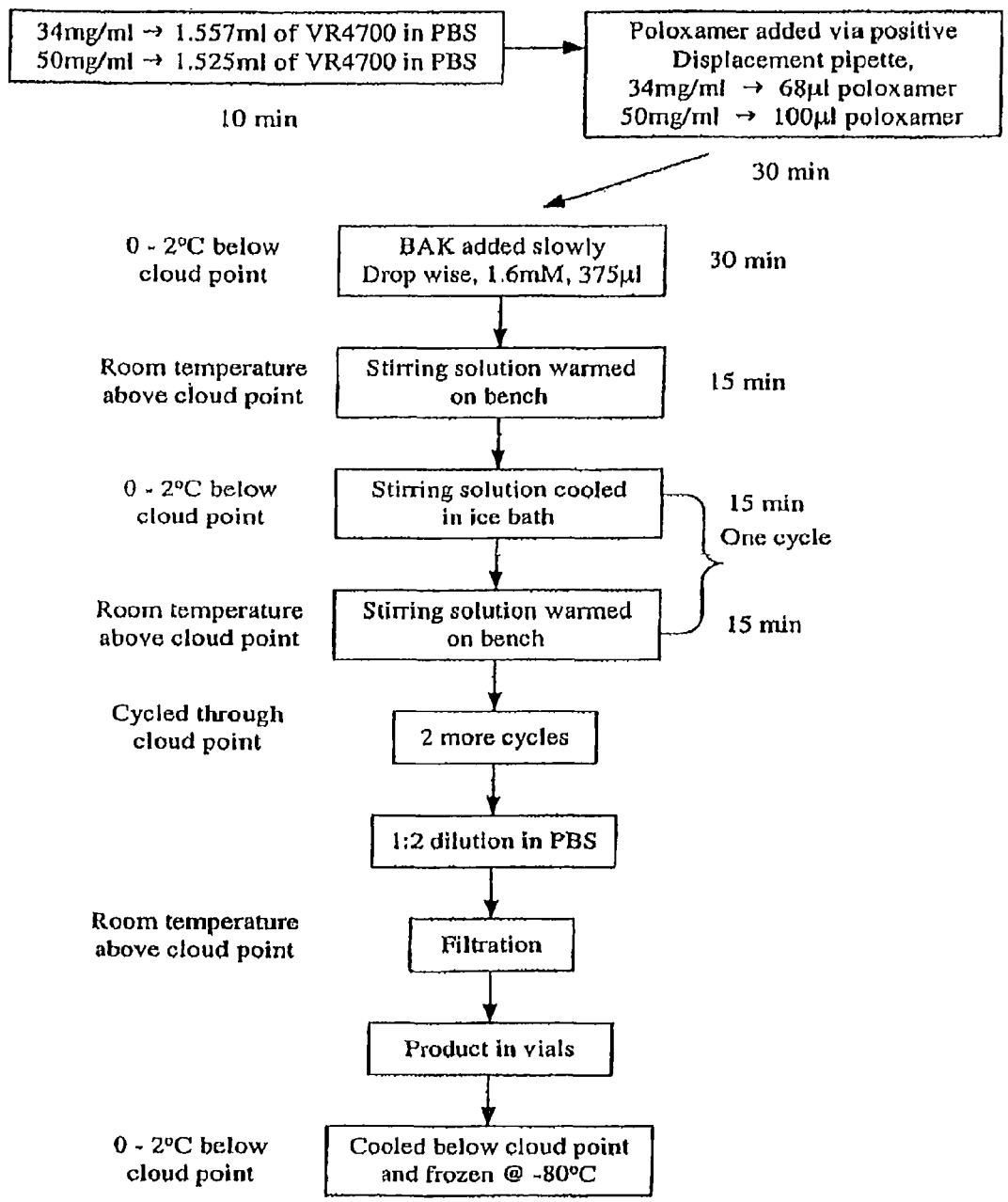
FIG. 9 shows the protocol for the preparation of a formulation comprising 0.3 mM BAK, 34 mg/ml or 50 mg/ml CRL 1005, and 2.5 mg/ml DNA in a final volume of 4.0 ml, through the use of thermal cycling.

This example describes the preparation of a formulation comprising 0.3 mM BAK, 34 mg/ml or 50 mg/ml CRL 1005, and 2.5 mg/ml of DNA in a final volume of 4.0 ml. The ingredients are combined together at a temperature below the cloud point, then the formulation is thermally cycled to room temperature (above the cloud point) several times, diluted, and filtered according to the protocol outlined in FIG. 9.

Plasmids VCL-6365 and VCL-6368, and optionally, additional plasmids encoding, e.g., additional HCMV antigens, e.g., VLC-6520, are mixed together at desired proportions in PBS. For the formulation containing 34 mg/ml CRL 1005, 1.55 ml of a solution containing about 3.2 mg/ml VCL-6365 and about 3.2 mg/ml VCL-6368 (about 6.4 mg/ml total DNA) is placed into the 15 ml round bottom flask fitted with a magnetic stirring bar, and for the formulation containing 50 mg/ml CRL 1005, 1.52 ml of a solution containing about 3.2 mg/ml VCL-6365 and about 3.2 mg/ml VCL-6368 (about 6.4 mg/ml total DNA) is placed into the 15 ml round bottom flask fitted with a magnetic stirring bar, and the solutions are stirred with moderate speed, in an ice bath on top of a stirrer/hotplate (hotplate off) for 10 minutes. CRL 1005 (68 µl for 34 mg/ml final concentration, and 100 µl for 50 mg/ml final concentration) is then added using a 100 µl positive displacement pipette and the solution is stirred for a further 30 minutes on ice. A 1.6 mM solution of BAK is prepared in PBS, and 375 µl is then added drop wise, slowly, to the stirring 34 mg/ml or 50 mg/ml mixtures, over 1 min using a 1 ml pipette. The solutions at this point are clear since they are below the cloud point of the poloxamer and are stirred on ice for 30 min. The ice baths are then removed; the solutions stirred at ambient temperature for 15 minutes to produce cloudy solutions as the poloxamer passes through the cloud point.

The flasks are then placed back into the ice baths and stirred for a further 15 minutes to produce clear solutions as the mixtures cooled below the poloxamer cloud point. The ice baths are again removed and the solutions stirred for a further 15 minutes. Stirring for 15 minutes above and below the cloud point (total of 30 minutes), is defined as one thermal cycle. The mixtures are cycled two more times.

In the meantime, two Steriflip® 50 ml disposable vacuum filtration devices, each with a 0.22 µm Millipore Express® membrane (available from Millipore, cat #SCGP00525) are placed in an ice bucket, with a vacuum line attached and left for 1 hour to allow the devices to equilibrate to the temperature of the ice. The poloxamer formulations are then diluted to 2.5 mg/ml DNA with PBS and filtered under vacuum.

The resulting formulations may be used immediately, or may be transferred to glass vials, cooled below the cloud point, and frozen at −80° C. for use at a later time.

C. A Simplified Method without Thermal Cycling

Figure 10:
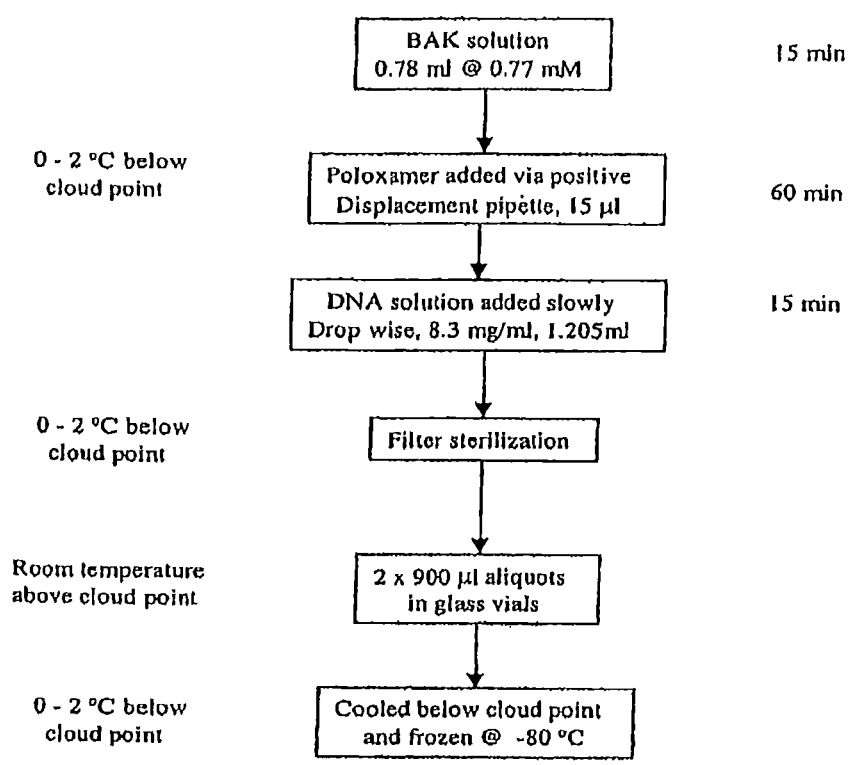
FIG. 10 shows the protocol for the simplified preparation (without thermal cycling) of a formulation comprising 0.3 mM BAK, 7.5 mg/ml CRL 1005, and 5 mg/ml DNA.

This example describes a simplified preparation of a formulation comprising 0.3 mM BAK, 7.5 mg/ml CRL 1005, and 5 mg/ml of DNA in a total volume of 3.6 ml. The ingredients are combined together at a temperature below the cloud point and then the formulation is simply filtered and then used or stored, according to the protocol outlined in FIG. 10.

A 0.77 mM solution of BAK is prepared in PBS, and 780 µl of the solution is placed into a 15 ml round bottom flask fitted with a magnetic stirring bar, and the solution is stirred with moderate speed, in an ice bath on top of a stirrer/hotplate (hotplate off) for 15 minutes. CRL 1005 (15 µl) is then added using a 100 µl positive displacement pipette and the solution is stirred for a further 60 minutes on ice. Plasmids VCL-6365 and VCL-6368, and optionally, additional plasmids encoding, e.g., additional HCMV antigens, e.g., VLC-6250, are mixed together at desired proportions in PBS. In the present example, about 1.2 ml of a solution containing about 4.1 mg/ml VCL-6365 and about 4.2 mg/ml VCL-6368 (about 8.3 mg/ml total DNA) is added drop wise, slowly, to the stirring solution over 1 min using a 5 ml pipette. The solution at this point (on ice) is clear since it is below the cloud point of the poloxamer and is further stirred on ice for 15 min.

In the meantime, two Steriflip® 50 ml disposable vacuum filtration devices, each with a 0.22 µm Millipore Express® membrane (available from Millipore, cat #SCGP00525) are placed in an ice bucket, with a vacuum line attached and left for 1 hour to allow the devices to equilibrate to the temperature of the ice. The poloxamer formulation was then filtered under vacuum, below the cloud point and then allowed to warm above the cloud point. The resulting formulations may be used immediately, or may be transferred to glass vials, cooled below the cloud point and then frozen at −80° C. for use at a later time.

Example 5

Animal Immunization

The immunogenicity of expression products encoded by one or more of the codon-optimized polynucleotides described in Examples 1, 2 and 3, and optionally the codon-optimized polynucleotides described in Example 4, are evaluated based on each plasmid's ability to mount an immune response in vivo. Plasmids are tested individually and in combinations by injecting single constructs as well as multiple constructs. Immunizations are initially carried out in animals, such as mice, rabbits, goats, sheep, primates, or other suitable animal, by intramuscular (IM) injections. Serum is collected from immunized animals, and the immune response is quantitated. The tests of immunogenicity further include measuring antibody titer, neutralizing antibody titer, T cell cytokine production and T cell cytolytic activity. Correlation to protective levels in humans are made according to methods well known by those of ordinary skill in the art. See "immune correlates," above.

A. DNA Formulations

Plasmid DNA is formulated by any of the methods described in Example 4. Alternatively, plasmid DNA is prepared as described above and dissolved at a concentration of about 0.1 mg/ml to about 10 mg/ml, preferably about 1 mg/ml, in PBS with or without transfection-facilitating cationic lipids, e.g., DMRIE/DOPE at a 4:1 DNA:lipid mass ratio. Alternative DNA formulations include 150 mM sodium phosphate instead of PBS, adjuvants, e.g., Vaxfectin™ at a 4:1 DNA:Vaxfectin™ mass ratio, mono-phosphoryl lipid A (detoxified endotoxin) from *S. minnesota* (MPL) and trehalosedicorynomycolateAF (TDM), in 2% oil (squalene)-Tween 80-water (MPL+TDM, available from Sigma/Aldrich, St. Louis, Mo., (catalog #M6536)), a solubilized mono-phosphoryl lipid A formulation (AF, available from Corixa), or (±)-N-(3-Acetoxypropyl)-N,N-dimethyl-2,3-bis(octyloxy)-1-propanaminium chloride (compound # VC1240) (see Shriver, J. W. et al., *Nature* 415:331-335 (2002), and P.C.T. Publication No. WO 02/00844 A2, each of which is incorporated herein by reference in its entirety).

B. Animal Immunizations

Codon-optimized and wild type DNA plasmids encoding secreted gB and pp65, and their respective mutant variants, as described above, are injected into BALB/c mice as single plasmids, as either DNA in PBS or formulated with the poloxamer-based delivery system: 3 mg/ml DNA, 34 or 50 mg/ml CRL 1005, and 0.3 mM BAK. Groups of 10 mice are immunized three times, at biweekly intervals, and serum is obtained to determine antibody titers to each of the antigens. Groups are also included in which mice are immunized with a trivalent preparation, containing each of the three plasmids in equal mass. The study design for each plasmid is shown in Table 10, and a typical immunization protocol is shown in Table 11.

TABLE 10

Study Design for Plasmids

| Group | Number of animals |
| --- | --- |
| DNA in PBS | 10 |
| DNA formulated with CRL 1005 and BAK | 10 |
| Plasmid backbone (VR10551), DNA in PBS | 5 |

TABLE 11

Immunization Schedule

| Day | Immunization |
| --- | --- |
| −3 | Pre-bleed |
| 0 | Plasmid injections, intramuscular, bilateral in rectus femoris, 25 µg/leg |
| 14 | Plasmid injections, intramuscular, bilateral in rectus femoris, 25 µg/leg |
| 20 | Serum collection |
| 28 | Plasmid injections, intramuscular, bilateral in rectus femoris, 25 µg/leg |
| 35 | Serum collection |

Serum antibody titers are determined by ELISA with recombinant proteins or transfection supernatants and lysates from transfected VM-92 cells or virus-infected cell lysates.

C. Production of HCMV pp65 and gB Antisera in Animals

Plasmid DNA encoding HCMV pp65, gB, IE1 or fragments, variants or derivatives thereof is prepared according to the immunization scheme described above and injected into a suitable animal for generating polyclonal antibodies. Serum is collected and the antibody titered as above. The titer of anti-HCMV peptide antibodies in serum from immunized animals may be increased by selection of anti-peptide antibodies, for instance, by adsorption to the peptide on a solid support and elution of the selected antibodies according to methods well known in the art.

Monoclonal antibodies are also produced using hybridoma technology (Kohler, et al., *Nature* 256:495 (1975); Kohler, et al., *Eur. J. Immunol.* 6:511 (1976); Kohler, et al, *Eur. J. Immunol.* 6:292 (1976); Hammerling, et al., in *Monoclonal Antibodies and T-Cell Hybridomas*, Elsevier, N.Y., (1981), pp. 563-681, each of which is incorporated herein by reference in its entirety). In general, such procedures involve immunizing an animal (preferably a mouse) as described above. Suitable cells can be recognized by their capacity to bind anti-HCMV pp65, gB antibody or IE1 antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2/0), available from the American Type Culture Collection, Rockville, Md. After fusion, the resulting hybridoma cells are selectively maintained in HAT medium, and then cloned by limiting dilution as described by Wands et al., *Gastroenterology* 80:225-232 (1981), incorporated herein by reference in its entirety. The hybridoma cells obtained through such a selection are then assayed to identify clones which secrete antibodies capable of binding HCMV pp65 or gB.

Alternatively, additional antibodies capable of binding to HCMV pp65 or gB may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, HCMV pp65 or gB specific antibodies are used to immunize an animal, preferably a mouse. The splenocytes of such an animal are then used to produce hybridoma cells, and the hybridoma cells are screened to identify clones which produce an antibody whose ability to bind to the HCMV protein-specific antibody can be blocked by HCMV pp65 or gB. Such antibodies comprise anti-idiotypic antibodies to the HCMV protein-specific antibody and can be used to immunize an animal to induce formation of further HCMV pp65 or gB-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, HCMV pp65 or gB-binding fragments can be produced through the application of recombinant DNA technology or through synthetic chemistry.

It may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., *Nature* 312:643 (1984); Neuberger, et al., *Nature* 314:268 (1985).

These antibodies are used, for example, in diagnostic assays, as a research reagent, or to further immunize animals to generate HCMV-specific anti-idiotypic antibodies. Non-limiting examples of uses for anti-HCMV antibodies include use in Western blots, ELISA (competitive, sandwich, and direct), immunofluorescence, immunoelectron microscopy, radioimmunoassay, immunoprecipitation, agglutinatione assays, immunodiffisuon, immunoelectrophoresis, and epitope mapping (Weir, D. Ed. *Handbook of Experimental Immunology*, $4^{th}$ ed. Vols. I and II, Blackwell Scientific Publications (1986)).

Example 6

Quantitative, Real Time RT-PCR Analysis of mRNA Expression of Constructs Encoding HCMV pp65 and gB, and Fragments, Variants and Derivatives Thereof Quantitation of the mRNA levels expressed from the HCMV pp65, gB and IE1 constructs is a valuable biological marker for gene activity. Various methods can be used to measure the levels of mRNA, such as Northern blots, slot blots, and other techniques known to those skilled in the art. However, a rapid method based on real-time RT-PCR provides an efficient, reliable means to monitor gene activity. One such system is the TaqMan® RT-PCR assay used with an ABI PRISM® Sequence Detection System, both available from Applied Biosystems, Inc. (Foster City, Calif.).

Briefly, RNA is extracted using conventional or commercially available techniques. After extraction, the RNA is aliquotted into optically transparent tubes or wells of a microtiter plate containing the provided buffers, enzymes, and reagents supplied with the appropriate kit, e.g., TaqMan® Gold RT-PCR Kit (Applied Biosystems, Inc., Foster City, Calif.). Additionally, the construct specific primers and probe, which can be designed by a person skilled in the art based on the sequences described herein, or commercially, e.g., ABI PRISM®. Primers & TaqMan® Probes Synthesis Service (Applied Biosystems, Inc., Foster City, Calif.) are added. The samples are placed in the ABI PRISM® Sequence Detection System, a thermocycler coupled to a laser capable of exciting the fluorophores present on the probe and a suitable detection system. Initially, the RNA is reverse transcribed into DNA, then thermostable DNA polymerase and sequence-specific primers contained in the reaction solution initiate the temperature-controlled amplification cycles. The probe used for detection of the amplification product is labeled with a low energy fluorophore (the reporter) and a high energy fluorophore (the quencher), which prevents emissions of the reporter from being detected if the quencher is closely associated with the reporter through fluorescence resonance energy transfer (FRET). At the beginning of the reaction cycle, the probe is in excess, so the majority remains unhybrized and intact, resulting in no signal. However, as the DNA product accumulates, a higher proportion of the probe is bound to the DNA. The bound probe is then degraded by the 5' nuclease activity of the DNA polymerase used for the amplification, which releases the reporter from the quencher and creates a detectable signal. As the PCR reaction progresses and the amplified product accumulates, more of the probe is degraded, inducing a greater signal that is recorded. The number of amplification cycles necessary to detect a signal (Ct) is directly proportional to the amount of starting template, or construct mRNA. By comparing Ct values between the sample and controls starting with a known amount of RNA, it is possible to quantitate the amount of mRNA expressed in cells transfected with plasmids containing the HCMV constructs. See the Applied Biosystem, Inc. tutorial "Real-Time PCR Vs. Traditional PCR" on the world wide web www_appliedbiosystems_com/support/tutorials/, visited Nov. 15, 2002. Other real time detection systems include "Molecular Beacon" probes, see, e.g., U.S. Pat. No. 6,103,476 to Kramer and Tyagi, which is incorporated herein by reference.

For the in vitro studies, suitable cells are seeded into 24 well tissue culture plates. Once the cells are at an appropriate cell density, plasmid DNA containing codon-optimized and non-codon-optimized HCMV constructs or appropriate controls, e.g. negative controls containing the plasmid backbone with no HCMV construct, is used to transfect the cells. At various time-points post-transfection, the cells are collected for RNA extraction, for example with 4M guanidinium thiocyanate followed by phenol extraction. Cells collected from in vivo studies are also used for RNA extraction. The extracted total RNA is quantitated by measuring the absorbance of the sample at 260 nm, diluted according to the Taqman® kit instructions (Applied Biosystems, Inc., Foster City, Calif.), and aliquotted into 386 well plates suitable for real-time PCR containing the buffers, nucleotides, and enzymes necessary. Controls containing known amounts of starting RNA are included in the assay, and optionally an internal standard may be included in the samples for quality assurance. This internal standard is typically an unrelated gene product, usually an abundant endogenous RNA. Primers and probes specific for the construct and optionally internal standard are also included. The primers are designed and synthesized in the same manner as conventional PCR primers, which is a routine task for one of skill in the art. To ensure reproducibility and specificity, multiple primer sets are used in the reaction, each targeting different regions of the construct. The primer is synthesized in a similar manner, but the fluorophores, e.g. FAM and TAMRA, are covalently attached by conventional methods. The reaction proceeds as described above, and the resulting Ct values of the samples are compared to those of the controls. Starting quantities of the mRNA are interpolated using the control Ct values.

After mRNA quantitation, the mRNA level is correlated with protein expression, both intracellular and secreted. Supernatant is collected from the tissue culture medium (or from the supernatant of centrifuged cells collected in vivo) at various time-points post-transfection. Additionally, a suitable number of cells are retained after harvesting for use in protein extraction. Western blots, slot blots, ELISA and other protein quantitation techniques are used to measure the HCMV protein levels produced by the transfected cells.

Example 7

Demonstration of Immunogenicity Plasmids Encoding Human CMV Antigens

General Experimental Procedure

The experimental procedure for the following example is as described above, with particular parameters and materials employed as described herein.

Plasmids

As described above, constructs of the present invention were inserted into the expression vector VR10551.

VR10551 is an expression vector without any transgene insert (backbone for the HCMV plasmids).

VR6365 contains the coding sequence for a secreted version of human CMV gB (amino acids 1-713) cloned into the VR10551 expression vector (Example 1). The DNA was prepared using Qiagen plasmid purification kits, and was characterized and formulated with the VF-P1205-02A poloxamer-based delivery system.

VR6368 contains the coding sequence of the full-length HCMV pp65, deleted of residues $^{435}$RKRK$^{438}$ in the putative kinase domain, cloned into the VR10551 expression vector (Example 2). The DNA was prepared using Qiagen plasmid purification kits, and was characterized and formulated with the VF-P1205-02A poloxamer-based delivery system, as above.

Poloxamer Formulation

The VF-P1205-02A poloxamer-based delivery system was formulated using a protocol equivalent to Example 4B, with an initial DNA, poloxamer and BAK concentration of 5.0 mg/ml, 7.5 mg/ml and 0.3 mM, respectively. Formulations were diluted with PBS at room temperature to the required experimental concentrations prior to injection.

Vaccination Regimen

Groups of nine, 6- to 8-week old female BALB/c mice (Harlan-Sprague-Dawley) received intramuscular (rectus femoris) injections containing 100 μg of pp65 DNA, 100 μg of gB DNA, or 100 μg each of pp65 and gB DNA delivered with PBS or the CRL 1005 poloxamer formulation described above. Control mice received 100 μg of pp65 DNA or 100 μg of gB DNA mixed with 100 μg of non-coding, vector DNA (VR10551) delivered with PBS or VF-P1205-02A. All mice received two vaccinations (administered on days 0 and 13) containing a total of 200 μg of DNA, 100 μg pp65 DNA and the 100 μg gB DNA. Sera were collected after the first (day 11) and second (day 22) vaccinations, and gB- and pp65-specific antibody responses were measured by ELISA and immunoblot analysis, respectively.

Recombinant gB Enzyme Linked Immunosorbent Assay (ELISA)

Sera were collected from the mice vaccinated according to the regimen described above. Anti-gB IgG titers were determined using a recombinant CMV gB Enzyme Linked Immunosorbent Assay (ELISA).

Ninety six-well, half area, high-binding EIA (Enzyme ImmunoAssay) plates were coated with recombinant CMV gB at a concentration of 0.05 μg/well (50 μL/well) in Borate Buffered Saline (BBS) buffer at 4° C. overnight. Plates were covered with an adhesive plate sealer for all incubations. After coating, plates were blotted on paper towels and 100 μL of blocking buffer (0.1% [w/v] BSA in BBS) was added to each well. Sealed plates were incubated at room temperature for 2 hours and were then stored at 4° C. until sera had been diluted. Sera were diluted in 0.5% (w/v) BSA in BBS in Eppendorf tubes, and were mixed by inversion and brief vortexing. Blocked plates were blotted and 100 μL of diluted serum was added to each well. Plates were sealed and incubated overnight at 4° C. Plates were then washed on a four wash cycle on an automated plate washer with 0.1% (v/v) Tween-20 in BBS and were blotted on paper towels. Alkaline phosphate labeled anti-mouse IgG Fc secondary antibody was diluted 1:2000 in 0.5% (w/v) BSA in BBS and 80 μL of diluted secondary antibody was added to each well. Plates were sealed and were incubated at room temperature for 2 hours. Plates were washed again on the four wash cycle on the automated plate washer and were blotted on paper towels. Fifty microliters of developing solution (1 mg/ml para-nitrophenyl phosphate in 50 mM sodium bicarbonate buffer, pH 9.8 and 1 mM MgCl$_2$) was added to each well, plates were sealed and incubated at room temperature. Absorbance at 405 nm, A$_{405}$, (single wavelength) was read on the plate reader. Titers were determined as the dilution at which the mean absorbance value of the immune serum was at least twice that of the mean absorbance value for the pre-immune serum at a dilution of 1:100.

Immunoblots to Detect pp65

Lysates from murine melanoma VM92 cells transfected with either VR6368 or VR10551 were made directly in 1× NuPAGE LDS sample buffer and were stored at −80° C. until needed. After thawing at room temperature, one tenth of the sample volume of 0.5 MM dithiothreitol was added to each sample. Samples were then heated at 85° C. for 10 min and were cooled immediately on ice prior to loading on NuPAGE 4-12% Bis-Tris gels. Electrophoresis was carried out at 200 V for 60 minutes at room temperature. For transfer of proteins, polyvinylidene difluoride (PVDF) membranes were first soaked in methanol for 30 s and then equilibrated in 1× NuPAGE transfer buffer containing 20% (v/v) methanol. Proteins were transferred from gels to PVDF membranes at 30V for 60 min at room temperature. After protein transfer, membranes were rinsed in milli-Q water and then blocked for 45 min at room temperature in 1% (w/v) BSA in BBS on an orbital shaker. After blocking, membranes were stored at 4° C. in 1% (w/v) BSA in BBS for no longer than 24 hr. Blots were cut into strips and were incubated in mouse immune serum diluted in 0.5% (w/v) BSA in BBS at room temperature overnight on an orbital shaker. After washing in BBS, the strips were incubated in secondary antibody (goat anti-mouse IgG Fcγ conjugated to alkaline phosphatase) at room temperature for 2.5 hr. Strips were then washed again in BBS and were developed in alkaline phosphatase substrate solution for 10 min at room temperature. Strips were then rinsed thoroughly in distilled water and were allowed to dry at room temperature between paper towels.

Mice were vaccinated with gB plasmid (VR6365) or gB/pp65 plasmid combination, as described above. The anti-gB IgG titers, measured after two vaccinations in mice vaccinated with gB plasmid (VR6365), alone or in combination with pp65 plasmid (VR6368) are given below:

TABLE 12

Anti-gB IgG Titers Following 2$^{nd}$ Vaccination

| Group | mean reciprocal titer (range) | geometric mean reciprocal titer |
| --- | --- | --- |
| gB (poloxamer formulation) | 42,667 (12,800-102,400) | 34,836 |
| Combination (poloxamer formulation) | 17,244 (1,600-25,600) | 13,825 |
| gB (naked DNA) | 29,867 (12,800-51,200) | 27,650 |
| Combination (naked DNA) | 10,667 (3,200-25,600) | 8,709 |

All mice vaccinated with plasmid DNA encoding HCMV gB alone or in combination, either with or without VF-P1205-02A, had detectable anti-gB IgG titers after two injections of DNA. Sera from mice injected with pp65 DNA only were pooled and tested. The binding activity for the pp65 only group was the same as for the pre-bleed sera, indicating that gB specific antibodies were not detected.

pp65 Immunoblots

Mouse sera collected after the second DNA vaccination were tested on immunoblots of lysates from cells transfected with pp65 plasmid (VR6368) as described above to determine, qualitatively, the difference in the antibody responses to pp65 in mice vaccinated with VR6368 alone and mice vaccinated with the plasmid combination. In the first set of immunoblots, pooled sera from each group of mice vaccinated with VR6368 were tested at dilutions of 1:200, 1:400, 1:800, 1:1000 and 1:2000. A sample of pooled sera from mice vaccinated with VR6365 (gB) formulated in VF-P1205-02A was included as a negative control. A pp65-specific murine monoclonal antibody was included as a positive control. Each immunoblot strip had a lane of molecular weight standards, a lane containing VR6368-transfected cell lysate, and a VR10551 transfected cell lysate control lane. All mice (nine of nine) vaccinated with pp65 DNA formulated with VF-P1205-02A had detectable antibody to pp65 by immunoblot when sera were tested at dilution of 1:200. Six of nine mice vaccinated with the bivalent HCMV plasmid vaccine formulated with VF-P1205-02A had detectable antibody to pp65 by immunoblot when tested at a dilution of 1:200. Immunoblot titration of pooled sera from the mice vaccinated with either the pp65 DNA formulated with VF-P1205-02A, or the bivalent HCMV plasmid vaccine formulated with VF-P1205-02A did not reveal a marked difference in the antibody response to pp65 between the groups. No pp65 antibody was detected in mice vaccinated with gB DNA alone.

Thus, plasmids VR6365 (gB) and VR6368 (pp65) elicited the production of antigen-specific antibodies in mice that received two injections of the plasmids either alone or in combination. Although we cannot quantify the anti-pp65 antibody response using immunoblots, they do show that the majority of mice had a detectable antibody response to pp65, and that the combination of the two plasmids did not result in complete suppression of the response to pp65. Antibody responses to pp65 in this study served as an additional readout for confirmation of production of this protein in vivo after vaccination with VR6368.

pp65-Specific IFN-γ ELISpot Assay

T cell responses to the DNA-encoded pp65 were determined by IFN-γ ELISpot assay. Splenocytes of vaccinated mice were stimulated with two separate pools of overlapping peptides, that, together, span the entire pp65 protein and should contain all possible T cell epitopes. Therefore, the type of the T cell (e.g., $CD8^+$ or $CD4^+$) that is producing IFN-γ in response to the peptide stimulation cannot be distinguished by this assay method. Theoretically, these peptides can be presented in the context of class I or class II MHC, thus stimulating both $CD8^+$ and $CD4^+$ T cells within the same splenocyte preparation.

In these assays the number of antigen-specific spots were usually >10-fold more than the number in control wells. IFN-γ producing cells were detected in splenocyte preparations from VR6368-vaccinated mice stimulated with either of the peptide pools, but approximately three times as many spots were detected in response to Pool I than to Pool II. Few to no spots were produced by splenocytes of gB-vaccinated mice in response to stimulation with either of the peptide pools.

These data demonstrate that the HCMV DNA vaccine component pp65 was expressed in vivo at levels sufficient to induce cellular immune responses, either when it was administered alone or in combination, in the VF-P1205-02A formulation.

Example 8

Confirmation of Immunogenicity Plasmids Encoding Human CMV Antigens

General Experimental Procedure

The experimental procedure for the following example is as described above, with particular parameters and materials employed as described herein.

Plasmids

As described above, constructs of the present invention, VR6365 and VR 6368 were constructed by inserting the appropriate inserts into the expression vector VR10551, and were formulated with poloxamer formulation VF-P1205-02A where noted.

Vaccination Regimen

Groups of nine, 6- to 8-week old female BALB/c mice (Harlan-Sprague-Dawley) received bilateral, intramuscular (rectus femoris) injections (50 μl/leg) containing plasmid DNA encoding pp65, gB, or pp65 and gB with or without VF-P1205-02A on days 0, 21, and 49. Each mouse received 200 μg of DNA per vaccination. For formulations containing a single gB or pp65 coding plasmid, 100 μg of blank DNA (VCL10551), which served as a filler, was included. The effect of the blank DNA was tested by vaccinating mice with 100 μg of the single plasmid DNAs delivered with or without VF-P1205-02A in the absence of the filler DNA. Serum samples were collected prior to the first vaccination (day−1) and after each vaccination (days 20, 48, and 63) and gB-specific antibodies were measured by ELISA.

Recombinant gB Enzyme Linked Immunosorbent Assay (ELISA)

Sera were collected from the vaccinated mice, and anti-gB IgG titers were determined using a recombinant CMV gB Enzyme Linked Immunosorbent Assay (ELISA) as described in Example 7.

The anti-gB IgG titers in sera from mice vaccinated with VCL-6365, either alone or in combination with VCL-6368 are given below:

TABLE 13

Anti-gB IgG Titers

| Immunogen | Bleed 2 (Day 48) $Log_{10}$ mean titer (range) | Bleed 3 (Day 63) $Log_{10}$ mean titer (range) |
|---|---|---|
| gB + pp65 in PBS | 4.6 (4.4-4.7) | 4.78 (4.4-5.0) |
| gB + pp65 + VF-P1205-02A | 4.7 (4.1-5.0) | 4.96 (4.7-5.3) |
| gB + neg. control plasmid | 4.98 (3.8-5.3) | 5.25 (4.1-5.6) |
| gB + neg. control plasmid + VF-P1205-02A | 4.87 (4.4-5.3) | 5.14 (4.7-5.6) |
| gB in PBS | 4.82 (4.4-5.3) | 5.15 (4.7-5.6) |
| gB + VF-P1205-02A | 4.73 (4.4-5.0) | 5.1 (4.7-5.3) |

Plasmid VCL6365 (gB) elicited the production of gB-specific antibodies in mice that received three injections of the plasmids either alone or in combination. All mice vaccinated with VCL6365 had detectable anti-gB IgG titers after two injections. These data confirm the immunogenicity of the gB plasmid product in vivo when VCL6365 is delivered in combination with VCL6368 in the VF-P1205-02A formulation.

Example 9

Plasmid Encoding Human CMV IE1 is Immunogenic

General Experimental Procedure

The experimental procedure for the following example is as described above, with particular parameters and materials employed as described herein.

Vaccination Regimen

Mice received bilateral, intramuscular injections into the rectus femoris of the IE1 plasmid VR6250. The total DNA doses as shown below were each in a 100 μl volume in PBS, but was administered as two equal volume injections, one into each rectus femoris muscle of each mouse. The negative control group contained 5 mice and all other groups contained 10 mice. Mice received injections on days 0 and 14. Splenocytes were analyzed for IE1 reactivity by ELISpot assay in which splenocytes were stimulated with a pool of 98 overlapping 15mer peptides (overlapping by 11 amino acids) that span the entire IE1 protein encoded on the VR6250 construct. Splenocytes from the negative control group were harvested on day 24 and were analyzed for non-specific stimulation of IFN-γ secreting T-cells with the IE1 peptide pool. Splenocytes from the groups injected with IE1 DNA were harvested for analysis of antigen specific, IFN-γ secreting, T-cell responses on days 27-29. Two spleens from each group were pooled for the assay. Two pools from each group were analyzed on days 27 and 28, one pool from each group was analyzed on day 29. The values reported below represent the average of 5 splenocyte pools per experimental group.

IFN-γ ELISpot Assay

T cell responses to the DNA vaccines were determined by quantifying the number of splenocytes secreting IFN-γ in response to antigen-specific stimulation as measured by IFN-γ ELISpot assay. ImmunoSpot plates (Cellular Technology Limited, Cleveland, Ohio) were coated with rat anti-mouse IFN-γ monoclonal antibody (BD Biosciences, San Diego, Calif.), and blocked with RPMI-1640 medium. Splenocyte suspensions were isolated from individual vaccinated mice and added to ELISpot plates at $1 \times 10^6$ or $3.3 \times 10^5$ cells/well in RPMI medium containing 5 μg/mL of each of the overlapping IE1 peptides as stimulating antigen. Control wells contained $1 \times 10^6$ splenocytes incubated in medium (no antigen). After a 20-hour incubation at 37° C., captured IFN-γ was detected by the sequential addition of biotin-labeled rat anti-mouse IFN-γ monoclonal antibody and avidin-horseradish peroxidase. Spots produced by the conversion of the colorimetric substrate, 3-amino-9-ethylcarbazole (AEC), were quantified by an ImmunoSpot Analyzer (Cellular Technology Limited, Cleveland, Ohio). The results are expressed as spot forming units (SFU) per $10^6$ cells.

TABLE 14

IE1 ELISpot Results

| DNA & Dose | 100 μg Blank | 1 μs VR6250 | 3 μg VR6250 | 10 μg VR6250 | 30 μg VR6250 | 100 μg VR6250 |
|---|---|---|---|---|---|---|
| SFU/$10^6$ cells | 6 | 5 | 77 | 289 | 367 | 501 |

The data shows that administering the IE1 plasmid VR6250 induced an antigen specific immune response, and that the immune response was DNA dose dependent. Additionally, this indirectly confirms that the IE1 protein was expressed in vivo.

Example 10

Formulation Selection Studies

The potency of different vaccine formulations was evaluated in two experimental mouse immunogenicity studies using murine CMV M84. Murine CMV M84 is considered a homolog of the human CMV pp65, and thus served as a surrogate for the pp65 antigen. The first study measured lipid dose responses using a fixed quantity of DNA while the second study evaluated clinically relevant doses of DNA by dose escalation.

Formulations

DMRIE/DOPE in a 1:1 molar ration was produced as a lipid film containing 46.2% DMRIE and 53.8% DOPE by weight (5.14 mg total dried lipid). Prior to injection, the dried, mixed lipid film was hydrated in sterile water for injection to form cationic liposomes that were then added to DNA at the appropriate concentration in 2×PBS. DNA was formulated with DMRIE/DOPE as follows:

TABLE 15

DNA Formulations

| DNA Concentration (mg/mL) | DNA:Lipid* |
|---|---|
| 0.5 | 2:1 |
| 1.0 | 4:1 |
| 3.0 | 10:1 |

*DNA (assigned MW = 333 gr/mol):cationic lipid molar ratio

For the lipid dose response studies the DMRIE/DOPE formulations listed above were diluted to a final vaccinating concentration of 0.5 mg/mL of M84 DNA. For the DNA dose escalation studies the formulations were not diluted prior to injection.

Poloxamer formulations for the lipid dose response study were produced with 5 mg/mL of M84 DNA, 7.5 mg/mL of CRL 1005, and 0.3 mM of benzylalkonium chloride (BAK) surfactant. Prior to injection, the formulations for the lipid dose response study were diluted to a final vaccinating concentration of 0.5 mg/mL of M84 DNA. In the DNA dose escalation studies, the formulations were produced with 3 mg/mL of the appropriate plasmid DNA, 4.5 mg/mL of CRL 1005, and 0.18 mM BAK. These formulations were not diluted prior to injection.

Vaccination Regimen

Groups of nine, six- to eight-week old BALB/c mice (Harlan-Sprague-Dawley) received bilateral (50 μL/leg) intramuscular (rectus femoris) injections of plasmid DNA formulated with DMRIE/DOPE or CRL 1005 in PBS. Control mice received DNA in PBS alone. All mice were boosted on (approximately) days 21 and 49. Two weeks after the last immunization, splenocytes were harvested from three mice/group/day for three sequential days, and antigen specific T cell responses were measured by IFN-γ ELISpot assay.

Cell Culture Media

Splenocyte cultures were grown in RPMI-1640 medium containing 25 mM HEPES buffer and L-glutamine and supplemented with 10% (v/v) FBS, 55 μM β-mercaptoethanol, 100 U/mL of penicillin G sodium salt, and 100 μg/mL of streptomycin sulfate.

IFN-γ ELISpot Assay

T cell responses to the DNA vaccines were determined by quantifying the number of splenocytes secreting IFN-γ in response to antigen-specific stimulation as measured by IFN-γ ELISpot assay. ImmunoSpot plates (Cellular Technology Limited, Cleveland, Ohio) were coated with rat anti-mouse IFN-γ monoclonal antibody (BD Biosciences, San Diego, Calif.), and blocked with RPMI-1640 medium. Splenocyte suspensions were produced from individual vaccinated mice and seeded in ELISpot plates at $1\times10^6$, $3\times10^5$, or $1\times10^5$ cells/well in RPMI medium containing 1 μg/mL of the appropriate MHC class I-restricted peptide (M84, $^{297}$AYAGLFTPL$^{305}$, (SEQ ID NO:32) Imgenex, San Diego, Calif.), 1 U/mL of recombinant murine IL-2 (Roche, Indianapolis, Ind.). Control wells contained $1\times10^6$ splenocytes incubated in medium with IL-2 only (no antigen). After a 20-hour incubation at 37° C., captured IFN-γ was detected by the sequential addition of biotin-labeled rat anti-mouse IFN-γ monoclonal antibody and avidin-horseradish peroxidase. Spots produced by the conversion of the colorimetric substrate, 3-amino-9-ethylcarbazole (AEC), were quantified by an ImmunoSpot reader (Cellular Technology Limited, Cleveland, Ohio). Statistically significant differences between the T cell responses of mice vaccinated with lipid- or poloxamer-formulated DNA and naked DNA was determined using a Student's t-test with $\alpha=0.05$.

The M84-specific CD8+ T cell responses of mice vaccinated with 50 μg of M84 DNA formulated with DMRIE/DOPE ("DID") at the DNA:lipid molar ratios indicated, CRL 1005, or PBS alone are given below.

TABLE 16

CD8+ T Cell Responses

| Vaccine Formulation | Mean SFU/$10^6$ Splenocytes CD8+ T cells |
|---|---|
| PBS | 299 |
| 2:1 D/D | 243 |
| 4:1 D/D | 179 |
| 10:1 D/D | 299 |
| CRL 1005 | 344 |

The M84-specific CD8+ T cell responses of mice vaccinated with escalating doses of M84 DNA formulated with DMRIE/DOPE (D/D) at the DNA:lipid molar ratios indicated versus M84 DNA formulated with CRL 1005 or PBS alone are given below.

TABLE 17

CD8+ T Cell Responses

| Vaccine Formulation (DNA Dose) | Mean SFU/$10^6$ Splenocytes CD8+ T cells |
|---|---|
| PBS (300 μg) | 533 |
| 2:1 D/D (50 μg) | 184 |
| 4:1 D/D (100 μg) | 158 |
| 10:1 D/D (300 μg) | 243 |
| CRL 1005 (300 μg) | 416 |

Example 11

Experiments Employing HCMV Antigens

Vaccination Regimen

Groups of nine, 6- to 8-week old female BALB/c mice (Harlan-Sprague-Dawley) received bilateral, intramuscular (rectus femoris) injections (50 μl/leg) containing plasmid DNA encoding pp65, gB, or pp65 and gB with or without CRL 1005 (the VF-P1205-02A formulation) on days 0 and 13. Each mouse received 200 μg of DNA per vaccination. For formulations containing a single gB or pp65 coding plasmid, 100 μg of blank DNA (VR10551) was added to yield 200 μg of total DNA. Beginning approximately three weeks after the primary immunization (on day 22), splenocytes were harvested from vaccinated mice and pp65-specific T cell responses were measured by IFN-g ELISpot assay. Three ELISpot assays were performed: assay one measured the immune response from a pool of splenocytes from three mice per group and assays two and three measured the immune response from a pool of splenocytes from two mice per group. The immune responses of the additional two mice in each group were not measured in this series of assays.

IFN-γ ELISpot Assay

T cell responses to DNA-encoded pp65 were determined by quantifying the number of splenocytes secreting IFN-γ in response to stimulation with pp65-derived peptides (Bio-Synthesis, Lewisville, Tex.). ImmunoSpot plates (Millipore, Billerica, Mass.) were coated with rat anti-mouse IFN-γ monoclonal antibody (BD Biosciences, San Diego, Calif.) and blocked with RPMI-1640 medium containing 25 mM HEPES buffer and L-glutamine and supplemented with 10% (v/v) heat inactivated FBS, 55 mM b-mercaptoethanol, 100 U/mL of penicillin G sodium salt, and 100 μg/mL of streptomycin sulfate (10% RPMI). Splenocyte suspensions were produced from vaccinated mice, resuspended in 10% RPMI medium at a density of $2\times10^7$ cells/mL, and seeded in triplicate wells of two separate ImmunoSpot plates at a density of $5\times10^5$ or $2.5\times10^5$ cells/well. Splenocytes were stimulated with two separate pools of overlapping pp65 peptides (one pool per plate) that, together, span the entire pp65 protein and should include all possible T cell epitopes. Therefore, the type of T cell (e.g., CD8+ or CD4+) that is producing IFN-γ in response to the peptide stimulation cannot be distinguished by this assay method. Theoretically, these peptides can be presented in the context of class I or class II MHC, thus stimulating both CD8+ and CD4+ T cells within the same splenocyte preparation. The peptide pools contained 68 (pool I) or 69 (pool II) peptides of 15 amino acids each (except one 13 amino acid peptide in pool II), and each peptide was represented at a final concentration of 5 μg/mL in the assay well. Control wells contained $5\times10^5$ cells in medium only (no peptide antigen). After a 21-hour incubation at 37° C., captured IFN-γ was detected by the sequential addition of biotin-labeled rat anti-mouse IFN-γ monoclonal antibody (BD Biosciences, San Diego, Calif.) and avidin-horseradish peroxidase. Spots produced by the conversion of the colorimetric substrate, 3-amino-9-ethylcarbazole (AEC), were quantified by an ImmunoSpot reader (Cellular Technology Limited, Cleveland, Ohio). Data are presented as the number of Spot Forming Units (SFU), produced in response to antigen-specific stimulation, per million cells assayed. The antigen-specific stimulation was calculated by subtracting the mean number of spots in wells containing splenocytes incubated in medium alone (the non-specific, background response) from the number of spots in wells containing the identical splenocyte preparation incubated with a pool of pp65-derived peptides. Three replicate wells were used to determine the mean non-specific background response. Each SFU corresponds to one pp65-specific T cell. Due to the small sample size (n=3), a statistical analysis of the difference of the means was not performed.

Experiment 1—See TABLES 18 and 19.

TABLE 18

T Cell Responses to CMV pp65 Peptide Pool I

| DNA Vaccine | Mean SFU/$10^6$ Cells | Fold Increase versus pp65 + gB |
|---|---|---|
| pp65 + gB | 170 | — |
| pp65 + gB + CRL 1005 | 705 | 4.1 |
| pp65 + Blank | 681 | 4.0 |
| pp65 + Blank + CRL 1005 | 780 | 4.6 |
| gB + Blank | 1 | 0 |
| gB + Blank + CRL 1005 | 2 | 0 |

TABLE 19

T Cell Responses to CMV pp65 Peptide Pool II

| DNA Vaccine | Mean SFU/$10^6$ Cells | Fold Increase versus pp65 + gB |
|---|---|---|
| pp65 + gB | 80 | — |
| pp65 + gB + CRL 1005 | 208 | 2.6 |
| pp65 + Blank | 374 | 4.7 |
| pp65 + Blank + CRL 1005 | 225 | 2.8 |
| gB + Blank | 0 | 0 |
| gB + Blank + CRL 1005 | 0 | 0 |

Experiment 2

The experiment above was repeated, and although the pp65+gB group had responses to peptide pool I that were 2.4-fold higher than that measured in the study reported in detail above, the results were similar.

TABLE 20

T CELL RESPONSES TO CMV PP65 PEPTIDE POOL I

| DNA Vaccine | Mean SFU/$10^6$ Cells | Fold Increase versus pp65 + gB |
|---|---|---|
| pp65 + gB | 407 | — |
| pp65 + gB + CRL 1005 | 444 | 1.1 |
| pp65 + Blank | 435 | 1.1 |
| pp65 + Blank + CRL 1005 | 762 | 1.9 |
| gB + Blank | ND | — |
| gB + Blank + CRL 1005 | ND | — |

TABLE 21

T Cell Responses to CMV pp65 Peptide Pool II

| DNA Vaccine | Mean SFU/$10^6$ Cells | Fold Increase versus pp65 + gB |
|---|---|---|
| pp65 + gB | 100 | — |
| pp65 + gB + CRL 1005 | 158 | 1.6 |
| pp65 + Blank | 140 | 1.4 |
| pp65 + Blank + CRL 1005 | 225 | 2.3 |
| gB + Blank | 0 | — |
| gB + Blank + CRL 1005 | 0 | — |

Experiment 3

Vaccination Regimen

Groups of nine, 6- to 8-week old female BALB/c mice (Harlan-Sprague-Dawley) received bilateral, intramuscular (rectus femoris) injections (50 μl/leg) containing plasmid DNA encoding pp65, gB, or pp65 and gB with or without CRL 1005 (the VF-P1205-02A formulation) on days 0, 21, and 49. Each mouse received 200 μg of DNA per vaccination. For formulations containing a single gB or pp65 coding plasmid, 100 μg of blank DNA (VCL10551) was added to yield a 200 μg dose of total DNA. The effect of the blank DNA was tested by vaccinating mice with 100 μg of the single plasmid DNAs delivered with or without CRL 1005 in the absence of the blank DNA. Splenocytes were harvested beginning day 66 and pp65-specific T cell responses were analyzed by IFN-γ ELISpot as above. Based on previous results, no pp65-specific T cell responses were anticipated for mice vaccinated with gB+blank DNA or gB+blank DNA+CRL 1005. Therefore, these mice were not evaluated in the ELISpot assays. Statistically significant differences between the mean T cell responses of vaccinated mice versus pp65+gB was determined using a Student's t-test with α=0.05.

TABLE 22

T Cell Responses to CMV pp65 Peptide Pool I

| DNA Vaccine | Mean SFU/$10^6$ Cells | Fold Increase versus pp65 + gB | p-value |
|---|---|---|---|
| pp65 + gB | 783 | — | — |
| pp65 + gB + CRL 1005 | 1360 | 1.7 | 0.03 |
| pp65 + Blank | 1265 | 1.6 | 0.02 |
| pp65 + Blank + CRL 1005 | 1308 | 1.7 | 0.03 |
| pp65 | 1184 | 1.5 | NS |
| pp65 + CRL 1005 | 1767 | 2.3 | 0.01 |

NS = not significant

TABLE 23

T Cell Responses to CMV pp65 Peptide Pool II

| DNA Vaccine | Mean SFU/$10^6$ Cells | Fold Increase versus pp65 + gB | p-value |
|---|---|---|---|
| pp65 + gB | 234 | — | — |
| pp65 + gB + CRL 1005 | 544 | 2.3 | 0.04 |
| pp65 + Blank | 496 | 2.1 | 0.04 |
| pp65 + Blank + CRL 1005 | 651 | 2.8 | 0.008 |
| pp65 | 581 | 2.5 | 0.02 |
| pp65 + CRL 1005 | 704 | 3.0 | 0.01 |

Example 12

Vaccine Combinations

DNA and Protein Combination

General Experimental Procedure

The experimental procedure for the following example is as described above, with particular parameters and materials employed as described herein.

Vaccination Regimen

BALB/c female mice, 6/group, were injected in each rectus femoris with 20 μg of HCMV bivalent DNA vaccine in a 50 μl volume+/−poloxamer VF-P1205-02A ("02A"), DMRIE:DOPE, ("D/D") and/or gB protein as indicated below. Plasmid VR6365 encodes HCMV gB, plasmid VR6368 encodes HCMV pp65. Full-length gB protein purified from CHO cells was obtained from Austral Biologicals. (San Ramon, Calif.). Mice received injections on days 0 and 14 and were bled for determination of gB antibody titers on day 13 and day 26. Splenocytes from two mice per group were harvested on days 26, 27, and 28 for pp65 IFN-γ ELISpot analyses (splenocytes from individual mice were assayed, n=6 per group).

TABLE 24

Immunization Schedule

| Group | DNA (total/injection/mouse) |
|---|---|
| A | 10 µg VR 6368 + 10 µg VR6365 + 02A |
| B | 10 µg VR 6368 + 10 µg VR6365 + 02A + 4.5 µg gB protein |
| C | 10 µg VR 6368 + 10 µg VR6365 + 02A + 1.5 µg gB protein |
| D | 10 µg VR 6368 + 10 µg VR6365 + 02A + 0.5 µg gB protein |
| E | 10 µg VR 6368 + 10 µg VR6365 + D/D + 4.5 µg gB protein |
| F | 10 µg VR 6368 + 10 µg VR6365 |

Recombinant gB Enzyme Linked Immunosorbent Assay (ELISA)

The ELISA for detecting gB specific serum antibodies was performed with 96 well Costar ½ well EIA plates coated with recombinant CMV gB at a concentration of 0.1 µg/well in borate buffered saline (BBS) buffer. After coating with antigen, the plates were sealed and incubated at 4° C. overnight. Plates were washed 4× with BBS containing 0.1% Tween-20 (BBST) using an automated plate washer. Non-specific binding was blocked by incubating plates for 1 hr at room temperature with 100 µL of assay buffer (10% fetal calf serum in BBS). Blocking buffer was then decanted and serially diluted sera (diluted in assay buffer) added at 50 µl/well. Plates were sealed, incubated at room temperature for 2 hours, then washed 4× with BBS containing 0.1% Tween-20 (BBST) using an automated plate washer. Goat anti-mouse IgG Fc specific secondary antibody diluted at 1:5000 in assay buffer was added at 50 µl/well; plates were sealed and incubated at room temperature for 2 hours. Plates were washed 4× with BBS containing 0.1% Tween-20 (BBST) using an automated plate washer. Substrate, consisting of p-nitrophenylphosphate at 1 mg/ml in 50 nM Sodium Bicarbonate buffer, pH 9.8 and $MgCl_2$ at 1 mM was added at 50 µl/well, plates were sealed and incubated at room temperature for 60 minutes. Absorbance of each well was determined at 405 nm. Endpoint titer=the reciprocal of the last dilution resulting in a mean absorbance value that is greater than or equal to twice the mean absorbance value of background wells.

TABLE 25

Anti-gB IgG Titers and ELISpot Results

| Group | HCMV pp65 SFU/10$^6$ splenocytes | HCMV gB antibody titers Day 13 | HCMV gB antibody titers Day 26 |
|---|---|---|---|
| A | 368 | 325 | 5867 |
| B | 576 | 467 | 22400 |
| C | 451 | 717 | 25600 |
| D | 260 | 500 | 14400 |
| E | 523 | 1800 | 187733 |
| F | 465 | 75 | 1867 |

Adding gB protein to the bivalent gB, pp65 DNA vaccine formulated in poloxamer increased the anti-gB antibody response up to 14-fold vs. the bivalent vaccine alone (bivalent vaccine+02A+1.5 µg gB protein (Group C) vs. bivalent vaccine alone (Group F), p=0.005) and up to 4-fold vs. bivalent DNA in poloxamer (bivalent vaccine+02A+1.5 µg gB protein (Group C) vs. bivalent vaccine+02A (Group A), p=0.01). Adding gB protein to the bivalent DNA vaccine formulated in cationic lipid increased the anti-gB antibody response 101-fold vs. bivalent vaccine alone (bivalent vaccine+D/D+4.5 µg gB protein (Group E) vs. bivalent vaccine alone (Group F), p=0.00006) and 32-fold vs. bivalent DNA in poloxamer (bivalent vaccine+D/D+4.5 µg gB protein (Group E) vs. bivalent vaccine+02A (Group A), p=0.00005). The pp65 response was similar for all groups indicating that combining protein with the bivalent DNA vaccine to improve the antibody component of the response did not decrease the cellular component of the response.

Example 13

Vaccine Combinations

Trivalent Vaccine Combination

Vaccination Regimen

Groups of 10 mice were injected in each rectus femoris with 50 µL of PBS containing multiple DNA plasmids as shown below. Plasmid VR6365 encodes HCMV gB, Plasmid VR6368 encodes HCMV pp65, Plasmid VR6250 encodes HCMV IE1, and "blank" refers to an equivalent plasmid backbone but lacking any antigen coding sequence. All DNA was formulated with the "02A" poloxamer based formulation as described in Example 4. Two sets of injections were given on days 0 and 14. Serum was drawn at day 26 for determination of gB antibody titers.

TABLE 26

Immunization Schedule

| Group | Dose (per leg) |
|---|---|
| A | 6.6 µgr VR6368 (pp65) + 6.6 µgr VR6250 (IE1) + 6.6 µgr VR6365 (gB) |
| B | 6.6 µgr VR6368 (pp65) + 6.6 µgr blank + 6.6 µgr VR6365 (gB) |
| C | 6.6 µgr blank + 6.6 µgr VR6250 (IE1) + 6.6 µgr VR6365 (gB) |

Recombinant gB Enzyme Linked Immunosorbent Assay (ELISA)

Sera were collected from the vaccinated mice according to the regimen described in Example 7 above. Anti-gB IgG titers were determined using a recombinant CMV gB Enzyme Linked Immunosorbent Assay (ELISA), as described in Example 12 above.

IFN-γ ELISpot Assay

Spleens were harvested for analysis of antigen specific, IFN-γ secreting, T-cell responses on days 27-29. Two spleens from each group were pooled for the assay. Two pools from each group were analyzed on days 27 and 28, one pool from each group was analyzed on day 29. Splenocytes were processed and analyzed for pp65 reactivity by ELISpot assay as described in Example 7. Splenocytes were analyzed for IE1 reactivity by ELISpot assay as described for pp65 ELISpot assay except, splenocytes were stimulated with a pool of 98 overlapping 15 mer peptides (overlapping by 11 amino acids) that span the entire IE1 protein encoded on the VR6250 construct. (See Example 3).

TABLE 27

Anti-gB IgG Titers and ELISpot Results

| Analysis | Group A | Group B | Group C |
|---|---|---|---|
| gB antibody titer | 18,560 | 24,320 | 62,720 |
| pp65 ELISpot | 348 | 231 | 1 |

TABLE 27-continued

Anti-gB IgG Titers and ELISpot Results

| Analysis | Group A | Group B | Group C |
|---|---|---|---|
| (SFU/$10^6$ splenocytes) | | | |
| IE1 ELISpot (SFU/$10^6$ splenocytes) | 218 | 1 | 319 |

Earlier experiments showed that administering each antigen encoding DNA alone elicits an immune response in vivo. The present data show that each antigen encoding DNA induces a specific immunological response when combined with other antigens. Thus, combining the antigens and simultaneously administering multiple antigen encoding DNAs allows generation of immune responses to all the antigens simultaneously.

Example 14

Electrically-Assisted Plasmid Delivery

In vivo gene delivery may be enhanced through the application of brief electrical pulses to injected tissues, a procedure referred to herein as electrically-assisted plasmid delivery. See, e.g., Aihara, H. & Miyazaki, J. *Nat. Biotechnol*. 16:867-70 (1998); Mir, L. M. et al., *Proc. Natl Acad. Sci. USA* 96:4262-67 (1999); Hartikka, J. et al.; *Mol. Ther*. 4:407-15 (2001); and Mir, L. M. et al.; Rizzuto, G. et al., *Hum Gene Ther* 11:1891-900 (2000); Widera, G. et al, *J. of Immuno*. 164: 4635-4640 (2000). The use of electrical pulses for cell electropermeabilization has been used to introduce foreign DNA into prokaryotic and eukaryotic cells in vitro. Cell permeabilization can also be achieved locally, in vivo, using electrodes and optimal electrical parameters that are compatible with cell survival.

The electroporation procedure can be performed with various electroporation devices. These devices include external plate type electrodes or invasive needle/rod electrodes and can possess two electrodes or multiple electrodes placed in an array. Distances between the plate or needle electrodes can vary depending upon the number of electrodes, size of target area and treatment subject.

The TriGrid needle array, as described herein, is a three electrode array comprising three elongate electrodes in the approximate shape of a geometric triangle. Needle arrays may include single, double, three, four, five, six or more needles arranged in various array formations. The electrodes are connected through conductive cables to a high voltage switching device that is connected to a power supply.

The electrode array is placed into the muscle tissue, around the site of nucleic acid injection, to a depth of approximately 3 mm to 3 cm. The depth of insertion varies depending upon the target tissue and size of patient receiving electroporation. After injection of foreign nucleic acid, such as plasmid DNA, and a period of time sufficient for distribution of the nucleic acid, square wave electrical pulses are applied to the tissue. The amplitude of each pulse ranges from about 100 volts to about 1500 volts, e.g., about 100 volts, about 200 volts, about 300 volts, about 400 volts, about 500 volts, about 600 volts, about 700 volts, about 800 volts, about 900 volts, about 1000 volts, about 1100 volts, about 1200 volts, about 1300 volts, about 1400 volts, or about 1500 volts or about 1-1.5 kV/cm, based on the spacing between electrodes. Each pulse has a duration of about 1 μs to about 1000 μs, e.g., about 1 μs, about 10 μs, about 50 μs, about 100 μs, about 200 μs, about 300 μs, about 400 μs, about 500 μs, about 600 μs, about 700 μs, about 800 μs, about 900 μs, or about 1000 μs, and a pulse frequency on the order of about 1-10 Hz. The polarity of the pulses may be reversed during the electroporation procedure by switching the connectors to the pulse generator. Pulses are repeated multiple times. The electroporation parameters (e.g. voltage amplitude, duration of pulse, number of pulses, depth of electrode insertion and frequency) will vary based on target tissue type, number of electrodes used and distance of electrode spacing, as would be understood by one of ordinary skill in the art.

Immediately after completion of the pulse regimen, subjects receiving electroporation can be optionally treated with membrane stabilizing agents to prolong cell membrane permeability as a result of the electroporation. Examples of membrane stabilizing agents include, but are not limited to, steroids (e.g. dexamethasone, methylprednisone and progesterone), angiotensin II and vitamin E. A single dose of dexamethasone, approximately 0.1 mg per kilogram of body weight, should be sufficient to achieve a beneficial affect.

EAPD techniques such as electroporation can also be used for plasmids contained in liposome formulations. The liposome-plasmid suspension is administered to the animal or patient and the site of injection is treated with a safe but effective electrical field generated, for example, by a TriGrid needle array, or a four needle array. The electroporation may aid in plasmid delivery to the cell by destabilizing the liposome bilayer so that membrane fusion between the liposome and the target cellular structure occurs. Electroporation may also aid in plasmid delivery to the cell by triggering the release of the plasmid, in high concentrations, from the liposome at the surface of the target cell so that the plasmid is driven across the cell membrane by a concentration gradient via the pores created in the cell membrane as a result of the electroporation.

Electroporation Study in Rabbits

Electroporation assisted DNA vaccine delivery was compared to DNA formulated with DMRIE:DOPE or CRL 1005 and DNA in PBS in a New Zealand White Rabbit model using CMV gB DNA. Rabbits (5 per group) were injected in the tibialis muscle at 0 and 28 days with 50 μg DNA/500 μl/leg. Electroporation was performed immediately after injection using the BTX-ECM830 pulse generator with a 5 mm×8.6 mm 4 needle array at 200V (232 V/cm), 60 msec, 2 pulses, and 2 Hz.

Serum endpoint titers were measured at days 2, 14, 28, 42 and 56 by gB ELISA. The ELISA for detecting gB specific serum antibodies was performed with 96 well Costar ½ well EIA plates coated with recombinant CMV gB at a concentration of 0.1 μg/well in borate buffered saline (BBS) buffer. After coating with antigen, the plates were sealed and incubated at 4° C. overnight. Plates were washed 4× with BBS containing 0.1% Tween-20 (BBST) using an automated plate washer. Non-specific binding was blocked by incubating plates for 1 hr at room temperature with 100 μL of assay buffer (10% fetal calf serum in BBS). Blocking buffer was then decanted and serially diluted sera (diluted in assay buffer) added at 50 μl/well. Plates were sealed, incubated at room temperature for 2 hours, then washed 4× with BBS containing 0.1% Tween-20 (BBST) using an automated plate washer. Goat anti-rabbit IgG Fc specific secondary antibody diluted at 1:5000 in assay buffer was added at 50 μl/well; plates were sealed and incubated at room temperature for 2 hours. Plates were washed 4× with BBS containing 0.1% Tween-20 (BBST) using an automated plate washer. Substrate, consisting of p-nitrophenylphosphate at 1 mg/ml in 50 nM Sodium Bicarbonate buffer, pH 9.8 and MgCl$_2$ at 1 mM was added at 50 µl/well, plates were sealed and incubated at room temperature for 60 minutes. Absorbance was determined at 405 nm using an automated 96 well plate reader. Endpoint titer=the reciprocal of the last dilution resulting in a mean absorbance value that is greater than or equal to twice the mean absorbance value of background wells.

TABLE 28

Serum endpoint titers

| Group | Pre-bleed | Day 14 | Day 28 | Day 42 | Day 56 |
|---|---|---|---|---|---|
| CRL 1005 | 140 | 420 | 4830 | 46720 | 55040 |
| DMRIE: DOPE | 240 | 1360 | 5120 | 354987 | 218453 |
| PBS + Electroporation | 180 | 79360 | 221867 | 2703360 | 1884160 |
| PBS | 115 | 135 | 2240 | 35840 | 35840 |

The mean anti-gB titers for the CRL 1005 group were slightly higher (up to 3 fold higher) than the titers for the PBS group, but the differences were not statistically significant at any time point. The mean anti-gB titers for the DMRIE: DOPE group were 2-10 fold higher (p<0.05 at all post-injection time points) than for gB DNA in PBS. Electroporation after injection of gB DNA in PBS increased anti-gB titers 53-588 fold over gB DNA in PBS without electroporation (p<0.05 at all post-injection time points), 34-189 fold over the CRL 1005 group (p<0.05 at all post-injection time points) and 8-58 fold over the DMRIE:DOPE group (p<0.05 at all post-injection time points).

Example 15

Treating Patients Using Compositions Comprising Human Codon-Optimized HCMV pp65 and gB, and Fragments and Variants Thereof The plasmid immunotherapeutic products are produced according to current FDA Good Manufacturing Procedures (GMP) and are administered to human subjects under an approved Investigational New Drug application.

A. Initial Studies

Thirty-two healthy adults are immunized by i.m. injection with 0.5 mg or 2.5 mg each of plasmid DNA encoding optimized gB and pp65 on separate plasmids at 0, 2, and 8 weeks. Blood samples are drawn preimmunization and at 2, 4, 8, 10, and 16 weeks for immunogenicity studies, including ELISpot assays to measure CD4+ and CD8+ T cell responses and antibody titers for HCMV gB.

B. Administration to Hematopoetic Stem Cell (HSC) Transplant Donors and Recipients Following the procedures above, healthy HSC donors are immunized with the plasmid compositions at 4 and 2 weeks prior to donation. Immunogenicity assays are performed using blood drawn from the donors at preimmunization, and every two weeks for 16 weeks post immunization. Recipients are divided into two groups. The first group receives the HSC from the immunized donors, but not be immunized themselves. The second group receives the HSC from the immunized donors and are immunized with the same plasmid compositions as the donors approximately four weeks after HSC transplantation, and immunogenicity assays are performed at pretransplantation and every two weeks as above. Immunizations may be repeated every two weeks for both donors and recipients.

What is claimed is:

1. An isolated polynucleotide comprising a nucleotide sequence comprising SEQ ID NO:13 and either SEQ ID NO:5, or an isolated polynucleotide comprising a nucleotide sequence encoding the amino acid sequence of SEQ ID NO:6.

2. The polynucleotide of claim 1, further comprising SEQ ID NO:28 or 30.

3. A composition comprising: (a) an isolated polynucleotide comprising SEQ ID NO:13 and (b) either an isolated polynucleotide comprising SEQ ID NO:5 or an isolated polynucleotide comprising a polynucleotide encoding the amino acid sequence of SEQ ID NO:6.

4. The composition of claim 3, wherein the nucleotide sequence encoding SEQ ID NO:6 is human codon-optimized.

5. The composition of claim 3, further comprising an isolated polynucleotide comprising a polynucleotide encoding IE1, an immunogenic fragment, variant, or derivative thereof.

6. The composition of claim 5, wherein the polynucleotide comprises SEQ ID NO:28 or 30.

7. An isolated polynucleotide comprising SEQ ID NO:28 or 30.

8. A composition comprising a plasmid comprising SEQ ID NO:28, and an isolated polynucleotide comprising SEQ ID NO:5 or an isolated polynucleotide comprising a nucleotide sequence encoding the amino acid sequence of SEQ ID NO:6.

9. A method of eliciting an immune response to human cytomegalovirus (CMV) in a human or in a human tissue comprising administering an effective amount of the polynucleotide of claim 1.

10. The method of claim 9, further comprising administering an effective amount of SEQ ID NO:28 or 30.

* * * * *

SEQUENCE LISTING

```
<160> NUMBER OF SEQ ID NOS: 50

<210> SEQ ID NO 1
<211> LENGTH: 1683
<212> TYPE: DNA
<213> ORGANISM: Human cytomegalovirus
<220> FEATURE:
<221> NAME/KEY: CDS
<222> LOCATION: (1)..(1683)

<400> SEQUENCE: 1 atg gag tcg cgc ggt cgc cgt tgt ccc gaa atg ata tcc gta ctg ggt      48
Met Glu Ser Arg Gly Arg Arg Cys Pro Glu Met Ile Ser Val Leu Gly
1               5                   10                  15 ccc att tcg ggg cac gtg ctg aaa gcc gtg ttt agt cgc ggc gat acg      96
Pro Ile Ser Gly His Val Leu Lys Ala Val Phe Ser Arg Gly Asp Thr
            20                  25                  30 ccg gtg ctg ccg cac gag acg cga ctc ctg cag acg ggt atc cac gta     144
Pro Val Leu Pro His Glu Thr Arg Leu Leu Gln Thr Gly Ile His Val
        35                  40                  45 cgc gtg agc cag ccc tcg ctg atc ttg gta tcg cag tac acg ccc gac     192
Arg Val Ser Gln Pro Ser Leu Ile Leu Val Ser Gln Tyr Thr Pro Asp
    50                  55                  60 tcg acg cca tgc cac cgc ggc gac aat cag ctg cag gtg cag cac acg     240
Ser Thr Pro Cys His Arg Gly Asp Asn Gln Leu Gln Val Gln His Thr
65                  70                  75                  80 tac ttt acg ggc agc gag gtg gag aac gtg tcg gtc aac gtg cac aac     288
Tyr Phe Thr Gly Ser Glu Val Glu Asn Val Ser Val Asn Val His Asn
                85                  90                  95
```

```
ccc acg ggc cga agc atc tgc ccc agc cag gag ccc atg tcg atc tat      336
Pro Thr Gly Arg Ser Ile Cys Pro Ser Gln Glu Pro Met Ser Ile Tyr
            100                 105                 110 gtg tac gcg ctg ccg ctc aag atg ctg aac atc ccc agc atc aac gtg      384
Val Tyr Ala Leu Pro Leu Lys Met Leu Asn Ile Pro Ser Ile Asn Val
        115                 120                 125 cac cac tac ccg tcg gcg gcc gag cgc aaa cac cga cac ctg ccc gta      432
His His Tyr Pro Ser Ala Ala Glu Arg Lys His Arg His Leu Pro Val
    130                 135                 140 gct gac gct gtg att cac gcg tcg ggc aag cag atg tgg cag gcg cgt      480
Ala Asp Ala Val Ile His Ala Ser Gly Lys Gln Met Trp Gln Ala Arg
145                 150                 155                 160 ctc acg gtc tcg gga ctg gcc tgg acg cgt cag cag aac cag tgg aaa      528
Leu Thr Val Ser Gly Leu Ala Trp Thr Arg Gln Gln Asn Gln Trp Lys
                165                 170                 175 gag ccc gac gtc tac tac acg tca gcg ttc gtg ttt ccc acc aag gac      576
Glu Pro Asp Val Tyr Tyr Thr Ser Ala Phe Val Phe Pro Thr Lys Asp
            180                 185                 190 gtg gca ctg cgg cac gtg gtg tgc gcg cac gag ctg gtt tgc tcc atg      624
Val Ala Leu Arg His Val Val Cys Ala His Glu Leu Val Cys Ser Met
        195                 200                 205 gag aac acg cgc gca acc aag atg cag gtg ata ggt gac cag tac gtc      672
Glu Asn Thr Arg Ala Thr Lys Met Gln Val Ile Gly Asp Gln Tyr Val
    210                 215                 220 aag gtg tac ctg gag tcc ttc tgc gag gac gtg ccc tcc ggc aag ctc      720
Lys Val Tyr Leu Glu Ser Phe Cys Glu Asp Val Pro Ser Gly Lys Leu
225                 230                 235                 240 ttt atg cac gtc acg ctg ggc tct gac gtg gaa gag gac ctg acg atg      768
Phe Met His Val Thr Leu Gly Ser Asp Val Glu Glu Asp Leu Thr Met
                245                 250                 255 acc cgc aac ccg caa ccc ttc atg cgc ccc cac gag cgc aac ggc ttt      816
Thr Arg Asn Pro Gln Pro Phe Met Arg Pro His Glu Arg Asn Gly Phe
            260                 265                 270 acg gtg ttg tgt ccc aaa aat atg ata atc aaa ccg ggc aag atc tcg      864
Thr Val Leu Cys Pro Lys Asn Met Ile Ile Lys Pro Gly Lys Ile Ser
        275                 280                 285 cac atc atg ctg gat gtg gct ttt acc tca cac gag cat ttt ggg ctg      912
His Ile Met Leu Asp Val Ala Phe Thr Ser His Glu His Phe Gly Leu
    290                 295                 300 ctg tgt ccc aag agc atc ccg ggc ctg agc atc tca ggt aac ctg ttg      960
Leu Cys Pro Lys Ser Ile Pro Gly Leu Ser Ile Ser Gly Asn Leu Leu
305                 310                 315                 320 atg aac ggg cag cag atc ttc ctg gag gta caa gcc ata cgc gag acc     1008
Met Asn Gly Gln Gln Ile Phe Leu Glu Val Gln Ala Ile Arg Glu Thr
                325                 330                 335 gtg gaa ctg cgt cag tac gat ccc gtg gct gcg ctc ttt ttc gat         1056
Val Glu Leu Arg Gln Tyr Asp Pro Val Ala Ala Leu Phe Phe Phe Asp
            340                 345                 350 atc gac ttg ctg ctg cag cgc ggg cct cag tac agc gag cac ccc acc     1104
Ile Asp Leu Leu Leu Gln Arg Gly Pro Gln Tyr Ser Glu His Pro Thr
        355                 360                 365 ttc acc agc cag tat cgc atc cag ggc aag ctt gag tac cga cac acc     1152
Phe Thr Ser Gln Tyr Arg Ile Gln Gly Lys Leu Glu Tyr Arg His Thr
    370                 375                 380 tgg gac cgg cac gac gag ggt gcc gcc cag ggc gac gac gac gtc tgg     1200
Trp Asp Arg His Asp Glu Gly Ala Ala Gln Gly Asp Asp Asp Val Trp
385                 390                 395                 400 acc agc gga tcg gac tcc gac gaa gaa ctc gta acc acc gag cgc aag     1248
Thr Ser Gly Ser Asp Ser Asp Glu Glu Leu Val Thr Thr Glu Arg Lys
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     | 405 |     |     |     |     | 410 |     |     |     |     | 415 |     |      |
| acg | ccc | cgc | gtc | acc | ggc | ggc | ggc | gcc | atg | gcg | ggc | gcc | tcc | act | tcc  | 1296 |
| Thr | Pro | Arg | Val | Thr | Gly | Gly | Gly | Ala | Met | Ala | Gly | Ala | Ser | Thr | Ser  |
|     |     | 420 |     |     |     |     | 425 |     |     |     |     | 430 |     |     |      |
| gcg | ggc | cgc | aaa | cgc | aaa | tca | gca | tcc | tcg | gcg | acg | gcg | tgc | acg | tcg  | 1344 |
| Ala | Gly | Arg | Lys | Arg | Lys | Ser | Ala | Ser | Ser | Ala | Thr | Ala | Cys | Thr | Ser  |
|     | 435 |     |     |     |     | 440 |     |     |     |     | 445 |     |     |     |      |
| ggc | gtt | atg | aca | cgc | ggc | cgc | ctt | aag | gcc | gag | tcc | acc | gtc | gcg | ccc  | 1392 |
| Gly | Val | Met | Thr | Arg | Gly | Arg | Leu | Lys | Ala | Glu | Ser | Thr | Val | Ala | Pro  |
| 450 |     |     |     |     | 455 |     |     |     |     | 460 |     |     |     |     |      |
| gaa | gag | gac | acc | gac | gag | gat | tcc | gac | aac | gaa | atc | cac | aat | ccg | gcc  | 1440 |
| Glu | Glu | Asp | Thr | Asp | Glu | Asp | Ser | Asp | Asn | Glu | Ile | His | Asn | Pro | Ala  |
| 465 |     |     |     | 470 |     |     |     |     | 475 |     |     |     |     | 480 |      |
| gtg | ttc | acc | tgg | ccg | ccc | tgg | cag | gcc | ggc | atc | ctg | gcc | cgc | aac | ctg  | 1488 |
| Val | Phe | Thr | Trp | Pro | Pro | Trp | Gln | Ala | Gly | Ile | Leu | Ala | Arg | Asn | Leu  |
|     |     |     |     | 485 |     |     |     |     | 490 |     |     |     |     | 495 |      |
| gtg | ccc | atg | gtg | gct | acg | gtt | cag | ggt | cag | aat | ctg | aag | tac | cag | gaa  | 1536 |
| Val | Pro | Met | Val | Ala | Thr | Val | Gln | Gly | Gln | Asn | Leu | Lys | Tyr | Gln | Glu  |
|     |     |     | 500 |     |     |     |     | 505 |     |     |     |     | 510 |     |      |
| ttc | ttc | tgg | gac | gcc | aac | gac | atc | tac | cgc | atc | ttc | gcc | gaa | ttg | gaa  | 1584 |
| Phe | Phe | Trp | Asp | Ala | Asn | Asp | Ile | Tyr | Arg | Ile | Phe | Ala | Glu | Leu | Glu  |
|     |     | 515 |     |     |     |     | 520 |     |     |     |     | 525 |     |     |      |
| ggc | gta | tgg | cag | ccc | gct | gcg | caa | ccc | aaa | cgt | cgc | cgc | cac | cgg | caa  | 1632 |
| Gly | Val | Trp | Gln | Pro | Ala | Ala | Gln | Pro | Lys | Arg | Arg | Arg | His | Arg | Gln  |
|     | 530 |     |     |     |     | 535 |     |     |     |     | 540 |     |     |     |      |
| gac | gcc | ttg | ccc | ggg | cca | tgc | atc | gcc | tcg | acg | ccc | aaa | aag | cac | cga  | 1680 |
| Asp | Ala | Leu | Pro | Gly | Pro | Cys | Ile | Ala | Ser | Thr | Pro | Lys | Lys | His | Arg  |
| 545 |     |     |     |     | 550 |     |     |     |     | 555 |     |     |     |     | 560  |
| ggt |     |     |     |     |     |     |     |     |     |     |     |     |     |     |      | 1683 |
| Gly |     |     |     |     |     |     |     |     |     |     |     |     |     |     |      |

<210> SEQ ID NO 2
<211> LENGTH: 561
<212> TYPE: PRT
<213> ORGANISM: Human cytomegalovirus

<400> SEQUENCE: 2

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Asn Gln Trp Lys
           165                 170                 175

Glu Pro Asp Val Tyr Tyr Thr Ser Ala Phe Val Phe Pro Thr Lys Asp
       180                 185                 190

Val Ala Leu Arg His Val Val Cys Ala His Glu Leu Val Cys Ser Met
   195                 200                 205

Glu Asn Thr Arg Ala Thr Lys Met Gln Val Ile Gly Asp Gln Tyr Val
210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
               245                 250                 255

Thr Arg Asn Pro Gln Pro Phe Met Arg Pro His Glu Arg Asn Gly Phe
           260                 265                 270

Thr Val Leu Cys Pro Lys Asn Met Ile Ile Lys Pro Gly Lys Ile Ser
       275                 280                 285

His Ile Met Leu Asp Val Ala Phe Thr Ser His Glu His Phe Gly Leu
   290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
               325                 330                 335

Val Glu Leu Arg Gln Tyr Asp Pro Val Ala Ala Leu Phe Phe Phe Asp
           340                 345                 350

Ile Asp Leu Leu Leu Gln Arg Gly Pro Gln Tyr Ser Glu His Pro Thr
       355                 360                 365

Phe Thr Ser Gln Tyr Arg Ile Gln Gly Lys Leu Glu Tyr Arg His Thr
   370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
               405                 410                 415

Thr Pro Arg Val Thr Gly Gly Gly Ala Met Ala Gly Ala Ser Thr Ser
           420                 425                 430

Ala Gly Arg Lys Arg Lys Ser Ala Ser Ser Ala Thr Ala Cys Thr Ser
       435                 440                 445

Gly Val Met Thr Arg Gly Arg Leu Lys Ala Glu Ser Thr Val Ala Pro
   450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
               485                 490                 495

Val Pro Met Val Ala Thr Val Gln Gly Gln Asn Leu Lys Tyr Gln Glu
           500                 505                 510

Phe Phe Trp Asp Ala Asn Asp Ile Tyr Arg Ile Phe Ala Glu Leu Glu
       515                 520                 525

Gly Val Trp Gln Pro Ala Ala Gln Pro Lys Arg Arg Arg His Arg Gln
   530                 535                 540

Asp Ala Leu Pro Gly Pro Cys Ile Ala Ser Thr Pro Lys Lys His Arg
545                 550                 555                 560

Gly

<210> SEQ ID NO 3

```
<211> LENGTH: 1683
<212> TYPE: DNA
<213> ORGANISM: Artificial Sequence
<220> FEATURE:
<223> OTHER INFORMATION: codon-optimized sequence of hCMV pp65
<220> FEATURE:
<221> NAME/KEY: CDS
<222> LOCATION: (1)..(1683)

<400> SEQUENCE: 3 atg gag tcc cgc ggt cgc cgc tgt ccc gaa atg ata tcc gta ctg ggt      48
Met Glu Ser Arg Gly Arg Arg Cys Pro Glu Met Ile Ser Val Leu Gly
1               5                   10                  15 ccc att tcc ggg cac gtg ctg aaa gcc gtg ttt agt cgc ggc gat acc      96
Pro Ile Ser Gly His Val Leu Lys Ala Val Phe Ser Arg Gly Asp Thr
            20                  25                  30 ccc gtg ctg ccc cac gag acc cga ctc ctg cag acc ggt atc cac gta     144
Pro Val Leu Pro His Glu Thr Arg Leu Leu Gln Thr Gly Ile His Val
        35                  40                  45 cgc gtg agc cag ccc tcc ctg atc ttg gta tcc cag tac acc ccc gac     192
Arg Val Ser Gln Pro Ser Leu Ile Leu Val Ser Gln Tyr Thr Pro Asp
    50                  55                  60 tcc acc cca tgc cac cgc ggc gac aat cag ctg cag gtg cag cac acc     240
Ser Thr Pro Cys His Arg Gly Asp Asn Gln Leu Gln Val Gln His Thr
65                  70                  75                  80 tac ttt acc ggc agc gag gtg gag aac gtg tcc gtc aac gtg cac aac     288
Tyr Phe Thr Gly Ser Glu Val Glu Asn Val Ser Val Asn Val His Asn
                85                  90                  95 ccc acc ggc cga agc atc tgc ccc agc cag gag ccc atg tcc atc tat     336
Pro Thr Gly Arg Ser Ile Cys Pro Ser Gln Glu Pro Met Ser Ile Tyr
            100                 105                 110 gtg tac gcc ctg ccc ctc aag atg ctg aac atc ccc agc atc aac gtg     384
Val Tyr Ala Leu Pro Leu Lys Met Leu Asn Ile Pro Ser Ile Asn Val
        115                 120                 125 cac cac tac ccc tcc gcc gcc gag cgc aaa cac cga cac ctg ccc gta     432
His His Tyr Pro Ser Ala Ala Glu Arg Lys His Arg His Leu Pro Val
    130                 135                 140 gct gac gct gtg att cac gcc tcc ggc aag cag atg tgg cag gcc cgc     480
Ala Asp Ala Val Ile His Ala Ser Gly Lys Gln Met Trp Gln Ala Arg
145                 150                 155                 160 ctc acc gtc tcc gga ctg gcc tgg acc cgc cag cag aac cag tgg aaa     528
Leu Thr Val Ser Gly Leu Ala Trp Thr Arg Gln Gln Asn Gln Trp Lys
                165                 170                 175 gag ccc gac gtc tac tac acc tca gcc ttc gtg ttt ccc acc aag gac     576
Glu Pro Asp Val Tyr Tyr Thr Ser Ala Phe Val Phe Pro Thr Lys Asp
            180                 185                 190 gtg gca ctg cgg cac gtg gtg tgc gcc cac gag ctg gtt tgc tcc atg     624
Val Ala Leu Arg His Val Val Cys Ala His Glu Leu Val Cys Ser Met
        195                 200                 205 gag aac acc cgc gca acc aag atg cag gtg ata ggt gac cag tac gtc     672
Glu Asn Thr Arg Ala Thr Lys Met Gln Val Ile Gly Asp Gln Tyr Val
    210                 215                 220 aag gtg tac ctg gag tcc ttc tgc gag gac gtg ccc tcc ggc aag ctc     720
Lys Val Tyr Leu Glu Ser Phe Cys Glu Asp Val Pro Ser Gly Lys Leu
225                 230                 235                 240 ttt atg cac gtc acc ctg ggc tct gac gtg gaa gag gac ctg acc atg     768
Phe Met His Val Thr Leu Gly Ser Asp Val Glu Glu Asp Leu Thr Met
                245                 250                 255 acc cgc aac ccc caa ccc ttc atg cgc ccc cac gag cgc aac ggc ttt     816
Thr Arg Asn Pro Gln Pro Phe Met Arg Pro His Glu Arg Asn Gly Phe
            260                 265                 270
```

| | | |
|---|---|---|
| acc gtg ttg tgt ccc aaa aat atg ata atc aaa ccc ggc aag atc tcc<br>Thr Val Leu Cys Pro Lys Asn Met Ile Ile Lys Pro Gly Lys Ile Ser<br>275 280 285 | | 864 |
| cac atc atg ctg gat gtg gct ttt acc tca cac gag cat ttt ggg ctg<br>His Ile Met Leu Asp Val Ala Phe Thr Ser His Glu His Phe Gly Leu<br>290 295 300 | | 912 |
| ctg tgt ccc aag agc atc ccc ggc ctg agc atc tca ggt aac ctg ttg<br>Leu Cys Pro Lys Ser Ile Pro Gly Leu Ser Ile Ser Gly Asn Leu Leu<br>305 310 315 320 | | 960 |
| atg aac ggg cag cag atc ttc ctg gag gta caa gcc ata cgc gag acc<br>Met Asn Gly Gln Gln Ile Phe Leu Glu Val Gln Ala Ile Arg Glu Thr<br>325 330 335 | | 1008 |
| gtg gaa ctg cgc cag tac gat ccc gtg gct gcc ctc ttc ttt ttc gat<br>Val Glu Leu Arg Gln Tyr Asp Pro Val Ala Ala Leu Phe Phe Phe Asp<br>340 345 350 | | 1056 |
| atc gac ttg ctg ctg cag cgc ggg cct cag tac agc gag cac ccc acc<br>Ile Asp Leu Leu Leu Gln Arg Gly Pro Gln Tyr Ser Glu His Pro Thr<br>355 360 365 | | 1104 |
| ttc acc agc cag tat cgc atc cag ggc aag ctt gag tac cga cac acc<br>Phe Thr Ser Gln Tyr Arg Ile Gln Gly Lys Leu Glu Tyr Arg His Thr<br>370 375 380 | | 1152 |
| tgg gac cgg cac gac gag ggt gcc gcc cag ggc gac gac gac gtc tgg<br>Trp Asp Arg His Asp Glu Gly Ala Ala Gln Gly Asp Asp Asp Val Trp<br>385 390 395 400 | | 1200 |
| acc agc gga tcc gac tcc gac gaa gaa ctc gta acc acc gag cgc aag<br>Thr Ser Gly Ser Asp Ser Asp Glu Glu Leu Val Thr Thr Glu Arg Lys<br>405 410 415 | | 1248 |
| acc ccc cgc gtc acc ggc ggc ggc gcc atg gcc ggc gcc tcc act tcc<br>Thr Pro Arg Val Thr Gly Gly Gly Ala Met Ala Gly Ala Ser Thr Ser<br>420 425 430 | | 1296 |
| gcc ggc cgc aaa cgc aaa tca gca tcc tcc gcc acc gcc tgc acc tcc<br>Ala Gly Arg Lys Arg Lys Ser Ala Ser Ser Ala Thr Ala Cys Thr Ser<br>435 440 445 | | 1344 |
| ggc gtt atg aca cgc ggc cgc ctt aag gcc gag tcc acc gtc gcc ccc<br>Gly Val Met Thr Arg Gly Arg Leu Lys Ala Glu Ser Thr Val Ala Pro<br>450 455 460 | | 1392 |
| gaa gag gac acc gac gag gat tcc gac aac gaa atc cac aat ccc gcc<br>Glu Glu Asp Thr Asp Glu Asp Ser Asp Asn Glu Ile His Asn Pro Ala<br>465 470 475 480 | | 1440 |
| gtg ttc acc tgg cca ccc tgg cag gcc ggc atc ctg gcc cgc aac ctg<br>Val Phe Thr Trp Pro Pro Trp Gln Ala Gly Ile Leu Ala Arg Asn Leu<br>485 490 495 | | 1488 |
| gtg ccc atg gtg gct acc gtt cag ggt cag aat ctg aag tac cag gaa<br>Val Pro Met Val Ala Thr Val Gln Gly Gln Asn Leu Lys Tyr Gln Glu<br>500 505 510 | | 1536 |
| ttc ttc tgg gac gcc aac gac atc tac cgc atc ttc gcc gaa ttg gaa<br>Phe Phe Trp Asp Ala Asn Asp Ile Tyr Arg Ile Phe Ala Glu Leu Glu<br>515 520 525 | | 1584 |
| ggc gta tgg cag ccc gct gcc caa ccc aaa cgc cgc cgc cac cgg caa<br>Gly Val Trp Gln Pro Ala Ala Gln Pro Lys Arg Arg Arg His Arg Gln<br>530 535 540 | | 1632 |
| gac gcc ttg ccc ggg cca tgc atc gcc tcc acc ccc aaa aag cac cga<br>Asp Ala Leu Pro Gly Pro Cys Ile Ala Ser Thr Pro Lys Lys His Arg<br>545 550 555 560 | | 1680 |
| ggt<br>Gly | | 1683 |

<210> SEQ ID NO 4
<211> LENGTH: 561
<212> TYPE: PRT

<213> ORGANISM: Artificial Sequence
<220> FEATURE:
<223> OTHER INFORMATION: codon-optimized sequence of hCMV pp65

<400> SEQUENCE: 4

```
Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
```

```
                385                 390                 395                 400
            Thr Ser Gly Ser Asp Ser Asp Glu Glu Leu Val Thr Thr Glu Arg Lys
                            405                 410                 415

Thr Pro Arg Val Thr Gly Gly Ala Met Ala Gly Ala Ser Thr Ser
                        420                 425                 430

Ala Gly Arg Lys Arg Lys Ser Ala Ser Ser Ala Thr Ala Cys Thr Ser
                        435                 440                 445

Gly Val Met Thr Arg Gly Arg Leu Lys Ala Glu Ser Thr Val Ala Pro
                    450                 455                 460

Glu Glu Asp Thr Asp Glu Asp Ser Asp Asn Glu Ile His Asn Pro Ala
            465                 470                 475                 480

Val Phe Thr Trp Pro Pro Trp Gln Ala Gly Ile Leu Ala Arg Asn Leu
                                485                 490                 495

Val Pro Met Val Ala Thr Val Gln Gly Gln Asn Leu Lys Tyr Gln Glu
                            500                 505                 510

Phe Phe Trp Asp Ala Asn Asp Ile Tyr Arg Ile Phe Ala Glu Leu Glu
                        515                 520                 525

Gly Val Trp Gln Pro Ala Ala Gln Pro Lys Arg Arg Arg His Arg Gln
                    530                 535                 540

Asp Ala Leu Pro Gly Pro Cys Ile Ala Ser Thr Pro Lys Lys His Arg
            545                 550                 555                 560

Gly

<210> SEQ ID NO 5
<211> LENGTH: 1671
<212> TYPE: DNA
<213> ORGANISM: Artificial Sequence
<220> FEATURE:
<223> OTHER INFORMATION: codon-optimized sequence of hCMV pp65

<400> SEQUENCE: 5
atggagtccc gcgtcgccg ctgtcccgaa atgatatccg tactgggtcc catttccggg        60
cacgtgctga agccgtgtt tagtcgcggc gataccccg tgctgcccca cgagacccga       120
ctcctgcaga ccggtatcca cgtacgcgtg agccagccct ccctgatctt ggtatcccag       180
tacacccccg actccacccc atgccaccgc ggcgacaatc agctgcaggt gcagcacacc       240
tactttaccg gcagcgaggt ggagaacgtg tccgtcaacg tgcacaaccc caccggccga       300
agcatctgcc ccagccagga gcccatgtcc atctatgtgt acgccctgcc cctcaagatg       360
ctgaacatcc ccagcatcaa cgtgcaccac tacccctccg ccgccgagcg caaacaccga       420
cacctgcccg tagctgacgc tgtgattcac gcctccggca gcagatgtg gcaggcccgc       480 ctcaccgtct ccggactggc ctggaccccg cagcagaacc agtggaaaga gcccgacgtc       540
tactacacct cagccttcgt gtttcccacc aaggacgtgg cactgcggca cgtggtgtgc       600
gcccacgagc tggtttgctc catggagaac acccgcgcaa ccaagatgca ggtgataggt       660
gaccagtacg tcaaggtgta cctggagtcc ttctgcgagg acgtgccctc cggcaagctc       720
tttatgcacg tcaccctggg ctctgacgtg aagaggacc tgaccatgac ccgcaacccc       780
caacccttca tgcgccccca cgagcgcaac ggctttaccg tgttgtgtcc caaaaatatg       840
ataatcaaac ccggcaagat ctcccacatc atgctggatg tggcttttac ctcacacgag       900
cattttgggc tgctgtgtcc caagagcatc cccggcctga acatctcagg taacctgttg       960
atgaacgggg agcagatctt cctggaggta caagccatac gcgagaccgt ggaactgcgc      1020
cagtacgatc ccgtggctgc cctcttcttt tcgatatcg acttgctgct gcagcgcggg      1080
```

```
cctcagtaca gcgagcaccc caccttcacc agccagtatc gcatccaggg caagcttgag    1140
taccgacaca cctgggaccg gcacgacgag ggtgccgccc agggcgacga cgacgtctgg    1200
accagcggat ccgactccga cgaagaactc gtaaccaccg agcgcaagac cccccgcgtc    1260
accggcggcg cgccatggcc ggcgcctcc acttccgccg gctcagcatc ctccgccacc     1320
gcctgcacct ccggcgttat gacacgcggc cgccttaagg ccgagtccac cgtcgccccc    1380
gaagaggaca ccgacgagga ttccgacaac gaaatccaca atcccgccgt gttcacctgg    1440
ccaccctggc aggccggcat cctggcccgc aacctggtgc ccatggtggc taccgttcag    1500
ggtcagaatc tgaagtacca ggaattcttc tgggacgcca acgacatcta ccgcatcttc    1560
gccgaattgg aaggcgtatg cagcccgct gcccaaccca aacgccgccg ccaccggcaa     1620
gacgccttgc ccgggccatg catcgcctcc accccaaaa agcaccgagg t               1671
```

<210> SEQ ID NO 6
<211> LENGTH: 557
<212> TYPE: PRT
<213> ORGANISM: Artificial Sequence
<220> FEATURE:
<223> OTHER INFORMATION: codon-optimized sequence of hCMV pp65

<400> SEQUENCE: 6

```
Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255
```

```
Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
        290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
            355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
            420                 425                 430

Ala Gly Ser Ala Ser Ser Ala Thr Ala Cys Thr Ser Gly Val Met Thr
        435                 440                 445

Arg Gly Arg Leu Lys Ala Glu Ser Thr Val Ala Pro Glu Glu Asp Thr
450                 455                 460

Asp Glu Asp Ser Asp Asn Glu Ile His Asn Pro Ala Val Phe Thr Trp
465                 470                 475                 480

Pro Pro Trp Gln Ala Gly Ile Leu Ala Arg Asn Leu Val Pro Met Val
                485                 490                 495

Ala Thr Val Gln Gly Gln Asn Leu Lys Tyr Gln Glu Phe Phe Trp Asp
            500                 505                 510

Ala Asn Asp Ile Tyr Arg Ile Phe Ala Glu Leu Glu Gly Val Trp Gln
            515                 520                 525

Pro Ala Ala Gln Pro Lys Arg Arg Arg His Arg Gln Asp Ala Leu Pro
530                 535                 540

Gly Pro Cys Ile Ala Ser Thr Pro Lys Lys His Arg Gly
545                 550                 555

<210> SEQ ID NO 7
<211> LENGTH: 1683
<212> TYPE: DNA
<213> ORGANISM: Artificial Sequence
<220> FEATURE:
<223> OTHER INFORMATION: codon-optimized sequence of hCMV pp65

<400> SEQUENCE: 7
atggagagca ggggcaggag gtgccccgag atgatcagcg tgctgggccc catcagcggc      60
cacgtgctga aggccgtgtt cagcaggggc gacacccccg tgctgcccca cgagaccagg     120
ctgctgcaga ccggcatcca cgtgagggtg agccagccca gcctgatcct ggtgagccag     180
tacacccccg acagcacccc ctgccacagg ggcgacaacc agctgcaggt gcagcacacc     240
tacttcaccg gcagcgaggt ggagaacgtg agcgtgaacg tgcacaaccc caccggcagg     300
agcatctgcc ccagccagga gcccatgagc atctacgtgt acgccctgcc cctgaagatg     360
```

```
ctgaacatcc ccagcatcaa cgtgcaccac taccccagcg ccgccgagag gaagcacagg      420
cacctgcccg tggccgacgc cgtgatccac gccagcggca agcagatgtg gcaggccagg      480
ctgaccgtga gcggcctggc ctggaccagg cagcagaacc agtggaagga gcccgacgtg      540
tactacacca gcgccttcgt gttccccacc aaggacgtgg ccctgaggca cgtggtgtgc      600
gcccacgagc tggtgtgcag catggagaac accagggcca ccaagatgca ggtgatcggc      660
gaccagtacg tgaaggtgta cctggagagc ttctgcgagg acgtgcccag cggcaagctg      720
ttcatgcacg tgaccctggg cagcgacgtg gaggaggacc tgaccatgac caggaacccc      780
cagcccttca tgaggcccca cgagaggaac ggcttcaccg tgctgtgccc caagaacatg      840
atcatcaagc ccggcaagat cagccacatc atgctggacg tggccttcac cagccacgag      900
cacttcggcc tgctgtgccc caagagcatc cccggcctga gcatcagcgg caacctgctg      960
atgaacggcc agcagatctt cctggaggtg caggccatca gggagaccgt ggagctgagg     1020
cagtacgacc ccgtggccgc cctgttcttc ttcgacatcg acctgctgct gcagaggggc     1080
ccccagtaca gcgagcaccc caccttcacc agccagtaca ggatccaggg caagctggag     1140
tacaggcaca cctgggacag gcacgacgag ggcgccgccc agggcgacga cgacgtgtgg     1200
accagcggca gcgacagcga cgaggagctg gtgaccaccg agaggaagac ccccagggtg     1260
accggcggcg gcgccatggc cggcgccagc accagcgccg gcaggaagag gaagagcgcc     1320
agcagcgcca ccgcctgcac cagcggcgtg atgaccaggg gcaggctgaa ggccgagagc     1380
accgtggccc ccgaggagga caccgacgag gacagcgaca cgagatccaa caccccgcc      1440 gtgttcacct ggcccccctg gcaggccggc atcctggcca ggaacctggt gcccatggtg     1500
gccaccgtgc agggccagaa cctgaagtac caggagttct ctgggacgc caacgacatc      1560 tacaggatct tcgccgagct ggagggcgtg tggcagcccg ccgcccagcc caagaggagg     1620
aggcacaggc aggacgccct gcccggcccc tgcatcgcca gcacccccaa gaagcacagg     1680
ggc                                                                    1683

<210> SEQ ID NO 8
<211> LENGTH: 1683
<212> TYPE: DNA
<213> ORGANISM: Artificial Sequence
<220> FEATURE:
<223> OTHER INFORMATION: codon-optimized sequence of hCMV pp65

<400> SEQUENCE: 8
atggagagcc gcgggagaag atgtcccgag atgatcagtg tcctgggccc aatatctggc       60
cacgtgctga aggctgtctt ctcgagggga gatacaccag ttcttcctca cgaaaccaga      120
ctgctccaga caggtattca gtccgcgtg tctcagccgt cactcatcct tgttagccag       180
tacactccgg atagtactcc atgccatagg ggcgacaacc agctccaagt tcagcatacg      240
tattttacag ggtccgaggt ggagaatgtg agcgtcaatg tgcacaaccc caccggacgt      300
tcaatatgcc catctcagga acctatgtct atctacgttt atgcactgcc tttgaagatg      360
ctgaacatcc ccagtattaa tgttcaccat tacccctctg ctgctgaacg caagcacagg      420
catctccccg tggccgacgc tgtgatccat gctagtggca aacagatgtg gcaggcacga      480
ttaacagtaa gcgggttggc atggacacgg cagcagaatc agtggaaaga gcccgacgta      540
tactatacca gtgcctttgt ctttcctacc aaggacgtcg ccttaagaca tgttgtctgc      600
gcgcacgagc tggtgtgtag catggaaaac actcgtgcaa ctaaaatgca ggtgattggc      660
gatcagtatg ttaaggtcta tctggagtca ttctgtgagg acgtcccatc cgggaaacta      720
```

```
ttcatgcacg tcactcttgg ttcggatgtg gaagaagatc tgacaatgac ccggaacccc      780 caaccctta tgcggcctca cgaacggaac gggttcacag tgctatgccc caaaaatatg       840
atcattaaac ccgtaagat atcccatatc atgctcgatg tggctttcac ctcccacgaa       900
cacttcgggc tgctgtgtcc caagtccatc ccaggactca gcatatccgg caatttattg      960
atgaacggtc aacagatctt cctggaggtg caggcaatca gagaaacagt ggaactccgc     1020
cagtatgacc ctgtggcggc tctgttttc tttgacattg atctgttgct caacgagga      1080 ccacaatatt ctgagcatcc aacatttact tcccagtacc gtatccaagg caagctcgaa     1140
tacaggcaca cgtgggacag gcacgacgag ggggctgccc aagggacga tgacgtatgg     1200 acatccggct ccgatagtga tgaggagctt gtgaccaccg agcggaagac cccaagagtg     1260
acgggcggag gtgcaatggc cggagcatct accagcgccg gcggaagcg aaaatctgcc      1320 tcatcagcaa ctgcttgcac cagcggtgta atgacgaggg gacgcctaaa ggctgagagc     1380
accgtggccc ctgaggaaga tactgacgag gactcagaca cgaaattca caatcctgcc     1440 gtgttcacat ggcctccttg gcaggccgga attctggccc ggaacttggt accgatggtg     1500
gccactgttc agggccagaa cctgaaatac caggagtttt tctgggatgc caatgacatc     1560
tacagaattt ttgcggaact ggagggagtg tggcagccag ccgcacaacc caagcgccgg     1620
cgccataggc aggatgccct gccgggccct tgcattgcga gcaccccaaa aaagcaccga     1680
ggc                                                                   1683

<210> SEQ ID NO 9
<211> LENGTH: 1683
<212> TYPE: DNA
<213> ORGANISM: Artificial Sequence
<220> FEATURE:
<223> OTHER INFORMATION: codon-optimized sequence of hCMV pp65

<400> SEQUENCE: 9
atggaatctc gaggtagacg ttgtccggag atgatcagcg tgctaggacc aataagtggg       60
cacgtcctga aggctgtgtt ttcaaggggg gatacgccag tgctcccaca cgagaccccgc     120 ctgctacaaa caggtattca cgttagggtc tcacagccca gcctaattt ggttagccag       180 tatacacccg actccacccc ttgtcatcgc ggcgacaacc agctgcaagt ccagcatact      240
tatttcacag gcagcgaggt ggaaaatgtg tcggtcaatg tgcataaccc taccgggcgt      300
tccatctgcc cttcacagga gcctatgtct atctacgtgt atgctttacc tttgaagatg      360
ttaaacatcc cctctatcaa tgtgcaccat tatccttcag cggctgagcg gaaacaccgc      420
cacttacccg tggctgacgc agtcatacac gcgagcggta agcagatgtg gcaagcacga      480
ctgacggtct ccggtctggc ttggactaga cagcagaatc agtggaagga acctgatgtg      540
tactacacca gcgcatttgt cttcccaacc aaagacgtgg cactgcgcca cgtagtgtgc      600
gcccatgaac tggtgtgttc catggagaac cccgggcaa ccaagatgca ggtaattggc       660
gatcagtatg tgaaagttta ccttgagtcc ttttgtgagg atgtacccag cggcaagctg      720
ttcatgcatg tgacgttggg cagtgacgtg gaagaggacc tgacaatgac tcgaaatcca     780
caaccattta tgaggccgca cgaaagaaac gggtttacag tgctctgccc aaagaacatg      840
atcatcaagc ccgggaagat tagtcatatt atgctcgatg ttgccttcac cagtcacgaa      900 catttttggac tcctttgccc caaatccatc ccaggcttgt caatttcagg caatctcctc     960
atgaacggac agcagatttt cctggaggtg caagcgatcc gggagactgt agagctgaga    1020
```

```
cagtatgatc ctgttgcagc cctgttcttc ttcgatatcg accttctcct tcagcgaggc    1080
ccgcagtaca gcgaacaccc aacctttaca tctcagtacc gcatccaagg gaaactggag    1140
tatcgtcata cctgggacag gcatgacgaa ggggccgctc aaggagacga tgatgtgtgg    1200
acaagtggct cggattccga tgaggagttg gtgacaaccg aaagaaagac tcccagggtt    1260
accggaggag gagcaatggc aggtgcttcc actagcgctg gcaggaaacg gaaaagcgcc    1320
tccagtgcca cagcctgcac ttctggcgtc atgacgaggg gcggctgaa agccgaatct    1380 actgtagccc ctgaggagga cactgacgag gattctgaca atgaaattca caatcccgcg    1440
gtttttacat ggccccccttg gcaggccgga attctggccc ggaaccttgt gcccatggtc    1500
gccacagtcc aaggccagaa cctgaagtac caggaatttt tctgggatgc caacgacata    1560
tacagaatct tcgcagaact ggagggagtt tggcagcccg ctgctcagcc taaacgcaga    1620
cggcacagac aggacgccct cccagggccg tgcatagcct taccccaaa gaagcaccgc    1680 ggt                                                                  1683

<210> SEQ ID NO 10
<211> LENGTH: 1683
<212> TYPE: DNA
<213> ORGANISM: Artificial Sequence
<220> FEATURE:
<223> OTHER INFORMATION: codon-optimized sequence of hCMV pp65

<400> SEQUENCE: 10
atggaatcgc gtggcaggcg atgtcccgaa atgatttcag tcttaggccc aatctccggg      60
cacgtgctca aagcagtctt ctccaggggg atacccccag tgctccctca cgagacgagg     120
cttctgcaga ccggcataca tgtcagagtt ctcagcccca gccttatttt ggtatctcag     180
tacaccccgg acagtacacc gtgtcacaga ggagacaacc agctccaagt ccagcataca     240
tacttcacag gctcggaagt ggaaaacgtg tctgtgaacg tccataaccc aactggccgg     300
tcaatttgcc cctctcagga gcctatgagt atctatgtgt atgctctgcc ctcaaaatg      360 ctgaacatcc aagtattaa tgtccatcat taccctagcg cagccgagag aaagcatcgc     420
cacctgcctg tggctgacgc tgtgatacac gcttcaggta gcaaatgtg gcaggcccgc     480 cttacagtgt ctggattggc atggacacgg cagcagaacc agtggaagga gcccgatgtg     540
tactatacta gcgcttttgt gttcccacg aaagatgtcg ccttacgaca cgttgtatgc     600
gcacacgagc tagtgtgtag tatggagaac acacgtgcca ccaaaatgca ggtcatcggc     660
gatcaatacg tcaaggtgta cctggagagt ttttgcgaag atgttccttc ggcaaattg      720 ttcatgcatg tgaccctggg ttctgatgtt gaggaggatc tgacaatgac tcgaaatccc     780
cagcctttca tgcgccctca cgaacggaac gggtttacag tgctgtgccc gaagaacatg     840
attatcaaac ccggaaaaat tcccacattt atgttggatg tagcctttac cagccatgaa     900
cacttcggac ttctctgtcc aaagtcaatt ccagggctgt ctataagcgg aaccttcta      960 atgaatggcc agcagatctt tctcgaggtg caggccataa gagagactgt ggagctccgg    1020
caatacgatc cggttgcggc cctcttcttt ttcgacatcg acctgttact gcagcgcggt    1080
ccacagtata gcgaacaccc aacttttcacc agtcagtatc gtatccaagg taagctggag    1140
tatagacaca cgtgggatcg ccatgacgaa ggtgcagccc aaggcgacga cgacgtttgg    1200
acctccggat ctgactcaga tgaggagctg gttaccacag aaagaaagac tcccagggtc    1260
actggaggtg gggctatggc tggagcaagc actagcgcag gccggaaacg aaagtccgcc    1320
agctccgcca cagcttgcac ctcaggcgta atgacgcggg gaagactgaa agccgagtcc    1380
```

```
actgtggcac ctgaagagga cacagacgaa gattccgaca atgaaatcca caatcccgca    1440
gtttttacct ggccaccttg gcaggcgggg attctggcgc gcaatctggt gcccatggtg    1500
gctaccgtac aaggccagaa tttgaagtac caggagttct tttgggacgc caatgacatc    1560
tatagaatct ttgccgaact ggaggggtg tggcagccag ccgctcaacc aaagaggagg    1620
```
*(note: line 1620 begins "tatagaatct ttgccgaact ggaggggtg" as shown)*

```
cgccaccggc aggatgcgct acccggacct tgcatcgcca gcaccctaa gaagcatagg     1680 ggg                                                                  1683

<210> SEQ ID NO 11
<211> LENGTH: 2718
<212> TYPE: DNA
<213> ORGANISM: Human cytomegalovirus
<220> FEATURE:
<221> NAME/KEY: CDS
<222> LOCATION: (1)..(2718)

<400> SEQUENCE: 11 atg gaa tcc agg atc tgg tgc ctg gta gtc tgc gtt aac ctg tgt atc     48
Met Glu Ser Arg Ile Trp Cys Leu Val Val Cys Val Asn Leu Cys Ile
1               5                   10                  15 gtc tgt ctg ggt gct gcg gtt tcc tct tct agt act tcc cat gca act     96
Val Cys Leu Gly Ala Ala Val Ser Ser Ser Ser Thr Ser His Ala Thr
            20                  25                  30 tct tct act cac aat gga agc cat act tct cgt acg acg tct gct caa    144
Ser Ser Thr His Asn Gly Ser His Thr Ser Arg Thr Thr Ser Ala Gln
        35                  40                  45 acc cgg tca gtc tat tct caa cac gta acg tct tct gaa gcc gtc agt    192
Thr Arg Ser Val Tyr Ser Gln His Val Thr Ser Ser Glu Ala Val Ser
    50                  55                  60 cat aga gcc aac gag act atc tac aac act acc ctc aag tac gga gat    240
His Arg Ala Asn Glu Thr Ile Tyr Asn Thr Thr Leu Lys Tyr Gly Asp
65                  70                  75                  80 gtg gtg gga gtc aac act acc aag tac ccc tat cgc gtg tgt tct atg    288
Val Val Gly Val Asn Thr Thr Lys Tyr Pro Tyr Arg Val Cys Ser Met
                85                  90                  95 gcc cag ggt acg gat ctt att cgc ttt gaa cgt aat atc atc tgc acc    336
Ala Gln Gly Thr Asp Leu Ile Arg Phe Glu Arg Asn Ile Ile Cys Thr
            100                 105                 110 tcg atg aag cct atc aat gaa gac ttg gat gag ggc atc atg gtg gtc    384
Ser Met Lys Pro Ile Asn Glu Asp Leu Asp Glu Gly Ile Met Val Val
        115                 120                 125 tac aag cgc aac atc gtg gcg cac acc ttt aag gta cgg gtc tac caa    432
Tyr Lys Arg Asn Ile Val Ala His Thr Phe Lys Val Arg Val Tyr Gln
    130                 135                 140 aag gtt ttg acg ttt cgt cgt agc tac gct tac atc tac acc act tat    480
Lys Val Leu Thr Phe Arg Arg Ser Tyr Ala Tyr Ile Tyr Thr Thr Tyr
145                 150                 155                 160 ctg ctg ggc agc aat acg gaa tac gtg gcg cct cct atg tgg gag att    528
Leu Leu Gly Ser Asn Thr Glu Tyr Val Ala Pro Pro Met Trp Glu Ile
                165                 170                 175 cat cac atc aac aag ttt gct caa tgc tac agt tcc tac agc cgc gtt    576
His His Ile Asn Lys Phe Ala Gln Cys Tyr Ser Ser Tyr Ser Arg Val
            180                 185                 190 ata gga ggc acg gtt ttc gtg gca tat cat agg gac agt tat gaa aac    624
Ile Gly Gly Thr Val Phe Val Ala Tyr His Arg Asp Ser Tyr Glu Asn
        195                 200                 205 aaa acc atg caa tta att ccc gac gat tat tcc aac acc cac agt acc    672
Lys Thr Met Gln Leu Ile Pro Asp Asp Tyr Ser Asn Thr His Ser Thr
    210                 215                 220
```

```
cgt tac gtg acg gtc aag gat cag tgg cac agc cgc ggc agc acc tgg      720
Arg Tyr Val Thr Val Lys Asp Gln Trp His Ser Arg Gly Ser Thr Trp
225                 230                 235                 240 ctc tat cgt gag acc tgt aat ctg aac tgt atg ctg acc atc act act      768
Leu Tyr Arg Glu Thr Cys Asn Leu Asn Cys Met Leu Thr Ile Thr Thr
                245                 250                 255 gcg cgc tcc aag tat cct tat cat ttt ttt gca act tcc acg ggt gat      816
Ala Arg Ser Lys Tyr Pro Tyr His Phe Phe Ala Thr Ser Thr Gly Asp
            260                 265                 270 gtg gtt tac att tct cct ttc tac aac gga acc aat cgc aat gcc agc      864
Val Val Tyr Ile Ser Pro Phe Tyr Asn Gly Thr Asn Arg Asn Ala Ser
        275                 280                 285 tac ttt gga gaa aac gcc gac aag ttt ttc att ttc ccg aac tac acc      912
Tyr Phe Gly Glu Asn Ala Asp Lys Phe Phe Ile Phe Pro Asn Tyr Thr
    290                 295                 300 atc gtt tcc gac ttt gga aga ccc aac gct gcg cca gaa acc cat agg      960
Ile Val Ser Asp Phe Gly Arg Pro Asn Ala Ala Pro Glu Thr His Arg
305                 310                 315                 320 ttg gtg gct ttt ctc gaa cgt gcc gac tcg gtg atc tct tgg gat ata     1008
Leu Val Ala Phe Leu Glu Arg Ala Asp Ser Val Ile Ser Trp Asp Ile
                325                 330                 335 cag gac gag aag aat gtc acc tgc cag ctc acc ttc tgg gaa gcc tcg     1056
Gln Asp Glu Lys Asn Val Thr Cys Gln Leu Thr Phe Trp Glu Ala Ser
            340                 345                 350 gaa cgt act atc cgt tcc gaa gcc gaa gac tcg tac cac ttt tct tct     1104
Glu Arg Thr Ile Arg Ser Glu Ala Glu Asp Ser Tyr His Phe Ser Ser
        355                 360                 365 gcc aaa atg act gca act ttt ctg tct aag aaa caa gaa gtg aac atg     1152
Ala Lys Met Thr Ala Thr Phe Leu Ser Lys Lys Gln Glu Val Asn Met
    370                 375                 380 tcc gac tcc gcg ctg gac tgc gta cgt gat gag gct ata aat aag tta     1200
Ser Asp Ser Ala Leu Asp Cys Val Arg Asp Glu Ala Ile Asn Lys Leu
385                 390                 395                 400 cag cag att ttc aat act tca tac aat caa aca tat gaa aaa tac gga     1248
Gln Gln Ile Phe Asn Thr Ser Tyr Asn Gln Thr Tyr Glu Lys Tyr Gly
                405                 410                 415 aac gtg tcc gtc ttc gaa acc agc ggc ggt ctg gtg gtg ttc tgg caa     1296
Asn Val Ser Val Phe Glu Thr Ser Gly Gly Leu Val Val Phe Trp Gln
            420                 425                 430 ggc atc aag caa aaa tct ttg gtg gaa ttg gaa cgt ttg gcc aat cga     1344
Gly Ile Lys Gln Lys Ser Leu Val Glu Leu Glu Arg Leu Ala Asn Arg
        435                 440                 445 tcc agt ctg aat atc act cat agg acc aga aga agt acg agt gac aat     1392
Ser Ser Leu Asn Ile Thr His Arg Thr Arg Arg Ser Thr Ser Asp Asn
    450                 455                 460 aat aca act cat ttg tcc agc atg gaa tcg gtg cac aat ctg gtc tac     1440
Asn Thr Thr His Leu Ser Ser Met Glu Ser Val His Asn Leu Val Tyr
465                 470                 475                 480 gcc cag ctg cag ttc acc tat gac acg ttg cgc ggt tac atc aac cgg     1488
Ala Gln Leu Gln Phe Thr Tyr Asp Thr Leu Arg Gly Tyr Ile Asn Arg
                485                 490                 495 gcg ctg gcg caa atc gca gaa gcc tgg tgt gtg gat caa cgg cgc acc     1536
Ala Leu Ala Gln Ile Ala Glu Ala Trp Cys Val Asp Gln Arg Arg Thr
            500                 505                 510 cta gag gtc ttc aag gaa ctc agc aag atc aac ccg tca gcc att ctc     1584
Leu Glu Val Phe Lys Glu Leu Ser Lys Ile Asn Pro Ser Ala Ile Leu
        515                 520                 525 tcg gcc att tac aac aaa ccg att gcc gcg cgt ttc atg ggt gat gtc     1632
Ser Ala Ile Tyr Asn Lys Pro Ile Ala Ala Arg Phe Met Gly Asp Val
```

-continued

|     | 530 |     |     |     | 535 |     |     |     | 540 |     |     |      |
|---|---|---|---|---|---|---|---|---|---|---|---|---|
| ttg | ggc | ctg | gcc | agc | tgc | gtg | acc | atc | aac | caa | acc | agc | gtc | aag | gtg | 1680 |
| Leu | Gly | Leu | Ala | Ser | Cys | Val | Thr | Ile | Asn | Gln | Thr | Ser | Val | Lys | Val |  |
| 545 |     |     |     |     | 550 |     |     |     |     | 555 |     |     |     |     | 560 |  |

| ctg | cgt | gat | atg | aac | gtg | aag | gaa | tcg | cca | gga | cgc | tgc | tac | tca | cga | 1728 |
| Leu | Arg | Asp | Met | Asn | Val | Lys | Glu | Ser | Pro | Gly | Arg | Cys | Tyr | Ser | Arg |  |
|     |     |     |     | 565 |     |     |     |     | 570 |     |     |     |     | 575 |     |  |

| ccc | gtg | gtc | atc | ttt | aat | ttc | gcc | aac | agc | tcg | tac | gtg | cag | tac | ggt | 1776 |
| Pro | Val | Val | Ile | Phe | Asn | Phe | Ala | Asn | Ser | Ser | Tyr | Val | Gln | Tyr | Gly |  |
|     |     |     | 580 |     |     |     |     | 585 |     |     |     |     | 590 |     |     |  |

| caa | ctg | ggc | gag | gac | aac | gaa | atc | ctg | ttg | ggc | aac | cac | cgc | act | gag | 1824 |
| Gln | Leu | Gly | Glu | Asp | Asn | Glu | Ile | Leu | Leu | Gly | Asn | His | Arg | Thr | Glu |  |
|     |     | 595 |     |     |     |     | 600 |     |     |     |     | 605 |     |     |     |  |

| gaa | tgt | cag | ctt | ccc | agc | ctc | aag | atc | ttc | atc | gcc | ggg | aac | tcg | gcc | 1872 |
| Glu | Cys | Gln | Leu | Pro | Ser | Leu | Lys | Ile | Phe | Ile | Ala | Gly | Asn | Ser | Ala |  |
| 610 |     |     |     |     | 615 |     |     |     |     | 620 |     |     |     |     |     |  |

| tac | gag | tac | gtg | gac | tac | ctc | ttc | aaa | cgc | atg | att | gac | ctc | agc | agt | 1920 |
| Tyr | Glu | Tyr | Val | Asp | Tyr | Leu | Phe | Lys | Arg | Met | Ile | Asp | Leu | Ser | Ser |  |
| 625 |     |     |     |     | 630 |     |     |     |     | 635 |     |     |     |     | 640 |  |

| atc | tcc | acc | gtc | gac | agc | atg | atc | gcc | ctg | gat | atc | gac | ccg | ctg | gaa | 1968 |
| Ile | Ser | Thr | Val | Asp | Ser | Met | Ile | Ala | Leu | Asp | Ile | Asp | Pro | Leu | Glu |  |
|     |     |     |     | 645 |     |     |     |     | 650 |     |     |     |     | 655 |     |  |

| aat | acc | gac | ttc | agg | gta | ctg | gaa | ctt | tac | tcg | cag | aaa | gag | ctg | cgt | 2016 |
| Asn | Thr | Asp | Phe | Arg | Val | Leu | Glu | Leu | Tyr | Ser | Gln | Lys | Glu | Leu | Arg |  |
|     |     |     | 660 |     |     |     |     | 665 |     |     |     |     | 670 |     |     |  |

| tcc | agc | aac | gtt | ttt | gac | ctc | gaa | gag | atc | atg | cgc | gaa | ttc | aac | tcg | 2064 |
| Ser | Ser | Asn | Val | Phe | Asp | Leu | Glu | Glu | Ile | Met | Arg | Glu | Phe | Asn | Ser |  |
|     |     | 675 |     |     |     |     | 680 |     |     |     |     | 685 |     |     |     |  |

| tac | aag | cag | cgg | gta | aag | tac | gtg | gag | gac | aag | gta | gtc | gac | ccg | cta | 2112 |
| Tyr | Lys | Gln | Arg | Val | Lys | Tyr | Val | Glu | Asp | Lys | Val | Val | Asp | Pro | Leu |  |
| 690 |     |     |     |     | 695 |     |     |     |     | 700 |     |     |     |     |     |  |

| ccg | ccc | tac | ctc | aag | ggt | ctg | gac | gac | ctc | atg | agc | ggc | ctg | ggc | gcc | 2160 |
| Pro | Pro | Tyr | Leu | Lys | Gly | Leu | Asp | Asp | Leu | Met | Ser | Gly | Leu | Gly | Ala |  |
| 705 |     |     |     |     | 710 |     |     |     |     | 715 |     |     |     |     | 720 |  |

| gcg | gga | aag | gcc | gtt | ggc | gta | gcc | att | ggg | gcc | gtg | ggt | ggc | gcg | gtg | 2208 |
| Ala | Gly | Lys | Ala | Val | Gly | Val | Ala | Ile | Gly | Ala | Val | Gly | Gly | Ala | Val |  |
|     |     |     |     | 725 |     |     |     |     | 730 |     |     |     |     | 735 |     |  |

| gcc | tcc | gtg | gtc | gaa | ggc | gtt | gcc | acc | ttc | ctc | aaa | aac | ccc | ttc | gga | 2256 |
| Ala | Ser | Val | Val | Glu | Gly | Val | Ala | Thr | Phe | Leu | Lys | Asn | Pro | Phe | Gly |  |
|     |     |     | 740 |     |     |     |     | 745 |     |     |     |     | 750 |     |     |  |

| gcc | ttc | acc | atc | atc | ctc | gtg | gcc | ata | gcc | gta | gtc | att | atc | act | tat | 2304 |
| Ala | Phe | Thr | Ile | Ile | Leu | Val | Ala | Ile | Ala | Val | Val | Ile | Ile | Thr | Tyr |  |
|     |     |     | 755 |     |     |     |     | 760 |     |     |     |     | 765 |     |     |  |

| ttg | atc | tat | act | cga | cag | cgg | cgt | ctg | tgc | acg | cag | ccg | ctg | cag | aac | 2352 |
| Leu | Ile | Tyr | Thr | Arg | Gln | Arg | Arg | Leu | Cys | Thr | Gln | Pro | Leu | Gln | Asn |  |
| 770 |     |     |     |     | 775 |     |     |     |     | 780 |     |     |     |     |     |  |

| ctc | ttt | ccc | tat | ctg | gtg | tcc | gcc | gac | ggg | acc | acc | gtg | acg | tcg | ggc | 2400 |
| Leu | Phe | Pro | Tyr | Leu | Val | Ser | Ala | Asp | Gly | Thr | Thr | Val | Thr | Ser | Gly |  |
| 785 |     |     |     |     | 790 |     |     |     |     | 795 |     |     |     |     | 800 |  |

| agc | acc | aaa | gac | acg | tcg | tta | cag | gct | ccg | cct | tcc | tac | gag | gaa | agt | 2448 |
| Ser | Thr | Lys | Asp | Thr | Ser | Leu | Gln | Ala | Pro | Pro | Ser | Tyr | Glu | Glu | Ser |  |
|     |     |     |     | 805 |     |     |     |     | 810 |     |     |     |     | 815 |     |  |

| gtt | tat | aat | tct | ggt | cgc | aaa | gga | ccg | gga | cca | ccg | tcg | tct | gat | gca | 2496 |
| Val | Tyr | Asn | Ser | Gly | Arg | Lys | Gly | Pro | Gly | Pro | Pro | Ser | Ser | Asp | Ala |  |
|     |     |     | 820 |     |     |     |     | 825 |     |     |     |     | 830 |     |     |  |

| tcc | acg | gcg | gct | ccg | cct | tac | acc | aac | gag | cag | gct | tac | cag | atg | ctt | 2544 |
| Ser | Thr | Ala | Ala | Pro | Pro | Tyr | Thr | Asn | Glu | Gln | Ala | Tyr | Gln | Met | Leu |  |
|     |     | 835 |     |     |     |     | 840 |     |     |     |     | 845 |     |     |     |  |

| ctg | gcc | ctg | gcc | cgt | ctg | gac | gca | gag | cag | cga | gcg | cag | cag | aac | ggt | 2592 |

-continued

```
Leu Ala Leu Ala Arg Leu Asp Ala Glu Gln Arg Ala Gln Gln Asn Gly
            850                 855                 860 aca gat tct ttg gac gga cag act ggc acg cag gac aag gga cag aag      2640
Thr Asp Ser Leu Asp Gly Gln Thr Gly Thr Gln Asp Lys Gly Gln Lys
865                 870                 875                 880 cct aac ctg cta gac cgg ctg cga cat cgc aaa aac ggc tac aga cac      2688
Pro Asn Leu Leu Asp Arg Leu Arg His Arg Lys Asn Gly Tyr Arg His
                885                 890                 895 ttg aaa gac tcc gac gaa gaa gag aac gtc                              2718
Leu Lys Asp Ser Asp Glu Glu Glu Asn Val
                900                 905

<210> SEQ ID NO 12
<211> LENGTH: 906
<212> TYPE: PRT
<213> ORGANISM: Human cytomegalovirus

<400> SEQUENCE: 12

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
            85                  90                  95

Ala Gln Gly Thr Asp Leu Ile Arg Phe Glu Arg Asn Ile Ile Cys Thr
        100                 105                 110

Ser Met Lys Pro Ile Asn Glu Asp Leu Asp Glu Gly Ile Met Val Val
    115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300
```

```
Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
                420                 425                 430

Gly Ile Lys Gln Lys Ser Leu Val Glu Leu Glu Arg Leu Ala Asn Arg
            435                 440                 445

Ser Ser Leu Asn Ile Thr His Arg Thr Arg Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
        515                 520                 525

Ser Ala Ile Tyr Asn Lys Pro Ile Ala Ala Arg Phe Met Gly Asp Val
530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
                580                 585                 590

Gln Leu Gly Glu Asp Asn Glu Ile Leu Leu Gly Asn His Arg Thr Glu
            595                 600                 605

Glu Cys Gln Leu Pro Ser Leu Lys Ile Phe Ile Ala Gly Asn Ser Ala
610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
675                 680                 685

Tyr Lys Gln Arg Val Lys Tyr Val Glu Asp Lys Val Val Asp Pro Leu
            690                 695                 700

Pro Pro Tyr Leu Lys Gly Leu Asp Asp Leu Met Ser Gly Leu Gly Ala
705                 710                 715                 720
```

```
Ala Gly Lys Ala Val Gly Val Ala Ile Gly Ala Val Gly Gly Ala Val
            725                 730                 735

Ala Ser Val Val Glu Gly Val Ala Thr Phe Leu Lys Asn Pro Phe Gly
        740                 745                 750

Ala Phe Thr Ile Ile Leu Val Ala Ile Ala Val Val Ile Ile Thr Tyr
    755                 760                 765

Leu Ile Tyr Thr Arg Gln Arg Arg Leu Cys Thr Gln Pro Leu Gln Asn
770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
            805                 810                 815

Val Tyr Asn Ser Gly Arg Lys Gly Pro Gly Pro Pro Ser Ser Asp Ala
        820                 825                 830

Ser Thr Ala Ala Pro Pro Tyr Thr Asn Glu Gln Ala Tyr Gln Met Leu
    835                 840                 845

Leu Ala Leu Ala Arg Leu Asp Ala Glu Gln Arg Ala Gln Gln Asn Gly
850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
            885                 890                 895

Leu Lys Asp Ser Asp Glu Glu Asn Val
            900                 905

<210> SEQ ID NO 13
<211> LENGTH: 2139
<212> TYPE: DNA
<213> ORGANISM: Artificial Sequence
<220> FEATURE:
<223> OTHER INFORMATION: codon-optimized sequence of hCMV gB
<220> FEATURE:
<221> NAME/KEY: CDS
<222> LOCATION: (1)..(2139)

<400> SEQUENCE: 13 atg gaa tcc agg atc tgg tgc ctg gta gtc tgc gtt aac ctg tgt atc      48
Met Glu Ser Arg Ile Trp Cys Leu Val Val Cys Val Asn Leu Cys Ile
1               5                   10                  15 gtc tgt ctg ggt gct gcc gtt tcc tct tct agt act tcc cat gca act      96
Val Cys Leu Gly Ala Ala Val Ser Ser Ser Ser Thr Ser His Ala Thr
            20                  25                  30 tct tct act cac aat gga agc cat act tct cgc acc acc tct gct caa     144
Ser Ser Thr His Asn Gly Ser His Thr Ser Arg Thr Thr Ser Ala Gln
        35                  40                  45 acc cgg tca gtc tat tct caa cac gta acc tct tct gaa gcc gtc agt     192
Thr Arg Ser Val Tyr Ser Gln His Val Thr Ser Ser Glu Ala Val Ser
    50                  55                  60 cat aga gcc aac gag act atc tac aac act acc ctc aag tac gga gat     240
His Arg Ala Asn Glu Thr Ile Tyr Asn Thr Thr Leu Lys Tyr Gly Asp
65                  70                  75                  80 gtg gtg gga gtc aac act acc aag tac ccc tat cgc gtg tgt tct atg     288
Val Val Gly Val Asn Thr Thr Lys Tyr Pro Tyr Arg Val Cys Ser Met
                85                  90                  95 gcc cag ggt acc gat ctt att cgc ttt gaa cgc aat atc atc tgc acc     336
Ala Gln Gly Thr Asp Leu Ile Arg Phe Glu Arg Asn Ile Ile Cys Thr
            100                 105                 110 tcc atg aag cct atc aat gaa gac ttg gat gag ggc atc atg gtg gtc     384
Ser Met Lys Pro Ile Asn Glu Asp Leu Asp Glu Gly Ile Met Val Val
```

```
                115                    120                    125
tac aag cgc aac atc gtg gcc cac acc ttt aag gta cgg gtc tac caa        432
Tyr Lys Arg Asn Ile Val Ala His Thr Phe Lys Val Arg Val Tyr Gln
    130                 135                 140 aag gtt ttg acc ttt cgc cgc agc tac gct tac atc tac acc act tat        480
Lys Val Leu Thr Phe Arg Arg Ser Tyr Ala Tyr Ile Tyr Thr Thr Tyr
145                 150                 155                 160 ctg ctg ggc agc aat acc gaa tac gtg gcc cct cct atg tgg gag att        528
Leu Leu Gly Ser Asn Thr Glu Tyr Val Ala Pro Pro Met Trp Glu Ile
                165                 170                 175 cat cac atc aac aag ttt gct caa tgc tac agt tcc tac agc cgc gtt        576
His His Ile Asn Lys Phe Ala Gln Cys Tyr Ser Ser Tyr Ser Arg Val
            180                 185                 190 ata gga ggc acc gtt ttc gtg gca tat cat agg gac agt tat gaa aac        624
Ile Gly Gly Thr Val Phe Val Ala Tyr His Arg Asp Ser Tyr Glu Asn
        195                 200                 205 aaa acc atg caa tta att ccc gac gat tat tcc aac acc cac agt acc        672
Lys Thr Met Gln Leu Ile Pro Asp Asp Tyr Ser Asn Thr His Ser Thr
    210                 215                 220 cgc tac gtg acc gtc aag gat cag tgg cac agc cgc ggc agc acc tgg        720
Arg Tyr Val Thr Val Lys Asp Gln Trp His Ser Arg Gly Ser Thr Trp
225                 230                 235                 240 ctc tat cgc gag acc tgt aat ctg aac tgt atg ctg acc atc act act        768
Leu Tyr Arg Glu Thr Cys Asn Leu Asn Cys Met Leu Thr Ile Thr Thr
                245                 250                 255 gcc cgc tcc aag tat cct tat cat ttt ttt gca act tcc acc ggt gat        816
Ala Arg Ser Lys Tyr Pro Tyr His Phe Phe Ala Thr Ser Thr Gly Asp
            260                 265                 270 gtg gtt tac att tct cct ttc tac aac gga acc aat cgc aat gcc agc        864
Val Val Tyr Ile Ser Pro Phe Tyr Asn Gly Thr Asn Arg Asn Ala Ser
        275                 280                 285 tac ttt gga gaa aac gcc gac aag ttt ttc att ttc ccc aac tac acc        912
Tyr Phe Gly Glu Asn Ala Asp Lys Phe Phe Ile Phe Pro Asn Tyr Thr
    290                 295                 300 atc gtt tcc gac ttt gga aga ccc aac gct gcc cca gaa acc cat agg        960
Ile Val Ser Asp Phe Gly Arg Pro Asn Ala Ala Pro Glu Thr His Arg
305                 310                 315                 320 ttg gtg gct ttt ctc gaa cgc gcc gac tcc gtg atc tct tgg gat ata        1008
Leu Val Ala Phe Leu Glu Arg Ala Asp Ser Val Ile Ser Trp Asp Ile
                325                 330                 335 cag gac gag aag aat gtc acc tgc cag ctc acc ttc tgg gaa gcc tcc        1056
Gln Asp Glu Lys Asn Val Thr Cys Gln Leu Thr Phe Trp Glu Ala Ser
            340                 345                 350 gaa cgc act atc cgc tcc gaa gcc gaa gac tcc tac cac ttt tct tct        1104
Glu Arg Thr Ile Arg Ser Glu Ala Glu Asp Ser Tyr His Phe Ser Ser
        355                 360                 365 gcc aaa atg act gca act ttt ctg tct aag aaa caa gaa gtg aac atg        1152
Ala Lys Met Thr Ala Thr Phe Leu Ser Lys Lys Gln Glu Val Asn Met
    370                 375                 380 tcc gac tcc gcc ctg gac tgc gta cgc gat gag gct ata aat aag tta        1200
Ser Asp Ser Ala Leu Asp Cys Val Arg Asp Glu Ala Ile Asn Lys Leu
385                 390                 395                 400 cag cag att ttc aat act tca tac aat caa aca tat gaa aaa tac gga        1248
Gln Gln Ile Phe Asn Thr Ser Tyr Asn Gln Thr Tyr Glu Lys Tyr Gly
                405                 410                 415 aac gtg tcc gtc ttc gaa acc agc ggt ggt ctg gtg gtg ttc tgg caa        1296
Asn Val Ser Val Phe Glu Thr Ser Gly Gly Leu Val Val Phe Trp Gln
            420                 425                 430 ggc atc aag caa aaa tct ttg gtg gaa ttg gaa cgc ttg gcc aat cga        1344
```

```
Gly Ile Lys Gln Lys Ser Leu Val Glu Leu Glu Arg Leu Ala Asn Arg
            435                 440                 445 tcc agt ctg aat atc act cat agg acc aga aga agt acc agt gac aat    1392
Ser Ser Leu Asn Ile Thr His Arg Thr Arg Arg Ser Thr Ser Asp Asn
450                 455                 460 aat aca act cat ttg tcc agc atg gaa tcc gtg cac aat ctg gtc tac    1440
Asn Thr Thr His Leu Ser Ser Met Glu Ser Val His Asn Leu Val Tyr
465                 470                 475                 480 gcc cag ctg cag ttc acc tat gac acc ttg cgc ggt tac atc aac cgg    1488
Ala Gln Leu Gln Phe Thr Tyr Asp Thr Leu Arg Gly Tyr Ile Asn Arg
                485                 490                 495 gcc ctg gcc caa atc gca gaa gcc tgg tgt gtg gat caa cgg cgc acc    1536
Ala Leu Ala Gln Ile Ala Glu Ala Trp Cys Val Asp Gln Arg Arg Thr
            500                 505                 510 cta gag gtc ttc aag gaa ctc agc aag atc aac ccc tca gcc att ctc    1584
Leu Glu Val Phe Lys Glu Leu Ser Lys Ile Asn Pro Ser Ala Ile Leu
            515                 520                 525 tcc gcc att tac aac aaa ccc att gcc gcc cgc ttc atg ggt gat gtc    1632
Ser Ala Ile Tyr Asn Lys Pro Ile Ala Ala Arg Phe Met Gly Asp Val
530                 535                 540 ttg ggc ctg gcc agc tgc gtg acc atc aac caa acc agc gtc aag gtg    1680
Leu Gly Leu Ala Ser Cys Val Thr Ile Asn Gln Thr Ser Val Lys Val
545                 550                 555                 560 ctg cgc gat atg aac gtg aag gaa tcc cca gga cgc tgc tac tca cga    1728
Leu Arg Asp Met Asn Val Lys Glu Ser Pro Gly Arg Cys Tyr Ser Arg
                565                 570                 575 ccc gtg gtc atc ttt aat ttc gcc aac agc tcc tac gtg cag tac ggt    1776
Pro Val Val Ile Phe Asn Phe Ala Asn Ser Ser Tyr Val Gln Tyr Gly
            580                 585                 590 caa ctg ggc gag gac aac gaa atc ctg ttg ggc aac cac cgc act gag    1824
Gln Leu Gly Glu Asp Asn Glu Ile Leu Leu Gly Asn His Arg Thr Glu
            595                 600                 605 gaa tgt cag ctt ccc agc ctc aag atc ttc atc gcc ggg aac tcc gcc    1872
Glu Cys Gln Leu Pro Ser Leu Lys Ile Phe Ile Ala Gly Asn Ser Ala
610                 615                 620 tac gag tac gtg gac tac ctc ttc aaa cgc atg att gac ctc agc agt    1920
Tyr Glu Tyr Val Asp Tyr Leu Phe Lys Arg Met Ile Asp Leu Ser Ser
625                 630                 635                 640 atc tcc acc gtc gac agc atg atc gcc ctg gat atc gac ccc ctg gaa    1968
Ile Ser Thr Val Asp Ser Met Ile Ala Leu Asp Ile Asp Pro Leu Glu
                645                 650                 655 aat acc gac ttc agg gta ctg gaa ctt tac tcc cag aaa gag ctg cgc    2016
Asn Thr Asp Phe Arg Val Leu Glu Leu Tyr Ser Gln Lys Glu Leu Arg
            660                 665                 670 tcc agc aac gtt ttt gac ctc gaa gag atc atg cgc gaa ttc aac tcc    2064
Ser Ser Asn Val Phe Asp Leu Glu Glu Ile Met Arg Glu Phe Asn Ser
            675                 680                 685 tac aag cag cgg gta aag tac gtg gag gac aag gta gtc gac cca cta    2112
Tyr Lys Gln Arg Val Lys Tyr Val Glu Asp Lys Val Val Asp Pro Leu
            690                 695                 700 cct ccc tac ctc aag ggt ctg gac gac                                2139
Pro Pro Tyr Leu Lys Gly Leu Asp Asp
705                 710

<210> SEQ ID NO 14
<211> LENGTH: 713
<212> TYPE: PRT
<213> ORGANISM: Artificial Sequence
<220> FEATURE:
<223> OTHER INFORMATION: codon-optimized sequence of hCMV gB
```

```
<400> SEQUENCE: 14

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415
```

```
Asn Val Ser Val Phe Glu Thr Ser Gly Gly Leu Val Val Phe Trp Gln
            420                 425                 430
Gly Ile Lys Gln Lys Ser Leu Val Glu Leu Glu Arg Leu Ala Asn Arg
        435                 440                 445
Ser Ser Leu Asn Ile Thr His Arg Thr Arg Arg Ser Thr Ser Asp Asn
    450                 455                 460
Asn Thr Thr His Leu Ser Ser Met Glu Ser Val His Asn Leu Val Tyr
465                 470                 475                 480
Ala Gln Leu Gln Phe Thr Tyr Asp Thr Leu Arg Gly Tyr Ile Asn Arg
                485                 490                 495
Ala Leu Ala Gln Ile Ala Glu Ala Trp Cys Val Asp Gln Arg Arg Thr
            500                 505                 510
Leu Glu Val Phe Lys Glu Leu Ser Lys Ile Asn Pro Ser Ala Ile Leu
        515                 520                 525
Ser Ala Ile Tyr Asn Lys Pro Ile Ala Ala Arg Phe Met Gly Asp Val
    530                 535                 540
Leu Gly Leu Ala Ser Cys Val Thr Ile Asn Gln Thr Ser Val Lys Val
545                 550                 555                 560
Leu Arg Asp Met Asn Val Lys Glu Ser Pro Gly Arg Cys Tyr Ser Arg
                565                 570                 575
Pro Val Val Ile Phe Asn Phe Ala Asn Ser Ser Tyr Val Gln Tyr Gly
            580                 585                 590
Gln Leu Gly Glu Asp Asn Glu Ile Leu Leu Gly Asn His Arg Thr Glu
        595                 600                 605
Glu Cys Gln Leu Pro Ser Leu Lys Ile Phe Ile Ala Gly Asn Ser Ala
    610                 615                 620
Tyr Glu Tyr Val Asp Tyr Leu Phe Lys Arg Met Ile Asp Leu Ser Ser
625                 630                 635                 640
Ile Ser Thr Val Asp Ser Met Ile Ala Leu Asp Ile Asp Pro Leu Glu
                645                 650                 655
Asn Thr Asp Phe Arg Val Leu Glu Leu Tyr Ser Gln Lys Glu Leu Arg
            660                 665                 670
Ser Ser Asn Val Phe Asp Leu Glu Glu Ile Met Arg Glu Phe Asn Ser
        675                 680                 685
Tyr Lys Gln Arg Val Lys Tyr Val Glu Asp Lys Val Val Asp Pro Leu
    690                 695                 700
Pro Pro Tyr Leu Lys Gly Leu Asp Asp
705                 710

<210> SEQ ID NO 15
<211> LENGTH: 2718
<212> TYPE: DNA
<213> ORGANISM: Artificial Sequence
<220> FEATURE:
<223> OTHER INFORMATION: codon-optimized sequence of hCMV gB

<400> SEQUENCE: 15
atggagagca ggatctggtg cctggtggtg tgcgtgaacc tgtgcatcgt gtgcctgggc      60
gccgccgtga gcagcagcag caccagccac gccaccagca gcacccacaa cggcagccac     120
accagcagga ccaccagcgc ccagaccagg agcgtgtaca gccagcacgt gaccagcagc     180
gaggccgtga gccacagggc caacgagacc atctacaaca ccaccctgaa gtacggcgac     240
gtggtgggcg tgaacaccac caagtacccc tacagggtgt gcagcatggc ccagggcacc     300
gacctgatca ggttcgagag gaacatcatc tgcaccagca tgaagcccat caacgaggac     360
```

```
ctggacgagg gcatcatggt ggtgtacaag aggaacatcg tggcccacac cttcaaggtg    420
agggtgtacc agaaggtgct gaccttcagg aggagctacg cctacatcta caccacctac    480
ctgctgggca gcaacaccga gtacgtggcc ccccccatgt gggagatcca ccacatcaac    540
aagttcgccc agtgctacag cagctacagc agggtgatcg gcggcaccgt gttcgtggcc    600
taccacaggg acagctacga gaacaagacc atgcagctga tccccgacga ctacagcaac    660
acccacagca ccaggtacgt gaccgtgaag gaccagtggc acagcagggg cagcacctgg    720
ctgtacaggg agacctgcaa cctgaactgc atgctgacca tcaccaccgc caggagcaag    780
tacccctacc acttcttcgc caccagcacc ggcgacgtgg tgtacatcag cccttctac     840 aacggcacca acaggaacgc cagctacttc ggcgagaacg ccgacaagtt cttcatcttc    900
cccaactaca ccatcgtgag cgacttcggc aggcccaacg ccgccccga cccacaggg    960 ctggtggcct tcctggagag ggccgacagc gtgatcagct gggacatcca ggacgagaag   1020
aacgtgacct gccagctgac cttctgggag gccagcgaga ggaccatcag gagcgaggcc   1080
gaggacagct accacttcag cagcgccaag atgaccgcca ccttcctgag caagaagcag   1140
gaggtgaaca tgagcgacag cgccctggac tgcgtgaggg acgaggccat caacaagctg   1200
cagcagatct tcaacaccag ctacaaccag acctacgaga gtacggcaa cgtgagcgtg    1260 ttcgagacca gcggcggcct ggtggtgttc tggcagggca tcaagcagaa gagcctggtg   1320
gagctggaga ggctggccaa caggagcagc ctgaacatca cccacaggac caggaggagc   1380
accagcgaca caacaccac ccacctgagc agcatggaga gcgtgcacaa cctggtgtac    1440
gcccagctgc agttcaccta cgacaccctg aggggctaca tcaacagggc cctggcccag   1500
atcgccgagg cctggtgcgt ggaccagagg aggaccctgg aggtgttcaa ggagctgagc   1560
aagatcaacc ccagcgccat cctgagcgcc atctacaaca gcccatcgc cgccaggttc   1620 atgggcgact gctgggcct ggccagctgc gtgaccatca accagaccag cgtgaaggtg    1680
ctgagggaca tgaacgtgaa ggagagcccc ggcaggtgct acagcaggcc cgtggtgatc   1740
ttcaacttcg ccaacagcag ctacgtgcag tacggccagc tgggcgagga caacgagatc   1800
ctgctgggca ccacaggac cgaggagtgc cagctgccca gcctgaagat cttcatcgcc   1860
ggcaacagcg cctacgagta cgtggactac ctgttcaaga ggatgatcga cctgagcagc   1920
atcagcaccg tggacagcat gatcgccctg gacatcgacc ccctggagaa caccgacttc   1980
agggtgctgg agctgtacag ccagaaggag ctgaggagca gcaacgtgtt cgacctggag   2040
gagatcatga gggagttcaa cagctacaag cagagggtga gtacgtgga ggacaaggtg    2100 gtggaccccc tgccccccta cctgaagggc ctggacgacc tgatgagcgg cctgggcgcc   2160
gccggcaagg ccgtgggcgt ggccatcggc gccgtgggcg cgccgtggc cagcgtggtg   2220 gagggcgtgg ccaccttcct gaagaacccc ttcggcgcct tcaccatcat cctggtggcc   2280
atcgccgtgg tgatcatcac ctacctgatc tacaccaggc agaggaggct gtgcacccag   2340
cccctgcaga acctgttccc ctacctggtg agcgccgacg gcaccaccgt gaccagcggc   2400
agcaccaagg acaccagcct gcaggccccc cccagctacg aggagagcgt gtacaacagc   2460
ggcaggaagg ccccggccc cccagcagc gacgccagca ccgccgcccc ccctacacc    2520 aacgagcagg cctaccagat gctgctggcc ctggcaggc tggacgccga gcagggcc     2580 cagcagaacg gcaccgacag cctggacggc cagaccggca cccaggacaa gggcagaag    2640 cccaacctgc tggacaggct gaggcacagg aagaacggct acaggcacct gaaggacagc   2700
```
gacgaggagg agaacgtg 2718

<210> SEQ ID NO 16
<211> LENGTH: 2718
<212> TYPE: DNA
<213> ORGANISM: Artificial Sequence
<220> FEATURE:
<223> OTHER INFORMATION: codon-optimized sequence of hCMV gB

<400> SEQUENCE: 16

| | |
|---|---|
| atggaatcca ggatctggtg tctcgtcgtc tgtgtcaacc tttgtatcgt ttgcttggga | 60 |
| gctgccgtta gtagcagctc cacaagtcat gccaccagca gtacccataa cggtagccac | 120 |
| acctcacgga caacgagcgc tcagactcgt tccgtgtact cgcagcacgt tacctcctca | 180 |
| gaggcagtgt cccatcgcgc taacgaaact atctacaaca ccacactcaa gtatggcgac | 240 |
| gtagtgggtg taaatacgac aaaatacccc atagagtgt gctcaatggc ccagggcacc | 300 |
| gatctgatcc ggttcgagag aaatataatc tgcacctcta tgaaacctat caatgaggat | 360 |
| ctggacgagg ggatcatggt ggtgtataag agaaatattg tcgcccatac ctttaaagtg | 420 |
| cgcgtttatc aaaaggtgtt aactttcaga aggtcctacg cttatatcta caccacgtac | 480 |
| ctgctcggct ccaatacaga gtacgtcgct cctcccatgt gggaaattca ccatatcaac | 540 |
| aagttcgccc agtgctactc ctcttactca cgcgtgatcg agggaccgt gttcgtggca | 600 |
| tatcaccgag attcttacga aaacaagaca atgcagctga tccctgatga ctactctaat | 660 |
| acacactcaa cccgttatgt gaccgtaaag gatcaatggc actcccgcgg gtctacctgg | 720 |
| ctctacaggg aaacgtgcaa cctgaattgt atgctgacaa taacgactgc taggtcaaag | 780 |
| tacccctacc actttttttgc aacctctacc ggcgacgtgg tttatattag tccttttctac | 840 |
| aacggaacca accgtaatgc gagttatttc ggtgaaaacg cagacaagtt tttcattttc | 900 |
| cccaactata ctatcgtgag tgacttcgga agacctaatg cagccccaga gactcatcgc | 960 |
| ctggtggcct cctcgaaaag agccgatagc gtgatctcct gggatattca ggacgagaag | 1020 |
| aacgtgactt gccaactcac ctttttggag gcgtctgagc gcactatacg aagcgaagcc | 1080 |
| gaagactctt atcattttcag cagtgcaaag atgacagcca ctttcttgtc caaaaaacag | 1140 |
| gaggttaaca tgtctgactc agcgctagac tgtgtgcggg acgaggcgat caacaaactg | 1200 |
| caacaaatat tcaacacgag ctacaaccag acctacgaga gtatggcaa tgtgtcagta | 1260 |
| tttgagacta gcggcggact ggtagtattt tggcagggga ttaaacagaa gtctctcgtc | 1320 |
| gaactcgagc ggctggccaa tcgcagtagt ctgaacatca cacacaggac acgaaggtct | 1380 |
| acttccgata ataataccac ccacctctcc tctatggagt cggtgcacaa cctggtgtac | 1440 |
| gctcagttgc agtttacata cgacaccctg cgcgggtata ttaacagagc gctggcacag | 1500 |
| atcgccgaag catggtgcgt cgaccaacgt cgaacgctgg aggtcttcaa ggagctatcc | 1560 |
| aagattaacc caagtgccat tctatctgca atttacaata gccgattgc cgctaggttt | 1620 |
| atgggcgatg ttctgggact ggcgagctgt gtgactataa accaaacgtc agtcaaggtg | 1680 |
| cttagggaca tgaacgttaa ggaatcccct ggccggtgtt attcgcggcc tgttgtcata | 1740 |
| tttaattttg ccaattcctc ttacgtgcag tacggccagt taggcgagga caacgaaatt | 1800 |
| ttattgggca atcatcgcac cgaggaatgc cagttgccga gcctgaaaat ctttatagct | 1860 |
| gggaacagcg cttacgagta cgtcgactat ctctttaagc ggatgattga tctgagctcg | 1920 |
| atcagcacac tcgactctat gatcgccctg gatattgacc cgctggagaa tacagatttc | 1980 |
| agagtgcttg aattatattc acagaaagag ctgcggagct caaatgtgtt cgatcttgag | 2040 |

```
gaaattatgc gggaattcaa cagctacaag caacgggtca agtacgtgga ggacaaggtg    2100
gtggacccac tgccccccta cttgaaaggt ctgatgatc tcatgagcgg tcttggagcg     2160
gctggcaaag ccgttggagt agcaatcggc gccgttggag gggccgtggc ttctgtagtg    2220
gagggcgttg ctaccttttt gaagaacccc ttcggggcct ttactatcat tctagtcgct    2280
attgcagtcg tgataatcac atatttgatc tatactcggc agagacgctt atgcacacag    2340 cccctttcaga atctcttccc ctatctggtc ccgcagatg gacaacagt gacaagtggc     2400 tcgactaagg ataccagctt gcaagctccc ccaagttacg aagagagcgt ttataactcc    2460
ggtaggaaag gaccaggtcc acctagctca gatgcatcaa ccgctgcccc accctatact    2520
aatgagcagg cctatcagat gctgcttgca ctcgccagac tggacgccga gcagcgagcc    2580
cagcagaatg gacagactc cctcgacggg cagactggaa cccaggataa aggacagaaa    2640
cctaatctgc ttgaccgact aagcacagg aaaaatggct acaggcacct taaagatagt    2700
gatgaagaag agaacgtc                                                  2718

<210> SEQ ID NO 17
<211> LENGTH: 2718
<212> TYPE: DNA
<213> ORGANISM: Artificial Sequence
<220> FEATURE:
<223> OTHER INFORMATION: codon-optimized sequence of hCMV gB

<400> SEQUENCE: 17
atggagagcc ggatttggtg tctggtcgtg tgcgtgaacc tgtgcatcgt ctgtttgggc      60
gctgccgttt catcctccag tacttcccat gctacatcct cgacacacaa tggctcacat     120
accagcagaa ctactctgc acaaactcgc tccgtgtact cacagcacgt cacttctagc      180
gaagcagtgt cccacagggc aaacgaaacg atctacaaca ccaccctgaa gtatggtgac     240
gtggtggggg tgaacaccac taaatatcct tatagagttt gtagtatggc acaagggaca     300
gatctgatca ggttcgagcg aaacattatt tgcacctcca tgaagcctat aaacgaagat     360
ctggacgagg gcatcatggt ggtgtacaag cgtaatatag tcgcccatac ctttaaggta     420
agggtgtacc agaaggtcct cacatttcgc agaagctatg cctatattta cactaccta t    480 ctactgggct ccaacactga atacgttgca ccccccatgt gggaaattca ccacatcaat    540
aaattcgccc agtgttattc cagctattct agggttatag aggcaccgt gtttgtggcc     600 taccaccggg atagctacga gaataagact atgcagctca tccctgacga ctacagcaat     660
acacattcca agatacgt caccgtcaag gatcagtggc attctagggg atctacatgg      720
ctttatcgcg agacatgcaa cttgaactgt atgcttacca tcaccacagc gcgttctaaa    780
tacccatatc attttttgc gactagtacg ggagacgtgg tgtatatctc accgttttat     840
aacggtacta accgtaatgc tagctatttt ggcgagaatg cagataaatt ttttatcttc   900
cccaactaca caatcgtaag tgacttcgga aggcccaatg ccgcccccga aacgcacagg    960
ctggtggcct tcctcgagcg agccgatagc gtaatttcat gggatataca ggatgagaaa   1020
aatgtgacct gccagcttac cttctgggaa gcttcagaga ggactatccg gagtgaagcc   1080
gaggattcct atcactttc cagtgctaag atgacggcaa cctttctctc aaagaagcag    1140
gaggtgaaca tgagcgactc ggctcttgat tgcgtgcggg acgaagcaat caacaaactg   1200
cagcaaatct tcaaccacag ctacaaccag acatacgaaa atatggaaa tgtgagcgtc    1260 ttcgagacta gcggtgggct ggtggtgttc tggcaggaa ttaagcagaa gtccttggtg     1320
```

| | |
|---|---|
| gaactggagc ggctggctaa ccggtcgtct ctaaatatca cccacagaac acgacgctct | 1380 |
| acgtctgata taacaccac acacctcagc agcatggaat ctgttcacaa cctcgtctac | 1440 |
| gcccaactac agttcaccta tgacactttg aggggggtata tcaatagagc tttagcccaa | 1500 |
| attgccgaag cctggtgtgt ggatcaacgg agaacactgg aggttttttaa ggagctctca | 1560 |
| aagattaacc cttcagcgat actgagcgcc atttacaata agccaatcgc agctagattc | 1620 |
| atgggtgacg tattgggctt agcaagttgt gttaccataa atcagacctc cgtgaaggtc | 1680 |
| ttacgcgaca tgaatgttaa ggagagccct gggcggtgct actcacggcc agttgtaatc | 1740 |
| ttcaatttcg caaactcctc atatgtccag tatggccaac taggagagga caacgagatt | 1800 |
| ctgctcggca accataggac agaggagtgc caactaccct ccctgaaaat tttcatcgct | 1860 |
| gggaattcgg cctatgagta cgtcgattac ctcttcaaac ggatgattga tctgagttct | 1920 |
| attagtaccg tggactccat gatcgctctt gacatagatc cactcgagaa taccgacttc | 1980 |
| cgggtccttg aactgtatag ccagaaagag cttcgctctt ctaacgtctt tgacttggaa | 2040 |
| gaaattatgc gagaatttaa ttcatataag cagcgtgtta aatacgttga agataaggtt | 2100 |
| gtggacccgt tacctcctta cctcaaaggc cttgacgatc tcatgagcgg gctcggcgca | 2160 |
| gccgggaaag cggtaggagt ggccatcggt gccgttggag gcgccgtagc cagtgtcgtg | 2220 |
| gaaggagtag caacgttcct gaaaaacccc ttcggtgctt ttacaattat cctcgtggcg | 2280 |
| atcgccgtgg tgatcattac ctacctgata tacactcgcc agcgacgcct gtgcacacaa | 2340 |
| ccattgcaga acttgtttcc ctacctggtc tcggcggacg ggactaccgt gacatctggg | 2400 |
| agtaccaaag atacgagctt acaggctccc ccatcttacg aggagtcagt gtacaattcc | 2460 |
| ggtagaaagg gtcctggccc tccgagtagt gacgctagca ccgctgcgcc cccatacaca | 2520 |
| aacgagcagg cctaccagat gctgctggcc ctggccagac tggatgctga gcagagagca | 2580 |
| cagcagaatg gaactgactc cctggatggg cagacaggca cgcaagataa gggccagaaa | 2640 |
| ccaaacttgc tggaccgcct tcgacaccgc aaaaatggct acaggcatct gaaggactct | 2700 |
| gacgaagaag agaatgtc | 2718 |

<210> SEQ ID NO 18
<211> LENGTH: 2718
<212> TYPE: DNA
<213> ORGANISM: Artificial Sequence
<220> FEATURE:
<223> OTHER INFORMATION: codon-optimized sequence of hCMV gB

<400> SEQUENCE: 18

| | |
|---|---|
| atggagagta ggatttggtg tctggtggtt tgcgtcaacc tttgcatcgt gtgcctgggg | 60 |
| gcagctgttt cgtcgtctag cactagccat gccacctcta gtactcacaa cgggtcacac | 120 |
| acatctcgga ccacatccgc acagaccagg agcgtataca gccagcatgt tacaagttcg | 180 |
| gaggcagtga gtcatcgagc aaatgagacc atctataata ccacactcaa gtatggcgac | 240 |
| gtcgtgggcg tgaatacaac caagtatcct taccgggtgt gcagcatggc acagggtacc | 300 |
| gatctcattc gcttcgagcg gaacattatc tgtacgagca tgaagcctat taacgaggac | 360 |
| ctcgatgaag gtatcatggt tgtttataaa cgcaatattg ttgcccacac gtttaaagtg | 420 |
| agagtttacc agaaggtgct gacattcagg aggtcgtacg cttacattta tactacatat | 480 |
| ctattagggt ccaacacaga gtacgtggcc ccgcccatgt gggaaatcca ccatatcaat | 540 |
| aagttcgctc agtgttattc ttcgtattcc agggtgatcg gcgggaccgt atttgtggct | 600 |
| taccacagag actcctacga gaacaaaaca atgcaactga ttcccgatga ctactctaat | 660 |

```
actcacagca ctcgctacgt gactgtcaag gatcagtggc actctagggg ctcaacctgg      720
ctgtacaggg aaacatgtaa tctgaattgc atgctgacca ttactactgc acgcagcaag      780
tatccctatc acttttttcgc cacctccaca ggggatgtcg tttatatcag cccatttttac    840
aacggcacca atagaaacgc ttcctacttt ggagaaaatg ctgataaatt cttcatattc      900
ccgaattaca ctatcgtgag tgatttcggc cgaccaaacg cggcgcccga aacccacaga      960
ctggttgcct tccttgaacg ggctgacagc gttatcagtt gggatatcca ggatgagaag     1020
aacgtgacct gccagctgac ttttttgggaa gcatcagaga ggaccattag gtccgaagcc    1080
gaggactcct accatttcag cagtgctaaa atgaccgcca ctttcctgtc aaaaaagcag     1140
gaggtgaaca tgtcagactc tgcactggat tgtgtccggg acgaagcaat caacaagctg     1200
cagcagatat tcaataccct ctacaaccaa acctacgaaa aatacggcaa tgtgtcagtg     1260
tttgagacgt ctggcggact ggtggtattt tggcagggaa taaaacagaa atccctcgtc     1320
gagttggagc gcttagccaa cagaagtagc ctgaacatca ctcacaggac acgccggtca     1380
acgagtgata ataataccac ccacctgagc agcatggagt ccgtccataa cctagtgtac     1440
gcccaactcc aattcactta tgacacactt cgaggttaca ttaaccgagc actcgcccag     1500
attgcagagg cctggtgtgt tgatcagcgg agaaccttgg aagtgtttaa ggaactctct     1560
aagataaacc cttccgctat cttatccgcc atttataata aacctatcgc agcacgcttc     1620
atgggtgacg tactggggct tgcctcttgt gtgacgatca accagacatc tgtgaaagtc     1680
ctgcgggata tgaatgtcaa ggagtcacca ggacgttgct acagccgccc agtcgtgatt     1740
tttaacttcg ctaattccag ctatgtgcaa tatgggcagt tgggagagga caatgagatc     1800
ctccttggta atcatcgcac tgaagaatgc cagttgcctt ctctgaagat ctttatcgcc     1860
ggcaacagcg cgtatgagta cgtagattac ctctttaagc gtatgataga cctttcctca     1920
atctccacag ttgatagtat gattgccctg gacatcgacc ccctggagaa cactgatttc     1980
agagtcctcg agttgtattc tcagaaggaa ttaagatcct ctaacgtatt tgacctcgag     2040
gagattatgc gcgaatttaa tagctacaag caacgagtca aatatgtgga agataaggtc     2100
gtggacccac taccgcccta tctaaagggg ctggacgacc tgatgagtgg gttaggagcg     2160
gccggaaaag ccgtgggagt ggcgattggt gctgtgggcg gggctgtagc cagtgtggtc     2220
gagggagtcg ctacctttct caagaatccc ttcggcgcgt ttacaatcat tctggtggcc     2280
atagctgttg tcataatcac gtacttgata tacacccggc agagacggct gtgcactcag     2340
cctctgcaaa atcttttccc ttatctagtc tctgccgacg gcaaccgt aacaagcggc       2400
agcacaaaag atacttcact ccaggccccc ccatcctacg aagaatcagt gtataactcc     2460
ggccgaaaag gacccggccc tccaagctca gacgcatcaa ccgccgcccc ccttacacc     2520
aacgagcagg cttaccagat gttgttggct ctcgcccgtc tggatgcgga acagcgtgcc     2580
caacaaaacg gaacggacag tcttgatggc cagacgggta cacaagacaa gggccagaag     2640
ccaaaccttc tggacaggtt gcggcacaga aaaaacggtt atagacatct gaaagactct     2700
gatgaggagg aaaatgtg                                                    2718
```

<210> SEQ ID NO 19
<211> LENGTH: 1473
<212> TYPE: DNA
<213> ORGANISM: Human cytomegalovirus
<220> FEATURE:
<221> NAME/KEY: CDS
<222> LOCATION: (1)..(1473)

<400> SEQUENCE: 19

```
atg gag tcc tct gcc aag aga aag atg gac cct gat aat cct gac gag    48
Met Glu Ser Ser Ala Lys Arg Lys Met Asp Pro Asp Asn Pro Asp Glu
 1               5                  10                  15 ggc cct tcc tcc aag gtg cca cgg ccc gag aca ccc gtg acc aag gcc    96
Gly Pro Ser Ser Lys Val Pro Arg Pro Glu Thr Pro Val Thr Lys Ala
             20                  25                  30 acg acg ttc ctg cag act atg ttg agg aag gag gtt aac agt cag ctg   144
Thr Thr Phe Leu Gln Thr Met Leu Arg Lys Glu Val Asn Ser Gln Leu
         35                  40                  45 agt ctg gga gac ccg ctg ttt cca gag ttg gcc gaa gaa tcc ctc aaa   192
Ser Leu Gly Asp Pro Leu Phe Pro Glu Leu Ala Glu Glu Ser Leu Lys
 50                  55                  60 act ttt gaa caa gtg acc gag gat tgc aac gag aac ccc gag aaa gat   240
Thr Phe Glu Gln Val Thr Glu Asp Cys Asn Glu Asn Pro Glu Lys Asp
 65                  70                  75                  80 gtc ctg gca gaa ctc gtc aaa cag att aag gtt cga gtg gac atg gtg   288
Val Leu Ala Glu Leu Val Lys Gln Ile Lys Val Arg Val Asp Met Val
                 85                  90                  95 cgg cat aga atc aag gag cac atg ctg aaa aaa tat acc cag acg gaa   336
Arg His Arg Ile Lys Glu His Met Leu Lys Lys Tyr Thr Gln Thr Glu
            100                 105                 110 gag aaa ttc act ggc gcc ttt aat atg atg gga gga tgt ttg cag aat   384
Glu Lys Phe Thr Gly Ala Phe Asn Met Met Gly Gly Cys Leu Gln Asn
        115                 120                 125 gcc tta gat atc tta gat aag gtt cat gag cct ttc gag gag atg aag   432
Ala Leu Asp Ile Leu Asp Lys Val His Glu Pro Phe Glu Glu Met Lys
130                 135                 140 tgt att ggg cta act atg cag agc atg tat gag aac tac att gta cct   480
Cys Ile Gly Leu Thr Met Gln Ser Met Tyr Glu Asn Tyr Ile Val Pro
145                 150                 155                 160 gag gat aag cgg gag atg tgg atg gct tgt att aag gag ctg cat gat   528
Glu Asp Lys Arg Glu Met Trp Met Ala Cys Ile Lys Glu Leu His Asp
                165                 170                 175 gtg agc aag ggc gcc gct aac aag ttg ggg ggt gca ctg cag gct aag   576
Val Ser Lys Gly Ala Ala Asn Lys Leu Gly Gly Ala Leu Gln Ala Lys
            180                 185                 190 gcc cgt gct aaa aag gat gaa ctt agg aga aag atg atg tat atg tgc   624
Ala Arg Ala Lys Lys Asp Glu Leu Arg Arg Lys Met Met Tyr Met Cys
        195                 200                 205 tac agg aat ata gag ttc ttt acc aag aac tca gcc ttc cct aag acc   672
Tyr Arg Asn Ile Glu Phe Phe Thr Lys Asn Ser Ala Phe Pro Lys Thr
    210                 215                 220 acc aat ggc tgc agt cag gcc atg gcg gca ctg cag aac ttg cct cag   720
Thr Asn Gly Cys Ser Gln Ala Met Ala Ala Leu Gln Asn Leu Pro Gln
225                 230                 235                 240 tgc tcc cct gat gag att atg gct tat gcc cag aaa ata ttt aag att   768
Cys Ser Pro Asp Glu Ile Met Ala Tyr Ala Gln Lys Ile Phe Lys Ile
                245                 250                 255 ttg gat gag gag aga gac aag gtg ctc acg cac att gat cac ata ttt   816
Leu Asp Glu Glu Arg Asp Lys Val Leu Thr His Ile Asp His Ile Phe
            260                 265                 270 atg gat atc ctc act aca tgt gtg gaa aca atg tgt aat gag tac aag   864
Met Asp Ile Leu Thr Thr Cys Val Glu Thr Met Cys Asn Glu Tyr Lys
        275                 280                 285 gtc act agt gac gct tgt atg atg acc atg tac ggg ggc atc tct ctc   912
Val Thr Ser Asp Ala Cys Met Met Thr Met Tyr Gly Gly Ile Ser Leu
    290                 295                 300
```

```
tta agt gag ttc tgt cgg gtg ctg tgc tgc tat gtc tta gag gag act    960
Leu Ser Glu Phe Cys Arg Val Leu Cys Cys Tyr Val Leu Glu Glu Thr
305                 310                 315                 320 agt gtg atg ctg gcc aag cgg cct ctg ata acc aag cct gag gtt atc    1008
Ser Val Met Leu Ala Lys Arg Pro Leu Ile Thr Lys Pro Glu Val Ile
            325                 330                 335 agt gta atg aag cgc gcc att gag gag atc tgc atg aag gtc ttt gcc    1056
Ser Val Met Lys Arg Arg Ile Glu Glu Ile Cys Met Lys Val Phe Ala
            340                 345                 350 cag tac att ctg ggg gcc gat cct ctg aga gtc tgc tct cct agt gtg    1104
Gln Tyr Ile Leu Gly Ala Asp Pro Leu Arg Val Cys Ser Pro Ser Val
            355                 360                 365 gat gac cta cgg gcc atc gcc gag gag tca gat gag gaa gag gct att    1152
Asp Asp Leu Arg Ala Ile Ala Glu Glu Ser Asp Glu Glu Glu Ala Ile
    370                 375                 380 gta gcc tac act ttg gcc acc gct ggt gtc agc tcc tct gat tct ctg    1200
Val Ala Tyr Thr Leu Ala Thr Ala Gly Val Ser Ser Ser Asp Ser Leu
385                 390                 395                 400 gtg tca ccc cca gag tcc cct gta ccc gcg act atc cct ctg tcc tca    1248
Val Ser Pro Pro Glu Ser Pro Val Pro Ala Thr Ile Pro Leu Ser Ser
            405                 410                 415 gta att gtg gct gag aac agt gat cag gaa gaa agt gag cag agt gat    1296
Val Ile Val Ala Glu Asn Ser Asp Gln Glu Glu Ser Glu Gln Ser Asp
            420                 425                 430 gag gaa gag gag gag ggt gct cag gag gag cgg gag gac act gtg tct    1344
Glu Glu Glu Glu Glu Gly Ala Gln Glu Glu Arg Glu Asp Thr Val Ser
            435                 440                 445 gtc aag tct gag cca gtg tct gag ata gag gaa gtt gcc cca gag gaa    1392
Val Lys Ser Glu Pro Val Ser Glu Ile Glu Glu Val Ala Pro Glu Glu
    450                 455                 460 gag gag gat ggt gct gag gaa ccc acc gcc tct gga ggc aag agc acc    1440
Glu Glu Asp Gly Ala Glu Glu Pro Thr Ala Ser Gly Gly Lys Ser Thr
465                 470                 475                 480 cac cct atg gtg act aga agc aag gct gac cag                        1473
His Pro Met Val Thr Arg Ser Lys Ala Asp Gln
            485                 490
```

<210> SEQ ID NO 20
<211> LENGTH: 491
<212> TYPE: PRT
<213> ORGANISM: Human cytomegalovirus

<400> SEQUENCE: 20

```
Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
                20                  25                  30

Thr Thr Phe Leu Gln Thr Met Leu Arg Lys Glu Val Asn Ser Gln Leu
            35                  40                  45

Ser Leu Gly Asp Pro Leu Phe Pro Glu Leu Ala Glu Glu Ser Leu Lys
        50                  55                  60

Thr Phe Glu Gln Val Thr Glu Asp Cys Asn Glu Asn Pro Glu Lys Asp
65                  70                  75                  80

Val Leu Ala Glu Leu Val Lys Gln Ile Lys Val Arg Val Asp Met Val
                85                  90                  95

Arg His Arg Ile Lys Glu His Met Leu Lys Lys Tyr Thr Gln Thr Glu
                100                 105                 110

Glu Lys Phe Thr Gly Ala Phe Asn Met Met Gly Gly Cys Leu Gln Asn
            115                 120                 125
```

Ala Leu Asp Ile Leu Asp Lys Val His Glu Pro Phe Glu Met Lys
    130                 135                 140

Cys Ile Gly Leu Thr Met Gln Ser Met Tyr Glu Asn Tyr Ile Val Pro
145                 150                 155                 160

Glu Asp Lys Arg Glu Met Trp Met Ala Cys Ile Lys Glu Leu His Asp
                165                 170                 175

Val Ser Lys Gly Ala Ala Asn Lys Leu Gly Gly Ala Leu Gln Ala Lys
            180                 185                 190

Ala Arg Ala Lys Lys Asp Glu Leu Arg Arg Lys Met Met Tyr Met Cys
        195                 200                 205

Tyr Arg Asn Ile Glu Phe Phe Thr Lys Asn Ser Ala Phe Pro Lys Thr
    210                 215                 220

Thr Asn Gly Cys Ser Gln Ala Met Ala Ala Leu Gln Asn Leu Pro Gln
225                 230                 235                 240

Cys Ser Pro Asp Glu Ile Met Ala Tyr Ala Gln Lys Ile Phe Lys Ile
                245                 250                 255

Leu Asp Glu Glu Arg Asp Lys Val Leu Thr His Ile Asp His Ile Phe
            260                 265                 270

Met Asp Ile Leu Thr Thr Cys Val Glu Thr Met Cys Asn Glu Tyr Lys
        275                 280                 285

Val Thr Ser Asp Ala Cys Met Met Thr Met Tyr Gly Gly Ile Ser Leu
    290                 295                 300

Leu Ser Glu Phe Cys Arg Val Leu Cys Cys Tyr Val Leu Glu Glu Thr
305                 310                 315                 320

Ser Val Met Leu Ala Lys Arg Pro Leu Ile Thr Lys Pro Glu Val Ile
                325                 330                 335

Ser Val Met Lys Arg Arg Ile Glu Glu Ile Cys Met Lys Val Phe Ala
            340                 345                 350

Gln Tyr Ile Leu Gly Ala Asp Pro Leu Arg Val Cys Ser Pro Ser Val
        355                 360                 365

Asp Asp Leu Arg Ala Ile Ala Glu Glu Ser Asp Glu Glu Ala Ile
    370                 375                 380

Val Ala Tyr Thr Leu Ala Thr Ala Gly Val Ser Ser Ser Asp Ser Leu
385                 390                 395                 400

Val Ser Pro Pro Glu Ser Pro Val Pro Ala Thr Ile Pro Leu Ser Ser
                405                 410                 415

Val Ile Val Ala Glu Asn Ser Asp Gln Glu Glu Ser Glu Gln Ser Asp
            420                 425                 430

Glu Glu Glu Glu Glu Gly Ala Gln Glu Glu Arg Glu Asp Thr Val Ser
        435                 440                 445

Val Lys Ser Glu Pro Val Ser Glu Ile Glu Glu Val Ala Pro Glu Glu
    450                 455                 460

Glu Glu Asp Gly Ala Glu Glu Pro Thr Ala Ser Gly Gly Lys Ser Thr
465                 470                 475                 480

His Pro Met Val Thr Arg Ser Lys Ala Asp Gln
                485                 490

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer T7

<400> SEQUENCE: 21

-continued

```
taatacgact cactataggg                                              20

<210> SEQ ID NO 22
<211> LENGTH: 18
<212> TYPE: DNA
<213> ORGANISM: Artificial Sequence
<220> FEATURE:
<223> OTHER INFORMATION: oligonucleotide primer 65-delta-rev

<400> SEQUENCE: 22
aggatgctga gccggcgg                                                18

<210> SEQ ID NO 23
<211> LENGTH: 23
<212> TYPE: DNA
<213> ORGANISM: Artificial Sequence
<220> FEATURE:
<223> OTHER INFORMATION: oligonucleotide primer M13rev

<400> SEQUENCE: 23
cccagtcacg acgttgtaaa acg                                          23

<210> SEQ ID NO 24
<211> LENGTH: 18
<212> TYPE: DNA
<213> ORGANISM: Artificial Sequence
<220> FEATURE:
<223> OTHER INFORMATION: oligonucleotide primer 65-delta-for

<400> SEQUENCE: 24
ccgccggctc agcatcct                                                18

<210> SEQ ID NO 25
<211> LENGTH: 22
<212> TYPE: DNA
<213> ORGANISM: Artificial Sequence
<220> FEATURE:
<223> OTHER INFORMATION: oligonucleotide primer VR1051FOR

<400> SEQUENCE: 25
gagcagtact cgttgctgcc gc                                           22

<210> SEQ ID NO 26
<211> LENGTH: 32
<212> TYPE: DNA
<213> ORGANISM: Artificial Sequence
<220> FEATURE:
<223> OTHER INFORMATION: oligonucleotide primer hCMVpp65-R

<400> SEQUENCE: 26
gttacgtcta gatcaacctc ggtgcttttt gg                                32

<210> SEQ ID NO 27
<211> LENGTH: 28
<212> TYPE: DNA
<213> ORGANISM: Artificial Sequence
<220> FEATURE:
<223> OTHER INFORMATION: oligonucleotide primer hCMVgB-R

<400> SEQUENCE: 27
tctagatcag tcgtccagac ccttgagg                                     28

<210> SEQ ID NO 28
<211> LENGTH: 1236
<212> TYPE: DNA
```

<213> ORGANISM: Artificial Sequence
<220> FEATURE:
<223> OTHER INFORMATION: codon-optimized IE1 sequence
<220> FEATURE:
<221> NAME/KEY: CDS
<222> LOCATION: (16)..(1227)

<400> SEQUENCE: 28

```
gatatcgccg ccacc atg gag tct agc gcc aag agg aag atg gac ccc gac        51
                 Met Glu Ser Ser Ala Lys Arg Lys Met Asp Pro Asp
                  1               5                  10 aac cct gat gag ggc cct agc agc aag gtg ccc cgg gtg aag cag atc        99
Asn Pro Asp Glu Gly Pro Ser Ser Lys Val Pro Arg Val Lys Gln Ile
         15                  20                  25 aag gtg cgg gtg gac atg gtg cgg cac agg atc aag gaa cac atg ctg       147
Lys Val Arg Val Asp Met Val Arg His Arg Ile Lys Glu His Met Leu
 30                  35                  40 aag aag tac acc cag acc gag gag aag ttc acc ggc gcc ttc aat atg       195
Lys Lys Tyr Thr Gln Thr Glu Glu Lys Phe Thr Gly Ala Phe Asn Met
45                  50                  55                  60 atg ggc ggc tgc ctg cag aat gcc ctg gac atc ctg gac aag gtg cac       243
Met Gly Gly Cys Leu Gln Asn Ala Leu Asp Ile Leu Asp Lys Val His
                 65                  70                  75 gag ccc ttc gag gag atg aag tgc atc ggc ctg acc atg cag agc atg       291
Glu Pro Phe Glu Glu Met Lys Cys Ile Gly Leu Thr Met Gln Ser Met
             80                  85                  90 tac gag aac tac atc gtg ccc gag gac aag agg gag atg tgg atg gcc       339
Tyr Glu Asn Tyr Ile Val Pro Glu Asp Lys Arg Glu Met Trp Met Ala
         95                 100                 105 tgc atc gac gag ctg cgg cgg aag atg atg tac atg tgc tac cgg aac       387
Cys Ile Asp Glu Leu Arg Arg Lys Met Met Tyr Met Cys Tyr Arg Asn
110                 115                 120 atc gag ttc ttc acc aag aac agc gcc ttc ccc aag acc acc aac gga       435
Ile Glu Phe Phe Thr Lys Asn Ser Ala Phe Pro Lys Thr Thr Asn Gly
125                 130                 135                 140 tgc tct cag gcc atg gcc gcc ctg cag aat ctg cct cag tgc agc ccc       483
Cys Ser Gln Ala Met Ala Ala Leu Gln Asn Leu Pro Gln Cys Ser Pro
                145                 150                 155 gat gag atc atg gcc tac gcc cag aag atc ttc aag atc ctg gac gag       531
Asp Glu Ile Met Ala Tyr Ala Gln Lys Ile Phe Lys Ile Leu Asp Glu
            160                 165                 170 gag agg gat aag gtg ctg acc cac atc gac cac atc ttc atg gac atc       579
Glu Arg Asp Lys Val Leu Thr His Ile Asp His Ile Phe Met Asp Ile
        175                 180                 185 ctg acc acc tgc gtg gag acc atg tgc aac gag tac aag gtg acc agc       627
Leu Thr Thr Cys Val Glu Thr Met Cys Asn Glu Tyr Lys Val Thr Ser
    190                 195                 200 gac gcc tgc atg atg aca atg tac ggc ggc atc agc ctg ctg agc gag       675
Asp Ala Cys Met Met Thr Met Tyr Gly Gly Ile Ser Leu Leu Ser Glu
205                 210                 215                 220 ttc tgc aga gtg ctg tgc tgc tac gtg ctg gag gag acc tct gtg atg       723
Phe Cys Arg Val Leu Cys Cys Tyr Val Leu Glu Glu Thr Ser Val Met
                225                 230                 235 ctg gcc aag agg ccc ctg atc acc aag cct gag gtg atc agc gtg atg       771
Leu Ala Lys Arg Pro Leu Ile Thr Lys Pro Glu Val Ile Ser Val Met
            240                 245                 250 aag cgg cgg atc gag gag atc tgc atg aag gtg ttc gcc cag tac atc       819
Lys Arg Arg Ile Glu Glu Ile Cys Met Lys Val Phe Ala Gln Tyr Ile
        255                 260                 265 ctg gga gcc gac cct ctg aga gtg tgt agc ccc agc gtg gat gac ctg       867
Leu Gly Ala Asp Pro Leu Arg Val Cys Ser Pro Ser Val Asp Asp Leu
```

```
                 270                 275                 280
aga gcc atc gcc gag gaa tct gat gaa gag gag gcc atc gtg gcc tat    915
Arg Ala Ile Ala Glu Glu Ser Asp Glu Glu Glu Ala Ile Val Ala Tyr
285                 290                 295                 300 aca ctg gcc aca gcc ggc gtg tct agc agc gat agc ctg gtg agc cct    963
Thr Leu Ala Thr Ala Gly Val Ser Ser Ser Asp Ser Leu Val Ser Pro
                305                 310                 315 cct gag tct cct gtg cct gcc aca atc cct ctg agc agc gtg atc gtg    1011
Pro Glu Ser Pro Val Pro Ala Thr Ile Pro Leu Ser Ser Val Ile Val
            320                 325                 330 gcc gag aac agc gat cag gag gag agc gag cag tct gat gag gaa gag    1059
Ala Glu Asn Ser Asp Gln Glu Glu Ser Glu Gln Ser Asp Glu Glu Glu
        335                 340                 345 gaa gag gga gcc cag gag gag aga gag gat acc gtg agc gtg aag agc    1107
Glu Glu Gly Ala Gln Glu Glu Arg Glu Asp Thr Val Ser Val Lys Ser
    350                 355                 360 gag cct gtg agc gag atc gaa gag gtg gcc cct gag gaa gag gat        1155
Glu Pro Val Ser Glu Ile Glu Glu Val Ala Pro Glu Glu Glu Asp
365                 370                 375                 380 ggc gcc gag gag cct aca gcc agc ggc ggc aag tca aca cac ccc atg    1203
Gly Ala Glu Glu Pro Thr Ala Ser Gly Gly Lys Ser Thr His Pro Met
                385                 390                 395 gtg acc aga agc aag gcc gac cag taaggatcc                          1236
Val Thr Arg Ser Lys Ala Asp Gln
            400
```

<210> SEQ ID NO 29
<211> LENGTH: 404
<212> TYPE: PRT
<213> ORGANISM: Artificial Sequence
<220> FEATURE:
<223> OTHER INFORMATION: codon-optimized IE1 sequence

<400> SEQUENCE: 29

```
Met Glu Ser Ser Ala Lys Arg Lys Met Asp Pro Asp Asn Pro Asp Glu
1               5                   10                  15

Gly Pro Ser Ser Lys Val Pro Arg Val Lys Gln Ile Lys Val Arg Val
            20                  25                  30

Asp Met Val Arg His Arg Ile Lys Glu His Met Leu Lys Lys Tyr Thr
        35                  40                  45

Gln Thr Glu Glu Lys Phe Thr Gly Ala Phe Asn Met Met Gly Gly Cys
    50                  55                  60

Leu Gln Asn Ala Leu Asp Ile Leu Asp Lys Val His Glu Pro Phe Glu
65                  70                  75                  80

Glu Met Lys Cys Ile Gly Leu Thr Met Gln Ser Met Tyr Glu Asn Tyr
                85                  90                  95

Ile Val Pro Glu Asp Lys Arg Glu Met Trp Met Ala Cys Ile Asp Glu
            100                 105                 110

Leu Arg Arg Lys Met Met Tyr Met Cys Tyr Arg Asn Ile Glu Phe Phe
        115                 120                 125

Thr Lys Asn Ser Ala Phe Pro Lys Thr Thr Asn Gly Cys Ser Gln Ala
    130                 135                 140

Met Ala Ala Leu Gln Asn Leu Pro Gln Cys Ser Pro Asp Glu Ile Met
145                 150                 155                 160

Ala Tyr Ala Gln Lys Ile Phe Lys Ile Leu Asp Glu Glu Arg Asp Lys
                165                 170                 175

Val Leu Thr His Ile Asp His Ile Phe Met Asp Ile Leu Thr Thr Cys
            180                 185                 190
```

```
Val Glu Thr Met Cys Asn Glu Tyr Lys Val Thr Ser Asp Ala Cys Met
        195                 200                 205

Met Thr Met Tyr Gly Gly Ile Ser Leu Leu Ser Glu Phe Cys Arg Val
210                 215                 220

Leu Cys Cys Tyr Val Leu Glu Glu Thr Ser Val Met Leu Ala Lys Arg
225                 230                 235                 240

Pro Leu Ile Thr Lys Pro Glu Val Ile Ser Val Met Lys Arg Arg Ile
                245                 250                 255

Glu Glu Ile Cys Met Lys Val Phe Ala Gln Tyr Ile Leu Gly Ala Asp
                260                 265                 270

Pro Leu Arg Val Cys Ser Pro Val Asp Asp Leu Arg Ala Ile Ala
                275                 280                 285

Glu Glu Ser Asp Glu Glu Ala Ile Val Ala Tyr Thr Leu Ala Thr
        290                 295                 300

Ala Gly Val Ser Ser Ser Asp Ser Leu Val Ser Pro Pro Glu Ser Pro
305                 310                 315                 320

Val Pro Ala Thr Ile Pro Leu Ser Ser Val Ile Val Ala Glu Asn Ser
                325                 330                 335

Asp Gln Glu Glu Ser Glu Gln Ser Asp Glu Glu Glu Glu Gly Ala
                340                 345                 350

Gln Glu Glu Arg Glu Asp Thr Val Ser Val Lys Ser Glu Pro Val Ser
        355                 360                 365

Glu Ile Glu Glu Val Ala Pro Glu Glu Glu Asp Gly Ala Glu Glu
        370                 375                 380

Pro Thr Ala Ser Gly Gly Lys Ser Thr His Pro Met Val Thr Arg Ser
385                 390                 395                 400

Lys Ala Asp Gln

<210> SEQ ID NO 30
<211> LENGTH: 1236
<212> TYPE: DNA
<213> ORGANISM: Artificial Sequence
<220> FEATURE:
<223> OTHER INFORMATION: codon-optimized IE1 sequence
<220> FEATURE:
<221> NAME/KEY: CDS
<222> LOCATION: (16)..(1227)

<400> SEQUENCE: 30
gaattcgccg ccacc atg gag tcc tct gcc aag aga aag atg gac cct gat     51
                Met Glu Ser Ser Ala Lys Arg Lys Met Asp Pro Asp
                 1               5                  10 aat cct gac gag ggc cct tcc tcc aag gtg cca cgg gtc aaa cag att     99
Asn Pro Asp Glu Gly Pro Ser Ser Lys Val Pro Arg Val Lys Gln Ile
             15                  20                  25 aag gtt cga gtg gac atg gtg cgg cat aga atc aag gag cac atg ctg    147
Lys Val Arg Val Asp Met Val Arg His Arg Ile Lys Glu His Met Leu
 30                  35                  40 aaa aaa tat acc cag acg gaa gag aaa ttc act ggc gcc ttt aat atg    195
Lys Lys Tyr Thr Gln Thr Glu Glu Lys Phe Thr Gly Ala Phe Asn Met
45                  50                  55                  60 atg gga gga tgt ttg cag aat gcc tta gat atc tta gat aag gtt cat    243
Met Gly Gly Cys Leu Gln Asn Ala Leu Asp Ile Leu Asp Lys Val His
                 65                  70                  75 gag cct ttc gag gag atg aag tgt att ggg cta act atg cag agc atg    291
Glu Pro Phe Glu Glu Met Lys Cys Ile Gly Leu Thr Met Gln Ser Met
             80                  85                  90
```

```
tat gag aac tac att gta cct gag gat aag cgg gag atg tgg atg gct    339
Tyr Glu Asn Tyr Ile Val Pro Glu Asp Lys Arg Glu Met Trp Met Ala
         95                 100                 105 tgt att gat gaa ctt agg aga aag atg atg tat atg tgc tac agg aat    387
Cys Ile Asp Glu Leu Arg Arg Lys Met Met Tyr Met Cys Tyr Arg Asn
    110                 115                 120 ata gag ttc ttt acc aag aac tca gcc ttc cct aag acc acc aat ggc    435
Ile Glu Phe Phe Thr Lys Asn Ser Ala Phe Pro Lys Thr Thr Asn Gly
125                 130                 135                 140 tgc agt cag gcc atg gcg gca ctg cag aac ttg cct cag tgc tcc cct    483
Cys Ser Gln Ala Met Ala Ala Leu Gln Asn Leu Pro Gln Cys Ser Pro
                145                 150                 155 gat gag att atg gct tat gcc cag aaa ata ttt aag att tgt gat gag    531
Asp Glu Ile Met Ala Tyr Ala Gln Lys Ile Phe Lys Ile Leu Asp Glu
            160                 165                 170 gag aga gac aag gtg ctc acg cac att gat cac ata ttt atg gat atc    579
Glu Arg Asp Lys Val Leu Thr His Ile Asp His Ile Phe Met Asp Ile
        175                 180                 185 ctc act aca tgt gtg gaa aca atg tgt aat gag tac aag gtc act agt    627
Leu Thr Thr Cys Val Glu Thr Met Cys Asn Glu Tyr Lys Val Thr Ser
    190                 195                 200 gac gct tgt atg atg acc atg tac ggg ggc atc tct ctc tta agt gag    675
Asp Ala Cys Met Met Thr Met Tyr Gly Gly Ile Ser Leu Leu Ser Glu
205                 210                 215                 220 ttc tgt cgg gtg ctg tgc tgc tat gtc tta gag gag act agt gtg atg    723
Phe Cys Arg Val Leu Cys Cys Tyr Val Leu Glu Glu Thr Ser Val Met
                225                 230                 235 ctg gcc aag cgg cct ctg ata acc aag cct gag gtt atc agt gta atg    771
Leu Ala Lys Arg Pro Leu Ile Thr Lys Pro Glu Val Ile Ser Val Met
            240                 245                 250 aag cgc cgc att gag gag atc tgc atg aag gtc ttt gcc cag tac att    819
Lys Arg Arg Ile Glu Glu Ile Cys Met Lys Val Phe Ala Gln Tyr Ile
        255                 260                 265 ctg ggg gcc gat cct ctg aga gtc tgc tct cct agt gtg gat gac cta    867
Leu Gly Ala Asp Pro Leu Arg Val Cys Ser Pro Ser Val Asp Asp Leu
    270                 275                 280 cgg gcc atc gcc gag gag tca gat gag gaa gag gct att gta gcc tac    915
Arg Ala Ile Ala Glu Glu Ser Asp Glu Glu Glu Ala Ile Val Ala Tyr
285                 290                 295                 300 act ttg gcc acc gct ggt gtc agc tcc tct gat tct ctg gtg tca ccc    963
Thr Leu Ala Thr Ala Gly Val Ser Ser Ser Asp Ser Leu Val Ser Pro
                305                 310                 315 cca gag tcc cct gta ccc gcg act atc cct ctg tcc tca gta att gtg   1011
Pro Glu Ser Pro Val Pro Ala Thr Ile Pro Leu Ser Ser Val Ile Val
            320                 325                 330 gct gag aac agt gat cag gaa gaa agt gag cag agt gat gag gaa gag   1059
Ala Glu Asn Ser Asp Gln Glu Glu Ser Glu Gln Ser Asp Glu Glu Glu
        335                 340                 345 gag gag ggt gct cag gag gag cgg gag gac act gtg tct gtc aag tct   1107
Glu Glu Gly Ala Gln Glu Glu Arg Glu Asp Thr Val Ser Val Lys Ser
    350                 355                 360 gag cca gtg tct gag ata gag gaa gtt gcc cca gag gaa gag gag gat   1155
Glu Pro Val Ser Glu Ile Glu Glu Val Ala Pro Glu Glu Glu Glu Asp
365                 370                 375                 380 ggt gct gag gaa ccc acc gcc tct gga ggc aag agc acc cac cct atg   1203
Gly Ala Glu Glu Pro Thr Ala Ser Gly Gly Lys Ser Thr His Pro Met
                385                 390                 395 gtg act aga agc aag gct gac cag tgaggatcc                         1236
Val Thr Arg Ser Lys Ala Asp Gln
                400
```

<210> SEQ ID NO 31
<211> LENGTH: 404
<212> TYPE: PRT
<213> ORGANISM: Artificial Sequence
<220> FEATURE:
<223> OTHER INFORMATION: codon-optimized IE1 sequence

<400> SEQUENCE: 31

```
Met Glu Ser Ser Ala Lys Arg Lys Met Asp Pro Asp Asn Pro Asp Glu
1               5                   10                  15

Gly Pro Ser Ser Lys Val Pro Arg Val Lys Gln Ile Lys Val Arg Val
            20                  25                  30

Asp Met Val Arg His Arg Ile Lys Glu His Met Leu Lys Lys Tyr Thr
        35                  40                  45

Gln Thr Glu Glu Lys Phe Thr Gly Ala Phe Asn Met Met Gly Gly Cys
    50                  55                  60

Leu Gln Asn Ala Leu Asp Ile Leu Asp Lys Val His Glu Pro Phe Glu
65                  70                  75                  80

Glu Met Lys Cys Ile Gly Leu Thr Met Gln Ser Met Tyr Glu Asn Tyr
                85                  90                  95

Ile Val Pro Glu Asp Lys Arg Glu Met Trp Met Ala Cys Ile Asp Glu
            100                 105                 110

Leu Arg Arg Lys Met Met Tyr Met Cys Tyr Arg Asn Ile Glu Phe Phe
        115                 120                 125

Thr Lys Asn Ser Ala Phe Pro Lys Thr Thr Asn Gly Cys Ser Gln Ala
    130                 135                 140

Met Ala Ala Leu Gln Asn Leu Pro Gln Cys Ser Pro Asp Glu Ile Met
145                 150                 155                 160

Ala Tyr Ala Gln Lys Ile Phe Lys Ile Leu Asp Glu Glu Arg Asp Lys
                165                 170                 175

Val Leu Thr His Ile Asp His Ile Phe Met Asp Ile Leu Thr Thr Cys
            180                 185                 190

Val Glu Thr Met Cys Asn Glu Tyr Lys Val Thr Ser Asp Ala Cys Met
        195                 200                 205

Met Thr Met Tyr Gly Gly Ile Ser Leu Leu Ser Glu Phe Cys Arg Val
    210                 215                 220

Leu Cys Cys Tyr Val Leu Glu Glu Thr Ser Val Met Leu Ala Lys Arg
225                 230                 235                 240

Pro Leu Ile Thr Lys Pro Glu Val Ile Ser Val Met Lys Arg Arg Ile
                245                 250                 255

Glu Glu Ile Cys Met Lys Val Phe Ala Gln Tyr Ile Leu Gly Ala Asp
            260                 265                 270

Pro Leu Arg Val Cys Ser Pro Ser Val Asp Asp Leu Arg Ala Ile Ala
        275                 280                 285

Glu Glu Ser Asp Glu Glu Glu Ala Ile Val Ala Tyr Thr Leu Ala Thr
    290                 295                 300

Ala Gly Val Ser Ser Ser Asp Ser Leu Val Ser Pro Pro Glu Ser Pro
305                 310                 315                 320

Val Pro Ala Thr Ile Pro Leu Ser Ser Val Ile Val Ala Glu Asn Ser
                325                 330                 335

Asp Gln Glu Glu Ser Glu Gln Ser Asp Glu Glu Glu Glu Gly Ala
            340                 345                 350

Gln Glu Glu Arg Glu Asp Thr Val Ser Val Lys Ser Glu Pro Val Ser
        355                 360                 365
```

-continued

```
Glu Ile Glu Glu Val Ala Pro Glu Glu Glu Asp Gly Ala Glu Glu
        370                 375                 380

Pro Thr Ala Ser Gly Gly Lys Ser Thr His Pro Met Val Thr Arg Ser
385                 390                 395                 400

Lys Ala Asp Gln

<210> SEQ ID NO 32
<211> LENGTH: 9
<212> TYPE: PRT
<213> ORGANISM: Homo sapiens

<400> SEQUENCE: 32

Ala Tyr Ala Gly Leu Phe Thr Pro Leu
1               5

<210> SEQ ID NO 33
<211> LENGTH: 20
<212> TYPE: DNA
<213> ORGANISM: Artificial
<220> FEATURE:
<223> OTHER INFORMATION: synthetic primer 2944S

<400> SEQUENCE: 33
ctgcgcctta tccggtaact                                            20

<210> SEQ ID NO 34
<211> LENGTH: 20
<212> TYPE: DNA
<213> ORGANISM: Artificial
<220> FEATURE:
<223> OTHER INFORMATION: synthetic primer 5876

<400> SEQUENCE: 34
cagtgaggca cctatctcag                                            20

<210> SEQ ID NO 35
<211> LENGTH: 20
<212> TYPE: DNA
<213> ORGANISM: Artificial
<220> FEATURE:
<223> OTHER INFORMATION: synthetic primer 5760

<400> SEQUENCE: 35
caccatgagt gacgactgaa                                            20

<210> SEQ ID NO 36
<211> LENGTH: 20
<212> TYPE: DNA
<213> ORGANISM: Artificial
<220> FEATURE:
<223> OTHER INFORMATION: synthetic primer 5761

<400> SEQUENCE: 36
ttaatcgcgg cctcgagcaa                                            20

<210> SEQ ID NO 37
<211> LENGTH: 20
<212> TYPE: DNA
<213> ORGANISM: Artificial
<220> FEATURE:
<223> OTHER INFORMATION: synthetic primer 5762

<400> SEQUENCE: 37
ggctcatgtc caacattacc                                            20
```

<210> SEQ ID NO 38
<211> LENGTH: 20
<212> TYPE: DNA
<213> ORGANISM: Artificial
<220> FEATURE:
<223> OTHER INFORMATION: synthetic primer 931S

<400> SEQUENCE: 38
gagacgccat ccacgctgtt                                                 20

<210> SEQ ID NO 39
<211> LENGTH: 20
<212> TYPE: DNA
<213> ORGANISM: Artificial
<220> FEATURE:
<223> OTHER INFORMATION: synthetic primer 5874

<400> SEQUENCE: 39
cagacttagg cacagcacaa                                                 20

<210> SEQ ID NO 40
<211> LENGTH: 20
<212> TYPE: DNA
<213> ORGANISM: Artificial
<220> FEATURE:
<223> OTHER INFORMATION: synthetic primer 5104

<400> SEQUENCE: 40
gagcgaggaa gcggaagagt                                                 20

<210> SEQ ID NO 41
<211> LENGTH: 20
<212> TYPE: DNA
<213> ORGANISM: Artificial
<220> FEATURE:
<223> OTHER INFORMATION: synthetic primer 3054A

<400> SEQUENCE: 41
ccgcctacat acctcgctct                                                 20

<210> SEQ ID NO 42
<211> LENGTH: 20
<212> TYPE: DNA
<213> ORGANISM: Artificial
<220> FEATURE:
<223> OTHER INFORMATION: synthetic primer 5767

<400> SEQUENCE: 42
gagcattacg ctgacttgac                                                 20

<210> SEQ ID NO 43
<211> LENGTH: 20
<212> TYPE: DNA
<213> ORGANISM: Artificial
<220> FEATURE:
<223> OTHER INFORMATION: synthetic primer 5768

<400> SEQUENCE: 43
atgcctcttc cgaccatcaa                                                 20

<210> SEQ ID NO 44
<211> LENGTH: 20
<212> TYPE: DNA
<213> ORGANISM: Artificial
<220> FEATURE:

<223> OTHER INFORMATION: synthetic primer 5770

<400> SEQUENCE: 44
ggcggtaatg ttggacatga                                              20

<210> SEQ ID NO 45
<211> LENGTH: 20
<212> TYPE: DNA
<213> ORGANISM: Artificial
<220> FEATURE:
<223> OTHER INFORMATION: synthetic primer 847A

<400> SEQUENCE: 45
ggcggagttg ttacgacatt                                              20

<210> SEQ ID NO 46
<211> LENGTH: 20
<212> TYPE: DNA
<213> ORGANISM: Artificial
<220> FEATURE:
<223> OTHER INFORMATION: synthetic primer 5772

<400> SEQUENCE: 46
cattgtgctg tgcctaagtc                                              20

<210> SEQ ID NO 47
<211> LENGTH: 20
<212> TYPE: DNA
<213> ORGANISM: Artificial
<220> FEATURE:
<223> OTHER INFORMATION: synthetic primer GA seqF1

<400> SEQUENCE: 47
ccagaccgag gagaagttca                                              20

<210> SEQ ID NO 48
<211> LENGTH: 20
<212> TYPE: DNA
<213> ORGANISM: Artificial
<220> FEATURE:
<223> OTHER INFORMATION: synthetic primer GA seqF2

<400> SEQUENCE: 48
tgctggagga gacctctgtg                                              20

<210> SEQ ID NO 49
<211> LENGTH: 20
<212> TYPE: DNA
<213> ORGANISM: Artificial
<220> FEATURE:
<223> OTHER INFORMATION: synthetic primer GA seqR2

<400> SEQUENCE: 49
tcgatccgcc gcttcatcac                                              20

<210> SEQ ID NO 50
<211> LENGTH: 1236
<212> TYPE: DNA
<213> ORGANISM: Homo sapiens

<400> SEQUENCE: 50
gaattcgccg ccaccatgga gtcctctgcc aagagaaaga tggaccctga taatcctgac      60
gagggccctt cctccaaggt gccacgggtc aaacagatta aggttcgagt ggacatggtg     120
cggcatagaa tcaaggagca catgctgaaa aaatataccc agacggaaga gaaattcact     180

```
ggcgccttta atatgatggg aggatgtttg cagaatgcct tagatatctt agataaggtt    240
catgagcctt tcgaggagat gaagtgtatt gggctaacta tgcagagcat gtatgagaac    300
tacattgtac ctgaggataa gcgggagatg tggatggctt gtattgatga acttaggaga    360
aagatgatgt atatgtgcta caggaatata gagttcttta ccaagaactc agccttccct    420
aagaccacca atggctgcag tcaggccatg gcggcactgc agaacttgcc tcagtgctcc    480
cctgatgaga ttatggctta tgcccagaaa atatttaaga ttttggatga ggagagagac    540
aaggtgctca cgcacattga tcacatattt atggatatcc tcactacatg tgtggaaaca    600
atgtgtaatg agtacaaggt cactagtgac gcttgtatga tgaccatgta cgggggcatc    660
tctctcttaa gtgagttctg tcgggtgctg tgctgctatg tcttagagga gactagtgtg    720
atgctggcca agcggcctct gataaccaag cctgaggtta tcagtgtaat gaagcgccgc    780
attgaggaga tctgcatgaa ggtctttgcc cagtacattc tgggggccga tcctctgaga    840
gtctgctctc ctagtgtgga tgacctacgg gccatcgccg aggagtcaga tgaggaagag    900
gctattgtag cctacacttt ggccaccgct ggtgtcagct cctctgattc tctggtgtca    960
cccccagagt cccctgtacc cgcgactatc cctctgtcct cagtaattgt ggctgagaac   1020
agtgatcagg aagaaagtga gcagagtgat gaggaagagg aggagggtgc tcaggaggag   1080
cgggaggaca ctgtgtctgt caagtctgag ccagtgtctg agatagagga agttgcccca   1140
gaggaagagg aggatggtgc tgaggaaccc accgcctctg gaggcaagag caccacccct   1200
atggtgacta gaagcaaggc tgaccagtga ggatcc                             1236
```